United States Patent
Routier et al.

(10) Patent No.: US 11,932,638 B2
(45) Date of Patent: Mar. 19, 2024

(54) ION CHANNEL INHIBITOR COMPOUNDS FOR CANCER TREATMENT

(71) Applicants: Centre National de la Recherche Scientifique, Paris (FR); Universite d'Orleans, Orleans (FR); Université de Tours, Tours (FR); Institut National de la Santé et de la Recherche Médicale (INSERM), Paris (FR); CHU Nantes, Nantes (FR)

(72) Inventors: Sylvain Routier, Tigy (FR); Frédéric Buron, Olivet (FR); Nuno Rodrigues, Aubiere (FR); Gaëlle Fourriere-Grandclaude, Chelles (FR); Christophe Vandier, La Riche (FR); Aurélie Chantome, Tours (FR); Marie Potier-Cartereau, La Riche (FR); Maxime Gueguinou, Tours (FR); Séverine Marionneau-Lambot, Thouare sur Loire (FR)

(73) Assignees: CENTRE NATIONAL DE LA RECHERCHE SCIENTIFQUE, Paris (FR); UNIVERSITE D'ORLEANS, Orleans (FR); UNIVERSITE DE TOURS, Tours (FR); INSTITUT NATIONAL DE LA SANTE ET DE LA RECHERCHE SCIENTIFIQUE (INSERM), Paris (FR); CHU NANTES, Nantes (FR)

( * ) Notice: Subject to any disclaimer, the term of this patent is extended or adjusted under 35 U.S.C. 154(b) by 0 days.

(21) Appl. No.: 16/615,947

(22) PCT Filed: May 23, 2018

(86) PCT No.: PCT/EP2018/063543
§ 371 (c)(1),
(2) Date: Feb. 26, 2020

(87) PCT Pub. No.: WO2018/215557
PCT Pub. Date: Nov. 29, 2018

(65) Prior Publication Data
US 2021/0009581 A1 Jan. 14, 2021

(30) Foreign Application Priority Data
May 23, 2017 (FR) ..................................... 17 54564

(51) Int. Cl.
*C07D 471/04* (2006.01)
*A61P 35/04* (2006.01)
*C07D 487/04* (2006.01)
*C07D 491/048* (2006.01)
*C07D 495/04* (2006.01)
*C07D 513/04* (2006.01)

(52) U.S. Cl.
CPC ............ *C07D 471/04* (2013.01); *A61P 35/04* (2018.01); *C07D 487/04* (2013.01); *C07D 491/048* (2013.01); *C07D 495/04* (2013.01); *C07D 513/04* (2013.01)

(58) Field of Classification Search
CPC .......................... C07D 471/04; C07D 487/04; C07D 491/048; C07D 495/04; C07D 513/04; A61P 35/04
USPC ........................................................ 514/243
See application file for complete search history.

(56) References Cited

U.S. PATENT DOCUMENTS

| 5,654,307 A | 8/1997 | Bridges et al. |
| 6,395,733 B1 | 5/2002 | Arnold et al. |
| (Continued) | | |

FOREIGN PATENT DOCUMENTS

| CN | 103 664 903 A | 3/2014 |
| CN | 103664903 A | 3/2014 |
| (Continued) | | |

OTHER PUBLICATIONS

Cancer [online], [retrieved on Jul. 6, 2007] Retrieved from the Internet, URL: http://www.nlm.nih.gov/medlineplus/cancer.html (Year: 2007).*

(Continued)

*Primary Examiner* — Kristin A Vajda
(74) *Attorney, Agent, or Firm* — WCF IP

(57) ABSTRACT

The present invention concerns a compound of following general formula (I):

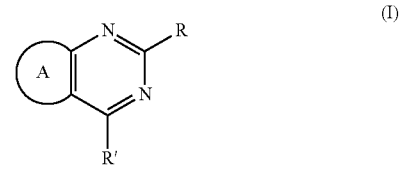

where:
either R is an $R_1$ group and R' is an $-A_1-Cy_1$ group, or R is an $-A_1-Cy_1$ group and R' is an $R_1$ group,
$R_1$ particularly being H or $(C_1-C_6)$alkyl group;
$A_1$ being an —NH— radical or —NH—CH$_2$— radical;
$Cy_1$ particularly being a phenyl group,
A is a fused (hetero)aromatic ring having 5 to 7 atoms, for use for treating cancer.

7 Claims, 1 Drawing Sheet

(56) References Cited

U.S. PATENT DOCUMENTS

| | | | |
|---|---|---|---|
| 6,734,180 B1 | 5/2004 | Nunokawa et al. | |
| 2008/0275045 A1 | 11/2008 | Eriksen et al. | |
| 2010/0105705 A1 | 4/2010 | Eriksen et al. | |
| 2013/0109693 A1 | 5/2013 | Routier | |
| 2017/0071944 A1 | 3/2017 | Geleziunas et al. | |
| 2018/0327411 A1* | 11/2018 | Castro | C07D 487/04 |
| 2020/0331917 A1 | 10/2020 | Castro et al. | |

FOREIGN PATENT DOCUMENTS

| | | |
|---|---|---|
| EP | 0 795 556 A1 | 9/1997 |
| EP | 1018514 A1 | 7/2000 |
| JP | 2008533087 A | 8/2008 |
| JP | 2010522719 A | 7/2010 |
| JP | 2020517734 A | 6/2020 |
| WO | 97/18212 A1 | 5/1997 |
| WO | 2000005234 A1 | 2/2000 |
| WO | 2006/097441 A1 | 9/2006 |
| WO | 2006097441 A1 | 9/2006 |
| WO | 2010/093419 A1 | 8/2010 |
| WO | 2010093419 A1 | 8/2010 |
| WO | 2011/135259 A1 | 11/2011 |
| WO | 2012125668 A1 | 9/2012 |
| WO | 2014/145512 A2 | 9/2014 |
| WO | 2014145512 A2 | 9/2014 |
| WO | 2015/027222 A2 | 2/2015 |

OTHER PUBLICATIONS

Lala et al., Role of nitric oxide in tumor progression: Lessons from experimental tumors, Cancer and Metastasis Reviews (1998), 17, 91-106 (Year: 1998).*

Golub et al., Molecular Classification of Cancer: Class Discovery and Class Prediction by Gene Expression Monitoring, Science (1999), vol. 286, 531-537 (Year: 1999).*

Lu et al., VTX-2337 Is a Novel TLR8 Agonist That Activates NK Cells and Augments ADCC, 2012, Clin Cancer Res, 18(2), 499-509 (Year: 2012).*

Michellys et al.; "Design and synthesis of novel selective anaplastic lymphoma kinase inhibitors"; Bioorganic & Medicinal Chemistry Letters, vol. 26, No. 3, Nov. 17, 2015, pp. 1090-1096.

Potier et al.; "Identification of SK3 channel as a new mediator of breast cancer cell migration"; Molecular Cancer Therapeutics, vol. 5, No. 11, Nov. 1, 2006, pp. 2946-2953.

Gilson, Paul R. et al., "Optimization of 2-Anilino 4-Amino Substituted Quinazolines into Potent Antimalarial Agents with Oral in Vivo Activity", Journal of Medicinal Chemistry vol. 60, Jan. 12, 2017.

Lepri, S. et al., "Structure-metabolism relationships in human-AOX: Chemical insights from a large database of aza-aromatic and amide compounds", PNAS, Apr. 3, 2017.

Wu, C. et al., "Discovery of Novel Stem Cell Mobilizers that Target the CXCR4 Receptor", Wiley ChemMedChem 7, 2012.

* cited by examiner

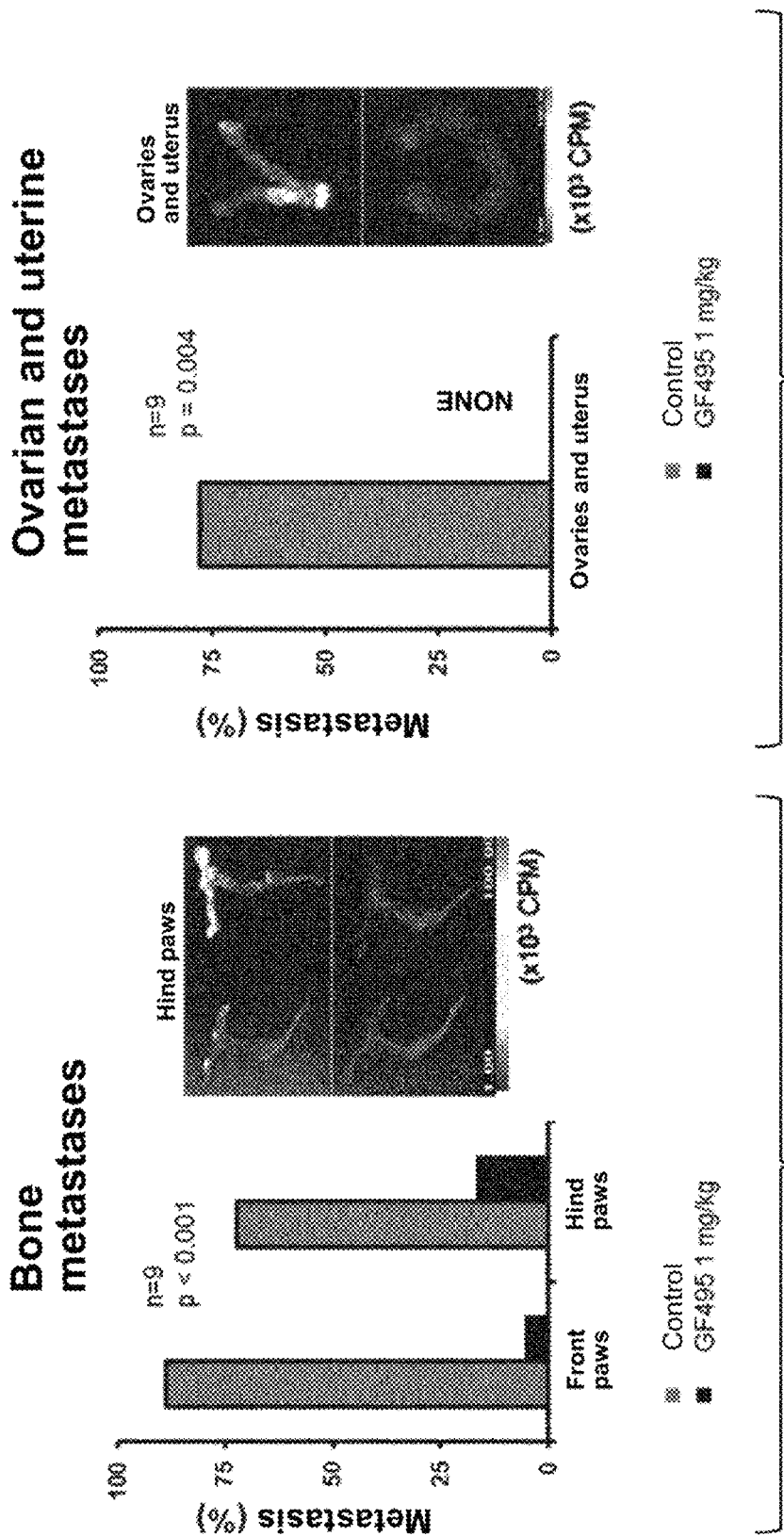

ION CHANNEL INHIBITOR COMPOUNDS FOR CANCER TREATMENT

The subject of the present invention concerns novel compounds in particular of pyridopyrimidine type having ion channel inhibitory properties, in particular of channel SK3. A further subject is the use of said compounds for cancer treatment.

The major therapies for early presentations of cancers are surgery and/or radiotherapy, with the adjunction of hormone therapy for breast cancer, and chemotherapy. The onset of visceral metastases after breast or prostate cancer generally corresponds to progression onto a palliative step. Patient survival time and quality depend upon the sensitivity of the disease to anticancer treatments. The treatment and prevention of metastases call for novel approaches. At the current time, various potential targets of biological routes are being researched to reach this objective.

In women, breast cancer represents the major cause of deaths by cancer over the world. Breast cancer has marked bony tropism and steroid hormone dependency, factors which promote tumour growth, cell survival and cell invasion.

When a cancer becomes metastatic, it is often life-threatening. During tumour growth (primary tumour) cancer cells detach themselves from the primary tumour and migrate, either via the lymphatic pathway (the lymph nodes are connected together by thin channels, the network forming the lymphatic system), or via the blood pathway. This ability of a cancer to metastasize is most certainly determined by a set of biological factors which, at the present time, form as many lines of research to block this metastatic property of cancer.

No targeted therapy currently exists against the migration or invasion of cancer cells, these properties nevertheless enabling tumour cells to leave the primary tumour and enter into lymphatic and blood circulation, leading to their remote development in non-tumoral tissues of the whole body. Research into this anti-metastasis area is scarcely developed or up until now has been unable to bring adequate response. This is the reason why the identification of new anti-metastatic targets, and of new «anti-metastatic» medicinal products, is a priority and must be intensified.

Ion channels and exchangers are transmembrane proteins having activity closely related to the condition of cell membranes.

Among the numerous ion channels, channel SK3—a channel in the family of small conductance calcium-activated potassium channels having oestrogen-regulated expression—promotes the migration of cancer cells.

Also, the inhibition of channel SK3 in breast epithelial cancer cells inhibits the development of bone metastases. In addition, prostate epithelial cancer cells express the SK3 protein contrary to non-cancerous epithelial cells. As a result, this discovery positions itself in an emerging field of investigation and indicates that channel SK3 could be a novel therapeutic target against any form of cancer having a tendency to metastasize, especially towards bone tissue.

It is the aim of the present invention to provide novel inhibitors of ion channels and in particular of channel SK3.

A further aim of the invention is to provide novel inhibitors of the SK3 and/or SK2 ion channels.

A yet further aim of the present invention is to provide compounds capable of inducing an anti-metastatic effect.

DESCRIPTION OF THE DRAWINGS

FIG. 1 is a graph and an image pertaining to the percentage of bone metastases for control mice and mice given compound 20 at 1 mg/kg.

FIG. 2 is a graph and an image pertaining to the percentage of ovarian and uterine metastases for control mice and mice given compound 20 at 1 mg/kg.

DESCRIPTION

The present invention therefore concerns a compound of following general formula (I):

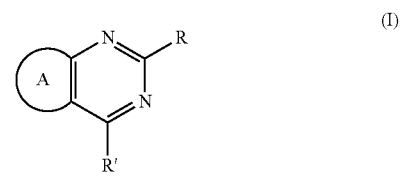

where:
either R is an $R_1$ group and R' is an $-A_1-Cy_1$ group,
or R is an $-A_1-Cy_1$ group and R' is an $R_1$ group,
  $R_1$ being H, a $(C_1-C_6)$alkyl group or radical selected from the group consisting of: $-OR_a$, $-NHR_a$, $-NR_aR_b$, $-NH-C(=O)R_a$, $-C(=O)R_a$, $-C(=O)OR_a$, $-NH-CN$, $-C(=O)NR_aR_b$, Cl, F, CN and nitrogen- or oxygen-containing heterocycles, $R_a$ and $R_b$, each independently being H, a $(C_1-C_6)$alkyl group or $(C_3-C_6)$cycloalkyl group;
  $A_1$ being an $-NH-$ radical or $-NH-CH_2-$ radical;
  $Cy_1$ being:
    either an optionally substituted phenyl group,
    or an aliphatic ring having at least 5 carbon atoms, optionally substituted and optionally fused to a (hetero)aryl ring having 2 to 6 carbon atoms,
    or a (hetero)aliphatic ring having at least 4 carbon atoms, optionally substituted and optionally fused to a (hetero)aryl ring having 2 to 6 carbon atoms;
  said (hetero)aliphatic rings being able to be substituted by at least one substituent selected from among $R_a$, $OR_a$, $OCH_2OCH_3$, $C(=O)R_a$, $C(=O)OR_a$, $NR_aR_b$ or F groups, $R_a$ and $R_b$ being such as defined above,
$Cy_1$ being a substituted phenyl group or substituted or unsubstituted (hetero)aliphatic ring when R is $-NH-Cy_1$ and R' is H;
A is a fused (hetero)aromatic ring having 5 to 10, preferably 5 to 7 atoms, in particular having 1 to 6 carbon atoms and optionally 1 to 3 heteroatoms particularly selected from among N, O and S,
A optionally being substituted by at least one substituent selected from among: halogen atoms, cyano groups, $NO_2$, $(C_1-C_6)$alkyls, (hetero)alkyls, (hetero)cycloalkyls, alkenes, alkynes, carbonyls or amides;
and the pharmaceutically acceptable salts thereof,
said compound of formula (I) being in pure stereoisomer form or in the form of a mixture of enantiomers and/or diastereoisomers, including racemic mixtures,
for its use for treating cancer.

The compounds of formula (I) may comprise one or more asymmetric carbon atoms. They can therefore exist in the form of enantiomers or diastereoisomers.

These enantiomers, diastereoisomers, and the mixtures thereof including racemic mixtures, are part of the invention.

The compounds of formula (I) can exist in the state of bases, or acid addition salts. Said addition salts are part of the invention.

These salts can be prepared with pharmaceutically acceptable acids, but the salts of other acids useful for example for purifying or isolating the compounds of formula (I) are also part of the invention.

In the invention, the term "(hetero)cycloalkyl" encompasses both the terms "cycloalkyl" and "heterocycloalkyl", these terms being such as defined below.

In the invention, the term "(hetero)alkyl" encompasses both the terms "alkyl" and "heteroalkyl", these terms being such as defined below.

In the invention, the term "(hetero)aryl" encompasses both the terms "aryl" and "heteroaryl", these terms being such as defined below.

In the invention, the term "(hetero)aromatic" encompasses both the terms "aromatic" and "heteroaromatic", these terms being such as defined below.

In the invention, the term "(hetero)aliphatic" encompasses both the terms "aliphatic" and "heteroaliphatic", these terms being such as defined below.

In the present invention, by ($C_t$-$C_z$) group it is meant a group comprising a carbon chain possibly having from t to z carbon atoms e.g. $C_1$-$C_6$ a carbon chain that can have 1 to 6 carbon atoms.

In the present invention, the term "halogen atom" designates fluorine chlorine, bromine or iodine atoms.

In the invention, the term "alkyl" designates linear or branched, saturated hydrocarbon aliphatic groups having 1 to 6 carbon atoms unless otherwise stated. As examples, mention can be made of methyl, ethyl, n-propyl, isopropyl, butyl, isobutyl, tertbutyl or pentyl groups.

In the invention, the term "heteroalkyl" designates linear or branched, saturated hydrocarbon aliphatic groups having 1 to 6 carbon atoms unless otherwise stated and comprising at least one heteroatom. As examples, mention can be made of ($C_1$-$C_6$)alkoxy groups, or amine groups, these groups possibly also being substituted. Among these groups, O-$A_2$-O-$A'_2$—$NH_2$ or —NH-$A_2$-$NH_2$ groups can be cited, the radicals $A_2$ and $A'_2$ being alkylene radicals having 1 to 4 carbon atoms.

In the invention, the term "cycloalkyl" designates carbon ring groups having 3 to 6 carbon atoms unless otherwise stated. As examples, mention can be made of cyclopropyl, cyclobutyl, cyclopentyl or cyclohexyl groups.

In the invention, the aryl groups are aromatic ring groups having between 6 and 10 carbon atoms. As examples of aryl groups, the phenyl or naphthyl groups can be cited.

In the invention, the term "heteroaryl" designates an aromatic monocyclic or bicyclic group having 5 to 10 members and comprising 1 to 4 heteroatoms selected from among O, S or N.

Groups that can be cited as examples are imidazolyl, thiazolyl, oxazolyl, furanyl, thiophenyl, pyrazolyl, oxadiazolyl, tetrazolyl, pyridinyl, pyrazinyl, pyrimidinyl, pyridazinyl, indolyl, benzofuranyl, benzothiophenyl, benzoxazolyl, benzimidazolyl, indazolyl, benzothiazolyl, isobenzothiazolyl, benzotriazolyl, quinoleinyl, isoquinoleinyl.

As heteroaryl having 5 to 6 atoms including 1 to 4 nitrogen atoms, particular mention is made of the following representative groups: pyrrolyl, pyrazolyl, 1,2,3-triazolyl, 1,2,4-triazolyl, tetrazolyl and 1,2,3-triazinyl.

As heteroaryl, mention can also be made of thiophenyl, oxazolyl, furanyl, 1,2,4-thiadiazolyl, naphthyridinyl, quinoxalinyl, phthalazinyl, imidazo[1,2-a]pyridine, imidazo[2,1-b]thiazolyl, cinnolinyl, benzofurazanyl, azaindolyl, benzimidazolyl, benzothiophenyl, thienopyridyl, thienopyrimidinyl, pyrrolopyridyl, imidazopyridyl, benzoazaindole, 1,2,4-triazinyl, indolizinyl, isoxazolyl, isoquinolinyl, isothiazolyl, purinyl, quinazolinyl, quinolinyl, isoquinolyl, 1,3,4-thiadiazolyl, thiazolyl, isothiazolyl, carbazolyl, and the corresponding groups derived from the fusion thereof or fusion with the phenyl core.

In the invention, the term "heterocycloalkyl" designates a saturated or partly saturated monocyclic or bicyclic group with 4 to 10 members, having one to three heteroatoms selected from among O, S or N, the heterocycloalkyl group possibly being attached to the remainder of the molecule by a carbon atom or heteroatom.

As saturated heterocycloalkyl having 5 to 6 atoms, mention can be made of oxetanyl, tetrahydrofuranyl, dioxolanyl, pyrrolidinyl, azepinyl, oxazepinyl, pyrazolidinyl, imidazolidinyl, tetrahydrothiophenyl, dithiolanyl, thiazolidinyl, tetrahydropyranyl, tetrahydropyridiny, dioxanyl, morpholinyl, piperidinyl, piperazinyl, tetrahydrothiopyranyl, dithianyl, thiomorpholinyl, or isoxazolidinyl.

The above-mentioned "alkyl", "cycloalkyl", "aryl", "heteroaryl" and "heterocycloalkyl" radicals can be substituted by one or more substituents. Among these substituents the following groups can be cited: amino, hydroxy, thiol, oxo, halogen, alkyl, alkoxy, alkylthio, alkylamino, aryloxy, arylalkoxy, cyano, trifluoromethyl, carboxy or carboxyalkyl.

If an alkyl radical is substituted by an aryl group, the term "arylalkyl" or "aralkyl" radical is used. "Arylalkyl" or "aralkyl" radicals are aryl-alkyl-radicals, the aryl and alkyl groups being such as defined above. Among arylalkyl radicals, particular mention can be made of the benzyl or phenethyl radical.

In the invention, the term "alkylthio" designates an —S-alkyl group, the alkyl group being such as defined above.

In the invention, the term "alkylamino" designates an —NH-alkyl or N(alkyl)$_2$ group, the alkyl group being such as defined above.

In the invention, the term "aryloxy" designates an —O-aryl group, the aryl group being such as defined above.

In the invention, the term "arylalkoxy" designates an aryl-alkoxy-group, the aryl and alkoxy groups being such as defined above.

In the invention, the term "carboxyalkyl" designates a HOOC-alkyl-group, the alkyl group being such as defined above. As examples of carboxyalkyl groups, carboxymethyl or carboxyethyl groups can be cited in particular.

In the invention, the term "carboxyl" designates a C(=O)OH group and the term "oxo" or "carbonyl" designates a C(=O) group.

In the invention, the term "alkene" designates a linear or branched, acyclic, hydrocarbon aliphatic group having a double carbon-carbon bond and meeting formula $C_nH_{2n}$. In the invention, alkenes have 2 to 6 carbon atoms unless otherwise stated. In the present invention, the "alkenyl" radical designates a radical corresponding to the above-mentioned alkene group from which a hydrogen atom has been removed.

In the invention, the term "alkyne" designates a linear or branched, acyclic, hydrocarbon aliphatic group having a triple carbon-carbon bond and meeting formula $C_nH_{2n-2}$. In the invention, the alkenes have 2 to 6 carbon atoms unless otherwise stated. In the present invention, the "alkynyl" radical designates a radical corresponding to the above-mentioned alkyne group from which a hydrogen atom has been removed. In the invention, the alkynyl radicals can be substituted e.g. by an alkyl group or alkylamino group.

In the invention, the term "carbonyl" designates both ketones and aldehydes, but also carboxylic acids and derivatives.

In the invention, the term "amide" designates a group derived from a carboxylic acid of the type R—C(=O)—NR'R".

In the invention, the fusion between ring A and the heterocycle of the compounds of formula (I) can be obtained via a heteroatom e.g. a nitrogen atom.

In one embodiment, when in formula (I) of the invention A is substituted by at least one substituent, the latter is selected for example from among halogen atoms, cyano groups, $NO_2$, $(C_1$-$C_6)$alkyls, (hetero)alkyls, (hetero)cycloalkyls, alkenyl or alkynyl radicals, or carbonyl-containing compounds (i.e. comprising a C(=O) group), or by an amido radical of the type —C(=O)—NR'R", R' and R" being $(C_1$-$C_6)$alkyl groups for example.

One family of preferred compounds used in the invention consists of compounds of following formula (II):

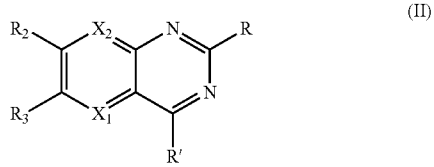

(II)

where:
R and R' are such as defined above in formula (I),
either $X_1$ is a nitrogen atom and $X_2$ is a $C(R_4)$ group,
or $X_1$ is a $C(R_5)$ group and $X_2$ is a nitrogen atom,
or $X_1$ and $X_2$ are a nitrogen atom,
$R_2$, $R_3$, $R_4$ and $R_5$ are each independently H or a substituent selected from the group consisting of: halogen atoms, $(C_1$-$C_6)$(cyclo)alkyl groups, $NR_aR_b$ groups and $OR_a$ groups, $R_a$ and $R_b$ each independently being H or $(C_1$-$C_6)$alkyl group.

In one embodiment, in formula (II), $X_1$ is a nitrogen atom and $X_2$ is a $C(R_4)$ group.

In one embodiment, in formula (II), $X_1$ is a $C(R_5)$ group and $X_2$ is a nitrogen atom.

In one embodiment, in formula (II), $X_1$ is a nitrogen atom, $X_2$ is a $C(R_4)$ group, R is an $R_1$ group and R' is an $-A_1$-$Cy_1$ group.

In one embodiment, in formula (II), $X_1$ is a $C(R_5)$ group, $X_2$ is a nitrogen atom, R is an $R_1$ group and R' is an $-A_1$-$Cy_1$ group.

In one embodiment, in formula (II), $X_1$ is a $C(R_5)$ group, $X_2$ is a nitrogen atom, R is an $R_1$ group and R' is an $-A_1$-$Cy_1$ group.

In one embodiment, in formula (II), $X_1$ is a nitrogen atom, $X_2$ is a $C(R_4)$ group, R is an $R_1$ group and R' is an $-A_1$-$Cy_1$ group.

One family of preferred compounds used in the invention consists of compounds of following formula (III):

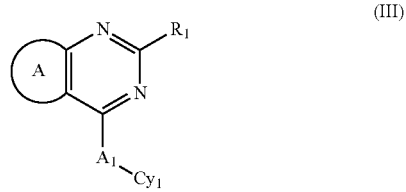

(III)

where A, $R_1$, $A_1$ and $Cy_1$ are such as defined above in formula (I).

A compound of formula (III) corresponds to a compound of formula (I) wherein R is an $R_1$ group and R' is an $-A_1$-$Cy_1$ group.

Preferably, in formula (III), A is a heteroaromatic fused ring having 5 to 7 atoms, comprising 1 to 6 carbon atoms and at least one nitrogen atom.

Preferably, in formula (III), $Cy_1$ is an aliphatic ring or heteroaliphatic ring such as defined above in formula (I), said aliphatic or heteroaliphatic rings optionally being fused to a heteroaryl ring such as defined above.

Another family of preferred compounds used in the invention is composed of compounds of following formula (III-1):

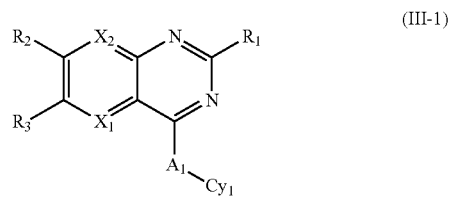

(III-1)

where:
$R_1$, $A_1$ and $Cy_1$ are such as defined above in formula (I),
either $X_1$ is a nitrogen atom $X_2$ is a $C(R_4)$ group,
or $X_1$ is a $C(R_5)$ group and $X_2$ is a nitrogen atom,
or $X_1$ and $X_2$ are a nitrogen atom,
$R_2$, $R_3$, $R_4$ and $R_5$ are each independently H or a substituent selected from the group consisting of: halogen atoms, $(C_1$-$C_6)$(cyclo)alkyl groups, $NR_aR_b$ groups, and $OR_a$ groups, $R_a$ and $R_b$ each independently being H or $(C_1$-$C_6)$alkyl group.

A compound of formula (III-1) corresponds to a compound of formula (III) in which A is a heteroaromatic fused ring optionally substituted (by $R_2$ and/or $R_3$), having 6 atoms including 4 or 5 carbon atoms and 1 or 2 nitrogen atoms, R is an $R_1$ group and R' is an $-A_1$-$Cy_1$ group.

One sub-family of preferred compounds used in the invention is composed of compounds of formula (III-1) such as defined above, where either $X_1$ is a nitrogen atom and $X_2$ is a $C(R_4)$ group, or $X_1$ is a $C(R_5)$ group and $X_2$ is a nitrogen atom.

One family of preferred compounds used in the invention is composed of compounds of following formula (IV):

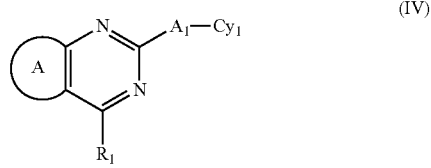

(IV)

where A, $R_1$, $A_1$ and $Cy_1$ are such as defined in claim 1.

A compound of formula (IV) corresponds to a compound of formula (I) in which R is an $-A_1$-$Cy_1$ group and R' is an $R_1$ group.

Preferably, in formula (IV), A is a heteroaromatic fused ring having 5 to 7 atoms, comprising 1 to 6 carbon atoms and at least one nitrogen atom.

Another family of preferred compounds used in the invention is composed of compounds of following formula (IV-1):

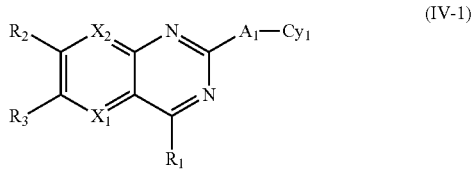

(IV-1)

where:
- $R_1$, $A_1$ and $Cy_1$ are such as defined in formula (I),
- either $X_1$ is a nitrogen atom and $X_2$ is a $C(R_4)$ group, or $X_1$ is a $C(R_5)$ group and $X_2$ is a nitrogen atom,
- $R_2$, $R_3$, $R_4$ and $R_5$ are each independently H or a substituent selected from the group consisting of: halogen atoms, $(C_1\text{-}C_6)$(cyclo)alkyl groups, $NR_aR_b$ groups, and $OR_a$ groups, $R_a$ and $R_b$ each independently being H or $(C_1\text{-}C_6)$alkyl group.

A compound of formula (IV-1) corresponds to a compound of formula (IV) in which A is a heteroaromatic fused ring, optionally substituted (by $R_2$ and/or $R_3$), having 6 atoms including 4 or 5 carbon atoms and 1 or 2 nitrogen atoms, R is an $R_1$ group and R' is an $-A_1\text{-}Cy_1$ group.

One sub-family of preferred compounds used in the invention is composed of compounds of formula (IV-1) such as defined above in which either $X_1$ is a nitrogen atom and $X_2$ is a $C(R_4)$ group, or $X_1$ is a $C(R_5)$ group and $X_2$ is a nitrogen atom.

In one embodiment, in above-mentioned formulas (II), (III-1) and (IV-1), $R_3$ is H.

In one embodiment, in above-mentioned formulas (II), (III-1) and (IV-1), $R_2$ and $R_3$ are H.

Another family of preferred compounds used in the invention is composed of compounds of following formula (III-2):

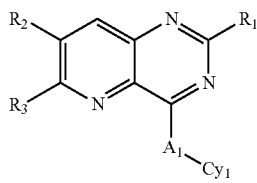

(III-2)

where:
- $R_1$, $A_1$ and $Cy_1$ are such as defined above in formula (I),
- $R_2$ and $R_3$ are each independently H or a substituent selected from the group consisting of: halogen atoms, $(C_1\text{-}C_6)$(cyclo)alkyl groups, $NR_aR_b$ groups, and $OR_a$ groups, $R_a$ and $R_b$ each independently being H or $(C_1\text{-}C_6)$alkyl group.

Preferably, in formula (III-2), $R_3$ is H.
Preferably, in formula (III-2), $R_2$ and $R_3$ are H.

Another family of preferred compounds used in the invention is composed of compounds of following formula (III-3):

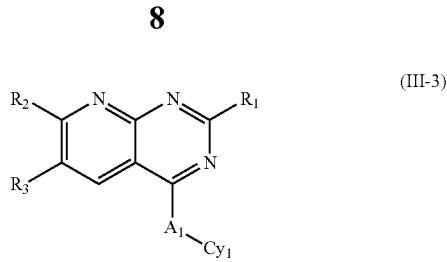

(III-3)

where:
- $R_1$, $A_1$ and $Cy_1$ are such as defined in formula (I),
- $R_2$ and $R_3$ are each independently H or a substituent selected from the group consisting of: halogen atoms, $(C_1\text{-}C_6)$(cyclo)alkyl groups, $NR_aR_b$ groups, and $OR_a$ groups, $R_a$ and $R_b$ each independently being H or $(C_1\text{-}C_6)$alkyl group.

Preferably, in formula (III-3), $R_3$ is H.
Preferably, in formula (III-3), $R_2$ and $R_3$ are H.

Another family of preferred compounds used in the invention is composed of compounds of following formula (IV-2):

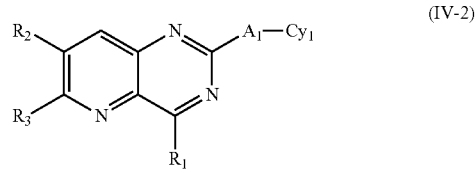

(IV-2)

where:
- $R_1$, $A_1$ and $Cy_1$ are such as defined above in formula (I),
- $R_2$ and $R_3$ are each independently H or a substituent selected from the group consisting of: halogen atoms, $(C_1\text{-}C_6)$(cyclo)alkyl groups, $NR_aR_b$ groups, and $OR_a$ groups, $R_a$ and $R_b$ each independently being H or $(C_1\text{-}C_6)$alkyl group.

Preferably, in formula (IV-2), $R_3$ is H.
Preferably, in formula (IV-2), $R_2$ and $R_3$ are H.

Another family of preferred compounds used in the invention is composed of compounds of following formula (IV-3):

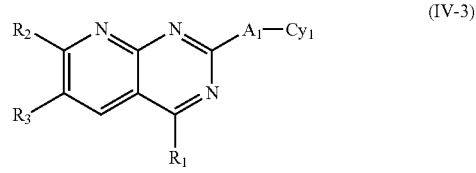

(IV-3)

where:
- $R_1$, $A_1$ and $Cy_1$ are such as defined above in formula (I),
- $R_2$ and $R_3$ are each independently H or a substituent selected from the group consisting of: halogen atoms, $(C_1\text{-}C_6)$(cyclo)alkyl groups, $NR_aR_b$ groups, and $OR_a$ groups, $R_a$ and $R_b$ each independently being H or $(C_1\text{-}C_6)$alkyl group.

Preferably, in formula (IV-3), $R_3$ is H.
Preferably, in formula (IV-3), $R_2$ and $R_3$ are H.

Another family of preferred compounds used in the invention is composed of compounds of following formula (III-4):

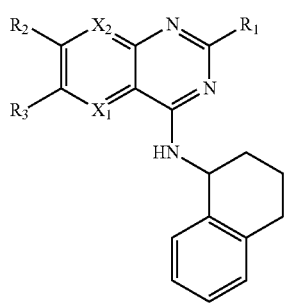

(III-4)

where:
- $X_1$, $X_2$ and $R_1$ are such as defined above in formula (I),
- $R_2$ and $R_3$ are each independently H or a substituent selected from the group consisting of: halogen atoms, $(C_1-C_6)$(cyclo)alkyl groups, $NR_aR_b$ groups, and $OR_a$ groups, $R_a$ and $R_b$ each independently being H or $(C_1-C_6)$alkyl group.

Preferably, in formula (III-4), $R_3$ is H.

Preferably, in formula (III-4), $R_2$ and $R_3$ are H.

Preferably, in formula (III-4), $X_1$ is a nitrogen atom and $X_2$ is a CH group.

Preferably, in formula (III-4), $X_1$ is a CH group and $X_2$ is a nitrogen atom.

Another family of preferred compounds used in the invention is composed of compounds of following formula (IV-4):

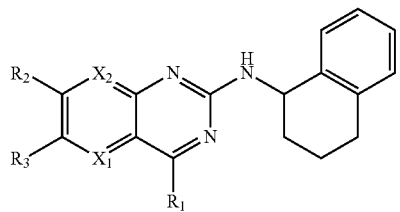

(IV-4)

where:
- $X_1$, $X_2$ and $R_1$ are such as defined above in formula (I),
- $R_2$ and $R_3$ are each independently H or a substituent selected from the group consisting of: halogen atoms, $(C_1-C_6)$(cyclo)alkyl groups, $NR_aR_b$ groups, and $OR_a$ groups, $R_a$ and $R_b$ each independently being H or $(C_1-C_6)$alkyl group.

Preferably, in formula (IV-4), $R_3$ is H.

Preferably, in formula (IV-4), $R_2$ and $R_3$ are H.

Preferably, in formula (IV-4), $X_1$ is a nitrogen atom and $X_2$ is a CH group.

Preferably, in formula (IV-4), $X_1$ is a CH group and $X_2$ is a nitrogen atom.

Among the preferred compounds used in the invention, the following compounds can be cited:

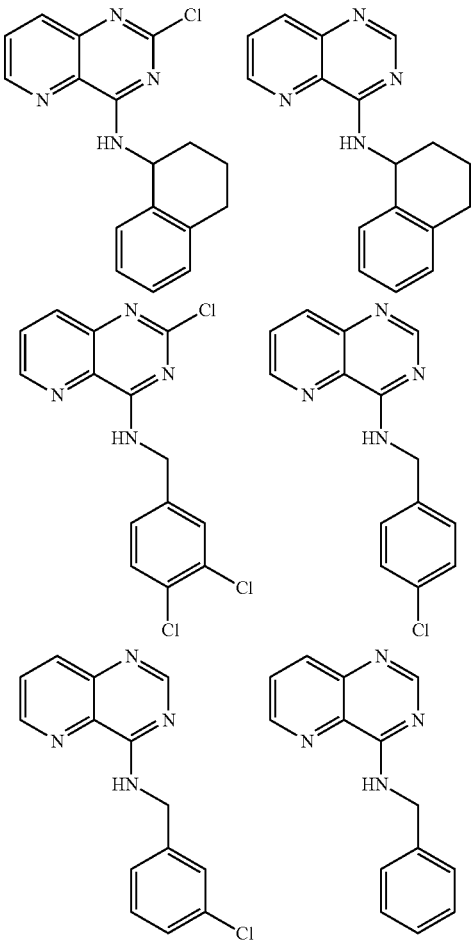

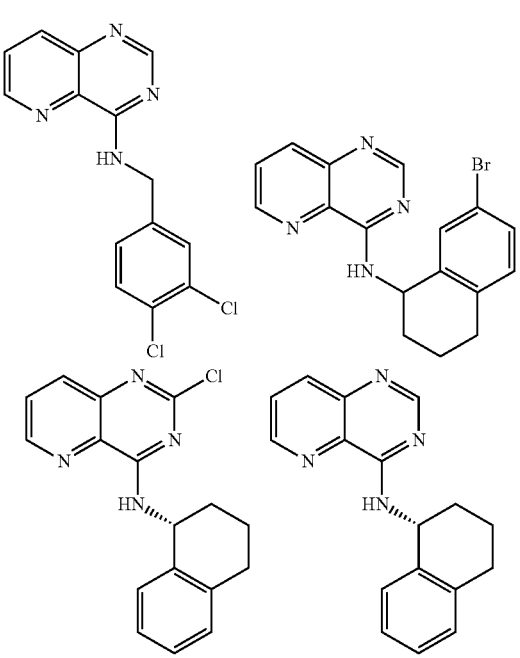

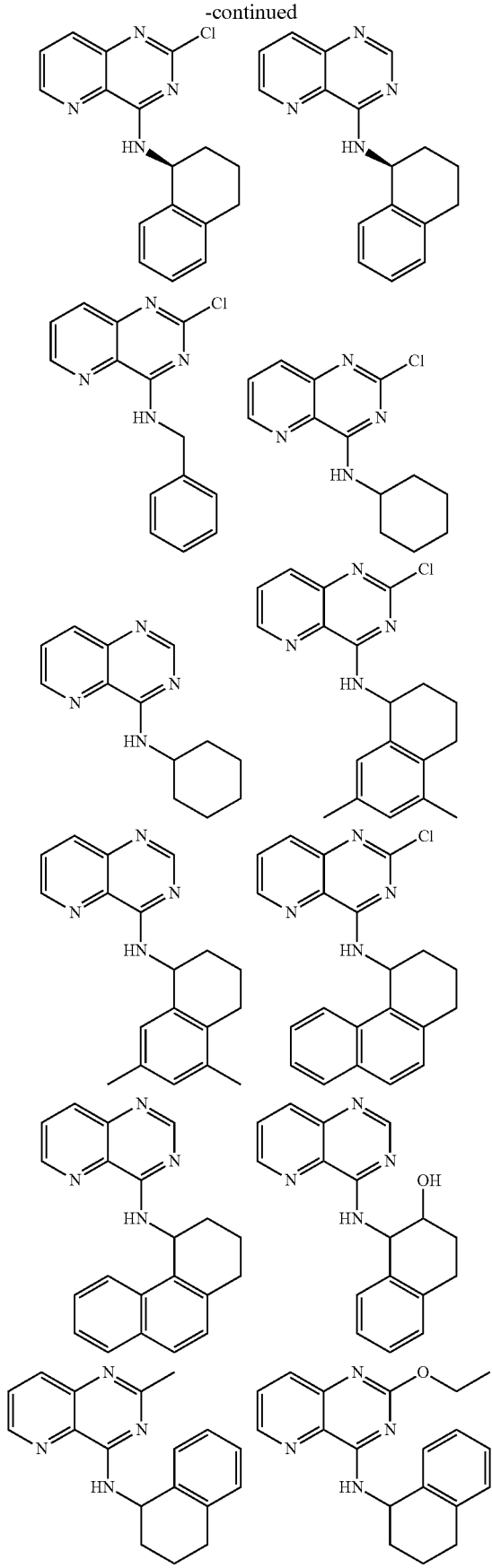
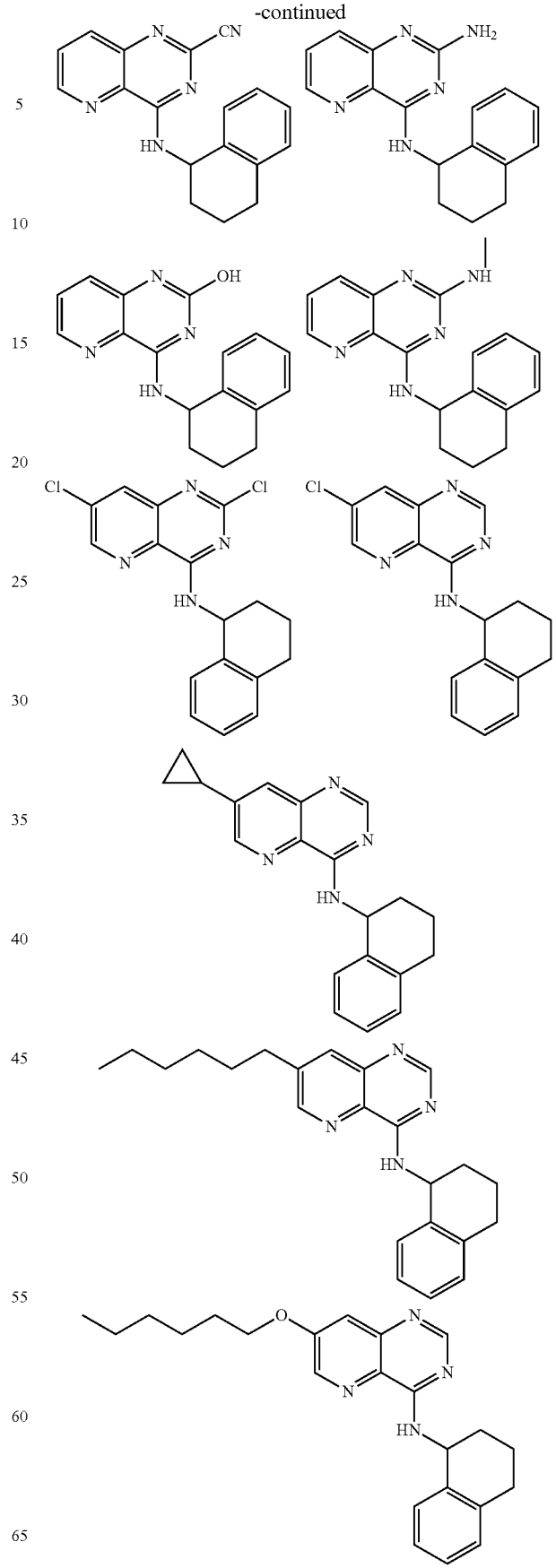

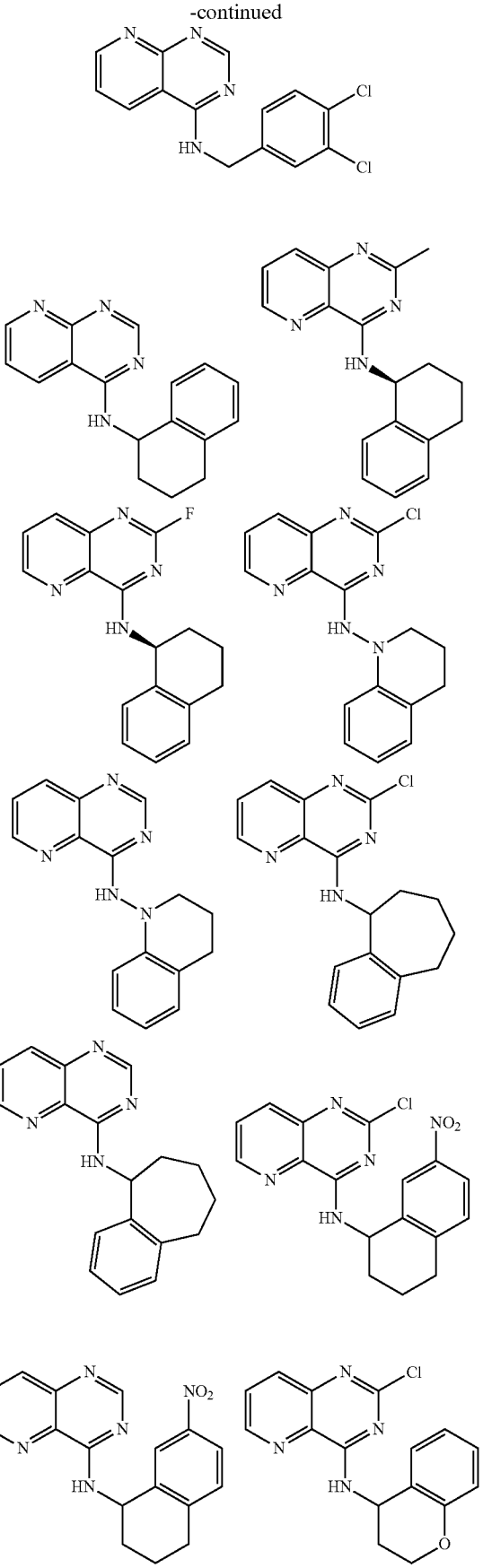
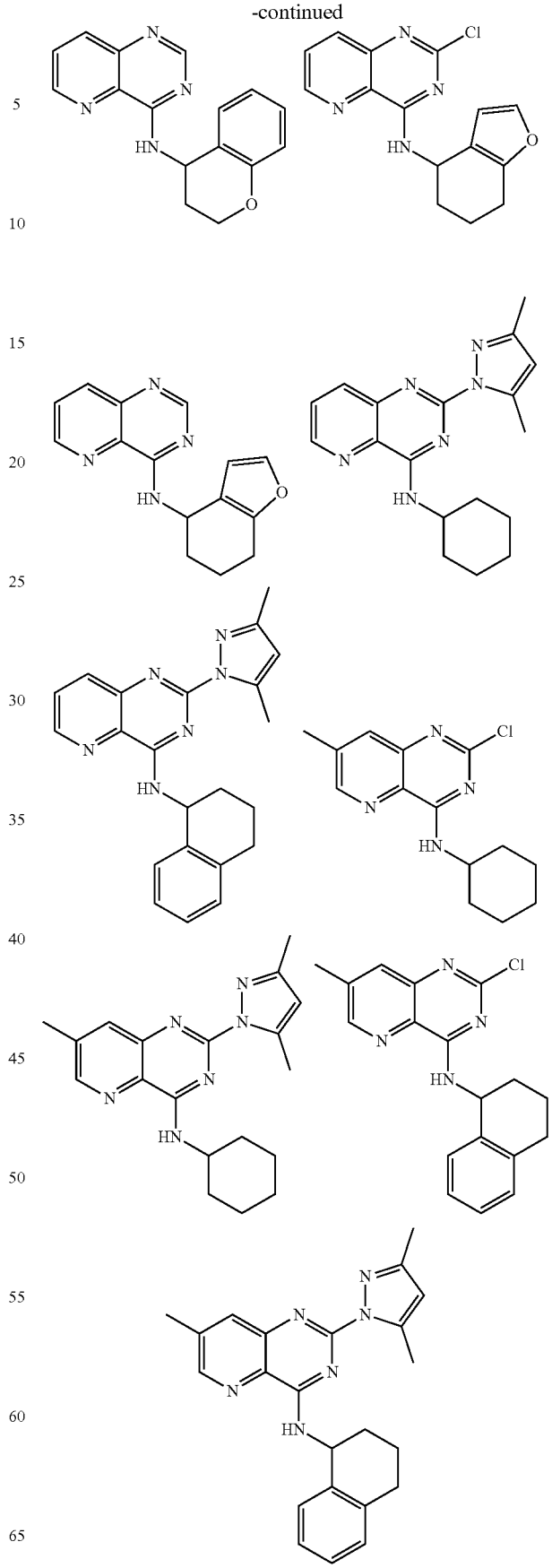

-continued
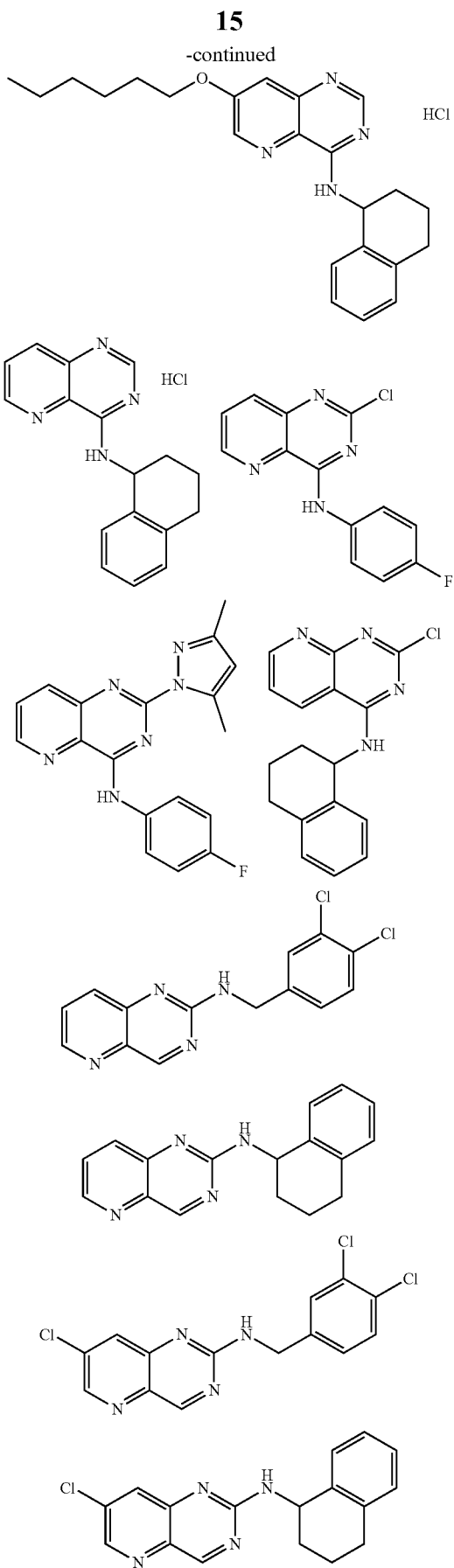
-continued
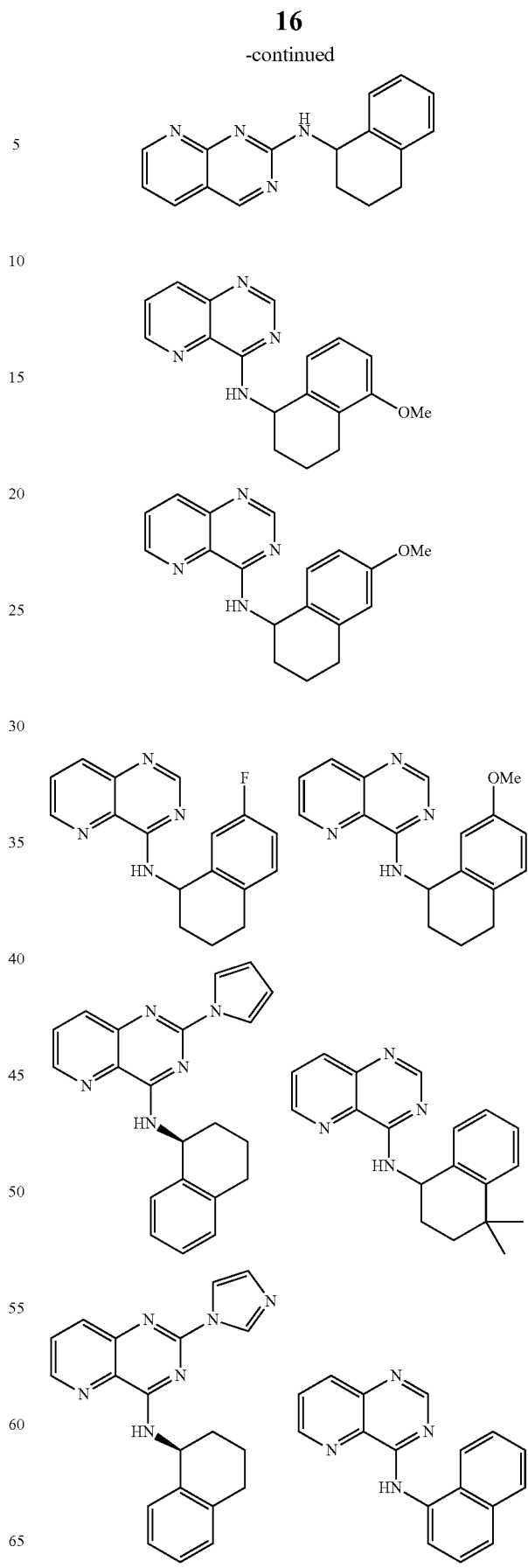

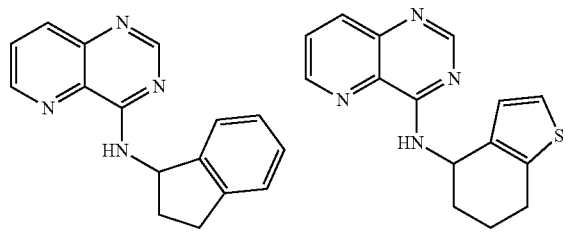
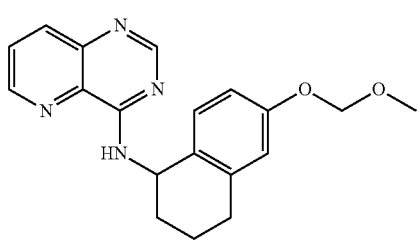
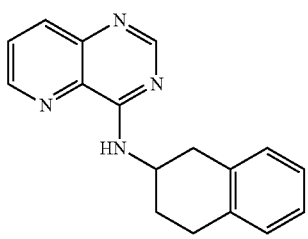
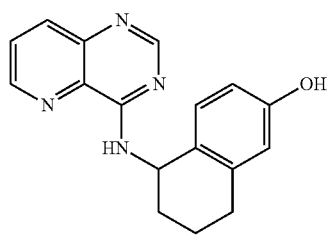
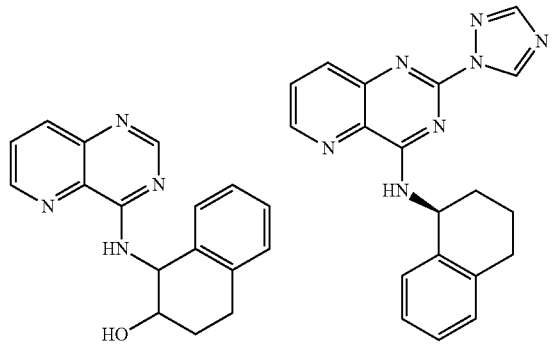
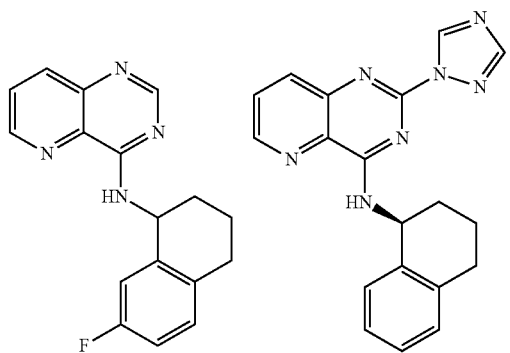
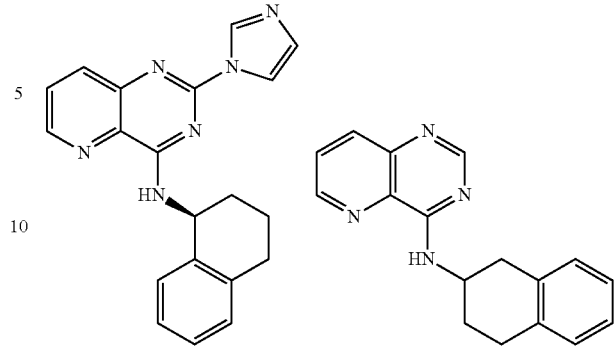
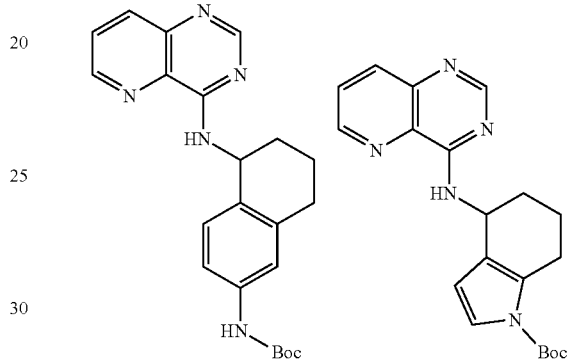
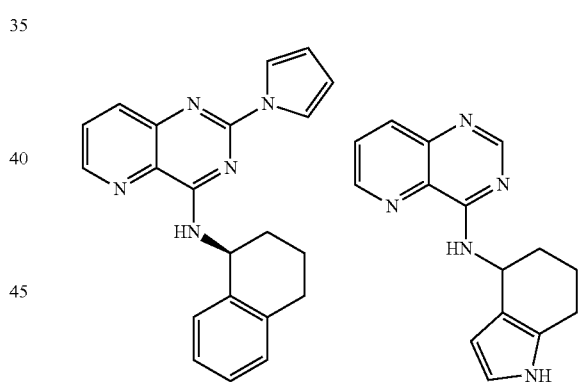
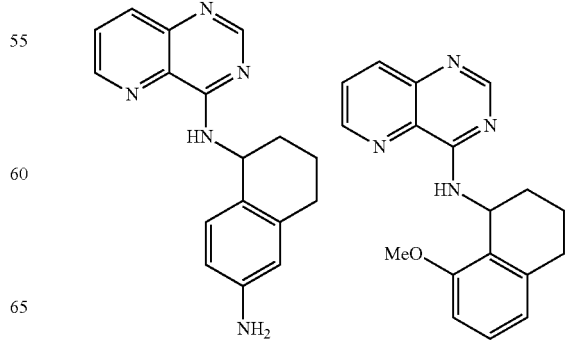

-continued
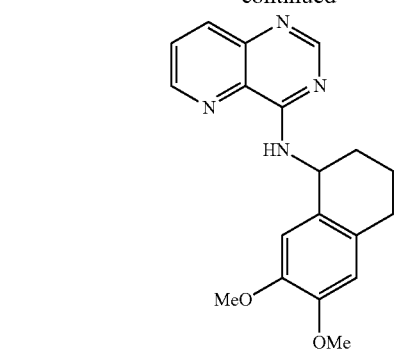
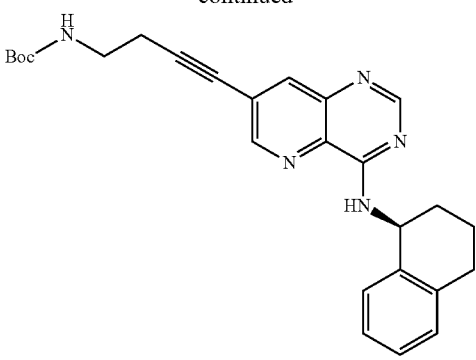
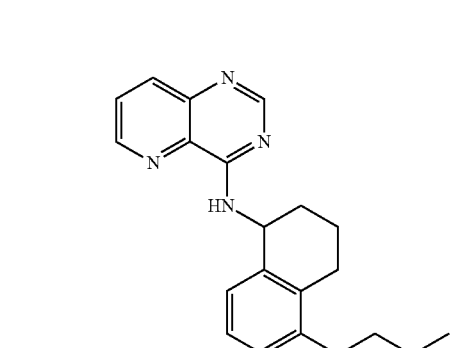
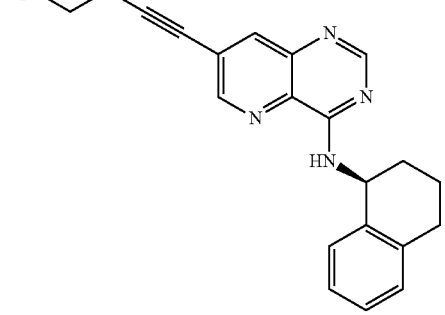
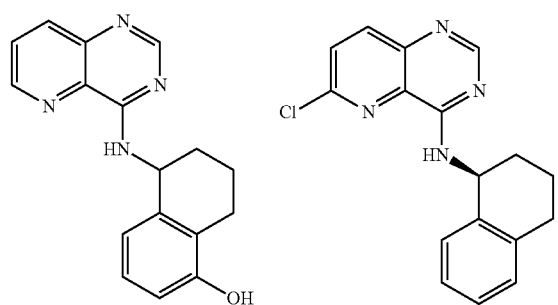
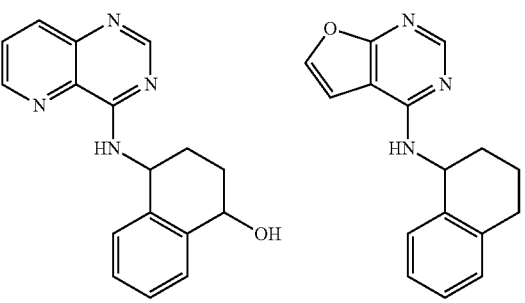
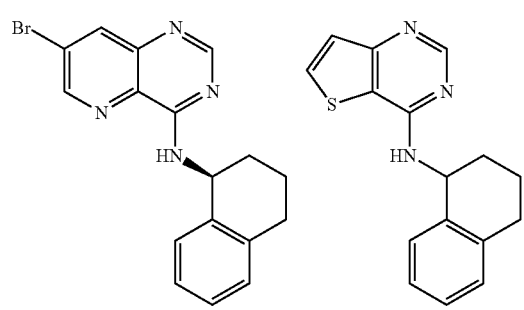
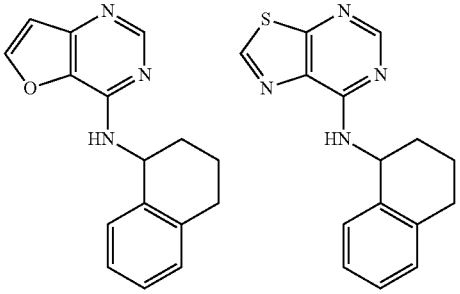
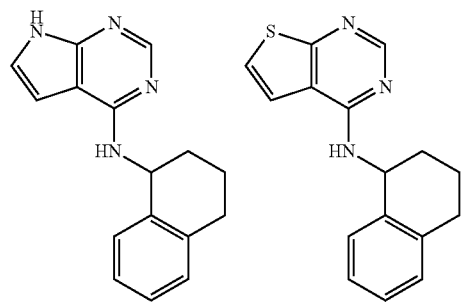
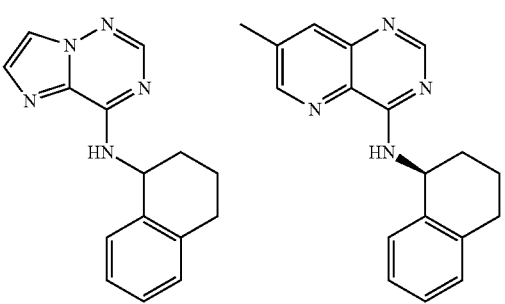

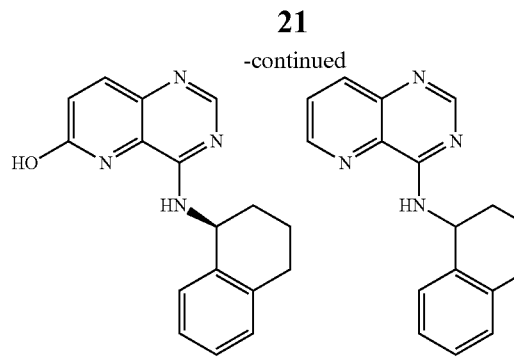

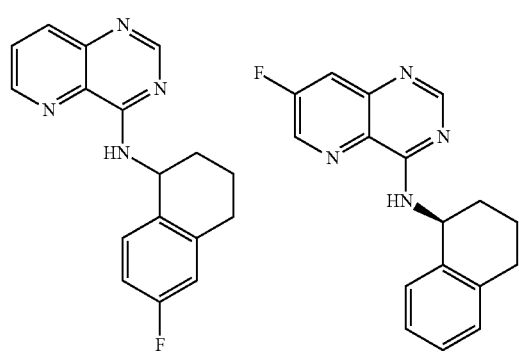

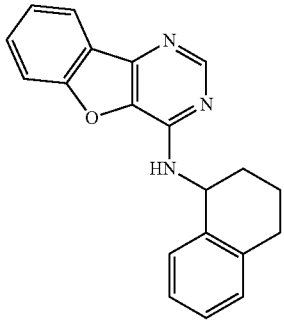

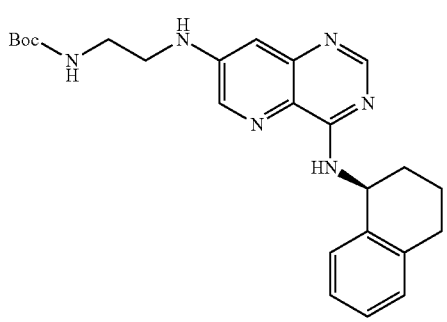

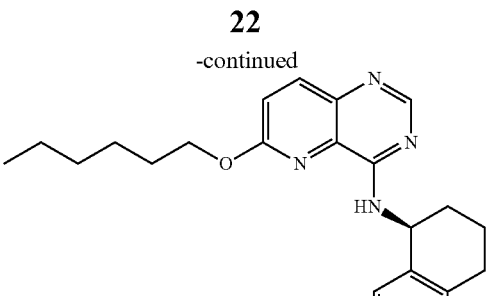

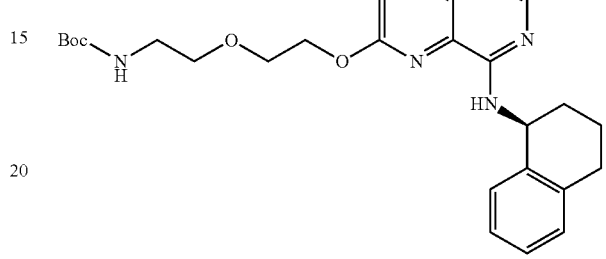

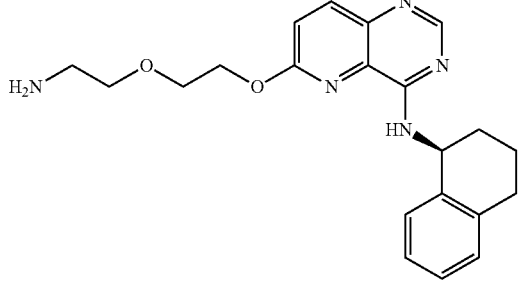

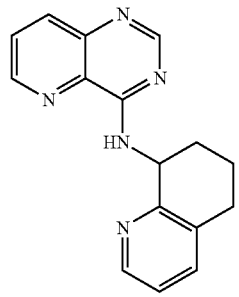

The present invention also concerns a compound of formula (I) such as defined above, or of formula (II), for use thereof in the treatment of breast cancer.

The present invention also concerns a compound of formula (V):

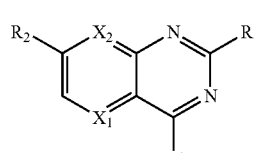

(V)

where:
R and R' are such as defined above in formula (I),
either $X_1$ is a nitrogen atom and $X_2$ is a $C(R_4)$ group,
or $X_1$ is a $C(R_5)$ group and $X_2$ is a nitrogen atom,
$R_2$, $R_4$ and $R_5$ are each independently H or a substituent selected from the group consisting of: halogen atoms, $(C_1-C_6)$(cyclo)alkyl groups, $NR_aR_b$ groups, and $OR_a$ groups, $R_a$ and $R_b$ each independently being H or $(C_1-C_6)$alkyl group.

and the pharmaceutically acceptable salts thereof, said compound of formula (I) being in the form of a pure stereoisomer or in the form of a mixture of enantiomers and/or diastereoisomers, including racemic mixtures, with the exception of the following compounds:

(a)
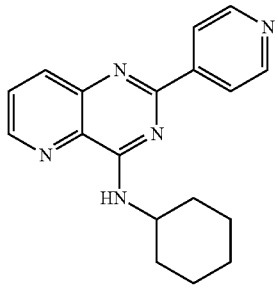

(b)
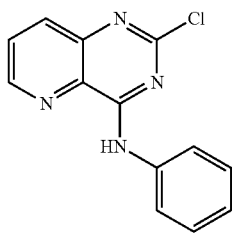

(c)
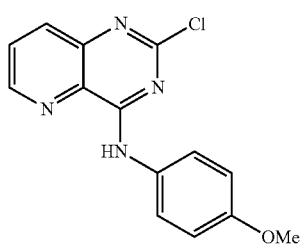

(d)
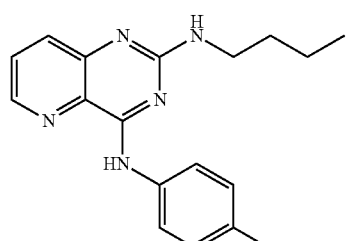

(e)
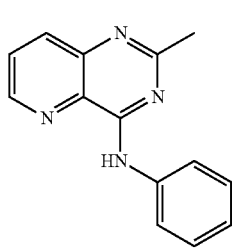

(f)
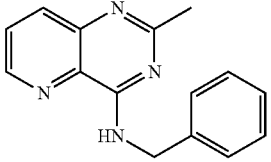

Preferably, in formula (V), $R_2$ is H.
Preferably, in formula (V), $X_1$ is a nitrogen atom and $X_2$ is a CH group.
Preferably, in formula (V), $X_1$ is a CH group and $X_2$ is a nitrogen atom.

In one embodiment, the compounds of the invention have the following general formula (VI):

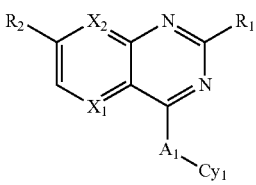

(VI)

where:
$R_1$, $A_1$ and $Cy_1$ are such as defined above in formula (I),
either $X_1$ is a nitrogen atom and $X_2$ is a $C(R_4)$ group, or $X_1$ is a $C(R_5)$ group and $X_2$ is a nitrogen atom,
$R_2$, $R_4$ and $R_5$ are each independently H or a substituent selected from the group consisting of: halogen atoms, $(C_1-C_6)$(cyclo)alkyl groups, $NR_aR_b$ groups, and $OR_a$ groups, $R_a$ and $R_b$ each independently being H or $(C_1-C_6)$alkyl group, with the exception of above-mentioned compounds (a), (b), (c), (d), (e) and (f).

Preferably, in formula (VI), $R_2$ is H.
Preferably, in formula (VI), $X_1$ is a nitrogen atom and $X_2$ is a CH group.
Preferably, in formula (VI), $X_1$ is a CH group and $X_2$ is a nitrogen atom.

In one embodiment, the compounds of the invention have the following general formula (VII):

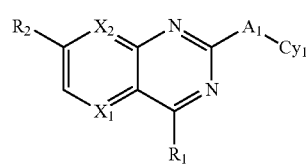

(VII)

where:
$R_1$, $A_1$ and $Cy_1$ are such as defined above in formula (I),
either $X_1$ is a nitrogen atom and $X_2$ is a $C(R_4)$ group, or $X_1$ is a $C(R_5)$ group and $X_2$ is a nitrogen atom,
$R_2$, $R_4$ and $R_5$ are each independently H or a substituent selected from the group consisting of: halogen atoms, $(C_1-C_6)$(cyclo)alkyl groups, $NR_aR_b$ groups, and $OR_a$ groups, $R_a$ and $R_b$ each independently being H or $(C_1-C_6)$alkyl group.

Preferably, in formula (VII), $R_2$ is H.
Preferably, in formula (VII), $X_1$ is a nitrogen atom and $X_2$ is a CH group.

Preferably, in formula (VII), $X_1$ is a CH group and $X_2$ is a nitrogen atom.

In one embodiment, the compounds of the invention have the following general formula (VI-1):

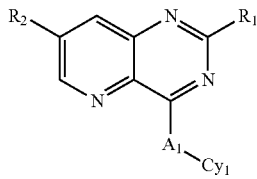

where:
$R_1$, $A_1$ and $Cy_1$ are such as defined above in formula (I),
$R_2$ is H or substituent selected from the group consisting of: halogen atoms, $(C_1-C_6)$(cyclo)alkyl groups, $NR_aR_b$ groups, and $OR_a$ groups, $R_a$ and $R_b$, each independently being H or $(C_1-C_6)$alkyl group, with the exception of above-mentioned compounds (a), (b), (c), (d), (e) and (f).

Preferably, in formula (VI-1), $R_2$ is H.

In one embodiment, the compounds of the invention have the following general formula (VI-2):

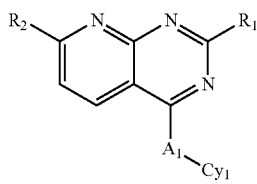

where:
$R_1$, $A_1$ and $Cy_1$ are such as defined above in formula (I),
$R_2$ is H or a substituent selected from the group consisting of: halogen atoms, $(C_1-C_6)$(cyclo)alkyl groups, $NR_aR_b$ groups, and $OR_a$ groups, $R_a$ and $R_b$ each independently being H or $(C_1-C_6)$alkyl group.

Preferably, in formula (VI-2), $R_2$ is H.

In one embodiment, the compounds of the invention have the following general formula (VII-1):

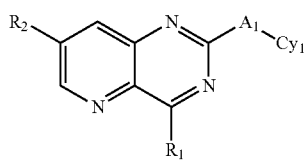

where:
$R_1$, $A_1$ and $Cy_1$ are such as defined above in formula (I),
$R_2$ is H or a substituent selected from the group consisting of: halogen atoms, $(C_1-C_6)$(cyclo)alkyl groups, $NR_aR_b$ groups, and $OR_a$ groups, $R_a$ and $R_b$ each independently being H or $(C_1-C_6)$alkyl group.

Preferably, in formula (VII-1), $R_2$ is H.

In one embodiment, the compounds of the invention have the following general formula (VII-2):

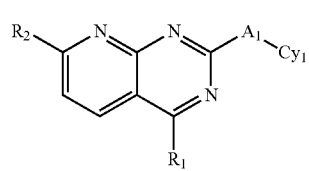

where:
$R_1$, A and $Cy_1$ are such as defined above in formula (I)
$R_2$ is H or a substituent selected from the group consisting of: halogen atoms, $(C_1-C_6)$(cyclo)alkyl groups, $NR_aR_b$ groups, and $OR_a$ groups, $R_a$ and $R_b$ each independently being H or $(C_1-C_6)$alkyl group.

Preferably, in formula (VII-2), $R_2$ is H.

The compounds of the invention can be used to prepare medicinal products, in particular medicinal products that are ion channel inhibitors, of SK3 and/or SK2 in particular.

The present invention therefore also concerns a compound of formula (V), (VI), (VI-1), (VI-2), (VII), (VII-1) or (VI-2) such as defined above, for use thereof as ion channel inhibitor, and of SK3 and/or SK2 in particular.

Therefore, in another aspect, the present invention concerns medicinal products which comprise a compound of formula (V), (VI), (VI-1), (VI-2), (VII), (VII-1) or (VI-2), or a pharmaceutically acceptable acid addition salt thereof.

These medicinal products find therapeutic use in particular for cancer treatment.

In another aspect, the present invention concerns pharmaceutical compositions comprising a compound of the invention as active ingredient. These pharmaceutical compositions contain an effective dose of at least one compound of the invention, or a pharmaceutically acceptable salt, and at least one pharmaceutically acceptable excipient.

Said excipients are selected as a function of the desired pharmaceutical form and administration mode from among usual excipients known to persons skilled in the art.

In the pharmaceutical compositions of the present invention for oral, sublingual, subcutaneous, intramuscular, intravenous, topical, local, intratracheal, intranasal, transdermal or rectal administration, the active ingredient of above formula (V), (VI), (VI-1), (VI-2), (VII), (VII-1) or (VI-2), or salt thereof, can be administered in unit administration form in a mixture with conventional pharmaceutical excipients, to animals and human beings for the treatment of the above disorders or diseases.

Suitable unit administration forms comprise forms via oral route such as tablets, soft or hard capsules, powders, granules and oral solutions or suspensions, sublingual, buccal, intratracheal, intraocular, intranasal or inhalation administration forms, topical, transdermal, subcutaneous, intramuscular or intravenous administration forms, rectal administration forms and implants. For topical application, the compounds of the invention can be used in creams, gels, ointments or lotions.

As is usual practice, the appropriate dosage for each patient is determined by the practitioner depending on administration mode, patient weight and response.

The present invention concerns a compound of formula (V), (VI), (VI-1), (VI-2), (VII), (VII-1) or (VI-2) of the present invention for use thereof in cancer treatment.

The present invention concerns a compound of formula (V), (VI), (VI-1), (VI-2), (VII), (VII-1) or (VI-2) such as defined above, or a pharmaceutically acceptable acid addition salt of this compound, for use thereof as medicinal product.

In another aspect, the present invention also concerns a method for treating the above-indicated pathologies which comprises the administering to a patient of an effective dose of a compound of the invention or one of the pharmaceutically acceptable salts thereof.

EXAMPLES

Preparation of Compounds of the Invention

The compounds of the invention are prepared in accordance with schemes 1 to 5 below:

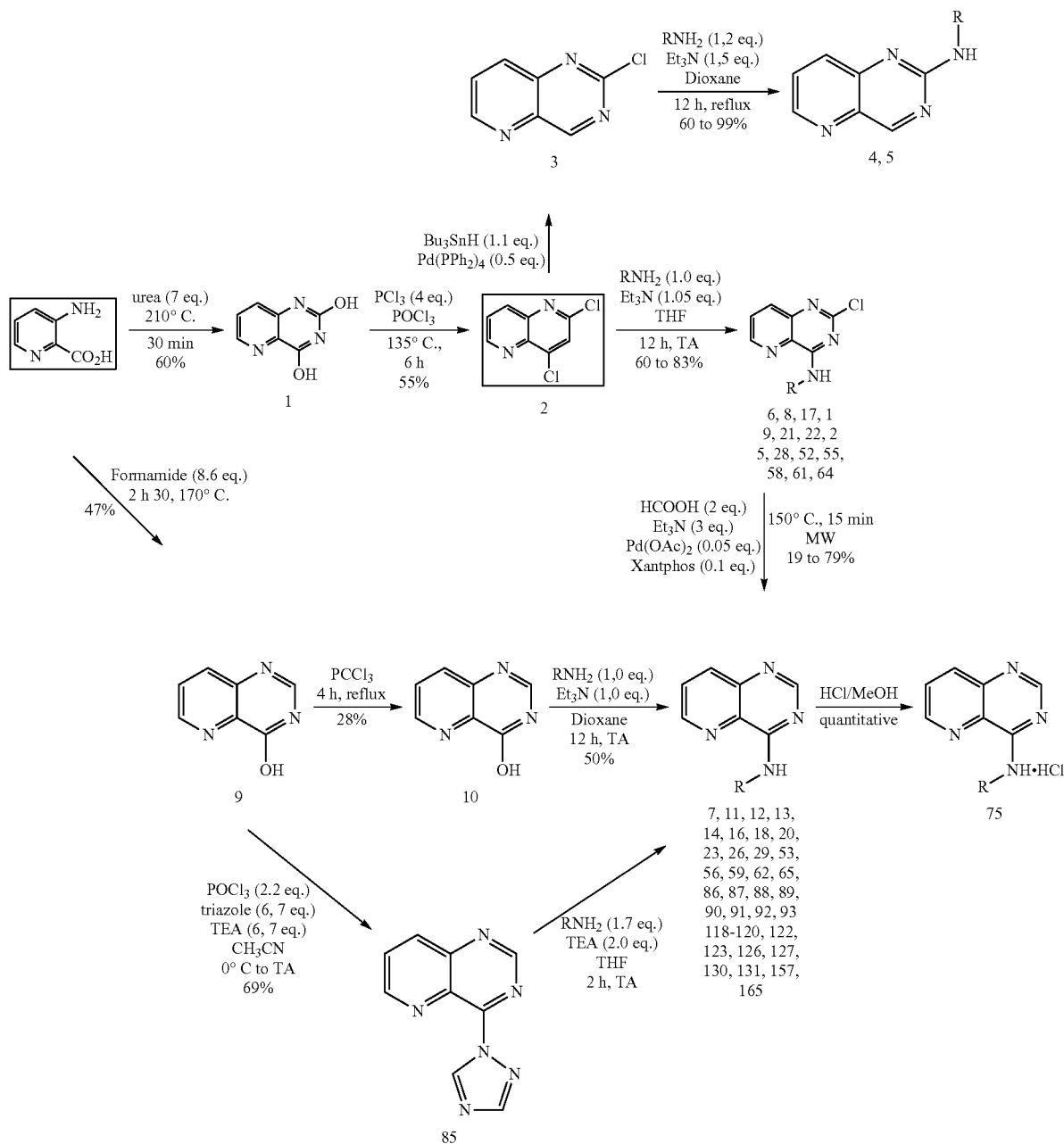

Scheme 2
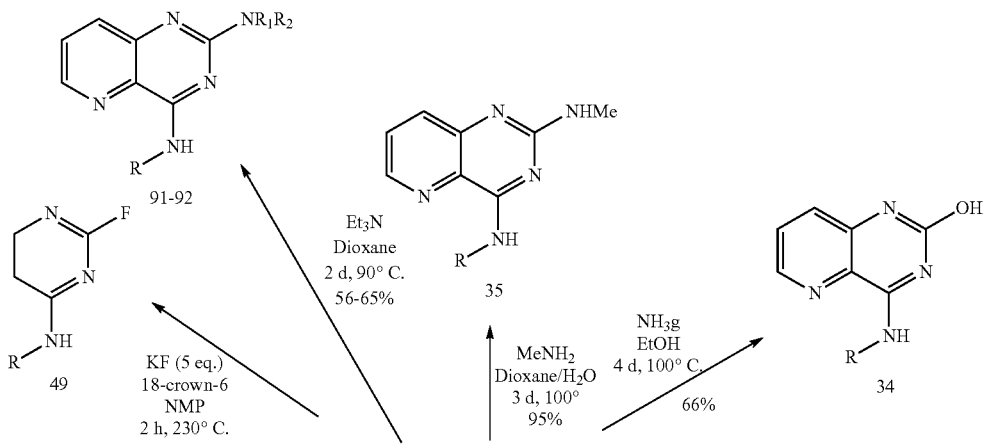
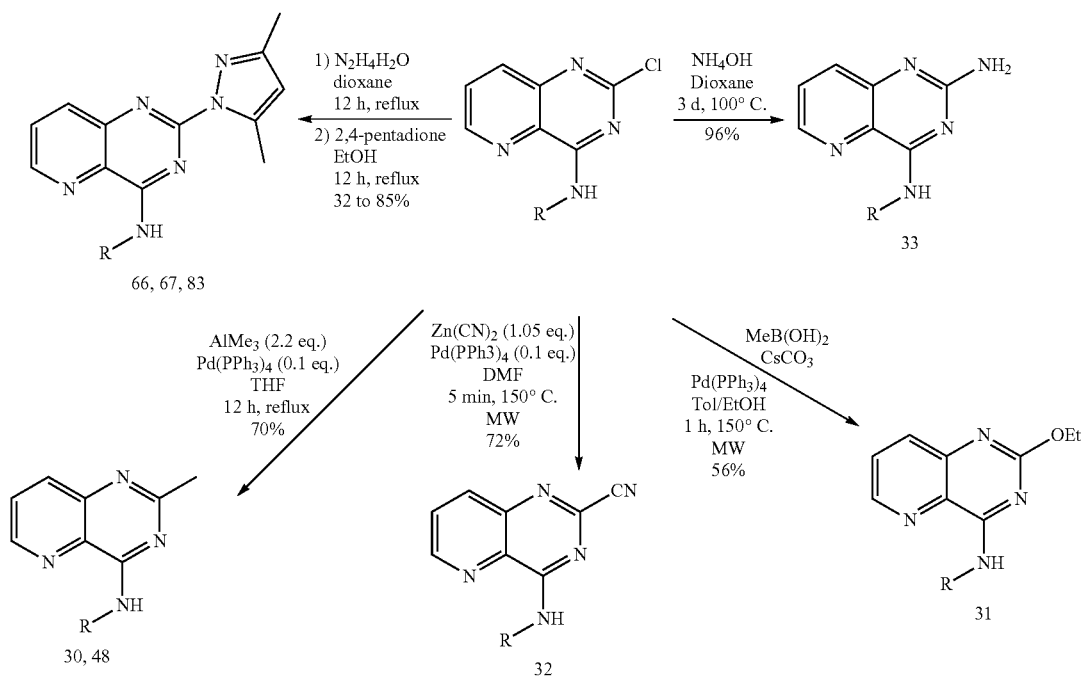
Scheme 3
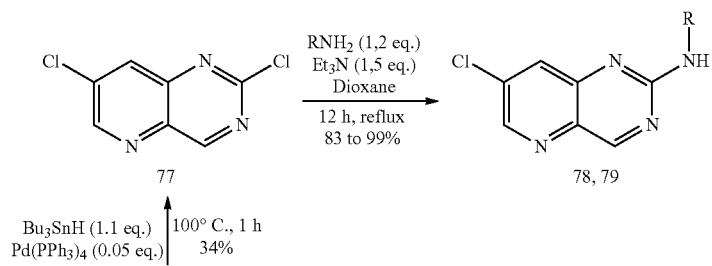

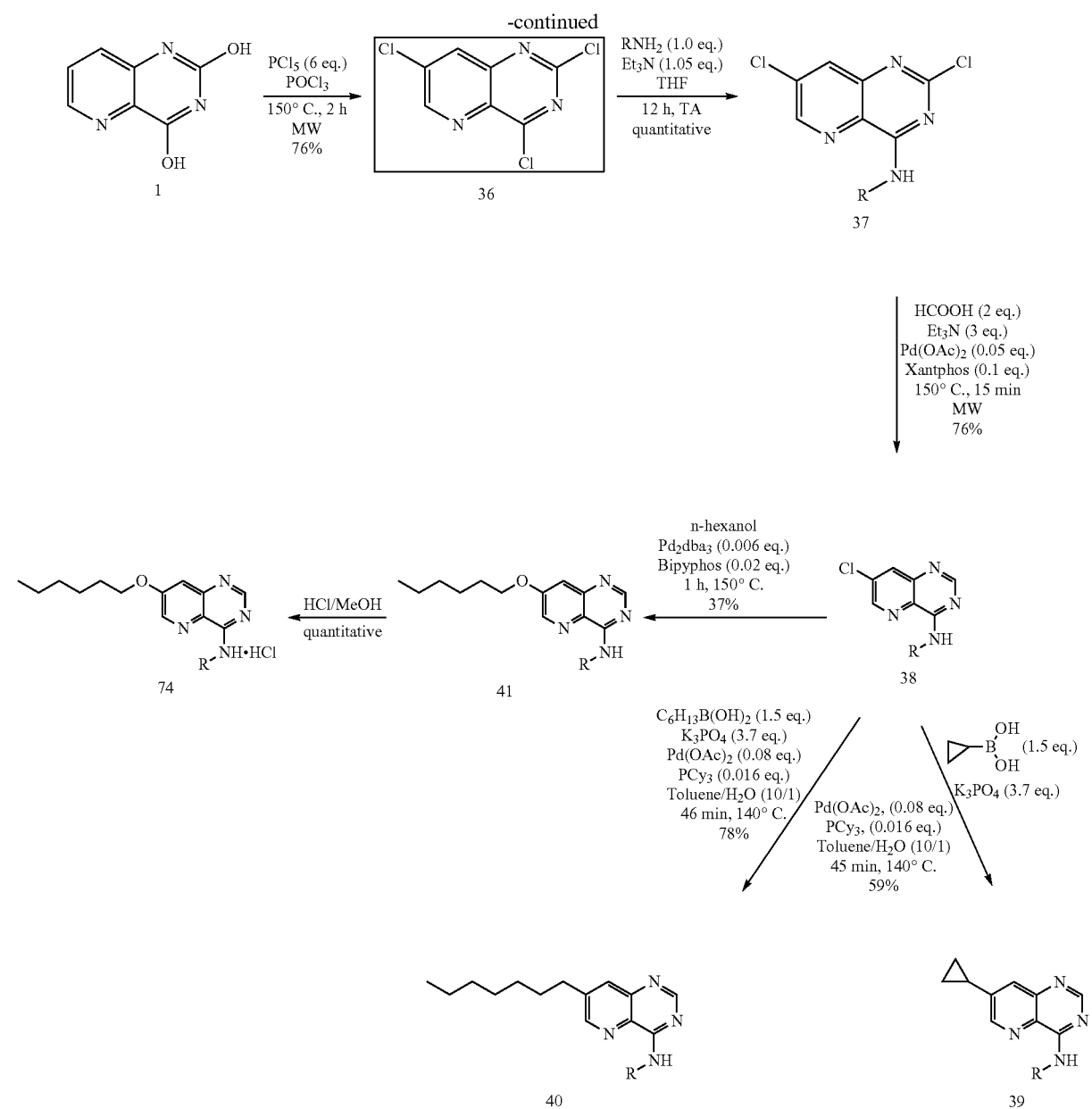
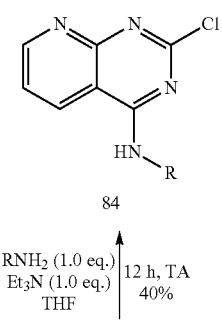

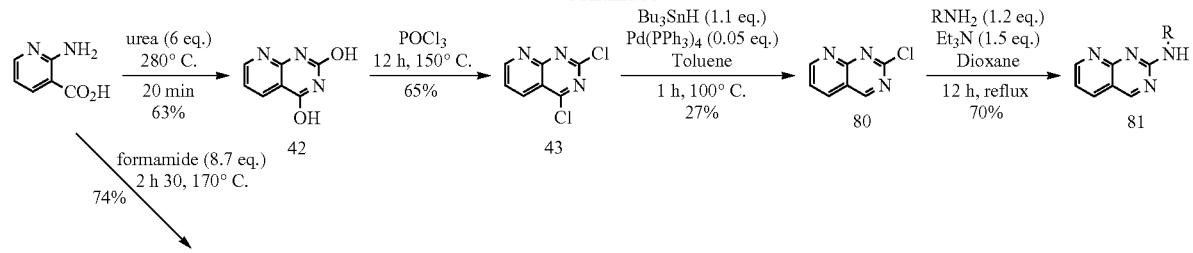
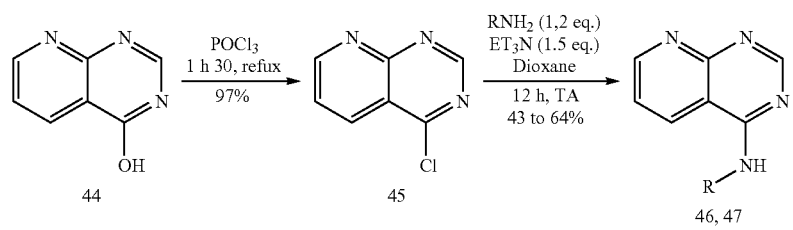
Scheme 5
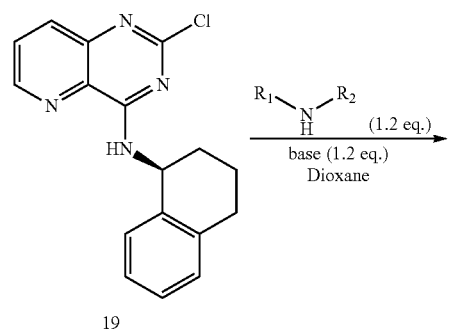
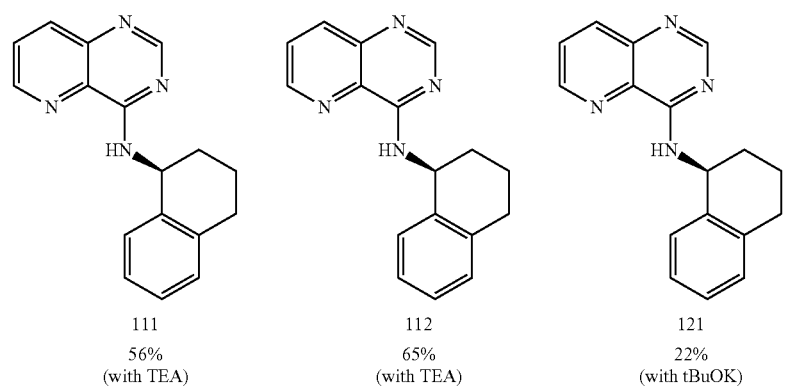

Scheme 6
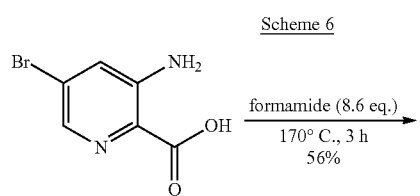
113
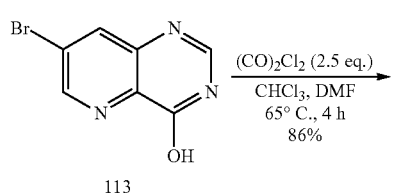
134
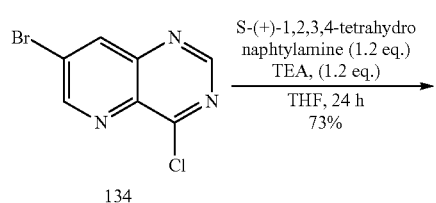
135
Scheme 7
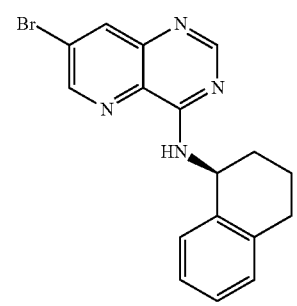
146
148
-continued
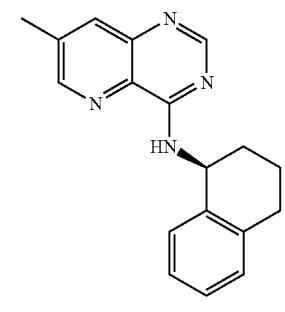
149
Scheme 8
114
132
133
151

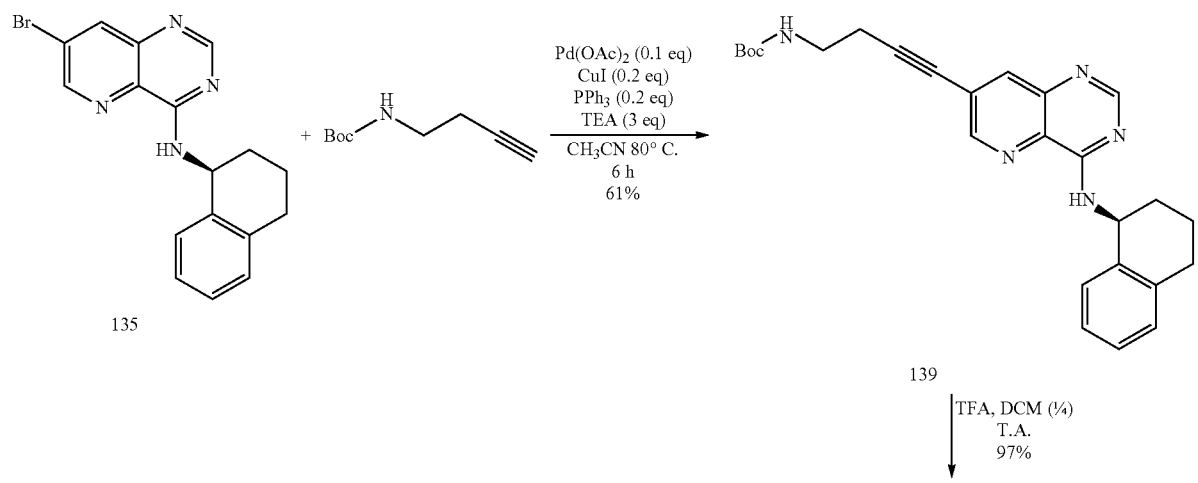
Scheme 9
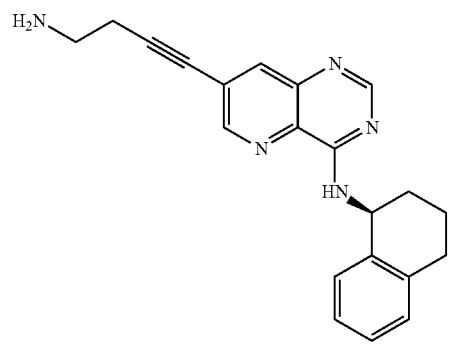
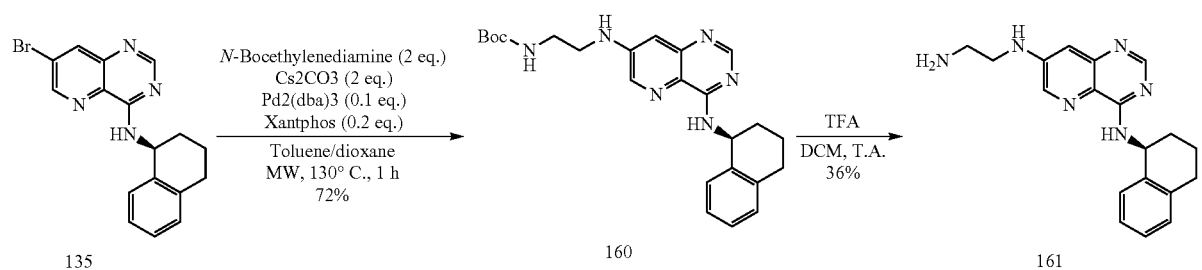

Scheme 10
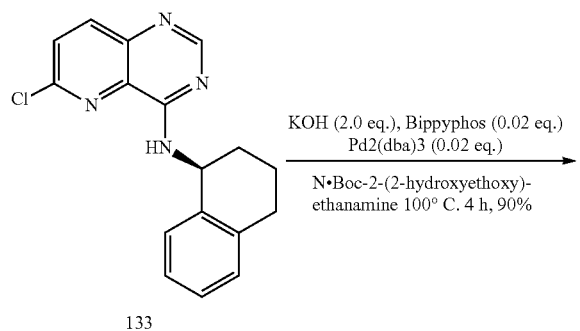
133
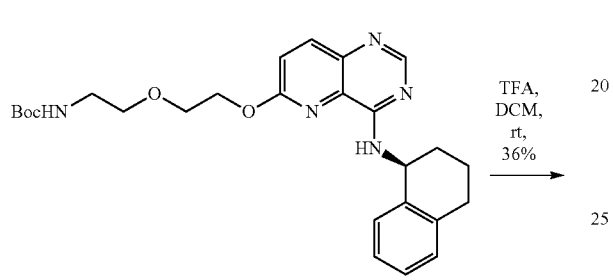
163
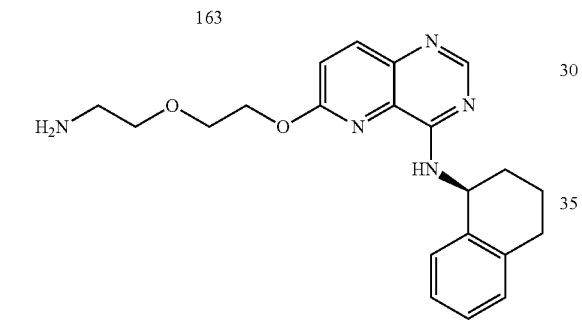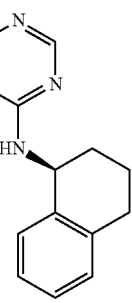
164
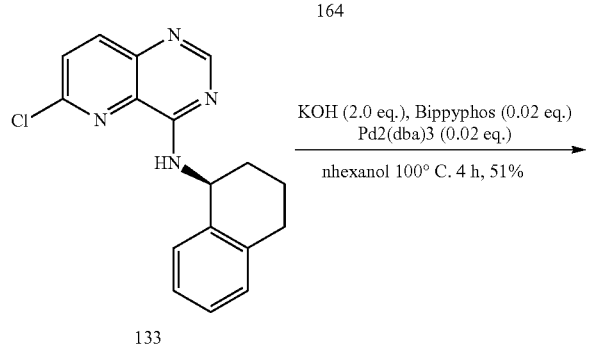
133
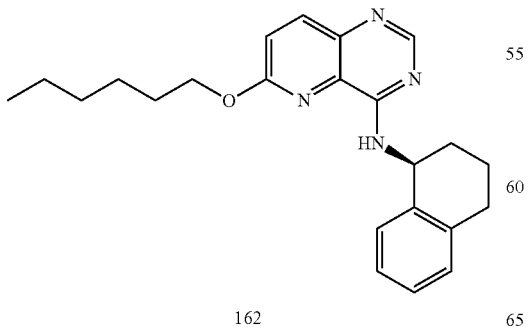
162
Scheme 11
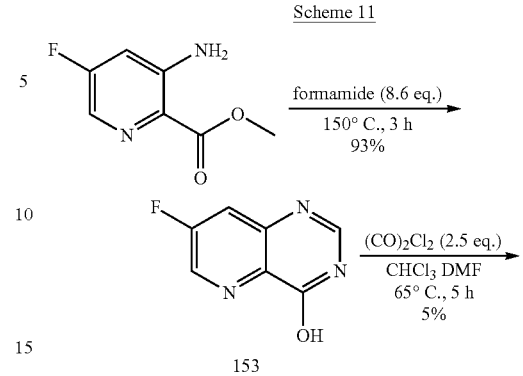
153
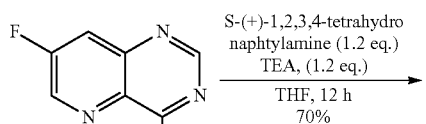
155
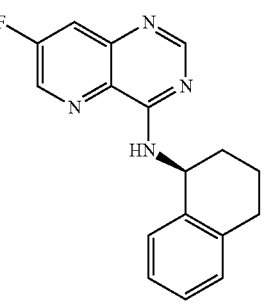
158
Scheme 12
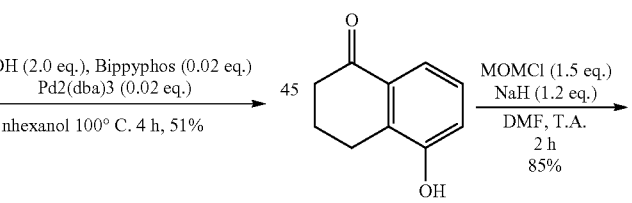
128
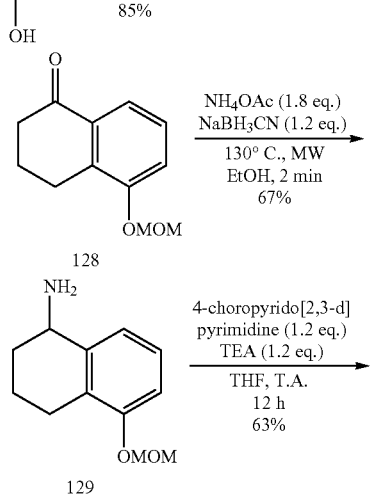
129

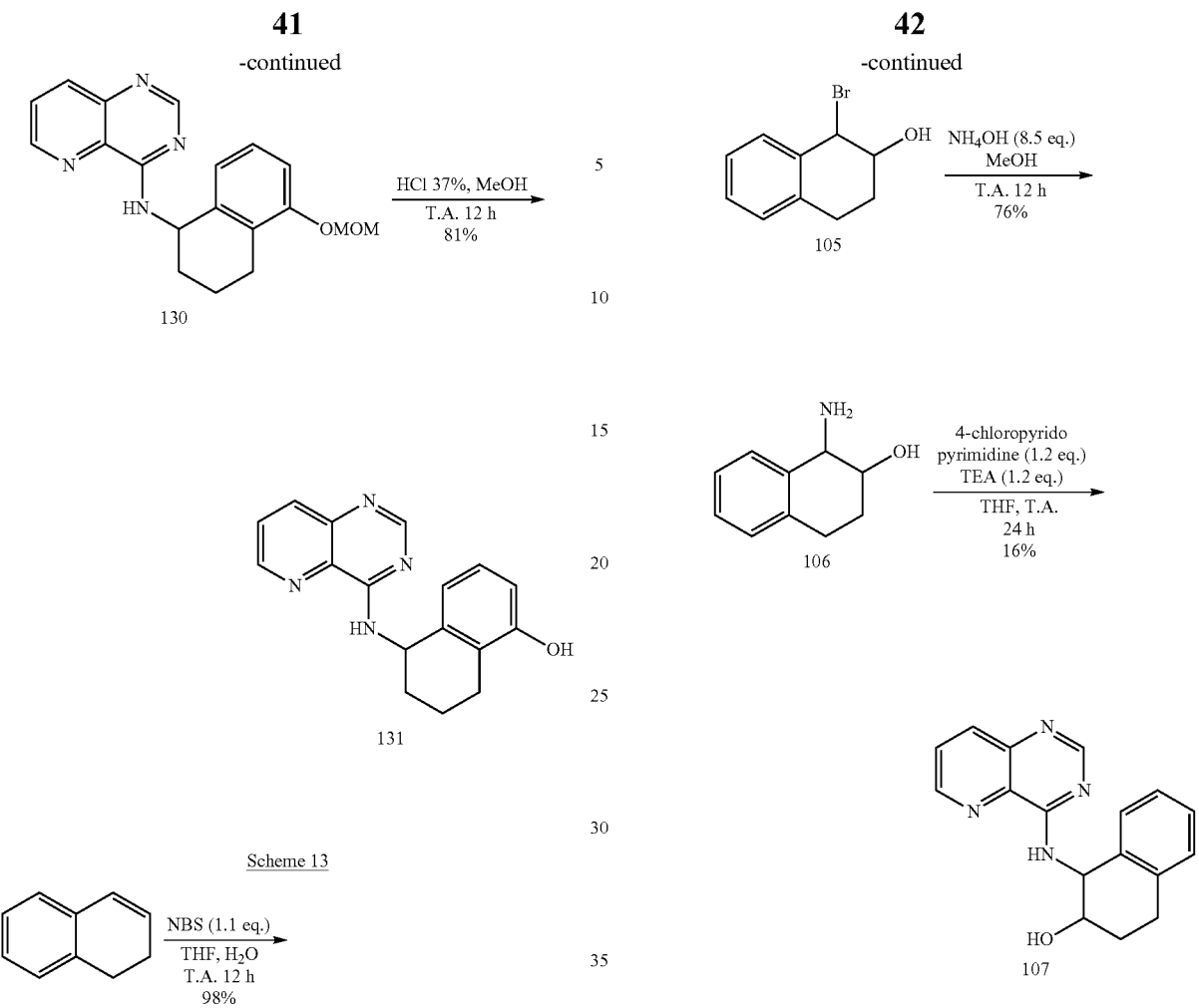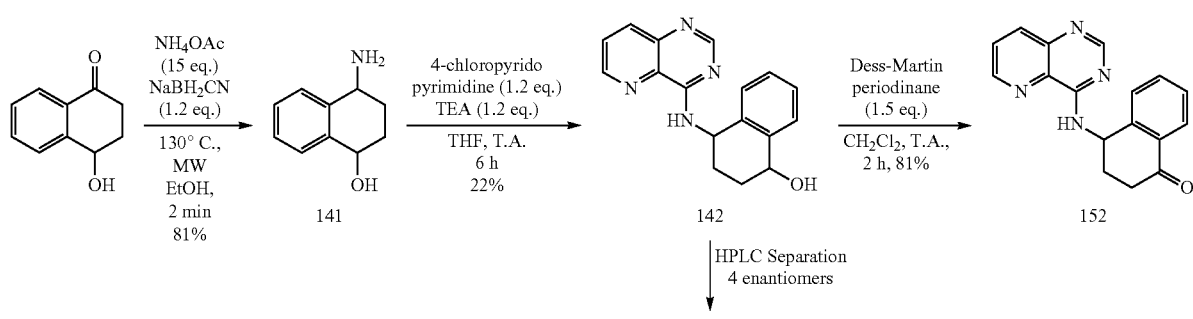

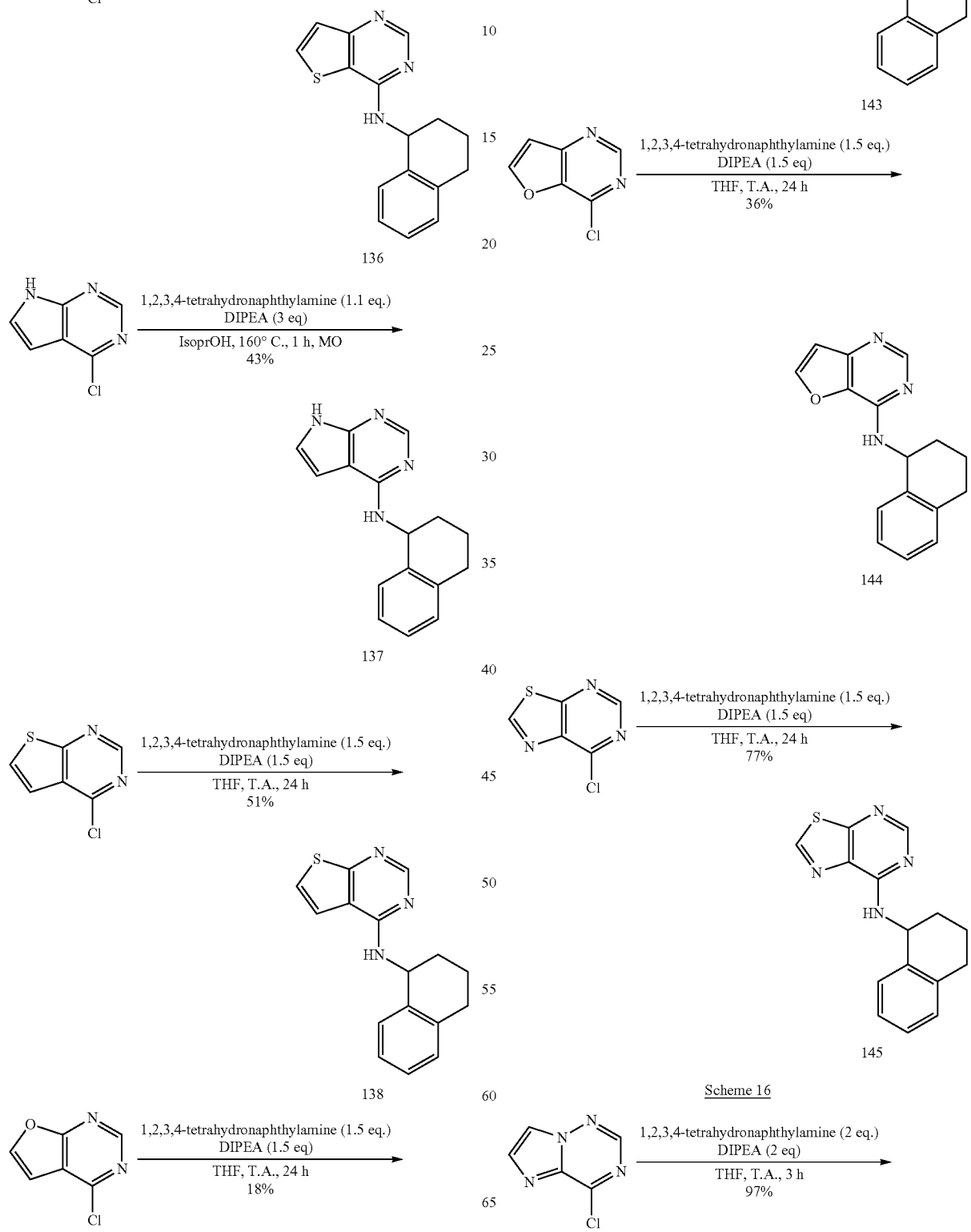

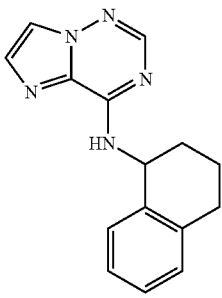

147

Scheme 17

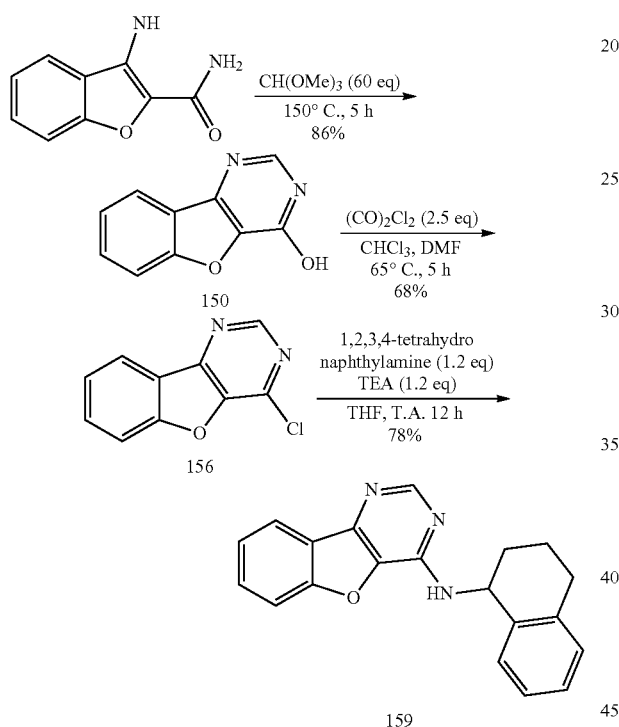

1. Preparation of Intermediate Compounds

Pyrido[3,2-d]pyrimidine-2,4(1H,3H)-dione (1)

CAS Number [37538-68-4]

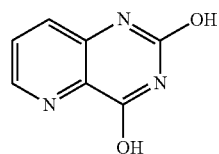 [SMILES: Oc1nc(O)c2ncccc2n1]

3-amino-picolinic acid (1 g, 7.2 mmol) and urea (3 g, 50 mmol, 7 eq.) were closely mixed and ground in a mortar. The mixture was placed in a 100 mL round-bottom flask and heated in a sand bath to 210° C. for 20 minutes. The reaction was complete when the residue had solidified. The mass obtained was dissolved under heat in 4 mL of 2 N sodium hydroxide. After cooling, the mixture was filtered and the filtrate acidified to pH 8 with the addition of concentrated hydrochloric acid. The precipitate formed was filtered, washed in a little cold water and dried to give the title product 42 (711 mg, 60%) in the form of a beige solid.

2,4-Dichloropyrido[3,2-d]pyrimidine (2)

CAS Number [39551-54-7]

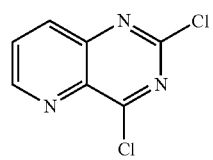

Product 1 (1 g, 6.1 mmol) was placed in suspension in POCl$_3$ (10 mL) after which PCl$_5$ was added (5.1 g, 24.5 mmol, 4.0 eq.). The whole was refluxed for 6 hours and the excess POCl$_3$ was evaporated under reduced pressure. The residue obtained was dissolved in 20 mL dichloromethane and poured onto 30 mL of a water/ice mixture. After 30-minute agitation the aqueous phase was extracted with 3×20 mL dichloromethane. The combined organic phases were dried over anhydrous magnesium sulfate and the solvents evaporated to give the title product 2 (673 mg, 55%) in the form of a yellow solid.

2-Chloropyrido[3,2-d]pyrimidine (3)

CAS Number [915302-21-5]

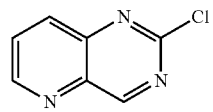

To a solution of product 2 (540 mg, 2.7 mmol) in anhydrous toluene (30 mL) under argon the addition was successively made of tributyltin hydride (0.8 mL, 3.0 mmol, 1.1 eq.) and Pd(PPh$_3$)$_4$ (156 mg, 0.135 mmol, 0.05 eq.). The mixture was brought to 100° C. for one hour. The toluene was evaporated and the residue obtained was solubilised in dichloromethane (20 mL) and hydrolysed with a saturated solution of potassium fluoride (20 mL). The mixture was left under vigorous stirring for 30 minutes then filtered through Celite® rinsing with dichloromethane (2×20 mL). The aqueous phase was extracted with dichloromethane (20 mL), and the combined organic phases dried over MgSO$_4$, filtered and concentrated in vacuo. The reaction product was chromatographed on silica gel (gradient EP to EP/AcOEt 80:20) to give the title product 3 (180 mg, 40%) in the form of a yellow solid.

4-Hydroxy-pyrido[3,2-d]pyrimidine (9)

CAS Number [37538-67-3]

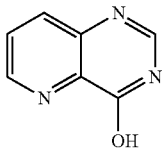 [SMILES: Oc1ncnc2cccnc12]

3-aminopicolinic acid (1 g, 7.2 mmol) was placed in a 100 mL round-bottom flask and formamide (2.3 mL, 57.6 mmol, 8.6 eq.) poured onto the acid. The paste obtained was brought to 170° C. for 2 h30; during the reaction the system becomes limpid and sets after cooling. The solid was recrystallized in 15 mL water and after filtration the crystals were washed with cold water (10 mL) to give the title product 9 (500 mg, 47%) in the form of brown crystals.

4-Chloropyrido[3,2-d]pyrimidine (10)

CAS Number [51674-77-2]

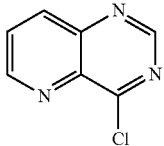

Product 9 (1 g, 6.80 mmol) was placed in a 100 mL round-bottom flask and phosphorus oxychloride (30 mL) poured onto the product. The assembly was refluxed under magnetic stirring for 4 h, the medium rapidly blackened. Excess oxychloride was evaporated under reduced pressure and there remained a black syrupy residue. The residue was placed 0° C. and about 20 mL of a water/ice mixture and 20 mL of dichloromethane were carefully added. The mixture was brought to pH 9/10 through the addition of solid sodium carbonate. The aqueous phase was rapidly extracted with dichloromethane (20 mL). The combined organic extracts were dried over MgSO$_4$ and the solvents were evaporated to give the title product 10 (310 mg, 28%) in the form of a purple solid to be given rapid use as such.

7-Bromo-1,2,3,4-tetrahydronaphthalen-1-amine (15)

CAS Number [865472-04-4]

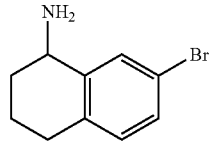 [SMILES: NC1CCCc2ccc(Br)cc21]

To a solution of 7-bromo-3,4-dihydronaphthalene (100 mg, 0.44 mmol) in ethanol (1 mL) the successive addition was made of ammonium acetate (514 mg, 6.66 mmol, 15.0 eq.) and sodium cyanoborohydride (33 mg, 0.52 mmol, 1.2 eq.). The mixture was brought to 130° C. under microwave radiation for 2 minutes then concentrated in vacuo. A 2 N sodium hydroxide solution was added until pH >10 was reached, and the product was extracted with ethyl acetate (2×20 mL). The combined organic phases were dried over MgSO$_4$, filtered and concentrated in vacuo to give the title product a (100 mg, quantitative) in the form of a colourless oil. R$_f$ (CH$_2$Cl$_2$/MeOH 95:05): 0.25. $^1$H NMR (400 MHz, CDCl$_3$) δ 7.55 (d, J=1.8 Hz, 1H), 7.24 (dd, J=8.2, 2.0 Hz, 1H), 6.94 (d, J=8.2 Hz, 1H), 3.94-3.90 (m, 1H), 2.82-2.58 (m, 2H), 2.05-1.95 (m, 1H), 1.95-1.86 (m, 1H), 1.83-1.70 (m, 1H), 1.70-1.56 (m, 3H). $^{13}$C NMR (101 MHz, CDCl$_3$) δ 143.5, 135.8, 130.9, 130.8, 129.7, 119.6, 49.4, 33.5, 29.1, 19.6. IR (Diamond ATR, cm$^{-1}$) ν 3359, 2927, 2858, 1590, 1477, 1266, 1169, 1083, 801. HRMS (EI-MS) m/z calculated for C$_{10}$H$_{12}$BrN [M+H]$^+$: 226.022588, found: 226.022470.

5,7-Dimethyl-1,2,3,4-tetrahydronaphthalen-1-amine (24)

CAS Number [59376-79-3]

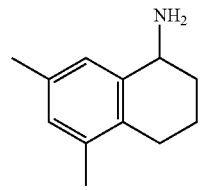

To a solution of 5,7-dimethyl-1-tetralone (100 mg, 0.57 mmol) in ethanol (1.3 mL) the successive addition was made of ammonium acetate (664 mg, 8.61 mmol, 15.0 eq.) and sodium cyanoborohydride (43 mg, 0.68 mmol, 1.2 eq.). The mixture was brought to 130° C. under microwave radiation for 2 minutes, then concentrated in vacuo. A 2 N sodium hydroxide solution was added until pH >10 was reached, and the product extracted with ethyl acetate (2×20 mL). The combined organic phases were dried over MgSO$_4$, filtered and concentrated in vacuo to give the title product 24 (100 mg, quantitative) in the form of a white solid.

1,2,3,4-Tetrahydrophenanthren-4-amine (27)

CAS Number [101561-96-0]

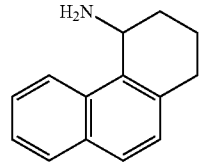 [SMILES: NC1CCCc2ccc3ccccc3c21]

To a solution of 1,2,3,4-tetrahydrophenanthren-4-one (150 mg, 0.96 mmol) in ethanol (2 mL) were successively added ammonium acetate (1.1 g, 14.4 mmol, 15.0 eq.) and sodium cyanoborohydride (72 mg, 1.15 mmol, 1.2 eq.). The mixture was brought to 130° C. under microwave radiation for 2 minutes, then concentrated in vacuo. A 2 N sodium hydroxide solution was added until pH >10 was reached, and the product extracted with ethyl acetate. The combined organic phases were dried over MgSO$_4$, filtered and concentrated in vacuo to give the title product 27 (140 mg, quantitative) in the form of a brown oil.

2,4,7-Trichloropyrido[3,2-d]pyrimidine (36)

CAS Number [1260663-38-4]

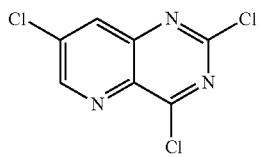 [SMILES: Clc1cnc2c(Cl)nc(Cl)nc2c1]

To a solution of product 1 (1.0 g, 6.1 mmol) in POCl₃ (10 mL), the addition was made of PCl₅ (7.65 g, 36.8 mmol, 6.0 eq.). The mixture was heated under microwave radiation to 150° C. for 2 hours. Excess POCl₃ was evaporated, the residue obtained was dissolved in dichloromethane then poured into 50 mL of a water/ice mixture. The whole was left under vigorous stirring for 30 minutes after which the aqueous phase was extracted with dichloromethane. The combined organic phases were dried over MgSO₄, filtered and concentrated in vacuo to give the title product 36 (1 g, 70%) in the form of a yellow solid.

2,4-Dihydroxy-pyrido[2,3-d]pyrimidine (42)

CAS Number [21038-66-4]

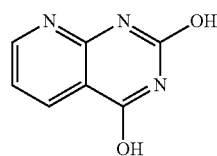 [SMILES: Oc1nc(O)c2cccnc2n1]

2-amino-nicotinic acid (5.0 g, 36 mmol) and urea (11.0 g, 180 mmol, 5 eq.) were closely mixed and ground in a mortar. The mixture was placed in a 250 mL round-bottom flask and heated in a sand bath to 280° C. for 20 minutes. The reaction was complete when the residue had solidified. The mass obtained was dissolved under heat in 100 mL of 2 N sodium hydroxide. After cooling, the mixture was filtered and the filtrate acidified to pH 8 through the addition of concentrated hydrochloric acid. The precipitate was filtered, washed with a little cold water and dried to give the title product 42 (3.7 g, 63%) in the form of a beige solid.

2,4-Dichloro-pyrido[2,3-d]pyrimidine (43)

CAS Number [126728-20-9]

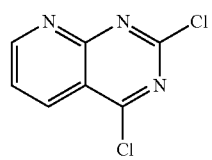 [SMILES: Clc1nc(Cl)c2cccnc2n1]

Product 42 (10.5 g, 65 mmol) was placed in a 500 mL round-bottom flask and phosphorus oxychloride (250 mL) poured onto the product. The mixture was left overnight at 150° C. under magnetic stirring. The excess oxychloride was evaporated under reduced pressure, and the residue placed at 0° C. and about 200 mL of a water/ice mixture and 300 mL of dichloromethane were carefully added. The mixture was brought to pH 8/9 using solid sodium carbonate. The aqueous phase was extracted with dichloromethane and the organic extracts dried over MgSO₄, after which the solvents were evaporated to give the title product 43 (8.42 mg, 65%) in the form of a beige solid to be given rapid use as such.

4-Hydroxy-pyrido[2,3-d]pyrimidine (44)

CAS Number [24410-19-3]

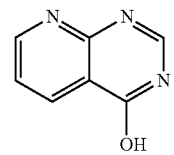 [SMILES: Oc1ncnc2ncccc12]

2-aminonicotinic acid (1 g, 7.2 mmol) was placed in a 100 mL round-bottom flask and formamide (2.3 mL, 57.6 mmol, 8.6 eq.) poured onto the acid. The paste obtained was brought to 170° C. for 2 h30, and became limpid during the reaction. After cooling, setting of the system was obtained. The solid was recrystallized in 15 mL of water and after filtration and washing in cold water gave the title product 44 (787 mg, 74%) in the form of beige crystals.

4-Chloropyrido[2,3-d]pyrimidine (45)

CAS Number [28732-79-8]

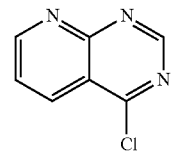 [SMILES: Clc1ncnc2ncccc12]

Product 44 (787 mg, 5.35 mmol) was placed in a 100 mL round-bottom flask and phosphorus oxychloride (12 mL) poured onto the product. The mixture was refluxed under magnetic stirring for 1 h30, the medium rapidly blackened. The excess oxychloride was evaporated under reduced pressure, leaving a black syrupy residue. The residue was placed at 0° C. and about 10 mL of a water/ice mixture and 10 mL of dichloromethane were carefully added. The mixture was brought to pH 9/10 with solid sodium carbonate. The aqueous phase was rapidly extracted with dichloromethane. The organic extracts were dried over MgSO₄ and the solvents evaporated to give the title product 45 (855 mg, 97%) in the form of a highly unstable orange solid to be given rapid use.

1-Nitroso-1,2,3,4-tetrahydroquinoline (50)

CAS Number [5825-44-5]

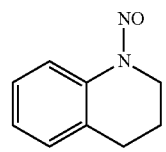

1,2,3,4-tetrahydroquinoline (0.94 mL, 7.50 mmol) and 10% HCl solution (3.01 mL, 9.76 mmol, 1.3 eq.) were stirred in a round bottom-flask at 0° C., under an argon atmosphere. A solution of NaNO₂ (829 mg, 12 mmol, 1.6 eq.) in water (5 mL) was added dropwise. After a stir time of 2 hours at ambient temperature the reaction mixture was diluted with 20 mL of water and extracted with ethyl acetate (2×20 mL). The organic phase was dried over magnesium sulfate and concentrated in vacuo but not to dryness since the product is sensitive. The residue was used directly at the following step without prior purification.

3,4-Dihydroquinolin-1(2H)-amine (51)

CAS Number [5825-45-6]

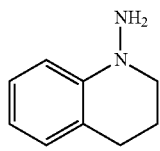

Product 50 (1.21 g, 7.51 mmol) was diluted in anhydrous THF (30 mL) at 0° C. in an argon atmosphere. Lithium aluminium hydride (1.14 g, 30 mmol, 4.0 eq.) was added portion-wise. The reaction mixture was stirred for 1 hour in a cold-water bath (15° C.). After return to 0° C., water (2 mL) was slowly added. The medium was filtered through Celite®, the filtrate diluted with water and extracted with dichloromethane. The organic phase was dried over magnesium sulfate and concentrated in vacuo. The reaction product was purified by silica gel chromatography (gradient eluent: EP to EP/AcOEt 80:20) to give the title product 51 in the form of a yellow/orange solid (800 mg, 70% in 2 steps).

6,7,8,9-Tetrahydro-5H-benzo[7]annulen-5-amine (54)

CAS Number [17910-26-8]

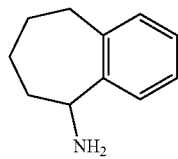 [SMILES: NC1CCCCc2ccccc21]

To a solution of 1-benzosuberone (0.62 mmol, 1.0 eq.) in ethanol (1.3 mL) were successively added ammonium acetate (721 mg, 0.93 mmol, 15.0 eq.) and sodium cyanoborohydride (47 mg, 0.75 mmol, 1.2 eq.). The mixture was brought to 130° C. under microwave radiation for 2 minutes, then concentrated in vacuo. A 2 N sodium hydroxide solution was added until pH >10 was obtained, after which the product was extracted with ethyl acetate (2×20 mL). The combined organic phases were dried over MgSO₄, filtered and concentrated in vacuo to give the title product 54 (119 mg, quantitative) in the form of a yellow oil.

7-Nitro-1,2,3,4-tetrahydronaphthalen-1-amine (57)

CAS Number [211372-31-5]

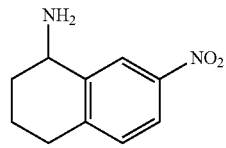 [SMILES: NC1CCCc2ccc([N+](=O)[O-])cc21]

To a solution of 7-nitro-1-tetralone (0.52 mmol, 1.0 eq.) in ethanol (1.3 mL) were successively added ammonium acetate (605 mg, 7.8 mmol, 15.0 eq.) and sodium cyanoborohydride (39 mg, 0.63 mmol, 1.2 eq.). The mixture was brought to 130° C. under microwave radiation for 2 minutes, then concentrated in vacuo. A 2 N sodium hydroxide solution was added until pH >10 was obtained, and the product extracted with ethyl acetate. The combined organic phases were dried over MgSO₄, filtered and concentrated in vacuo. The residue was purified eluting with EP/AE (80:20). The product was obtained in the form of a brown solid with a yield of 99% (100 mg).

3,4-Dihydro-2H-1-benzopyran-4-amine (60)

CAS Number [53981-38-7]

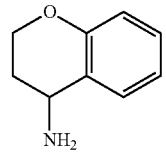 [SMILES: NC1CCOc2ccccc21]

To a solution of 4-Chromanone (3.57 mmol, 1.0 eq.) in ethanol (5.0 mL) were successively added ammonium acetate (4.0 g, 50.6 mmol, 15 eq.) and sodium cyanoborohydride (269 mg, 4.3 mmol, 1.2 eq.). The mixture was brought to 130° C. under microwave radiation for 2 minutes, then concentrated in vacuo. A 2 N sodium hydroxide solution was added until pH >10 was reached, and the product extracted with ethyl acetate. The combined organic phases were dried over MgSO₄, filtered and concentrated in vacuo. The residue was purified eluting with EP/AE (80:20). The product 60 was obtained in the form of a brown solid with a yield of 94% (500 mg).

4,5,6,7-Tetrahydro-1-benzofuran-4-amine (63)

CAS Number [389795-57-7]

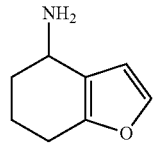

In a round-bottom flask under argon, 100 mg of 6-7-dihydro-1-benzofuran-4(5H)-one were solubilised in 5 mL of MeOH. 1 g of ammonium acetate (0.014 mol, 15.0 eq.), 122 mg of sodium cyanoborohydride (1.94 mol, 1.2 eq.) and 2 g of molecular sieve were added to the mixture. After refluxing for 4 h, the mixture was filtered through Celite® to remove the sieve. The excess MeOH was evaporated. The pH of the solution was increased to above 10 with 2 N NaOH. The aqueous phase was then extracted with EtOAc (3×25 mL). The organic phases were combined, dried over MgSO$_4$, filtered through cotton and evaporated in vacuo. 215 mg of compound 63 was obtained in the form of a brown oil with a yield of 99% (215 mg).

7-Methylpyrido[3,2-d]pyrimidine-2,4-diol (68)

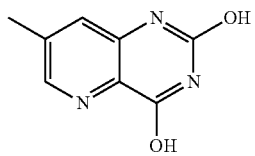

Under a carbon dioxide atmosphere and in a 20 mL vial, 400 mg (3.0 mmol, 1 eq.) of 3-amino-5-methylpyridine-2-carbonitrile was dissolved in 8 mL of anhydrous DMF. 448 µL (3.0 mmol, 1 eq.) of 1,8-diazabicyclo[5.4.0]undec-7-ne (DBU) were added. The solution was degassed for 15 minutes and the vial sealed. The mixture was heated to 105° C. for 6 hours (precipitation of the product). At 0° C., 2 mL of 1 M HCl were added. The precipitate was vacuum filtered allowing the isolation of a beige solid with a yield of 90%. $^1$H NMR (400 MHz, DMSO-d$_6$) δ: 11.07 (bs, 2H); 7.93 (s, 1H) 7.34 (s, 1H), 2.34 (s, 3H). $^{13}$C NMR (101 MHz, DMSO-d$_6$) δ: 161.7, 150.5, 146.2 139.7, 138.5, 129.7, 123.4, 18.6. HRMS (EI-MS): CH$_7$N$_3$O$_2$ [M+H]$^+$, calculated m/z 178.0617, found m/z 178.0611. IR (Diamond ATR, cm$^{-1}$) ν 3052, 1673, 1410, 1127, 846, 820, 686. T$_m$: >260° C.

2,4-Dichloro-7-methylpyrido[3,2-d]pyrimidine (69)

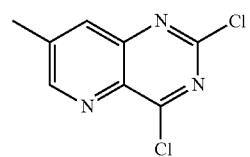

In a 50 mL round-bottom flask, 1 g (6.65 mmol; 1.0 eq.) of compound 68 was placed in suspension in 10 mL of phosphorus oxychloride and 4.7 g (22.60 mmol; 4.0 eq.) of PCl$_5$. The mixture was heated to 130° C. After a reaction time of 12 hours, the excess POCl$_3$ was evaporated under reduced pressure. The residue obtained was brought to 0° C. using an ice bath then solubilised in dichloromethane (150 mL), and the mixture poured in a water/ice mixture (200 mL) without any basification. After return to ambient temperature, the aqueous phase was extracted with dichloromethane (1×100 mL). The organic phases were dried over MgSO$_4$, filtered and concentrated under reduced pressure. The residue obtained was purified by silica gel column chromatography under pressure (AE/EP, 2:8) to give a white solid 69 with a yield of 70%. $^1$H NMR (400 MHz, CDCl$_3$) δ: 8.99 (d, J=2.0 Hz, 1H) 8.08 (m, 1H), 2.68 (m, 3H); $^{13}$C NMR (101 MHz, CDCl$_3$) δ: 166.7, 157.0, 156.6, 150.4, 143.2, 136.4, 135.8, 20.7. HRMS (EI-MS): C$_7$H2Cl$_3$N$_3$ [M+H]$^+$, calculated m/z 213.9939, found m/z 213.9933; IR (Diamond ATR, cm$^{-1}$) ν1539, 1439, 1398, 1255, 1137, 1004, 869, 698, 690 T$_m$: 146-168° C.

2,4,7-trichloropyrido[3,2-d]pyrimidine (77)

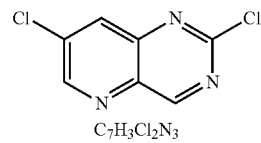 [SMILES: Clc1cnc2cnc(Cl)nc2c1 ; "C7H3Cl2N3"]

C$_7$H$_3$Cl$_2$N$_3$

To a solution of product 36 (310 mg, 1.32 mmol) in anhydrous toluene (15 mL) under argon the addition was successively made of tributyltin hydride (0.4 mL, 1.45 mmol, 1.1 eq.) and Pd(PPh$_3$)$_4$ (76 mg, 0.06 mmol, 0.05 eq.). The mixture was brought to 100° C. for one hour. The toluene was afterwards evaporated and the residue obtained was solubilised in dichloromethane and hydrolysed with a saturated solution of potassium fluoride. The mixture was left under vigorous stirring for 30 minutes then filtered through Celite® rinsing with dichloromethane. The aqueous phase was extracted with dichloromethane, dried over MgSO$_4$, filtered and concentrated in vacuo. The reaction product was chromatographed on silica gel (gradient: petroleum ether→petroleum ether/AcOEt 95:05) to give the title product 77 (90 mg, 34%) in the form of a yellow solid. $^1$H NMR (400 MHz, CDCl$_3$) δ 9.03 (d, J=2.2 Hz, 1H), 8.31 (d, J=2.2 Hz, 1H). $^{13}$C NMR (101 MHz, CDCl$_3$) δ 166.0, 157.0, 152.7, 148.8, 138.5, 135.1, 134.2. IR (Diamond ATR, cm$^{-1}$) ν 3048, 2167, 1579, 1531, 1430, 1324, 1253, 1136, 1001, 872. HRMS (EI-MS) m/z calculated for C$_7$H$_2$C$_3$N$_3$ [M+H]$^+$: 232.9314, found: 232.9323. T$_m$: 166° C.

2,4-Dichloro-pyrido[2,3-d]pyrimidine (80)

CAS Number [1060816-71-8]

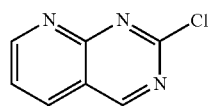

To a solution of product 43 (450 mg, 2.2 mmol) in anhydrous toluene (25 mL) under argon the addition was successively made of tributyltin hydride (0.67 mL, 2.5 mmol, 1.1 eq.) and Pd(PPh$_3$)$_4$ (130 mg, 0.113 mmol, 0.05 eq.). The mixture was brought to 100° C. for one hour. The toluene was afterwards evaporated and the residue obtained was solubilised in dichloromethane and hydrolysed with a saturated solution of potassium fluoride. The mixture was left under vigorous stirring for 30 minutes then filtered through Celite®, rinsing with dichloromethane. The aqueous phase was extracted with dichloromethane, dried over MgSO$_4$, filtered and concentrated in vacuo. The reaction product was chromatographed on silica gel (gradient petroleum ether→petroleum ether/AcOEt 80:20) to give the title product 80 (100 mg, 27%) in the form of an unstable white solid to be given rapid use. $^1$H NMR (250 MHz, CDCl$_3$) δ 9.33 (dd, J=2.0, 4.4 Hz, 1H), 8.64 (dd, J=2.0, 8.3 Hz, 1H), 7.72 (dd, J=4.4, 8.3 Hz, 1H). T$_m$: 134-136° C.

4-(1H-1,2,4-Triazol-1-yl)pyrido[3,2-d]pyrimidine (85)

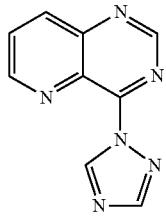 [SMILES: c1cnc2c(-n3cncn3)ncnc2c1]

In a 100 mL round-bottom flask, 1,2,4-triazole (3.15 g; 45.6 mmol) was dissolved in 22 mL of CH$_3$CN and the flask immersed in an ice bath. POCl$_3$ (1.4 mL; 15 mmol) was added at 0° C. followed by the dropwise addition of triethylamine (6.34 mL; 45.6 mmol). The solution became white and opaque. The solution was stirred at 0° C. for 40 minutes and then at ambient temperature for 30 minutes. Finally, compound 9 (1 g; 6.8 mmol) was added and the yellowish solution stirred overnight at ambient temperature. The reaction was monitored by TLC (solvent system: 98% CH$_2$Cl$_2$ and 2% MeOH) to verify disappearance of the starting compound. On completion of the reaction, the solution was diluted with 50 mL of water and the product extracted with 5×60 mL ethyl acetate. The organic phases were combined, washed with saturated aqueous NaCl solution and dried over MgSO$_4$. After filtration, the solvent was evaporated to obtain a yellow powder. After solid deposit on silica, the product was purified on a silica column using a solvent system of 98% CH$_2$Cl$_2$ and 2% MeOH. The product was obtained in the form of a yellow solid (920 mg; 69%). Rf (EP/AE 50:50): 0.52. $^1$H NMR (400 MHz, CDCl$_3$) δ 10.26 (1H; s), 9.38 (s, 1H), 9.18 (m, 1H), 8.50 (m, 1H), 8.30 (s, 1H), 7.96 (m, 1H). $^{13}$C NMR (100 MHz, CDCl$_3$) δ 155.4, 153.4, 153.2, 152.5, 149.2, 149.1, 137.6, 132.2, 129.2. IR (Diamond ATR, cm$^{-1}$) ν 3109, 1514, 1410, 1336, 1197, 1121, 969, 832, 661. HRMS (EI-MS): m/z calculated for C$_9$H$_7$N$_6$ [M+H]$^+$: 199.0726, found: 199.0728. T$_m$: 184-186° C.

General procedure A (synthesis of amines): In a sealed 10 mL tube, the ketone is dissolved in 6 mL of ethanol and the successive addition is made of NH$_4$Ac (15 eq.) and NaBH$_3$CN (1.2 eq.). The reaction is conducted in a microwave reactor at 130° C. under vigorous stirring. On completion of the reaction, the disappearance of the starting ketone is verified by TLC, and the ethanol is evaporated. A 2 M sodium hydroxide solution is added to reach pH 10 and the product then extracted with 3×20 mL ethyl acetate. The organic phases are combined and washed with saturated aqueous NaCl solution and finally dried over MgSO$_4$. After filtration, the solvent is evaporated and the product is purified on a silica column.

1-Indanamine (96)

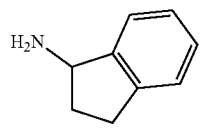

Compound 96 was obtained following procedure A with indanone (200 mg; 1.5 mmol), NH$_4$Ac (1.75 g; 28 mmol) and NaBH$_3$CN (114 mg; 1.8 mmol). The product was purified on a silica column with 90% CH$_2$Cl$_2$ and 10% MeOH solvent system. The product was obtained in the form of a white solid (108 mg; 54%). Rf (CH$_2$Cl$_2$/MeOH 90:10): 0.22. $^1$H NMR (400 MHz, CDCl$_3$) δ 7.28 (m, 4H), 4.36 (m, 1H), 2.97 (m, 1H), 2.82 (m, 1H), 2.51 (m, 1H), 1.90 (br s, 2H, NH$_2$), 1.70 (m, 1H). $^{13}$C NMR (100 MHz, CDCl$_3$) δ 147.3, 143.0, 127.2, 126.5, 124.6, 123.3, 57.2, 37.2, 30.1. IR (Diamond ATR, cm$^{-1}$) ν 3280, 2966, 1613, 1477, 1356, 1289, 1258, 1050, 813, 745, 579. HRMS (EI-MS): m/z calculated for C$_9$H$_{12}$N [M+H]$^+$: 134.0964, found: 134.0962. T$_m$: 102-104° C.

5-methoxy-1,2,3,4-tetrahydronaphthalen-1-amine (97)

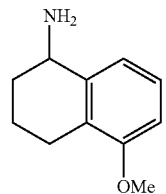 [SMILES: COc1cccc2c1CCCC2N]

Compound 97 was obtained following procedure A with 5-methoxytetralone (400 mg; 2.3 mmol), NH$_4$OAc (2.6 g; 34 mmol) and NaBH$_3$CN (174 mg; 2.8 mmol). The product was purified on a silica column, with 97% CH$_2$Cl$_2$ and 3% MeOH solvent system. The product was obtained in the form of a white solid (352 mg; 88%). Rf (CH$_2$Cl$_2$/MeOH 98:2): 0.35. $^1$H NMR (400 MHz, CD$_3$OD) 7.08 (m, 1H), 6.92 (m, 1H), 6.68 (m, 1H), 3.84 (m, 1H), 3.71 (s, 3H), 2.55 (m, 2H), 1.85 (m, 2H), 1.63 (m, 2H). $^{13}$C NMR (100 MHz, CD$_3$OD) 158.4, 142.3, 127.4, 126.5, 121.1, 108.9, 55.7, 50.1, 32.7, 24.1, 19.7. IR (Diamond ATR, cm$^{-1}$) ν 3396, 2920, 2840, 1549, 1245, 1066, 780, 717, 640. HRMS (EI-MS): m/z calculated for C$_{11}$H$_{16}$NO [M+H]$^+$: 178.1226, found: 178.1221. T$_m$: 115-117° C.

7-methoxy-1,2,3,4-tetrahydronaphthalen-1-amine (98)

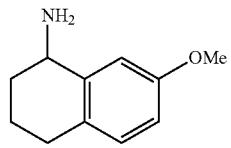 [SMILES: COc1ccc2c(c1)C(N)CCC2]

Compound 98 was obtained following procedure A with 7-methoxytetralone (150 mg; 0.85 mmol), NH$_4$OAc (986 mg; 12.8 mmol) and NaBH$_3$CN (64 mg; 1.02 mmol). The product was purified on a silica column, with 90% CH$_2$Cl$_2$ and 10% MeOH solvent system. The product was obtained in the form of a white solid (150 mg; 99%). Rf (CH2Cl2/MeOH 90:10): 0.21. $^1$H NMR (400 MHz, CDCl$_3$) δ 6.94 (m, 2H), 6.68 (m, 1H), 3.90 (m, 1H), 3.74 (s, 3H), 2.64 (m, 2H), 2.48 (br s, 2H; NH$_2$), 1.92 (m, 2H), 1.66 (m, 2H). $^{13}$C NMR (100 MHz, CDCl$_3$) δ 157.6, 141.4, 129.6, 128.5, 112.8, 112.3, 54.9, 49.3, 33.1, 28.4, 19.6. IR (Diamond ATR, cm$^{-1}$)

ν 3341, 2928, 1575, 1470, 1252, 1035, 815, 702. HRMS (EI-MS): m/z calculated for $C_{11}H_{16}NO$ [M+H]$^+$: 178.1226, found: 178.1223. $T_m$: 99-101° C.

7-fluoro-1,2,3,4-tetrahydronaphthalen-1-amine (99)

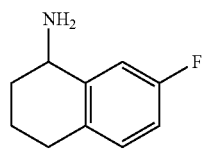 [SMILES: NC1CCCc2ccc(F)cc21]

Compound 99 was obtained following procedure A with 7-fluorotetralone (400 mg; 2.4 mmol), NH$_4$OAc (2.8 g; 56.5 mmol) and NaBH$_3$CN (181 mg; 2.88 mmol). The product was purified on a silica column with 97% CH$_2$Cl$_2$ and 3% MeOH solvent system. The product was obtained in the form of a white solid (271 mg; 68%). Rf (CH$_2$Cl$_2$/MeOH 98:2): 0.20. $^1$H NMR (250 MHz, CDCl$_3$) δ 7.08 (m, 1H), 6.96 (m, 1H), 6.78 (m, 1H), 3.86 (m, 1H), 2.66 (m, 2H), 1.98 (m, 1H), 1.87 (m, 3H), 1.72 (m, 1H), 1.58 (m, 1H). $^{13}$C NMR (62.5 MHz, CDCl$_3$) δ 161.1 (J=243.0 Hz), 142.9 (J=6.0 Hz), 132.1 (J=3.0 Hz), 130.1 (J=7.0 Hz), 114.0 (J=20.0 Hz), 113.6 (J=20.0 Hz), 49.4, 33.3, 28.7, 19.7. IR (Diamond ATR, cm$^{-1}$) ν 2944, 1551, 1471, 1372, 1250, 807, 705. HRMS (EI-MS): m/z calculated for $C_{10}H_{13}NF$ [M+H]$^+$: 166.1026, found: 166.1033. $T_m$: 95-97° C.

4,5,6,7-tetrahydrobenzo[b]thiophen-4-amine (100)

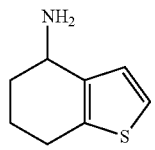

Compound 100 was obtained following procedure A with 6,7-dihydro-4-benzo[b]thiophenone (200 mg; 1.32 mmol), NH$_4$OAc (1.52 g; 19.8 mmol) and NaBH$_3$CN (100 mg; 1.58 mmol). The product was purified on a silica gel column with 95% CH$_2$Cl$_2$ and 5% MeOH solvent system. The product was obtained in the form of a yellow solid (157 mg; 79%). R$_f$ (CH$_2$Cl$_2$/MeOH 95:5): 0.28. $^1$H NMR (400 MHz, CD$_3$OD) δ 7.16 (m, 1H), 7.04 (m, 1H), 4.04 (m, 1H), 2.78 (m, 2H), 2.06 (m, 2H), 1.83 (m, 1H), 1.72 (m, 1H). $^{13}$C NMR (100 MHz, CD$_3$OD) 139.0, 138.2, 127.1, 123.7, 48.1, 32.4, 25.7, 21.8. IR (Diamond ATR cm$^{-1}$) ν 3307, 2931, 1607, 1474, 1307, 1152, 870, 814, 674. HRMS (EI-MS): m/z calculated for $C_8H_{12}NS$ [M+H]$^+$: 154.0685, found: 154.0683. $T_m$: 102-104° C.

4,4-dimethyl-1,2,3,4-tetrahydronaphthalen-1-amine (101)

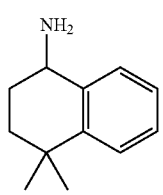

Compound 101 was obtained following procedure A with 4,4-dimethyl-1,2,3,4-tetrahydronaphthalen-1-one (500 mg; 2.9 mmol), NH$_4$OAc (3.32 g; 43.1 mmol) and NaBH$_3$CN (217 mg; 3.45 mmol). The product was purified on a silica gel column with 95% CH$_2$Cl$_2$ and 5% MeOH solvent system. The product was obtained in the form of a white solid (240 mg; 48%). Rf (CH$_2$C$_{12}$/MeOH 95:5): 0.24. $^1$H NMR (250 MHz, CDCl$_3$) δ 7.41 (m, 1H), 7.35 (m, 1H), 7.19 (m, 2H), 3.97 (m, 1H), 2.65 (br s, 2H), 2.08 (m, 1H), 1.87 (m, 1H), 1.74 (m, 1H), 1.63 (m, 1H), 1.34 (s, 3H), 1.28 (s, 3H). $^{13}$C NMR (62.5 MHz, CDCl$_3$) δ 145.3, 139.4, 127.9, 127.00, 126.6, 125.8, 50.0, 35.1, 33.9, 31.7, 29.5. IR (Diamond ATR, cm$^{-1}$) ν 3414, 3303, 2957, 2860, 1636, 1574, 1456, 1291, 1153, 1042, 762, 545, 508. HRMS (EI-MS): m/z calculated for $C_{12}H_{18}N$ [M+H]$^+$: 176.1433, found: 176.1434. $T_m$: 70-72° C.

6-(Methoxymethoxy)-3,4-dihydronaphthalen-1(2H)-one (102)

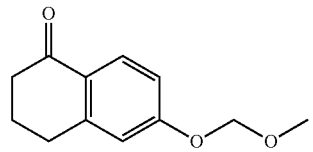

6-hydroxytetralone (200 mg, 1.23 mmol, 1.0 eq.) was dissolved in 3 mL DMF in a 25 mL round-bottom flask and the flask immersed in an ice bath at 0° C. Under stirring, sodium hydride (60 mg, 1.5 mmol, 1.2 eq.) was added and 10 min later the addition was made of chloromethyl methyl ether (0.14 mL, 1.85 mmol, 1.5 eq.). The mixture was stirred at ambient temperature for 2 hours. On completion of the reaction, the mixture was diluted with 90 mL AcOEt and washed with 3×70 mL water. The organic phase was washed with saturated aqueous NaCl solution (20 mL) and dried over MgSO$_4$. After filtration, the solvent was evaporated and the residue purified by silica gel chromatography (gradient 100 to 70% PE and 0 to 30% AE/). Product 102 was obtained in the form of a colourless oil (248 mg, 98%). R (petroleum ether/AcOEt 50:50) 0.90. $^1$H NMR (400 MHz, CDCl$_3$) δ 790 (d, J=87 Hz 1H), 685 (dd, J=8.7, 2.5 Hz, 1H), 6.78 (d, J=2.5 Hz, 1H), 5.14 (s, 2H), 3.40 (s, 3H), 2.3 (t, J=6.0 Hz, 2H), 2.51 (t, J=6.0 Hz, 2H), 2.02 (quin, J=6.0 Hz, 2H). $^{13}$C NMR (101 MHz, CDCl$_3$) δ 196.9, 161.0, 146.7, 129.3, 126.9, 114.7, 114.6, 93.8, 56.1, 38.8, 29.9, 23.2. IR (Diamond ATR cm$^{-1}$) ν 2942, 2828, 1672, 1570, 1491, 1080, 920, 826. HRMS (EI-MS): m/z calculated for $C_{12}H_{14}N_4NaO_3$ [M+Na]$^+$: 229.0835, found: 229.0833.

6-(Methoxymethoxy)-1,2,3,4-tetrahydronaphthalen-1-amine (103)

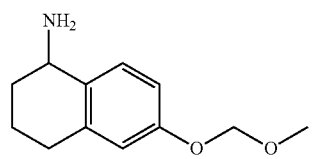

Compound 103 was obtained following procedure A with compound 102 (225 mg, 1.1 mmol, 1.0 eq.), NH$_4$OAc (1.27 g, 16.5 mmol, 15.0 eq.) and NaBH$_3$CN (83 mg, 1.32 mmol, 1.2 eq.). The residue was purified by silica gel chromatography (solvent system CH$_2$Cl$_2$/MeOH 90:10). The product was obtained in the form of a white solid (78 mg, 35%). R$_f$ (CH$_2$Cl$_2$/MeOH 95:5): 0.21. $^1$H NMR (400 MHz, CDCl$_3$) δ 7.31 (d, J=8.7 Hz, 1H), 6.87 (dd, J=8.7 and 2.5 Hz, 1H), 6.75 (d, J=2.5 Hz, 1H), 5.14 (s, 2H), 3.94 (m, 1H), 3.46 (s, 3H), 2.74 (m, 2H), 1.96 (m, 1H), 1.90 (m, 1H), 1.69 (m, 2H). $^{13}$C NMR (101 MHz, CDCl$_3$) δ 155.8, 138.2, 134.7, 129.3, 116.0, 114.5, 94.5, 56.0, 48.9, 33.7, 29.9, 19.5. IR (Diamond ATR, cm$^{-1}$): 3326, 2937, 2841, 1500, 1318, 1150, 1007, 824, 718. HRMS (EI-MS): m/z calculated for C$_{12}$H$_{17}$NNaO$_2$ [M+Na]$^+$: 230.1148, found: 230.1151. T$_m$: 99-101° C.

1-Bromo-1,2,3,4-tetrahydronaphthalen-2-ol (105)

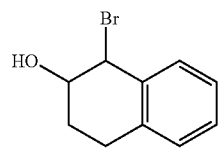 [SMILES: OC1CCc2ccccc2C1Br]

1,2-dihydronaphthalene (1 g, 7.7 mmol) and N-bromosuccinimide (1.51 g, 8.47 mmol) were dissolved in 7 mL THF and 4 mL water and the mixture stirred overnight at ambient temperature. The starting product disappeared and the succinimide precipitated in the form of a white solid. The mixture was diluted with 60 mL AcOEt and washed with 2×50 mL water. The organic phase was washed with saturated aqueous NaCl solution and dried over MgSO$_4$. After filtration, the solvent was evaporated and compound 105 was precipitated through the addition of pentane. The product was obtained in the form of a white solid (1.7 g, 98%). R$_f$ (PE/AE 60:40): 0.82. $^1$H NMR (400 MHz, DMSO-d$_6$) δ 7.37 (m, 1H), 7.19 (m, 2H), 7.10 (m, 1H), 5.85 (br s, 1H, OH), 4.67 (m, 1H), 4.47 (m, 1H), 2.85 (m, 2H), 2.44 (m, 1H), 2.11 (m, 1H). $^{13}$C NMR (101 MHz, DMSO-d$_6$) δ 136.6, 134.9, 129.4, 128.1, 127.3, 125.9, 71.8, 56.3, 27.7, 26.4. IR (Diamond ATR, cm$^{-1}$) ν 3242, 2910, 1693, 1434, 1188, 949, 878, 749, 652. HRMS (EI-MS): m/z calculated for C$_{19}$H$_{21}$N$_4$O$_2$ [M+H]$^+$: 337.1659, found: 337.1660. T$_m$: 104-106° C.

1-Amino-1,2,3,4-tetrahydronaphthalen-2-ol (106)

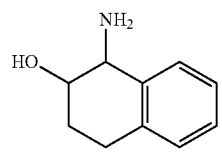 [SMILES: NC1c2ccccc2CCC1O]

Compound 105 (770 mg, 3.4 mmol) was dissolved in 2 mL of MeOH after which aqueous ammonium hydroxide (4 mL, 29 mmol) was added. The mixture was stirred overnight at ambient temperature. TLC verified disappearance of the starting product and the MeOH was evaporated. The residue was purified directly by silica gel chromatography (gradient system 0 to 10% MeOH/100 to 90% CH$_2$Cl$_2$). Product 106 was obtained in the form of a white solid (423 mg, 76%). R (AE 100): 0.19. $^1$H NMR (400 MHz, DMSO-d$_6$) δ 7.52 (m, 1H), 7.24 (m, 2H), 7.16 (m, 1H), 5.46 (br s, 1H, OH), 4.02 (m, 1H), 3.80 (m, 1H), 2.81 (m, 2H), 2.02 (m, 1H), 1.75 (m, 1H). $^{13}$C NMR (101 MHz, DMSO-d$_6$) δ 136.6, 132.9, 128.7, 128.0, 127.7, 126.1, 68.5, 55.3, 28.2, 26.3. IR (Diamond ATR, cm$^{-1}$) ν 2929, 1598, 1493, 1043, 774, 742, 552. HRMS (EI-MS): m/z calculated for C$_{10}$H$_{14}$NO [M+H]$^+$: 164.1069, found: 164.1070. T$_m$: 155-160° C.

7-Fluoro-1,2,3,4-tetrahydronaphthalen-1-amine (109)

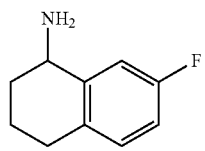 [SMILES: NC1CCCc2ccc(F)cc21]

Compound 109 was obtained following procedure B with 7-fluorotetralone (400 mg, 24 mmol, 1.0 eq.), NH$_4$OAc (2.8 g, 56.5 mmol, 15.0 eq.) and NaBH$_3$CN (181 mg, 2.88 mmol, 1.2 eq.). The residue was purified by silica gel chromatography (eluting with CH$_2$Cl$_2$/MeOH 97:3). The product was obtained in the form of a white solid (271 mg, 68%). R$_f$ (CH$_2$Cl$_2$/MeOH 98:2): 0.20. $^1$H NMR (400 MHz, CDCl$_3$) δ 7.08 (dd, J=10, 3 Hz, 1H), 6.96 (dd, J=8 et 6 Hz, 1H), 6.78 (td, J=8 et 3 Hz, 1H), 3.86 (t, J=6.0 Hz, 1H), 2.66 (m, 2H), 1.98 (m, 1H), 1.87 (m, 1H), 1.86 (br s, 2H, NH$_2$), 1.72 (m, 1H), 1.58 (m, 1H). $^{13}$C NMR (101 MHz, CDCl$_3$) δ 161.1 (J=243.0 Hz), 142.9 (J=6.0 Hz), 132.1 (J=3.0 Hz), 130.1 (J=7.0 Hz), 114.0 (J=20 Hz), 113.6 (J=20.0 Hz), 49.4, 33.3, 28.7, 19.7. IR (Diamond ATR, cm$^{-1}$) n 2944, 1551, 1471, 1372, 1250, 807, 705. HRMS (EI-MS): m/z calculated for C$_{10}$H$_{13}$NF [M+H]$^+$: 166.1026, found: 166.1033. T$_m$: 94-96° C.

7-Bromopyrido[3,2-d]pyrimidin-4-ol (113)

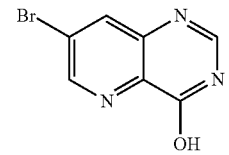

3-amino-5-bromopicolinic acid (500 mg, 2.3 mmol) was dissolved in 5 mL of formamide and the mixture heated to 170° C. for 12 h. On completion of the reaction, the solution was cooled down to ambient temperature and 20 mL of iced water was added. The product precipitated in the form of a brown solid that was isolated by filtration and oven dried (303 mg, 58%). R$_f$ (CH$_2$Cl$_2$/MeOH 90:10): 0.25. $^1$H NMR (400 MHz, CDCl$_3$) δ 12.66 (br s, 1H), 8.87 (d, J=8.0 Hz, 1H), 8.41 (d, J=8.0 Hz, 1H), 8.19 (s, 1H). $^{13}$C NMR (101 MHz, CDCl$_3$) δ 159.2, 149.7, 147.5, 146.5, 138.0, 137.3, 124.6. IR (Diamond ATR cm$^{-1}$) n 3025, 2820, 1719, 1568, 1222, 866, 737, 630, 540. HRMS (EI-MS): m/z calculated for C$_7$H$_5$BrN$_3$O [M+H]$^+$: 225.9610, found: 225.9614. T$_m$: >260° C.

6-Chloropyrido[3,2-d]pyrimidin-4-ol (114)

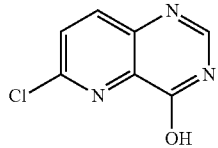

3-amino-6-chloropicolinic acid (500 mg, 2.9 mmol) was dissolved in 5 mL of formamide and the mixture heated to 170° C. for 12 h. On completion of the reaction, the solution was cooled down to ambient temperature and 20 mL of iced water was added. The product precipitated in the form of a brown solid that was isolated by filtration and oven dried (186 mg, 35%). $R_f$ (CH$_2$Cl$_2$/MeOH 90:10): 0.28. $^1$H NMR (400 MHz, DMSO-d$_6$) δ 8.18 (s, 1H), 8.14 (d, J=8.0 Hz, 1H), 7.87 (d, J=8.0 Hz, 1H). $^{13}$C NMR (101 MHz, DMSO-d$_6$) δ 158.6, 148.6, 146.9, 145.3, 139.6, 139.1, 130.0. IR (Diamond ATR, cm$^{-1}$) n 3038, 2907, 1651, 1465, 1275, 1096, 843, 633. HRMS (EI-MS): m/z calculated for C$_7$H$_5$ClN$_3$O [M+H]$^+$: 182.0115, found: 182.0116. T$_m$: >260° C.

tert-Butyl 4-amino-4,5,6,7-tetrahydroindole-1-carboxylate (115)

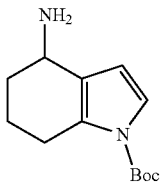 [SMILES: CC(C)(C)OC(=O)n1ccc2c1CCCC2N]

Compound 115 was obtained following procedure A with tert-butyl 4-oxo-6,7-dihydro-5H-indole-1-carboxylate (200 mg, 0.85 mmol, 1.0 eq.), NH$_4$OAc (983 mg, 12.8 mmol, 15.0 eq.) and NaBH$_3$CN (64 mg, 1.02 mmol, 1.2 eq.). The residue was purified by silica gel chromatography (eluting with CH$_2$Cl$_2$/MeOH 90:10). The product was obtained in the form of a brown oil (85 mg, 42%). $R_f$ (CH$_2$Cl$_2$/MeOH 90:10): 0.28. $^1$H NMR (400 MHz, CDCl$_3$) δ 7.12 (d, J=3.0 Hz, 1H), 6.20 (d, J=3.0 Hz, 1H), 3.85 (dt, J=3.0, 7.0 Hz, 1H), 2.79 (t, J=6.0 Hz, 2H), 2.55 (br s, 2H, NH$_2$), 1.93 (m, 2H), 1.71 (m, 1H), 1.55 (s, 9H), 1.48 (m, 1H). $^{13}$C NMR (101 MHz, CDCl$_3$) δ 149.6, 130.2, 126.1, 120.0, 109.3, 83.3, 46.1, 33.3, 28.1, 24.7, 20.6. IR (Diamond ATR, cm$^{-1}$): 2976, 2933, 2400, 1732, 1583, 1368, 1318, 1299, 1141, 1126, 1015, 851, 706. HRMS (EI-MS): m/z calculated for C$_{13}$H$_{20}$N$_2$NaO$_2$ [M+Na]$^+$: 259.1417, found: 259.1415.

tert-Butyl N-(1-aminotetralin-6-yl)carbamate (116)

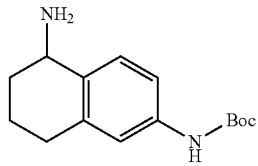 [SMILES: CC(C)(C)OC(=O)Nc1ccc2c(c1)CCCC2N]

Compound 116 was obtained following procedure A with tert-butyl N-(1-oxotetralin-6-yl)carbamate (150 mg, 0.57 mmol, 1.0 eq.), NH$_4$OAc (658 mg, 8.55 mmol, 15.0 eq.) and NaBH$_3$CN (44 mg, 0.69 mmol, 1.2 eq.). The residue was purified by silica gel chromatography (eluting with CH$_2$Cl$_2$/MeOH 90:10). The product was obtained in the form of a brown solid (90 mg, 60%). $R_f$ (CH$_2$Cl$_2$/MeOH 90:10): 0.25. $^1$H NMR (400 MHz, CDCl$_3$) δ 7.28 (d, J=8.0 Hz, 1H), 7.16 (br s, 1H, NH), 7.05 (dd, J=8.0, 2.0 Hz, 1H), 6.75 (br s, 1H), 3.95 (t, J=5.0 Hz, 1H), 2.70 (m, 2H), 2.57 (br s, 2H, NH$_2$), 1.97 (m, 1H), 1.89 (m, 1H), 1.70 (m, 2H), 1.49 (s, 9H). $^{13}$C NMR (101 MHz, CDCl$_3$) δ 153.0, 137.7, 137.0, 134.9, 128.7, 118.7, 116.8, 80.4, 49.0, 33.1, 29.7, 28.4, 19.5. IR (Diamond ATR, cm$^{-1}$) n 3305, 2929, 1698, 1529, 1239, 1155, 871, 770. HRMS (EI-MS): m/z calculated for C$_{15}$H$_{22}$N$_2$NaO$_2$ [M+Na]$^+$: 285.1573, found: 285.1575. T$_m$: 77-79° C.

Tetralin-2-amine (117)

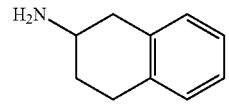 [SMILES: NC1CCc2ccccc2C1]

Compound 117 was obtained following procedure A with 2-tetralone (0.45 mL, 3.1 mmol, 1.0 eq.), NH$_4$OAc (3.58 g, 46.5 mmol, 15.0 eq.) and NaBH$_3$CN (234 mg, 3.72 mmol, 1.2 eq.). The residue was purified by silica gel chromatography (eluting with CH$_2$Cl$_2$/MeOH 90:10). The product was obtained in the form of a brown solid (325 mg, 71%). $R_f$ (CH$_2$Cl$_2$/MeOH 90:10): 0.22. $^1$H NMR (400 MHz, CDCl$_3$) δ 7.10 (m, 4H), 3.17 (m, 1H), 2.99 (m, 1H), 2.87 (m, 2H), 2.56 (dd, J=16.0, 9.0 Hz, 1H), 1.99 (m, 1H), 1.81 (br s, 2H), 1.59 (m, 1H). $^{13}$C NMR (101 MHz, CDCl$_3$) δ 135.6, 135.0, 129.1, 128.5, 125.7, 125.6, 47.1, 39.1, 32.6, 27.9. IR (Diamond ATR, cm$^{-1}$) n 3420, 3255, 3018, 2917, 1570, 1394, 738. HRMS (EI-MS): m/z calculated for C$_{10}$H$_{14}$N [M+H]$^+$: 148.1120, found: 148.1121. T$_m$: 100-102° C.

8-Methoxytetralin-1-amine (124)

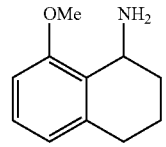 [SMILES: COc1cccc2c1C(N)CCC2]

Compound 124 was obtained following procedure A with 8-methoxytetralone (300 mg, 1.7 mmol, 1.0 eq.), NH$_4$OAc (1.97 g, 25.5 mmol, 15.0 eq.) and NaBH$_3$CN (129 mg, 2.84 mmol, 1.2 eq.). The residue was purified by silica gel chromatography (eluting with CH$_2$Cl$_2$/MeOH 90:10). The product was obtained in the form of an orange oil (211 mg, 71%). $R_f$ (CH$_2$Cl$_2$/MeOH 90:10): 0.19. $^1$H NMR (400 MHz, CDCl$_3$) δ 7.08 (t, J=8.0 Hz, 1H), 6.66 (m, 2H), 4.18 (t, J=4.0 Hz, 1H), 3.81 (s, 3H), 2.68 (m, 2H), 1.97 (br s, 2H, NH$_2$), 1.83 (m, 3H), 1.70 (m, 1H). $^{13}$C NMR (101 MHz, CDCl$_3$) δ 157.6, 137.6, 129.3, 126.8, 121.4, 107.3, 54.9, 43.4, 31.3, 29.6, 17.9. IR (Diamond ATR, cm$^{-1}$) n 3366, 2930, 2835, 1581, 1467, 1438, 1249, 1093, 1077, 767, 741, 521. HRMS (EI-MS): m/z calculated for $CH_{16}NO$ $[M+H]^+$: 178.1226, found: 178.1226.

6,7-Dimethoxytetralin-1-amine (125)

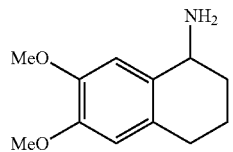 [SMILES: COc1cc2c(cc1OC)C(N)CCC2]

Compound 125 was obtained following procedure A with 6,7-dimethoxytetralone (300 mg, 1.45 mmol, 1.0 eq.), $NH_4OAc$ (1.68 g, 21.8 mmol, 15.0 eq.) and $NaBH_3CN$ (110 mg, 1.7 mmol, 1.2 eq.). The residue was purified by silica gel chromatography (eluting with $CH_2Cl_2$/MeOH 90:10). The product was obtained in the form of an orange oil (211 mg, 71%). $R_f$ ($CH_2Cl_2$/MeOH 90:10): 0.19. $^1H$ NMR (400 MHz, $CDCl_3$) δ 6.93 (s, 1H), 6.54 (s, 1H), 6.90 (m, 1H), 3.86 (s, 3H), 3.83 (s, 3H), 2.66 (m, 2H), 2.00 (br s, 2H, $NH_2$) 1.95 (m, 1H), 1.69 (m, 1H). 13C NMR (101 MHz, $CDCl_3$) δ 147.8, 147.4, 132.6, 128.9, 111.5, 111.1 56.1, 55.9, 49.2, 34.1, 29.2, 19.7. IR (Diamond ATR, $cm^{-1}$) n 3351, 2930, 2835, 1508, 1252, 1216, 1111, 1015, 861, 794. HRMS (EI-MS): m/z calculated for $C_{12}H_{17}NO_2Na$ $[M+Na]^+$: 230.1151, found: 230.1149.

5-(Methoxymethoxy)tetralin-1-one (128)

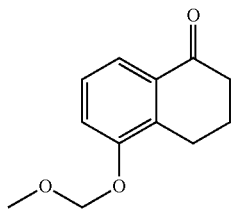

5-hydroxytetralone (300 mg, 1.85 mmol, 1.0 eq.) was dissolved in 3 mL of anhydrous THF in a 25 mL round-bottom flask and the flask immersed in an ice bath at 0° C. Under stirring, sodium hydride (90 mg, 2.22 mmol, 1.2 eq.) was added and after 10 min the addition was made of chloromethyl methyl ether (0.21 mL, 2.77 mmol, 1.5 eq.). The mixture was stirred at ambient temperature for 2 hours. On completion of the reaction, the mixture was diluted with 90 mL AcOEt then washed with 3×70 mL water. The organic phase was washed with saturated aqueous NaCl solution (20 mL) and dried over $MgSO_4$. After filtration, the solvent was evaporated and the residue purified by silica gel chromatography (eluting gradient 0 to 20% AcOEt/100 to 80% PE). Product 128 was obtained in the form of a colourless oil (334 mg, 85%). $R_f$ (PE/AcOEt 50:50): 0.35. $^1H$ NMR (400 MHz, $CDCl_3$) δ 7.66 (d, J=8.0 Hz, 1H), 7.15 (m, 1H), 5.18 (s, 2H), 3.46 (s, 3H), 2.90 (t, J=6.0 Hz, 2H), 2.62 (t, J=6.0 Hz, 2H), 2.10 (quin, J=6.0 Hz, 2H). $^{13}C$ NMR (101 MHz, $CDCl_3$) δ 198.3, 155.9, 138.3, 133.6, 130.1, 122.8, 113.3, 94.6, 56.2, 39.1, 29.1, 23.5. IR (Diamond ATR, $cm^{-1}$): 2945, 1680, 1606, 1492, 1427, 1322, 1274, 1151, 921, 821. HRMS (EI-MS): m/z calculated for $C_{12}H_{15}O_3$ $[M+H]^+$: 207.1015, found: 207.1018.

5-(Methoxymethoxy)tetralin-1-amine (129)

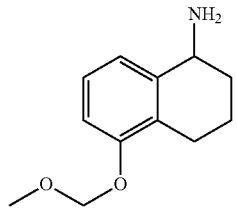

Compound 129 was obtained following procedure A with compound 128 (200 mg, 0.97 mmol, 1.0 eq.), $NH_4OAc$ (1.125 g, 14.6 mmol, 15.0 eq.) and $NaBH_3CN$ (74 mg, 1.16 mmol, 1.2 eq.). The residue was purified by silica gel chromatography (eluting with $CH_2Cl_2$/MeOH 90:10). The product was obtained in the form of an orange oil (134 mg, 67%). $R_f$ ($CH_2Cl_2$/MeOH 90:10): 0.24. $^1H$ NMR (400 MHz, $CDCl_3$) δ 7.08 (d, J=3.0 Hz, 1H), 6.98 (d, J=8.0 Hz, 1H), 6.84 (dd, J=8.0, 3.0 Hz, 1H), 5.14 (m, 2H), 3.93 (dd, J=6.0, 5.0 Hz, 1H), 3.46 (s, 3H), 2.70 (m, 2H), 1.94 (m, 2H), 1.69 (m, 2H). $^{13}C$ NMR (101 MHz, $CDCl_3$) δ 155.5, 142.1, 130.2, 129.9, 115.3, 115.2, 94.6, 55.9, 49.6, 33.4, 28.8, 19.8. IR (Diamond ATR, $cm^{-1}$): 2929, 1681, 1608, 1440, 1315, 1273, 1229, 1149, 999, 920, 814. HRMS (EI-MS): m/z calculated for $C_{12}H_{18}NO_2$ $[M+H]^+$: 208.1332, found: 208.1333.

4,6-Dichloropyrido[3,2-d]pyrimidine (132)

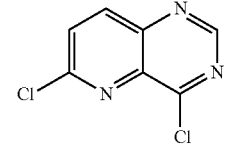 [SMILES: Clc1ccc2ncnc(Cl)c2n1]

Compound 114 (190 mg, 1.1 mmol, 1.0 eq.) was dissolved in 10 mL of $CHCl_3$ and a few drops of DMF were added. The round-bottom flask was then immersed in an ice bath at 0° C. and oxalyl chloride (0.24 mL, 2.76 mmol, 2.5 eq.) was added dropwise. The solution was heated to 65° C. for 4 to 5 hours under vigorous stirring. Disappearance of the starting reagent was monitored by TLC and at the end of the reaction the $CHCl_3$ and excess oxalyl chloride were evaporated. The deposit obtained was taken up in 30 mL dichloromethane and the product washed with 30 mL of saturated aqueous $Na_2CO_3$ solution. The organic phase was washed with saturated aqueous NaCl solution (40 mL) and dried over $MgSO_4$. After filtration, the solvent was evaporated and the residue purified on silica gel (eluting with $CH_2Cl_2$/Acetone 98:2). The product was obtained in the form of a brown solid (107 mg, 51%). $R_f$ (PE/AcOEt 60:40): 0.40. $^1H$ NMR (400 MHz, $CDCl_3$) δ 9.13 (s, 1H), 8.34 (d, J=8.0 Hz, 1H), 7.86 (d, J=8.0 Hz, 1H). $^{13}C$ NMR (101 MHz, $CDCl_3$) δ 163.1, 154.7, 153.7, 146.7, 139.9, 138.1, 131.6. IR (Diamond ATR, $cm^{-1}$) n 3068, 1728, 1643, 1552, 1413, 1306, 1133, 1010, 859, 688. HRMS (EI-MS): m/z calculated for $C_7H_4Cl_2N_3$ $[M+H]^+$: 199.9777, found: 199.9776. $T_m$: 161-163° C.

7-Bromo-4-chloro-pyrido[3,2-d]pyrimidine (134)

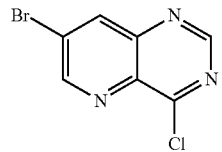

Compound 134 was obtained as described for 132 with 113 (1.00 g, 4.44 mmol, 1.0 eq.) and oxalyl chloride (0.953 mL, 11.1 mmol, 2.5 eq.). The product was purified by silica gel chromatography (eluting with $CH_2Cl_2$/Acetone 98:2). The product was obtained in the form of a white solid (946 mg, 86%). $R_f$ (PE/AcOEt 60:40): 0.82. $^1$H NMR (400 MHz, $CDCl_3$) δ 9.14 (d, J=8.0 Hz, 1H), 9.12 (s, 1H), 8.59 (d, J=8.0 Hz, 1H). $^{13}$C NMR (101 MHz, $CDCl_3$) δ 164.6, 155.5, 154.5, 147.9, 138.7, 136.7, 126.5. IR (Diamond ATR cm$^{-1}$) n 3037, 1553, 1533, 1430, 1361, 1317, 1074, 999, 921, 838, 677, 656. HRMS (EI-MS): m/z calculated for $C_7H_4ClBrN_3$ [M+H]$^+$: 243.9271, found: 243.9270. $T_m$: 188-190° C.

4-Aminotetralin-1-ol (141)

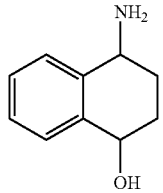 [SMILES: NC1CCC(O)c2ccccc21]

Compound 141 was obtained following procedure A with 4-hydroxy-3,4-dihydronaphthalenone (100 mg, 0.62 mmol, 1.0 eq.), $NH_4OAc$ (716 mg, 9.3 mmol, 15.0 eq.) and $NaBH_3CN$ (47 mg, 0.74 mmol, 1.2 eq.). The residue was purified by silica gel chromatography (solvent system $CH_2Cl_2$/MeOH 85:15). The product was obtained in the form of an orange oil (82 mg, 81%). $R_f$ ($CH_2Cl_2$/MeOH 90:10): 0.12. $^1$H NMR (400 MHz, $CDCl_3$) δ 7.35 (m, 4H), 4.72 (m, 1H), 3.99 (m, 1H), 2.33 (br s, 2H, $NH_2$), 2.22 (m, 1H), 1.86 (m, 3H). $^{13}$C NMR (101 MHz, $CDCl_3$) δ 140.5, 139.1, 128.4, 128.0, 127.4, 68.2, 49.4, 29.5, 28.8. IR (Diamond ATR, cm$^{-1}$) n 3268, 2861, 1567, 1448, 1330, 1043, 750, 583. HRMS (+ESI): m/z calculated for $C_{10}H_{14}NO$ [M+H]$^+$: 164.1069, found: 164.1070.

7-Methylpyrido[3,2-d]pyrimidin-4-ol (146)

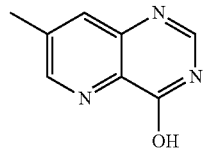

3-amino-5-methyl-pyridine-2-carboxylic acid amide (200 mg, 1.33 mmol) was dissolved in 7.5 mL of trimethylorthoformate (68.6 mmol) and the mixture heated to 120° C. for 16 h. On completion of the reaction, the solution was cooled down to ambient temperature and 20 mL of iced water was added. The product precipitated in the form of a brown solid that was isolated by filtration and oven dried (192 mg, 90%). $R_f$ ($CH_2Cl_2$/MeOH 90:10): 0.22. $^1$H NMR (400 MHz, $CDCl_3$) δ 12.44 (br s, 1H), 8.64 (d, J=8.0 Hz, 1H), 8.11 (s, 1H), 7.88 (d, J=8.0 Hz, 1H), 2.47 (s, 3H). $^{13}$C NMR (101 MHz, $CDCl_3$) δ 159.5, 150.4, 146.2, 145.6, 139.2, 136.0, 134.6, 18.1. IR (Diamond ATR, cm$^{-1}$) n 3440, 3276, 3033, 2789, 1715, 1595, 1303, 1284, 1212, 1184, 922, 898, 706, 687. HRMS (EI-MS): m/z calculated for $C_8H_8N_3O$ [M+H]$^+$: 162.0661, found: 162.0663. $T_m$: >260° C.

4-Chloro-7-methyl-pyrido[3,2-d]pyrimidine (148)

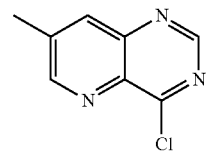

Compound 148 was obtained as described for 132 with 146 (130 mg, 0.81 mmol, 1.0 eq.), and oxalyl chloride (0.18 mL, 2.13 mmol, 2.5 eq.). The product was purified by silica gel chromatography (eluting with $CH_2Cl_2$/Acetone 99:1). The product was obtained in the form of a white solid (946 mg, 86%). $R_f$ ($CH_2Cl_2$/Acetone 99:01): 0.52. $^1$H NMR (400 MHz, $CDCl_3$) δ 9.07 (s, 1H), 8.98 (d, J=8.0 Hz, 1H), 8.14 (d, J=8.0 Hz, 1H), 2.65 (s, 3H). $^{13}$C NMR (101 MHz, $CDCl_3$) δ 163.9, 155.2, 154.5, 147.7, 140.7, 136.4, 135.5, 19.4. IR (Diamond ATR, cm$^{-1}$) n 2624, 1715, 1558, 1371, 1322, 1223, 999, 900, 837, 673. HRMS (EI-MS): m/z calculated for $C_8H_7ClN_3$ [M+H]$^+$: 180.0323, found: 180.0322. $T_m$: >260° C.

Benzofuro[3,2-d]pyrimidin-4-ol (150)

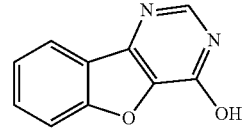 [SMILES: Oc1ncnc2c1oc1ccccc12]

3-aminobenzofuran-2-carboxylic acid amide (100 mg, 0.56 mmol) was dissolved in 5 mL of trimethylorthoformate (45.7 mmol) and the mixture heated to 150° C. for 2 h. On completion of the reaction, the solution was cooled down to ambient temperature and 20 mL of iced water was added. The product precipitated in the form of a yellow solid that was isolated by filtration and oven dried (100 mg, 86%). $R_f$ ($CH_2Cl_2$/MeOH 90:10): 0.33. $^1$H NMR (400 MHz, DMSO-$d_6$) δ 8.26 (s, 1H), 8.05 (d, J=8.0 Hz, 1H), 7.83 (d, J=8.0 Hz, 1H), 7.68 (t, J=7.0 Hz, 1H), 7.50 (t, J=7.0 Hz, 1H). $^{13}$C NMR (101 MHz, DMSO-$d_6$) δ 155.8, 152.5, 146.7, 143.1, 139.1, 129.9, 124.4, 122.1, 121.3, 112.9. IR (Diamond ATR, cm$^{-1}$) n 3326, 2577, 1646, 1444, 1360, 1279, 1230, 1189, 1113, 1081, 959, 864, 743. HRMS (EI-MS): m/z calculated $C_{10}H_7N_2O_2$ [M+H]$^+$: 187.0502, found: 187.0503. $T_m$: >260° C.

7-Fluoropyrido[3,2-d]pyrimidin-4-ol (153)

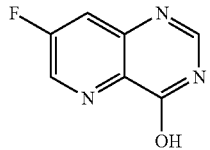

Methyl 3-amino-5-fluoropicolinate (100 mg, 0.59 mmol) was dissolved in 6 mL of formamide (151.0 mmol) and the mixture heated to 150° C. for 12 h. On completion of the reaction, the solution was cooled down to ambient temperature and 10 mL of iced water was added. The product precipitated in the form of a brown solid that was isolated by filtration and oven dried (90 mg, 93%). $R_f$ (CH$_2$Cl$_2$/MeOH 90:10): 0.25. $^1$H NMR (400 MHz, DMSO-d$_6$) δ 8.81 (d, J=3.0 Hz, 1H), 8.19 (s, 1H), 8.01 (dd, J=9.0, 3.0 Hz, 1H). $^{13}$C NMR (101 MHz, DMSO-d$_6$) δ 162.1, 159.5, 158.7, 147.6, 144.6, 139.1, 138.8, 136.3, 120.1, 119.9. IR (Diamond ATR, cm$^{-1}$) n 3044, 2847, 1678, 1593, 1463, 1376, 1301, 1208, 892, 733, 651. HRMS (EI-MS): m/z calculated for C$_7$H$_5$FN$_3$O [M+H]$^+$: 166.0411, found: 166.0413. $T_m$: >260° C.

6-Fluorotetralin-1-amine (154)

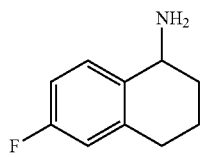 [SMILES: NC1CCCc2cc(F)ccc21]

Compound 154 was obtained following procedure A with compound 6-fluorotetralone (500 mg, 3.0 mmol, 1.0 eq.), NH$_4$OAc (3.46 g, 45.0 mmol, 15.0 eq.) and NaBH$_3$CN (227 mg, 3.6 mmol, 1.2 eq.). The residue was purified by silica gel chromatography (eluting with CH$_2$Cl$_2$/MeOH 95:5). The product was obtained in the form of a yellow powder (498 mg, 81%). $R_f$ (CH$_2$Cl$_2$/MeOH 95:5): 0.18. $^1$H NMR (400 MHz, CDCl$_3$) δ 7.28 (dd, J=8.0, 6.0 Hz, 1H), 6.77 (td, J=8.0, 3.0 Hz, 1H), 6.67 (dd, J=9.0, 3.0 Hz, 1H), 3.85 (t, J=6.0 Hz, 1H), 2.66 (m, 2H), 1.87 (m, 2H), 1.64 (m, 1H), 1.62 (m, 1H), 1.50 (br s, 2H, NH$_2$). $^{13}$C NMR (101 MHz, CDCl$_3$) δ 162.3, 159.9, 138.8, 138.7, 136.6, 129.6, 129.5, 114.7, 114.5, 112.8, 112.6, 48.7, 33.5, 29.5, 19.1. IR (Diamond ATR, cm$^{-1}$): 2929, 1617, 1473, 1357, 813, 572. HRMS (EI-MS: m/z calculated for C$_{10}$H$_{13}$FN [M+H]$^+$: 166.1026, found: 166.1029. $T_m$: 104-106° C.

4-Chloro-7-fluoro-pyrido[3,2-d]pyrimidine (155)

Compound 155 was obtained as described for 132 with 153 (100 mg, 0.61 mmol, 1.0 eq.) and oxalyl chloride (0.13 mL, 1.52 mmol, 2.5 eq.). The product was purified by silica gel chromatography (eluting gradient 0 to 40% AcOEt/100 to 60% PE). The product was obtained in the form of a beige solid (5 mg, 5%). $R_f$ (PE/AcOEt 50:50): 0.91. $^1$H NMR (400 MHz, CDCl$_3$) δ 9.09 (s, 1H), 9.01 (d, J=3.0 Hz, 1H), 8.00 (dd, J=8.0, 3.0 Hz, 1H). $^{13}$C NMR (101 MHz, CDCl$_3$) δ 164.0, 160.9 (d, J=270.0 Hz), 155.4, 148.7 (d, J=10.0 Hz), 144.7 (d, J=28.0 Hz), 135.4 (d, J=2.0 Hz), 119.9 (d, J=17.0 Hz). IR (Diamond ATR, cm$^{-1}$) n 3025, 2582, 1678, 1646, 1411, 1301, 1076, 867, 732, 584. HRMS (EI-MS): m/z calculated for C$_7$H$_4$ClFN$_3$ [M+H]$^+$: 184.0072, found: 184.0073. $T_m$: 148-150° C.

4-Chlorobenzofuro[3,2-d]pyrimidine (156)

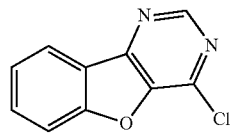 [SMILES: Clc1ncnc2c1oc1ccccc12]

Compound 156 was obtained as described for 132 with 150 (75 mg, 0.40 mmol, 1.0 eq.) and oxalyl chloride (0.10 mL, 1.0 mmol, 2.5 eq.). The product was purified by silica gel chromatography (eluting gradient 0 to 20% AcOEt/100 to 80% PE). The product was obtained in the form of a white solid (56 mg, 68%). $R_f$ (PE/AcOEt 70:30): 0.49. $^1$H NMR (400 MHz, CDCl$_3$) δ 8.99 (s, 1H), 8.25 (m, 1H), 7.75 (m, 1H), 7.54 (m, 1H). $^{13}$C NMR (101 MHz, CDCl$_3$) δ 158.1, 153.1, 151.4, 144.5, 142.8, 132.7, 125.0, 122.9, 121.6, 113.2. IR (Diamond ATR, cm$^{-1}$) n 3059, 1626, 1538, 1488, 1380, 1213, 1187, 1141, 1066, 874, 635. HRMS (EI-MS): m/z calculated for C$_{10}$H$_6$ClN$_2$O [M+H]$^+$: 205.0163, found: 205.0163. $T_m$: 133-135° C.

2. Preparation of Formula (I) Compounds of the Invention

Example 1: N-(3,4-Dichlorobenzyl)pyrido[3,2-d]pyrimidin-2-amine (4)

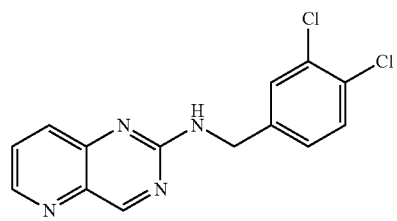 [SMILES: Clc1ccc(CNc2ncc3ncccc3n2)cc1Cl]

Product 3 (100 mg, 0.60 mmol) was dissolved in 1,4-dioxane (7 mL) and the successive addition was made of 3,4-dichlorobenzylamine (0.10 mL, 0.75 mmol, 1.2 eq.) and triethylamine (0.11 mL, 0.79 mmol, 1.5 eq.), and the mixture refluxed under stirring overnight. The 1,4-dioxane was evaporated and the residue obtained taken up in water (20 mL) and extracted with dichloromethane (2×20 mL). The combined organic phase was dried over magnesium sulfate, filtered and concentrated in vacuo. The reaction product was chromatographed on silica gel (gradient EP to EP/AcOEt 50:50) to give the title product 4 (110 mg, 60%) in the form of a yellow solid. $R_f$ (EP/AcOEt 60:40): 0.13. $^1$H NMR (400 MHz, CDCl$_3$) δ 9.20 (s, 1H), 8.66 (dd, J=4.1, 1.4 Hz, 1H), 7.89 (d, J=8.5 Hz, 1H), 7.57 (dd, J=8.6, 4.1 Hz, 1H), 7.50 (d, J=1.5 Hz, 1H), 7.39 (d, J=8.2 Hz, 1H), 7.23 (dd, J=8.2, 1.7 Hz, 1H), 5.93 (s, 1H), 4.73 (d, J=6.2 Hz, 2H). $^{13}$C NMR (101 MHz, CDCl$_3$) δ 163.7, 159.3, 148.3, 147.5, 139.5, 137.2, 133.9, 132.8, 131.4, 130.7, 129.6, 128.5, 127.0, 44.8. IR (Diamond ATR cm$^{-1}$) ν 3231, 3034, 2862, 1585, 1541, 1465, 1397, 1351, 1250, 1142, 1035, 936, 821. HRMS (EI-MS) m/z calculated for C$_{14}$H$_{10}$Cl$_2$N$_4$ [M+H]$^+$: 305.035528; found: 305.035355. T$_m$: 163-165° C.

Example 2: N-(1,2,3,4-Tetrahydronaphthalen-1-yl)pyrido[3,2-d]pyrimidin-2-amine (5)

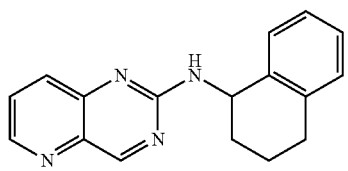 [SMILES: c1ccc2c(c1)CCCC2Nc1ncc2ncccc2n1]

Product 5 was obtained following the same operating mode as for 4 from 1,2,3,4-tetrahydronaphthylamine (0.12 mL, 0.83 mmol, 1.2 eq.) to give the title product 5 (190 mg, quantitative) in the form of a yellow solid. $R_f$ (EP/AcOEt 60:40): 0.18. $^1$H NMR (250 MHz, CDCl$_3$) δ 9.12 (s, 1H), 8.62 (dd, J=4.1, 1.5 Hz, 1H), 7.88 (s, 1H), 7.55 (dd, J=8.6, 4.1 Hz, 1H), 7.39 (d, J=7.2 Hz, 1H), 7.24-7.08 (m, 3H), 5.85 (d, J=8.5 Hz, 1H), 5.44 (dd, J=13.6, 5.9 Hz, 1H), 2.84 (dd, J=11.7, 5.9 Hz, 2H), 2.21-2.14 (m, 1H), 2.02-1.92 (m, 3H). $^{13}$C NMR (101 MHz, CDCl$_3$) δ 164.7, 163.6, 148.6, 146.9, 137.7, 137.4, 137.1, 133.8, 129.5, 129.3, 128.9, 128.4, 127.4, 126.3, 47.5, 29.5, 20.2. IR (Diamond ATR, cm$^{-1}$) ν 3238, 3046, 2927, 2858, 1607, 1585, 1536, 1407, 1313, 1248, 1099, 916, 821. HRMS (EI-MS) m/z calculated for C$_{17}$H$_{16}$N$_4$ [M+H]$^+$: 277.144773; found: 277.144824. T$_m$: 120-122° C.

Example 3: 2-Chloro-N-(1,2,3,4-tetrahydronaphthalen-1-yl)pyrido[3,2-d]pyrimidin-4-amine (6)

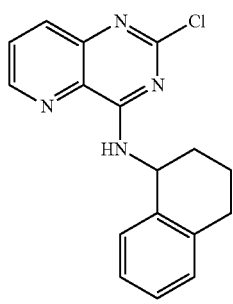 [SMILES: Clc1nc(NC2CCCc3ccccc32)c2ncccc2n1]

Product 2 (673 mg, 3.36 mmol) was dissolved in THF (32 mL) and the mixture placed at 0° C. The successive addition was made of 1,2,3,4-tetrahydronaphthylamine (0.48 mL, 3.36 mmol, 1.0 eq.) and triethylamine (0.50 mL, 3.53 mmol, 1.05 eq.) and the mixture stirred overnight at ambient temperature. The THF was evaporated and the residue obtained taken up in water (20 mL) and extracted with dichloromethane (2×20 mL). The combined organic phase was dried over magnesium sulfate, filtered and concentrated in vacuo. The reaction product was chromatographed on silica gel (gradient EP to EP/AcOEt 80:20) to give the title product 6 (869 mg, 83%) in the form of a white solid. $R_f$ (CH$_2$Cl$_2$/MeOH 99:01): 0.55. $^1$H NMR (250 MHz, CDCl$_3$) δ 8.61 (dd, J=4.3, 1.5 Hz, 1H), 8.03 (dd, J=8.5, 1.5 Hz, 1H), 7.64 (dd, J=8.5, 4.3 Hz, 1H), 7.58 (d, J=8.6 Hz, 1H), 7.32 (d, J=7.2 Hz, 1H), 7.23-7.14 (m, 3H), 5.63 (dd, J=14.7, 5.7 Hz, 1H), 2.87 (q, J=6.3 Hz, 2H), 2.30-2.14 (m, 1H), 2.11-2.03 (m, 1H), 1.99-1.92 (m, 2H). $^{13}$C NMR (101 MHz, CDCl$_3$) δ 160.3, 158.7, 148.4, 145.9, 137.9, 135.9, 135.2, 130.8, 129.5, 129.0, 128.5, 127.8, 126.6, 49.0, 29.7, 29.3, 20.1. IR (Diamond ATR, cm$^{-1}$) ν 3388, 2944, 1574, 1542, 1466, 1397, 1375, 1283, 1127, 1033, 957, 826. HRMS (EI-MS) m/z calculated for C$_{17}$H$_{15}$ClN$_4$ [M+H]$^+$: 311.105801, found: 311.105823. T$_m$: 146-148° C.

Example 4: N-(1,2,3,4-Tetrahydronaphthalen-1-yl)pyrido[3,2-d]pyrimidin-4-amine (7)

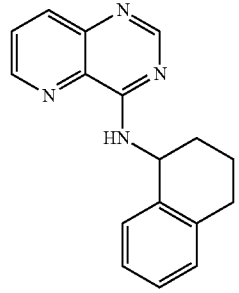 [SMILES: c1ccc2c(c1)CCCC2Nc1ncnc2cccnc12]

Product 6 (100 mg, 0.32 mmol) was dissolved in anhydrous THF (1 mL) under an argon atmosphere followed by the respective addition of triethylamine (0.13 mL, 0.97 mmol, 3.0 eq.) and formic acid (0.02 mL, 0.64 mmol, 2.0 eq.). After stirring for 5 minutes at ambient temperature, palladium acetate (7 mg, 0.032 mmol, 0.1 eq.) and Xantphos (37 mg, 0.064 mmol, 0.2 eq.) were added and the mixture brought to 150° C. under microwave radiation for 15 minutes. The reaction mixture was evaporated and the residue obtained taken up in water (20 mL) and extracted with dichloromethane (2×20 mL). The combined organic phase was dried over magnesium sulfate and concentrated in vacuo. The reaction product was purified by silica gel chromatography (gradient CH$_2$Cl$_2$ to CH$_2$Cl$_2$/MeOH 99.5:0.5) to give the title product 7 (70 mg, 79%) in the form of a yellow solid. $R_f$ (CH$_2$Cl$_2$/MeOH 98:02): 0.28. $^1$H NMR (250 MHz, CDCl$_3$) δ 8.68 (s, 1H), 8.63 (dd, J=4.2, 1.5 Hz, 1H), 8.10 (dd, J=8.5, 1.4 Hz, 1H), 7.63 (dd, J=8.5, 4.2 Hz, 1H), 7.46 (d, J=8.0 Hz, 1H), 7.34 (d, J=7.0 Hz, 1H), 7.24-7.08 (m, 3H), 5.63 (dd, J=14.3, 5.7 Hz, 1H), 2.87 (q, J=6.4 Hz, 2H), 2.28-2.16 (m, 1H), 2.13-1.86 (m, 3H). $^{13}$C NMR (101 MHz, CDCl$_3$) δ 159.2, 156.6, 148.2, 144.5, 137.8, 136.5, 135.9, 132.1, 129.4, 129.0, 127.8, 127.6, 126.4, 48.7, 29.8, 29.4, 20.1. IR (Diamond ATR, cm$^{-1}$) ν 3213, 2938, 1577, 1538, 1480, 1388, 1313, 1268, 1153, 917, 899. HRMS (EI-MS) m/z calculated for C$_{17}$H$_{16}$N$_4$ [M+H]$^+$: 277.144773, found: 277.145010. T$_m$: 96-98° C.

Example 5: 2-Chloro-N-(3,4-dichlorobenzyl)pyrido[3,2-d]pyrimidin-4-amine (8)

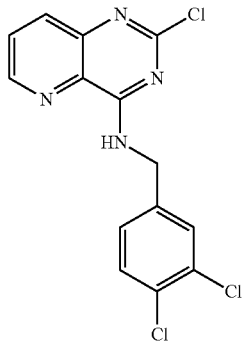 [SMILES: Clc1nc(NCc2ccc(Cl)c(Cl)c2)c2ncccc2n1]

Product 8 was obtained as described for 6 starting with 2 and 3,4 dichlorobenzylamine (0.10 mL, 0.75 mmol, 1.0 eq.) to give the title product 8 (163 mg, 64%) in the form of a white solid. $R_f$ (CH$_2$Cl$_2$/MeOH 95:05): 0.65. $^1$H NMR (250 MHz, CDCl$_3$) δ 8.67 (dd, J=4.3, 1.5 Hz, 1H), 8.05 (dd, J=8.5, 1.5 Hz, 1H), 7.68 (dd, J=8.5, 4.3 Hz, 1H), 7.60 (s, 1H), 7.49 (d, J=2.0 Hz, 1H), 7.43 (d, J=8.2 Hz, 1H), 7.25 (dd, J=7.7, 2.6 Hz, 1H), 4.83 (d, J=6.2 Hz, 2H). 13C NMR (101 MHz, CDCl$_3$) δ 160.9, 158.4, 148.7, 145.9, 137.6, 135.3, 133.0, 132.2, 130.9, 130.6, 130.0, 128.7, 127.5, 43.9. IR (Diamond ATR, cm$^{-1}$) ν 3372, 1587, 1546, 1427, 1375, 1279, 1209, 1130, 1028, 922, 869, 822. HRMS (EI-MS) m/z calculated for C$_{14}$H$_9$C$_3$N$_4$ [M+H]$^+$: 338.996556, found: 338.996507. T$_m$: 120-122° C.

Example 6: N-(4-Chlorobenzyl)pyrido[3,2-d]pyrimidin-4-amine (11)

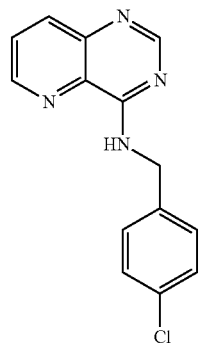 [SMILES: Clc1ccc(CNc2ncnc3cccnc23)cc1]

Product 10 (43 mg, 0.26 mmol) was dissolved in dioxane (2 mL) and the mixture placed at 0° C. The successive addition was made of 4-chlorobenzylamine (0.03 mL, 0.26 mmol, 1.0 eq.) then triethylamine (0.04 mL, 0.26 mmol, 1.0 eq.) and the mixture stirred overnight at ambient temperature. The dioxane was evaporated and the residue obtained taken up in water (20 mL) and extracted with dichloromethane (2×20 mL). The combined organic phase was dried over magnesium sulfate, filtered and concentrated in vacuo. The reaction product was chromatographed on silica gel (gradient EP to EP/AcOEt 40:60) to give the title product 11 (35 mg, 50%) in the form of a white solid. $R_f$ (EP/AcOEt 50:50): 0.18. $^1$H NMR (400 MHz, CDCl$_3$) δ 8.74-8.58 (m, 2H), 8.11 (dd, J=8.5, 1.5 Hz, 1H), 7.65 (dd, J=8.5, 4.2 Hz, 1H), 7.50 (s, 1H), 7.36-7.26 (m, 4H), 4.83 (d, J=6.1 Hz, 2H). $^{13}$C NMR (101 MHz, CDCl$_3$) δ 159.8, 156.4, 148.5, 144.5, 136.6, 136.1, 133.6, 132.1, 129.3 (×2), 129.0 (×2), 127.9, 44.1. IR (Diamond ATR, cm$^{-1}$) ν 3399, 3253, 2923, 1585, 1551, 1490, 1362, 1312, 1112, 1011, 920, 803. HRMS (EI-MS) m/z calculated for C$_{14}$H$_{11}$ClN$_4$ [M+H]$^+$: 271.074501, found: 271.074754. T$_m$: 141-143° C.

Example 7: N-(3-Chlorobenzyl)pyrido[3,2-d]pyrimidin-4-amine (12)

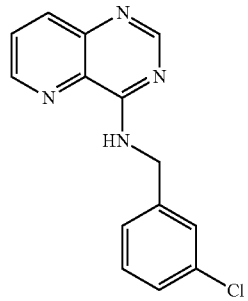 [SMILES: Clc1cccc(CNc2ncnc3cccnc23)c1]

Product 12 was obtained as described for 11 using product 10 and 3-chlorobenzylamine (0.03 mL, 0.22 mmol, 1.0 eq.) to give the title product 12 (30 mg, 50%) in the form of a colourless oil. $R_f$ (EP/AcOEt 70:30): 0.13. $^1$H NMR (400 MHz, CDCl$_3$) δ 8.77-8.60 (m, 2H), 8.12 (dd, J=8.5, 1.4 Hz, 1H), 7.66 (dd, J=8.5, 4.2 Hz, 1H), 7.53 (s, 1H), 7.39 (s, 1H), 7.31-7.24 (m, 3H), 4.85 (d, J=6.1 Hz, 2H). $^{13}$C NMR (101 MHz, CDCl$_3$) δ 159.8, 156.4, 148.5, 144.5, 140.1, 136.1, 134.8, 132.0, 130.2, 128.0 (×2), 126.0, 44.1. IR (Diamond ATR, cm$^{-1}$) ν 3248, 1581, 1553, 1482, 1416, 1310, 1196, 1077, 991, 894, 825. HRMS (EI-MS) m/z calculated for C$_{14}$H$_{11}$ClN$_4$ [M+H]$^+$: 271.074501, found: 271.074641. T$_m$: 87-89° C.

Example 8: N-Benzylpyrido[3,2-d]pyrimidin-4-amine (13)

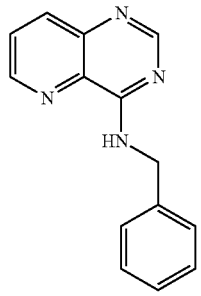 [SMILES: c1ccc(CNc2ncnc3cccnc23)cc1]

Product 13 was obtained as described for 11 using 10 (100 mg, 0.37 mmol), benzylamine and 3-chlorobenzylamine (0.03 mL, 0.37 mmol, 1.0 eq.) to give the title product 13 (30 mg, 34%) in the form of a yellow solid. $R_f$ (CH$_2$Cl$_2$/MeOH 99:01): 0.13. $^1$H NMR (400 MHz, CDCl$_3$) δ 8.68 (d, 1H) 8.67 (s, 1H), 8.11 (dd, J=8.5, 1.5 Hz, 1H), 7.65 (dd, J=8.5, 4.3 Hz, 1H), 7.50 (s, 1H), 7.46-7.28 (m, 5H), 4.87 (d, J=5.9 Hz, 2H). $^{13}$C NMR (101 MHz, CDCl$_3$) δ 159.9, 156.6, 148.5, 144.5, 138.1, 136.1, 132.3, 129.0 (×2), 128.1 (×2), 128.0, 127.9, 45.0. IR (Diamond ATR, cm$^{-1}$) ν 3257, 3057, 1578, 1483, 1421, 1382, 1352, 1312, 1142, 1023, 890, 825, 800. HRMS (EI-MS) m/z calculated for $C_{14}H_{12}N_4$ [M+H]$^+$: 237.113473, found: 237.113550. $T_m$: 84-86° C.

Example 9: N-(3,4-Dichlorobenzyl)pyrido[3,2-d]pyrimidin-4-amine (14)

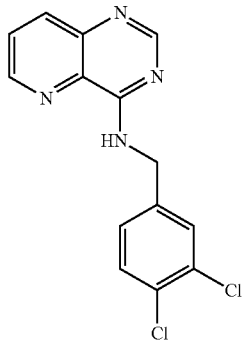 [SMILES: Clc1ccc(CNc2ncnc3cccnc23)cc1Cl]

Product 14 was obtained as described for 11 using product 10 (110 mg, 0.66 mmol) and 3,4 dichlorobenzylamine (0.18 mL, 1.33 mmol, 2 eq.) to give the title product 14 (59 mg, 30%) in the form of a white solid. $R_f$ ($CH_2Cl_2$/MeOH 97:03): 0.33. $^1$H NMR (400 MHz, CDCl$_3$) δ 8.67 (dt, J=4.2, 1.5 Hz, 1H), 8.64 (s, 1H), 8.10 (dt, J=8.5, 1.5 Hz, 1H), 7.65 (ddd, J=8.5, 4.2, 1.4 Hz, 1H), 7.56 (s, 1H), 7.46 (s, 1H), 7.37 (dd, J=8.2, 1.4 Hz, 1H), 7.24-7.16 (m, 1H), 4.81 (d, J=6.2 Hz, 2H). $^{13}$C NMR (101 MHz, CDCl$_3$) δ 159.8, 156.3, 148.5, 144.5, 138.5, 136.1, 132.8, 132.0, 131.7, 130.7, 129.7, 128.0, 127.1, 43.5. IR (Diamond ATR, cm$^{-1}$) ν 3257, 3066, 1578, 1551, 1469, 1371, 1310, 1127, 1027, 897, 827, 804. HRMS (EI-MS) m/z calculated for $C_{14}H_{10}Cl_2N_4$ [M+H]$^+$: 305.035528, found: 305.035598. $T_m$: 140-142° C.

Example 10: N-(7-Bromo-1,2,3,4-tetrahydronaphthalen-1-yl)pyrido[3,2-d]pyrimidin-4-amine (16)

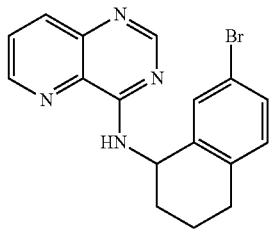

Product 16 was obtained as described for 11 from the amine 15 (217 mg, 0.96 mmol, 1 eq.) to give the title product 16 (149 mg, 43%) in the form of a colourless oil. $R_f$ (EP/AcOEt 50:50): 0.33. $^1$H NMR (400 MHz, CDCl$_3$) δ 8.65 (dd, J=6.9, 3.7 Hz, 2H), 8.10 (d, J=8.4 Hz, 1H), 7.64 (dd, J=8.5, 4.2 Hz, 1H), 7.44 (dd, J=15.5, 4.9 Hz, 2H), 7.29 (dd, J=8.2, 1.8 Hz, 1H), 7.00 (d, J=8.2 Hz, 1H), 5.61 (dd, J=14.4, 6.2 Hz, 1H), 2.78 (dt, J=12.8, 6.4 Hz, 2H), 2.23-2.10 (m, 1H), 2.05-1.86 (m, 3H). $^{13}$C NMR (101 MHz, CDCl$_3$) δ 159.2, 156.5, 148.3, 144.5, 138.8, 136.7, 136.0, 132.0, 131.5, 131.0, 130.7, 127.9, 119.8, 48.3, 29.6, 28.9, 20.0. IR (Diamond ATR, cm$^{-1}$) ν 3380, 2930, 2858, 1672, 1578, 1531, 1478, 1360, 1299, 1119, 1001, 873, 828, 802. HRMS (EI-MS) m/z calculated for $C_{17}H_{15}BrN_4$ [M+H]$^+$: 355.055285, found: 355.055432.

Example 11: (R)-2-Chloro-N-(1,2,3,4-tetrahydronaphthalen-1-yl)pyrido-[3,2-d]pyrimidin-4-amine (17)

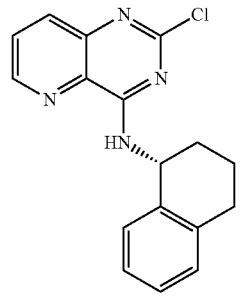 [SMILES: Clc1nc(N[C@@H]2CCCc3ccccc32)c2ncccc2n1]

Product 17 was obtained as described for 6 from 2 (150 mg, 0.75 mmol) and (R)-1,2,3,4-tetrahydronaphthylamine (0.10 mL, 0.75 mmol, 1.0 eq.) to give the title product 17 (150 mg, 64%) in the form of a white solid. $R_f$ ($CH_2Cl_2$/MeOH 99:01): 0.55. $^1$H NMR (400 MHz, CDCl$_3$) δ 8.57 (d, J=4.2 Hz, 1H), 8.00 (d, J=8.5 Hz, 1H), 7.69-7.48 (m, 2H), 7.31 (d, J=7.6 Hz, 1H), 7.22-7.12 (m, 3H), 5.61 (dd, J=14.3, 5.9 Hz, 1H), 2.99-2.68 (m, 2H), 2.24-2.16 (m, 1H), 2.07-1.81 (m, 3H). $^{13}$C NMR (101 MHz, CDCl$_3$) δ 160.1, 158.6, 148.3, 145.7, 137.7, 135.8, 135.0, 130.7, 129.4, 128.9, 128.4, 127.7, 126.4, 48.9, 29.6, 29.2, 20.0. IR (Diamond ATR, cm$^{-1}$) ν 3256, 2927, 1578, 1466, 1394, 1377, 1321, 1270, 1192, 1127, 958, 873, 824. HRMS (EI-MS) m/z calculated for $C_{17}H_{15}ClN_4$ [M+H]$^+$: 311.105801, found: 311.106246. $[α]_D$=+67.2 (c 1.0, CHCl$_3$). $T_m$: 180-182° C.

Example 12: (R)—N-(1,2,3,4-Tetrahydronaphthalen-1-yl)pyrido[3,2-d]pyrimidin-4-amine (18)

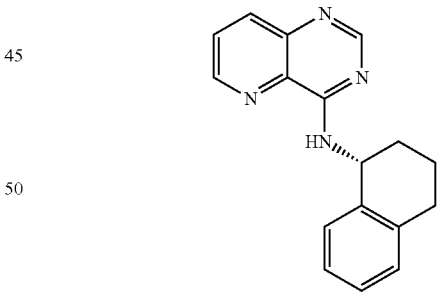

Product 18 was obtained as described for 7 from 17 (100 mg, 0.32 mmol) to give the title product 18 (60 mg, 67%) in the form of a yellow solid. $R_f$ ($CH_2Cl_2$/MeOH 98:02): 0.28. $^1$H NMR (400 MHz, CDCl$_3$) δ 8.68 (s, 1H), 8.62 (dd, J=4.2, 1.4 Hz, 1H), 8.11 (dd, J=8.5, 1.4 Hz, 1H), 7.63 (dd, J=8.5, 4.2 Hz, 1H), 7.48 (d, J=8.2 Hz, 1H), 7.34 (d, J=7.2 Hz, 1H), 7.22-7.11 (m, 3H), 5.63 (dd, J=14.3, 5.9 Hz, 1H), 3.05-2.65 (m, 2H), 2.23-2.17 (m, 1H), 2.10-1.84 (m, 3H). $^{13}$C NMR (101 MHz, CDCl$_3$) δ 159.2, 156.6, 148.2, 144.4, 137.8, 136.5, 135.9, 132.1, 129.0, 127.8, 127.6, 126.4, 48.8, 29.8, 29.4, 20.2. IR (Diamond ATR, cm$^{-1}$) ν 3373, 2934, 1582, 1536, 1365, 1311, 1137, 1111, 1001, 928, 830. HRMS (EI-MS) m/z calculated for $C_{17}H_{16}N_4$ [M+H]$^+$: 277.144773, found: 277.145111. $[\alpha]_D$=+8.3 (c 1.1, CHCl$_3$). T$_m$: 85-87° C.

Example 13: (S)-2-Chloro-N-(1,2,3,4-tetrahydronaphthalen-1-yl)pyrido[3,2-d]pyrimidin-4-amine (19)

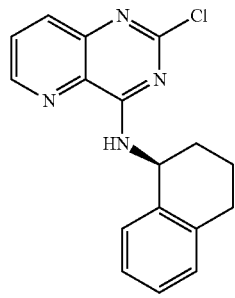 [SMILES: Clc1nc(N[C@H]2CCCc3ccccc32)c2ncccc2n1]

Product 19 was obtained as described for 6 from 2 (200 mg, 1.00 mmol) and (S)-1,2,3,4-tetrahydronaphthylamine (0.15 mL, 1.05 mmol, 1.0 eq.) to give the title product 19 (165 mg, 53%) in the form of a white solid. R$_f$ (CH$_2$Cl$_2$/MeOH 99:01): 0.55. $^1$H NMR (400 MHz, CDCl$_3$) δ 8.59 (dd, J=4.2, 1.5 Hz, 1H), 8.02 (dd, J=8.5, 1.5 Hz, 1H), 7.71-7.52 (m, 2H), 7.32 (d, J=7.5 Hz, 1H), 7.23-7.14 (m, 3H), 5.62 (dd, J=14.2, 5.9 Hz, 1H), 2.98-2.71 (m, 2H), 2.25-2.17 (m, 1H), 2.12-1.80 (m, 3H). $^{13}$C NMR (101 MHz, CDCl$_3$) δ 160.2, 158.7, 148.3, 145.8, 137.8, 135.8, 135.1, 130.8, 129.5, 129.0, 128.4, 127.8, 126.5, 49.0, 29.6, 29.3, 20.0. IR (Diamond ATR, cm$^{-1}$) ν 3256, 2927, 1578, 1533, 1394, 1321, 1270, 1127, 958, 873, 824. HRMS (EI-MS) m/z calculated for $C_{17}H_{15}ClN_4$ [M+H]$^+$: 311.105801, found: 311.106098. $[\alpha]_D$=−68.0 (c 1.0, CHCl$_3$). T$_m$: 179-181° C.

Example 14: (S)—N-(1,2,3,4-Tetrahydronaphthalen-1-yl)pyrido[3,2-d]pyrimidin-4-amine (20)

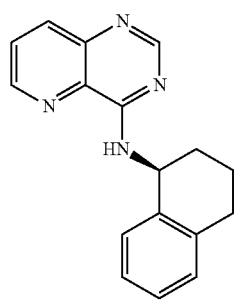 [SMILES: c1ccc2c(c1)CCC[C@@H]2Nc1ncnc2cccnc12]

Product 20 was obtained as described for 7 from 19 (100 mg, 0.32 mmol) to give the title product 20 (70 mg, 79%) in the form of a yellow solid. R$_f$ (CH$_2$Cl$_2$/MeOH 98:02): 0.28. $^1$H NMR (400 MHz, CDCl$_3$) δ 8.69 (s, 1H), 8.64 (dd, J=4.2, 1.4 Hz, 1H), 8.11 (dd, J=8.5, 1.4 Hz, 1H), 7.64 (dd, J=8.5, 4.2 Hz, 1H), 7.46 (d, J=8.3 Hz, 1H), 7.34 (d, J=7.3 Hz, 1H), 7.24-7.16 (m, 3H), 5.64 (dd, J=14.3, 6.0 Hz, 1H), 3.03-2.65 (m, 2H), 2.28-2.14 (m, 1H), 2.11-1.89 (m, 3H). $^{13}$C NMR (101 MHz, CDCl$_3$) δ 159.3, 156.7, 148.3, 144.5, 137.9, 136.6, 136.0, 132.2, 129.4, 129.0, 127.8, 127.6, 126.5, 48.8, 29.8, 29.4, 20.2. IR (Diamond ATR, cm$^{-1}$) ν 3373, 2934, 1582, 1536, 1365, 1311, 1137, 1111, 1001, 928, 830. HRMS (EI-MS) m/z calculated for $C_{17}H_{16}N_4$ [M+H]$^+$: 277.144773, found: 277.145203. $[\alpha]_D$=−8.1 (c 1.2, CHCl$_3$). T$_m$: 80-82° C.

Example 15: N-Benzyl-2-chloropyrido[3,2-d]pyrimidin-4-amine (21)

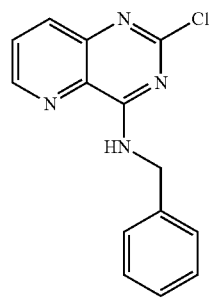 [SMILES: Clc1nc(NCc2ccccc2)c2ncccc2n1]

Product 21 was obtained as described for 6 starting with 2 (200 mg, 1.00 mmol) and benzylamine (0.11 mL, 1.00 mmol, 1 eq.) to give the title product 21 (181 mg, 67%) in the form of a white solid. R$_f$ (EP/AcOEt 70:30): 0.40. $^1$H NMR (400 MHz, CDCl$_3$) δ 8.62 (dd, J=4.3, 1.5 Hz, 1H), 8.01 (dd, J=8.5, 1.5 Hz, 1H), 7.68-7.55 (m, 2H), 7.42-7.29 (m, 5H), 4.84 (d, J=5.9 Hz, 2H). $^{13}$C NMR (101 MHz, CDCl$_3$) δ 160.8, 158.5, 148.4, 145.7, 137.2, 135.1, 130.7, 129.0 (×2), 128.5, 128.2 (×2), 128.0, 45.2. IR (Diamond ATR, cm$^{-1}$) ν 3401, 3036, 1578, 1543, 1456, 1377, 1323, 1282, 1220, 1132, 956, 873, 808. HRMS (EI-MS) m/z calculated for $C_{14}H_{11}ClN_4$ [M+H]$^+$: 271.074501, found: 271.074680. T$_m$: 130-132° C.

Example 16: 2-Chloro-N-cyclohexylpyrido[3,2-d]pyrimidin-4-amine (22)

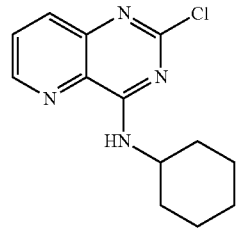 [SMILES: Clc1nc(NC2CCCCC2)c2ncccc2n1]

Product 22 was obtained as described for 6 from 2 (100 mg, 0.50 mmol) and cyclohexylamine (0.06 mL, 0.50 mmol, 1.0 eq.) to give the title product 22 (94 mg, 72%) in the form of a white solid. R$_f$ (EP/AcOEt 80:20): 0.44. $^1$H NMR (400 MHz, CDCl$_3$) δ 8.63 (dd, J=4.2, 1.4 Hz, 1H), 7.98 (dd, J=8.5, 1.4 Hz, 1H), 7.61 (dd, J=8.5, 4.3 Hz, 1H), 7.24 (s, 1H), 4.31-4.07 (m, 1H), 2.09 (dd, J=12.1, 3.1 Hz, 2H), 1.85-1.74 (m, 2H), 1.74-1.60 (m, 1H), 1.57-1.23 (m, 5H). $^{13}$C NMR (101 MHz, CDCl$_3$) δ 160.0, 158.7, 148.1 (×2), 145.6, 135.1 (×2), 130.8, 128.3 (×2), 49.5, 32.7, 25.61, 24.8. IR (Diamond ATR, cm$^{-1}$) ν 3267, 2924, 2854, 1585, 1538, 1470, 1381, 1323, 1272, 1133, 1066, 951, 871, 820. HRMS (EI-MS) m/z calculated for $C_{13}H_{15}ClN_4$ [M+H]$^+$: 263.105801, found: 263.106066. T$_m$: 80-82° C.

Example 17: N-Cyclohexylpyrido[3,2-d]pyrimidin-4-amine (23)

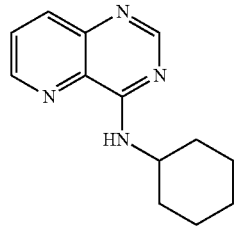 [SMILES: c1cnc2c(NC3CCCCC3)ncnc2c1]

Product 23 was obtained as described for 7 from 22 (70 mg, 0.27 mmol) to give the title product 23 (30 mg, 50%) in the form of a yellow oil. $R_f$ (EP/AcOEt 50:50): 0.23. $^1$H NMR (400 MHz, CDCl$_3$) δ 8.70-8.63 (m, 1H), 8.61 (s, 1H), 8.08 (d, J=8.4 Hz, 1H), 7.63 (dd, J=8.4, 4.2 Hz, 1H), 7.16 (d, J=6.3 Hz, 1H), 4.19 (dt, J=14.5, 8.4 Hz, 1H), 2.21-2.02 (m, 2H), 1.90-1.75 (m, 2H), 1.69 (dd, J=9.1, 3.8 Hz, 1H), 1.59-1.29 (m, 5H). $^{13}$C NMR (101 MHz, CDCl$_3$) δ 159.0, 156.5, 148.0 (×2), 144.2, 135.8, 132.2, 127.7 (×2), 49.4, 32.9, 25.7, 24.9. IR (Diamond ATR, cm$^{-1}$) ν 386, 2929, 2853, 1581, 1541, 1438, 1364, 1317, 1276, 914, 836, 828. HRMS (EI-MS) m/z calculated for C$_{13}$H$_{16}$N$_4$ [M+H]$^+$: 229.144773, found: 229.145034.

Example 18: 2-Chloro-N-(5,7-dimethyl-1,2,3,4-tetrahydronaphthalen-1-yl)pyrido[3,2-d]pyrimidin-4-amine (25)

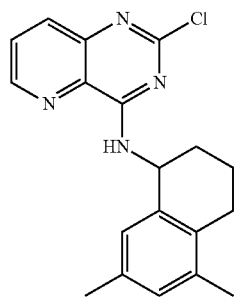 [SMILES: Cc1cc(C)c2c(c1)C(Nc1nc(Cl)nc3cccnc13)CCC2]

Product 25 was obtained as described for 6 from 2 (200 mg, 1.00 mmol) and the amine 24 (175 mg, 1.0 mmol, 1.0 eq.) to give the title product 25 (230 mg, 68%) in the form of a white solid. $R_f$ (EP/AcOEt 70:30): 0.55. $^1$H NMR (400 MHz, CDCl$_3$) δ 8.55 (dd, J=4.2, 1.1 Hz, 1H), 8.00 (dd, J=8.5, 1.1 Hz, 1H), 7.67 (d, J=8.6 Hz, 1H), 7.60 (dd, J=8.5, 4.2 Hz, 1H), 6.98 (s, 1H), 6.91 (s, 1H), 5.61-5.46 (m, 1H), 2.73-2.50 (m, 2H), 2.23 (s, 3H), 2.20 (s, 3H), 2.15-1.99 (m, 2H), 1.99-1.89 (m, 2H). $^{13}$C NMR (101 MHz, CDCl$_3$) δ 159.9, 158.6, 148.2, 145.6, 136.7, 135.4, 135.3, 134.9, 133.0, 130.7, 130.2, 128.2, 127.2, 49.3, 28.9, 26.2, 20.9, 19.6, 19.5. IR (Diamond ATR, cm$^{-1}$) ν 3271, 2930, 2861, 1577, 1537, 1466, 1389, 1322, 1271, 1190, 1127, 1035, 956, 873, 822. HRMS (EI-MS) m/z calculated for C$_{19}$H$_{19}$ClN$_4$ [M+H]$^+$: 339.137101, found: 339.137019. T$_m$: 55-57° C.

Example 19: N-(5,7-Dimethyl-1,2,3,4-tetrahydronaphthalen-1-yl)pyrido[3,2-d]pyrimidin-4-amine (26)

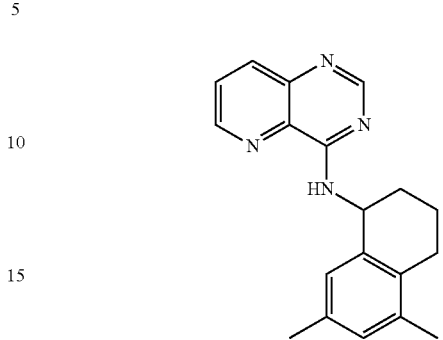

Product 26 was obtained as described 7 from 25 (100 mg, 0.30 mmol) to give the title product 26 (52 mg, 58%) in the form of a colourless oil. $R_f$ (EP/AcOEt 50:50): 0.32. $^1$H NMR (400 MHz, CDCl$_3$) δ 8.69 (s, 1H), 8.63 (dd, J=4.2, 1.5 Hz, 1H), 8.11 (dd, J=8.5, 1.5 Hz, 1H), 7.63 (dd, J=8.5, 4.2 Hz, 1H), 7.48 (d, J=8.3 Hz, 1H), 7.02 (s, 1H), 6.94 (s, 1H), 5.61-5.49 (m, 1H), 2.76-2.69 (m, 1H), 2.67-2.56 (m, 1H), 2.24 (s, 6H), 2.18-2.04 (m, 2H), 1.99-1.94 (m, 2H). $^{13}$C NMR (101 MHz, CDCl$_3$) δ 159.1, 156.7, 148.2, 144.4, 136.8, 136.2, 135.9, 135.5, 133.2, 132.2, 130.2, 127.8, 127.3, 49.1, 29.2, 26.4, 21.0, 19.8, 19.7. (Diamond ATR, cm$^{-1}$) ν 2929, 2861, 1578, 1533, 1478, 1439, 1360, 1305, 1192, 1112, 908, 857, 827, 802. HRMS (EI-MS) m/z calculated for C$_{19}$H$_{20}$N$_4$ [M+H]$^+$: 305.176073, found: 305.176343. IR

Example 20: 2-Chloro-N-(1,2,3,4-tetrahydrophenanthren-4-yl)pyrido[3,2-d]pyrimidin-4-amine (28)

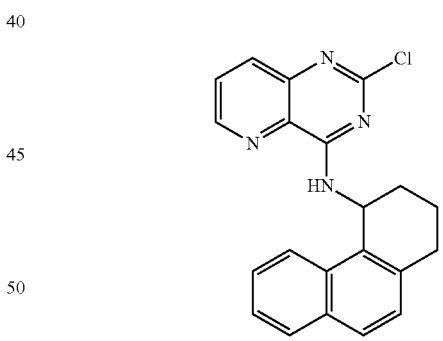

Product 28 was obtained as described for 6 from 2 (200 mg, 1.00 mmol) and the amine 27 (197 mg, 1.0 mmol, 1.0 eq.) to give the title product 28 (240 mg, 67%) in the form of a white solid. $R_f$ (EP/AcOEt 80:20): 0.43. $^1$H NMR (400 MHz, CDCl$_3$) δ 8.48 (d, J=4.2 Hz, 1H), 8.02 (d, J=8.5 Hz, 1H), 7.95-7.87 (m, 1H), 7.84-7.79 (m, 1H), 7.76 (d, J=8.5 Hz, 1H), 7.65-7.54 (m, 2H), 7.42 (dd, J=9.5, 4.9 Hz, 2H), 7.27 (d, J=8.3 Hz, 1H), 6.15 (d, J=8.2 Hz, 1H), 3.12-2.89 (m, 2H), 2.52 (d, J=8.6 Hz, 1H), 2.11-1.92 (m, 3H). $^{13}$C NMR (101 MHz, CDCl$_3$) δ 159.4, 158.7, 148.3, 145.8, 136.3, 135.1, 132.6, 132.4, 130.8, 129.2, 128.7, 128.7, 128.4, 128.1, 127.0, 125.4, 123.0, 45.0, 30.1, 28.7, 18.2. IR (Diamond ATR, cm$^{-1}$) ν 3383, 2930, 1575, 1534, 1466, 1435, 1389, 1324, 1273, 1190, 1127, 959, 874, 805. HRMS (EI-MS) m/z calculated for $C_{21}H_{17}ClN_4$ [M+H]$^+$: 361.121451, found: 361.121633. $T_m$: 70-72° C.

Example 21: N-(1,2,3,4-Tetrahydrophenanthren-4-yl)pyrido[3,2-d]pyrimidin-4-amine (29)

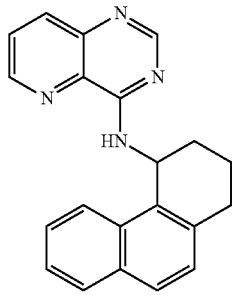 [SMILES: c1ccc2c3c(ccc2c1)CCCC3Nc1ncnc2cccnc12]

Product 29 was obtained as described for 7 from 28 (100 mg, 0.28 mmol) to give the title product 29 (70 mg, 77%) in the form of a yellow oil. $R_f$ (EP/AcOEt 70:30): 0.18. $^1$H NMR (400 MHz, CDCl$_3$) δ 8.81 (s, 1H), 8.52 (dd, J=4.2, 1.5 Hz, 1H), 8.11 (dd, J=8.5, 1.5 Hz, 1H), 7.93-7.85 (m, 1H), 7.80 (dd, J=6.2, 3.1 Hz, 1H), 7.75 (d, J=8.5 Hz, 1H), 7.59 (dd, J=8.5, 4.2 Hz, 1H), 7.50 (d, J=8.1 Hz, 1H), 7.43-7.33 (m, 2H), 7.31-7.24 (m, 1H), 6.18 (d, J=8.3 Hz, 1H), 3.14-2.87 (m, 2H), 2.57-2.41 (m, 1H), 2.09-1.92 (m, 3H). $^{13}$C NMR (101 MHz, CDCl$_3$) δ 158.4, 156.7, 148.3, 144.5, 136.3, 135.9, 132.6, 132.5, 132.2, 129.9, 128.6, 128.5, 128.1, 127.8, 127.0, 125.3, 123.1, 44.6, 30.2, 28.8, 18.3. IR (Diamond ATR, cm$^{-1}$) ν 3384, 3049, 2930, 1575, 1533, 1466, 1436, 1389, 1325, 1273, 1190, 1126, 959, 874, 805. HRMS (EI-MS) m/z calculated for $C_{21}H_{18}N_4$[M+H]$^+$: 327.160423, found: 327.160571.

Example 22: 2-Methyl-N-(1,2,3,4-tetrahydronaphthalen-1-yl)pyrido[3,2-d]pyrimidin-4-amine (30)

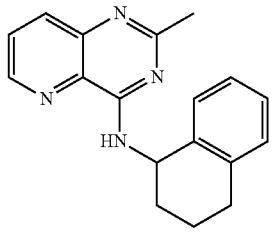 [SMILES: Cc1nc(NC2CCCc3ccccc32)c2ncccc2n1]

Product 6 (100 mg, 0.32 mmol) was dissolved in THF (3.5 mL) under argon and a solution of trimethyl aluminium in toluene (2M, 0.35 mL, 0.70 mmol, 2.2 eq.) was added dropwise. Pd(PPh$_3$)$_4$ (36 mg, 0.032 mmol, 0.1 eq.) was afterwards added and the medium heated under reflux overnight. After cooling, the solvent was evaporated. The reaction product was purified by silica gel chromatography (gradient CH$_2$Cl$_2$ to CH$_2$Cl$_2$/MeOH 99:01) to give the title product 30 (65 mg, 70%) in the form of a white solid. $R_f$ (CH$_2$Cl$_2$/MeOH 99:01): 0.20. $^1$H NMR (400 MHz, CDCl$_3$) δ 8.57 (dd, J=4.3, 1.5 Hz, 1H), 8.03 (dd, J=8.5, 1.6 Hz, 1H), 7.59 (dd, J=8.4, 4.2 Hz, 1H), 7.44-7.32 (m, 2H), 7.25-7.11 (m, 3H), 5.70 (dd, J=14.1, 6.2 Hz, 1H), 2.97-2.79 (m, 2H), 2.70 (s, 3H), 2.29-2.16 (m, 1H), 2.10-1.88 (m, 3H). $^{13}$C NMR (101 MHz, CDCl$_3$) δ 166.0, 158.9, 147.2, 144.7, 137.7, 136.9, 135.0, 130.6, 129.3, 128.9, 127.6, 127.4, 126.3, 48.3, 29.8, 29.4, 27.0, 20.2. IR (Diamond ATR, cm$^{-1}$) ν 3385, 2928, 1578, 1530, 1440, 1413, 1366, 1339, 1297, 1162, 1114, 1001, 825. HRMS (EI-MS) m/z calculated for $C_{18}H_{18}N_4$ [M+H]$^+$: 291.160423, found: 291.160771. $T_m$: 95-97° C.

Example 23: 2-Ethoxy-N-(1,2,3,4-tetrahydronaphthalen-1-yl)pyrido[3,2-d]pyrimidin-4-amine (31)

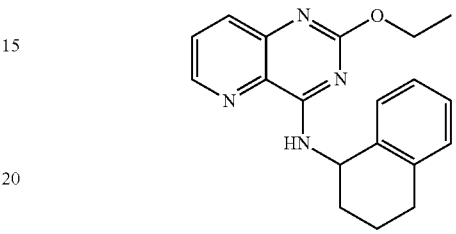

A suspension of product 6 (100 mg, 0.32 mmol), MeB(OH)$_2$ (29 mg, 0.48 mmol, 1.5 eq.), Pd(PPh$_3$)$_4$ (18 mg, 0.016 mmol, 0.05 eq.) and Cs$_2$CO$_3$ (313 mg, 0.96 mmol, 3 eq.) in a 3:1 toluene/ethanol mixture (4 mL) was heated under microwave radiation to 150° C. for 1 hour. After cooling, water (20 mL) was added to the mixture and the product extracted with dichloromethane (2×20 mL). The combined organic phase was dried over magnesium sulfate, filtered and concentrated in vacuo. The crude product was purified by silica gel chromatography (gradient EP to EP/AcOEt 85:15) to give product 31 (60 mg, 58%) in the form of a white solid. $R_f$ (EP/AcOEt 80:20): 0.37. $^1$H NMR (400 MHz, CDCl$_3$) δ 8.43 (dd, J=4.2, 1.5 Hz, 1H), 7.88 (dd, J=8.5, 1.4 Hz, 1H), 7.52 (dd, J=8.5, 4.2 Hz, 1H), 7.42 (d, J=8.5 Hz, 1H), 7.36-7.30 (m, 1H), 7.22-7.13 (m, 3H), 5.65 (dd, J=14.4, 6.0 Hz, 1H), 4.51 (q, J=7.1 Hz, 2H), 2.86 (dt, J=13.3, 6.4 Hz, 2H), 2.26-2.11 (m, 1H), 2.08-1.83 (m, 3H), 1.47 (t, J=7.1 Hz, 3H). $^{13}$C NMR (101 MHz, CDCl$_3$) δ 162.9, 160.9, 146.3, 145.3, 137.8, 136.6, 134.2, 130.3, 129.3, 129.1, 127.8, 127.5, 126.4, 63.3, 48.6, 29.9, 29.4, 20.2, 14.8. IR (Diamond ATR, cm$^{-1}$) ν3379, 2939, 1570, 1423, 1333, 1311, 1219, 1059, 825, 807. HRMS (EI-MS) m/z calculated for $C_{19}H_{20}N_4O$ [M+H]$^+$: 321.170988, found: 321.171136. $T_m$: 187-189° C.

Example 24: 4-(1,2,3,4-tetrahydronaphthalen-1-ylamino)pyrido[3,2-d]pyrimidine-2-carbonitrile (32)

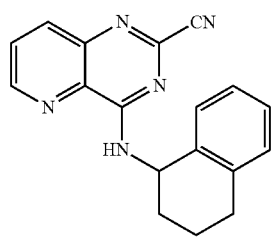 [SMILES: N#Cc1nc(NC2CCCc3ccccc32)c2ncccc2n1]

Under an argon atmosphere in a sealed tube, product 6 (100 mg, 0.32 mmol) was dissolved in DMF over sieve (1 mL) after which Zn(CN)$_2$ (38 mg, 0.32 mmol, 1.0 eq.) and Pd(PPh$_3$)$_4$ (37 mg, 0.032 mmol, 0.1 eq.) were added. The mixture was brought to 150° C. under microwave radiation for 5 minutes. The DMF was evaporated and the residue obtained taken up in water (20 mL) and extracted with ethyl acetate (2×20 mL). The organic phase was washed with saturated NaCl solution (20 mL), dried over MgSO$_4$ and concentrated under reduced pressure. The reaction product was purified by silica gel chromatography (gradient EP to EP/AcOEt 85:15) to give the title product 32 (70 mg, 72%) in the form of a beige solid. R$_f$(CH$_2$Cl$_2$/MeOH 99:01): 0.55. $^1$H NMR (400 MHz, CDCl$_3$) δ 8.74 (dd, J=4.2, 1.4 Hz, 1H), 8.16 (dd, J=8.5, 1.4 Hz, 1H), 7.73 (dd, J=8.5, 4.3 Hz, 1H), 7.64 (d, J=8.2 Hz, 1H), 7.33-7.07 (m, 4H), 5.64 (dd, J=14.3, 5.8 Hz, 1H), 3.04-2.66 (m, 2H), 2.37-2.14 (m, 1H), 2.14-1.84 (m, 3H). $^{13}$C NMR (101 MHz, CDCl$_3$) δ 159.3, 150.4, 144.3, 142.3, 137.9, 136.3, 135.7, 131.9, 129.6, 128.9, 128.7, 127.9, 126.6, 116.6, 49.2, 29.6, 29.3, 20.0. IR (Diamond ATR, cm$^{-1}$) ν 3280, 2938, 2359, 1399, 1557, 1467, 1440, 1387, 1324, 1291, 1163, 1116, 1072, 1039, 996, 888, 801. HRMS (EI-MS) m/z calculated for C$_{18}$H$_{15}$N$_5$ [M+H]$^+$: 302.140022, found: 302.139997. T$_m$: 159-161° C.

Example 25: N$^4$-(1,2,3,4-tetrahydronaphthalen-1-yl)pyrido[3,2-d]pyrimidine-2,4-diamine (33)

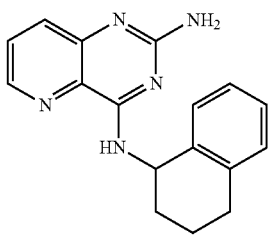 [SMILES: Nc1nc(NC2CCCc3ccccc32)c2ncccc2n1]

In a sealed tube, product 6 (100 mg, 0.32 mmol) was dissolved in dioxane (1 mL) and ammonia (2 mL) was added. The mixture was brought to 100° C. for 3 days. After cooling, the mixture was concentrated in vacuo. The crude product was taken up in water (20 mL) and extracted with dichloromethane (20 mL). The combined organic phases were dried over MgSO$_4$, filtered and concentrated in vacuo. The crude product was purified by silica gel chromatography (gradient CH$_2$Cl$_2$ to CH$_2$Cl$_2$/MeOH 98:02) to give the title product 33 (90 mg, 96%) in the form of a white solid. R$_f$ (CH$_2$Cl$_2$/MeOH 97:03): 0.20. H NMR (400 MHz, CDCl$_3$) δ 8.29 (dd, J=4.2, 1.4 Hz, 1H), 7.68 (dd, J=8.5, 1.4 Hz, 1H), 7.44 (dd, J=8.5, 4.2 Hz, 1H), 7.34 (d, J=7.3 Hz, 1H), 7.30 (d, J=8.6 Hz, 1H), 7.22-7.12 (m, 3H), 5.54 (dd, J=14.3, 6.2 Hz, 1H), 5.05 (s, 2H), 2.97-2.75 (m, 2H), 2.20-2.13 (m, 1H), 2.08-1.83 (m, 3H). $^{13}$C NMR (101 MHz, CDCl$_3$) δ 160.7, 159.9, 146.6, 143.7, 137.8, 136.9, 132.6, 129.3 (×2), 129.0, 127.8, 127.5, 126.4, 48.4, 29.9, 29.5, 20.3. IR (Diamond ATR, cm$^{-1}$) ν 3311, 3153, 2929, 1600, 1567, 1537, 1447, 1381, 1103, 906, 818. HRMS (EI-MS) m/z calculated for C$_{17}$H$_{17}$N$_5$ [M+H]$^+$: 292.155672, found: 292.155978. T$_m$: 152-154° C.

Example 26: 4-(1,2,3,4-tetrahydronaphthalen-1-ylamino)pyrido[3,2-d]pyrimidin-2-ol (34)

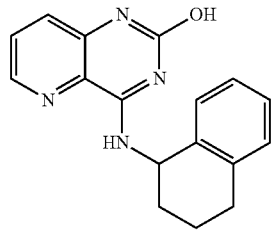 [SMILES: Oc1nc(NC2CCCc3ccccc32)c2ncccc2n1]

Product 6 (100 mg, 0.32 mmol) was dissolved in ethanol (2 mL) in a sealed tube and gaseous ammonia was bubbled through this solution at 0° C. for 15 minutes. The mixture was heated to 100° C. for 4 days. After cooling, the crude product was concentrated in vacuo and purified by silica gel chromatography (gradient CH$_2$Cl$_2$ to CH$_2$Cl$_2$/MeOH 96:04) to give product 34 (62 mg, 66%) in the form of a white solid. R$_f$ (CH$_2$Cl$_2$/MeOH 97:03): 0.10. $^1$H NMR (400 MHz, CDCl$_3$) δ 12.80 (s, 1H), 8.32 (dd, J=4.4, 1.4 Hz, 1H), 7.82 (dd, J=8.4, 1.4 Hz, 1H), 7.66 (d, J=8.9 Hz, 1H), 7.50 (dd, J=8.4, 4.4 Hz, 1H), 7.40-7.34 (m, 1H), 7.27-7.14 (m, 3H), 5.80 (dt, J=8.6, 5.9 Hz, 1H), 3.00-2.75 (m, 2H), 2.29-2.22 (m, 1H), 2.09-2.03 (m, 1H), 1.99-1.92 (m, 2H). $^{13}$C NMR (101 MHz, CDCl$_3$) δ 160.7, 159.5, 143.8, 138.0, 137.9, 136.1, 129.0, 129.2, 128.4, 127.6, 126.8, 126.5, 124.4, 48.5, 29.8, 29.4, 20.1. IR (Diamond ATR, cm$^{-1}$) ν 3354, 2923, 2857, 1654, 1597, 1535, 1466, 1333, 1160, 1089, 1002, 920, 804. HRMS (EI-MS) m/z calculated for C$_{17}$H$_{16}$N$_4$O [M+H]$^+$: 293.139688, found: 293.139965. T$_f$>260° C.

Example 27: N$^2$-methyl-N$^4$-(1,2,3,4-tetrahydronaphthalen-1-yl)pyrido[3,2-d]pyrimidine-2,4-diamine (35)

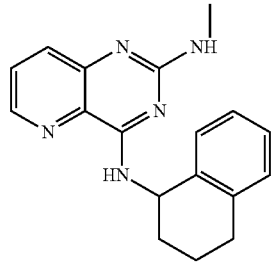 [SMILES: CNc1nc(NC2CCCc3ccccc32)c2ncccc2n1]

A sealed tube was charged with product 6 (100 mg, 0.32 mmol), dioxane (1 mL) and methylamine (40% in water, 3 mL). The reaction mixture was heated to 100° C. for 3 days. The mixture was then evaporated and the product extracted with dichloromethane (2×20 mL); the combined organic phases were dried over MgSO$_4$, filtered and concentrated in vacuo. The crude product was purified by silica gel chromatography (gradient EP to EP/AcOEt 40:60) to give the title product 35 (93 mg, 95%) in the form of a yellow solid. R$_f$(EP/AcOEt 40:60): 0.33. $^1$H NMR (250 MHz, CDCl$_3$) δ 8.24 (dd, J=4.2, 1.5 Hz, 1H), 7.73 (d, J=8.5 Hz, 1H), 7.46-7.29 (m, 2H), 7.25-7.10 (m, 4H), 5.54 (dd, J=13.8, 6.1 Hz, 1H), 5.13 (s, 1H), 3.08 (d, J=5.0 Hz, 3H), 2.85 (dd, J=13.5, 6.8 Hz, 2H), 2.22-2.08 (m, 1H), 2.02-1.77 (m, 3H).

$^{13}$C NMR (101 MHz, CDCl$_3$) δ 160.5, 159.3, 146.8, 142.8, 137.6, 137.1, 132.4, 129.2 (×2), 128.9, 127.5, 127.3, 126.3, 48.3, 29.8, 29.4, 28.6, 20.2. IR (Diamond ATR, cm$^{-1}$) v 3365, 3289, 2919, 2851, 1569, 1476, 1394, 1365, 1320, 1131, 815. HRMS (EI-MS) m/z calculated for C$_{18}$H$_{19}$N$_5$ [M+H]$^+$: 306.171322, found: 306.171542. T$_m$: 145-147° C.

Example 28: 2,7-dichloro-N-(1,2,3,4-tetrahydronaphthalen-1-yl)pyrido [3,2-d]pyrimidin-4-amine (37)

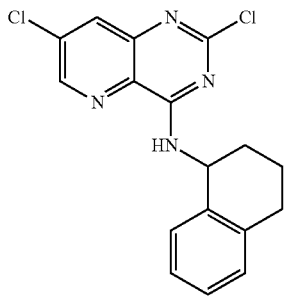 [SMILES: Clc1cnc2c(NC3CCCc4ccccc43)nc(Cl)nc2c1]

Product 36 (250 mg, 1.07 mmol) was dissolved in THF (10 mL) and the mixture placed at 0° C. The successive addition was made of 1,2,3,4-tetrahydronaphthylamine (0.15 mL, 1.07 mmol, 1 eq.) then triethylamine (0.16 mL, 1.12 mmol, 1.05 eq.) and the mixture left under stirring overnight at ambient temperature. The THF was evaporated and the residue obtained was taken up in water (20 mL) and extracted with dichloromethane (2×20 mL). The combined organic phase was dried over magnesium sulfate, filtered and concentrated in vacuo. The crude was chromatographed on silica gel (gradient EP to EP/AcOEt 98:02) to give the title product 37 (378 mg, quantitative) in the form of a white solid. R$_f$ (EP/AcOEt 95:05): 0.25. $^1$H NMR (400 MHz, CDCl$_3$) δ 8.49 (d, J=2.2 Hz, 1H), 7.97 (d, J=2.2 Hz, 1H), 7.50 (d, J=8.5 Hz, 1H), 7.29 (d, J=7.6 Hz, 1H), 7.24-7.14 (m, 3H), 5.61 (dt, J=11.7, 5.9 Hz, 1H), 2.95-2.73 (m, 2H), 2.29-2.12 (m, 1H), 2.11-1.82 (m, 3H). $^{13}$C NMR (101 MHz, CDCl$_3$) δ 159.8 (×2), 147.6, 146.2, 137.8, 136.2, 135.6, 133.5, 129.5, 128.9, 128.8, 127.9, 126.5, 49.1, 29.6, 29.3, 20.0. IR (Diamond ATR, cm$^{-1}$) v 3384, 3062, 2939, 1564, 1438, 1360, 1318, 1280, 1178, 1126, 1086, 959, 906, 791. HRMS (EI-MS) m/z calculated for C$_{17}$H$_{14}$Cl$_2$N$_4$ [M+H]$^+$: 345.066828, found: 345.066837. T$_m$: 185-187° C.

Example 29: 7-Chloro-N-(1,2,3,4-tetrahydronaphthalen-1-yl)pyrido[3,2-d]pyrimidin-4-amine (38)

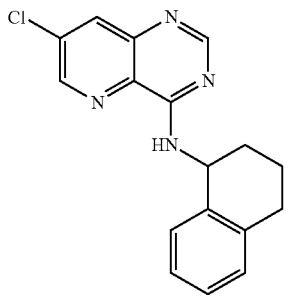 [SMILES: Clc1cnc2c(NC3CCCc4ccccc43)ncnc2c1]

Product 38 was obtained as described for 7 from 37 (50 mg, 0.14 mmol) to give the title product 38 (32 mg, 76%) in the form of a yellow oil. R$_f$(CH$_2$Cl$_2$/MeOH 95:05): 0.50. $^1$H NMR (400 MHz, CDCl$_3$) δ 8.67 (s, 1H), 8.55 (d, J=1.4 Hz, 1H), 8.11 (s, 1H), 7.40 (d, J=8.1 Hz, 1H), 7.32 (d, J=7.6 Hz, 1H), 7.25-7.13 (m, 3H), 5.63 (dd, J=13.7, 6.1 Hz, 1H), 2.98-2.77 (m, 2H), 2.26-2.16 (m, 1H), 2.13-1.86 (m, 3H). $^{13}$C NMR (101 MHz, CDCl$_3$) δ 159.1, 157.6, 147.6, 144.8, 137.9, 136.2, 135.5, 134.2, 130.1, 129.5, 128.9, 127.8, 126.5, 48.9, 29.7, 29.4, 20.1. IR (Diamond ATR, cm$^{-1}$) v3393, 2949, 2918, 1574, 1533, 1446, 1350, 1301, 1159, 1079, 936, 890. HRMS (EI-MS) m/z calculated for C$_{17}$H$_{15}$ClN$_4$ [M+H]$^+$: 311.105801, found: 311.105890. T$_m$: 145147° C.

Example 30: 7-Cyclopropyl-N-(1,2,3,4-tetrahydronaphthalen-1-yl)pyrido [3,2-d]pyrimidin-4-amine (39)

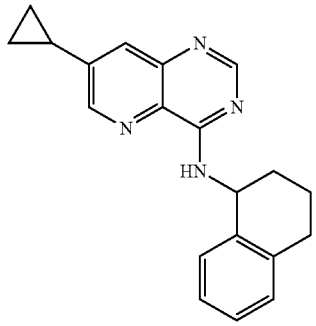 [SMILES: c1ccc2c(c1)CCCC2Nc1ncnc2cc(C3CC3)cnc12]

To a solution of product 38 (50 mg, 0.16 mmol) in a toluene/water mixture (10:1, 0.66 mL), cyclopropylboronic acid (18 mg, 0.21 mmol, 1.3 eq.), potassium phosphate (119 mg, 0.56 mmol, 3.5 eq.), tricyclohexylphosphine (7 mg, 0.026 mmol, 0.16 eq.) and palladium acetate (3 mg, 0.013 mmol, 0.08 eq.) were successively added. The mixture was brought to 140° C. under microwave radiation for 45 minutes, filtered through Celite® and rinsed with ethyl acetate (2×20 mL). The filtrate was washed with water (20 mL), dried over magnesium sulfate, filtered and concentrated in vacuo. The crude product was purified by silica gel chromatography (gradient EP to EP/AcOEt 60:40) to give the title product 39 (30 mg, 59%) in the form of a white solid. R$_f$ (EP/AcOEt 70:30): 0.18. $^1$H NMR (400 MHz, CDCl$_3$) δ 8.59 (s, 1H), 8.43 (d, J=1.4 Hz, 1H), 7.60 (d, J=1.7 Hz, 1H), 7.33 (d, J=6.9 Hz, 2H), 7.23-7.19 (m, 1H), 7.18-7.13 (m, 2H), 5.66 (dd, J=13.7, 5.7 Hz, 1H), 3.09-2.89 (m, 2H), 2.38-2.30 (m, 1H), 2.23-2.15 (m, 2H), 2.14-2.01 (m, 2H), 1.36-1.26 (m, 2H), 1.05 (td, J=6.0, 2.8 Hz, 2H). $^{13}$C NMR (100 MHz, CDCl$_3$) δ 158.8, 156.4, 147.9, 144.8, 144.3, 137.6, 136.5, 129.9, 129.8, 129.2, 128.8, 127.4, 126.3, 48.8, 30.1, 29.6, 20.4, 13.9, 10.7 (×2). IR (Diamond ATR, cm$^{-1}$) v 3374, 2952, 2906, 1577, 1463, 1490, 1454, 1441, 1369, 1300, 1215, 1164, 1136, 1020, 968, 910, 874. HRMS (EI-MS) m/z calculated for C$_{20}$H$_{20}$N$_4$ [M+H]$^+$: 317.176073, found: 317.176340. T$_m$: 135-137° C.

Example 31: 7-Hexyl-N-(1,2,3,4-tetrahydronaphthalen-1-yl)pyrido[3,2-d]pyrimidin-4-amine (40)

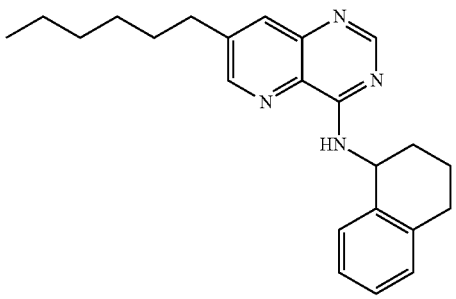 [SMILES: CCCCCCc1cnc2c(NC3CCCc4ccccc43)ncnc2c1]

Product 40 was obtained such as described for 39 from 38 (50 mg, 0.16 mmol) and n-hexylboronic acid (27 mg, 0.21 mmol, 1.3 eq.) to give the title product 40 (50 mg, 78%) in the form of a yellow oil. $R_f$ (EP/AcOEt 70:30): 0.50. $^1$H NMR (400 MHz, CDCl$_3$) δ 8.62 (s, 1H), 8.44 (d, J=1.9 Hz, 1H), 7.85 (d, J=1.9 Hz, 1H), 7.39 (d, J=8.5 Hz, 1H), 7.34 (d, J=6.8 Hz, 1H), 7.24-7.18 (m, 1H), 7.18-7.11 (m, 2H), 5.67 (dd, J=13.7, 5.9 Hz, 1H), 3.08-2.96 (m, 2H), 2.96-2.86 (m, 2H), 2.41-2.30 (m, 1H), 2.24-2.14 (m, 1H), 2.14-2.03 (m, 2H), 1.84 (dt, J=14.9, 7.3 Hz, 2H), 1.58-1.40 (m, 6H), 1.10-0.99 (m, 3H). $^{13}$C NMR (100 MHz, CDCl$_3$) δ 158.9, 156.3, 149.4, 144.2, 143.0, 137.6, 136.4, 133.9, 130.0, 129.2, 128.8, 127.4, 126.3, 48.8, 33.5, 31.9, 31.1, 30.0, 29.6, 29.1, 22.9, 20.4, 14.4. IR (Diamond ATR, cm$^{-1}$) ν 3391, 2926, 2856, 1577, 1528, 1445, 1366, 1305, 1203, 1159, 1119, 907, 848. HRMS (EI-MS) m/z calculated for C$_{23}$H$_{28}$N$_4$ [M+H]$^+$: 361.238673, found: 361.238688.

Example 32: 7-(hexyloxy)-N-(1,2,3,4-tetrahydronaphthalen-1-yl)pyrido [3,2-d]pyrimidin-4-amine (41)

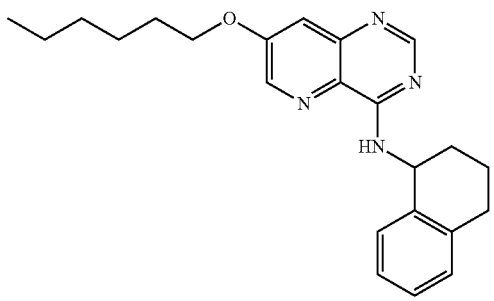 [SMILES: CCCCCCOc1cnc2c(NC3CCCc4ccccc43)ncnc2c1]

A solution of Pd$_2$(dba)$_3$ (1.4 mg, 16.10-4 mmol, 0.005 eq.) and Bippyphos (3.2 mg, 0.0064 mmol, 0.02 eq.) in n-hexanol (0.6 mL) was stirred at ambient temperature for 5 minutes, after which potassium hydroxide (27 mg, 0.48 mmol, 1.5 eq.) and product 38 (100 mg, 0.32 mmol) were added and the mixture brought to 150° C. under microwave radiation for one hour. Water (20 mL) was added and the product extracted with dichloromethane (2×20 mL). The combined organic phase was dried over MgSO$_4$, filtered and concentrated in vacuo. The crude product was purified by silica gel chromatography (gradient EP to EP/AcOEt 60:40) to give the title product 41 (45 mg, 37%) in the form of a white solid. $R_f$ (EP/AcOEt 70:30): 0.35. $^1$H NMR (400 MHz, CDCl$_3$) δ 8.57 (s, 1H), 8.31 (d, J=2.6 Hz, 1H), 7.35-7.32 (m, 2H), 7.23 (dd, J=7.2, 5.0 Hz, 1H), 7.19 (dd, J=6.7, 1.6 Hz, 1H), 7.15 (t, J=6.3 Hz, 2H), 5.69-5.61 (m, 1H), 4.17 (t, J=6.4 Hz, 2H), 3.07-2.88 (m, 2H), 2.39-2.28 (m, 1H), 2.22-2.04 (m, 3H), 2.04-1.93 (m, 2H), 1.64 (dt, J=14.2, 7.0 Hz, 2H), 1.51 (td, J=7.0, 3.6 Hz, 4H), 1.10-1.05 (m, 3H). $^{13}$C NMR (100 MHz, CDCl$_3$) δ 158.5, 158.1, 156.8, 145.9, 141.8, 137.6, 136.5, 129.2, 128.8, 127.4, 126.2, 125.5, 113.2, 69.0, 48.7, 31.8, 30.1, 29.6, 29.1, 25.9, 22.9, 20.4, 14.4. IR (Diamond ATR, cm$^{-1}$) ν 3419, 3050, 2930, 2855, 1577, 1526, 1441, 1389, 1329, 1281, 1136, 1073, 999, 891. HRMS (EI-MS) m/z calculated for C$_{23}$H$_{28}$N$_4$O [M+H]$^+$: 377.233588, found: 377.233647. $T_m$: 92-94° C.

Example 33: N-(3,4-dichlorobenzyl)pyrido[2,3-d]pyrimidin-4-amine (46)

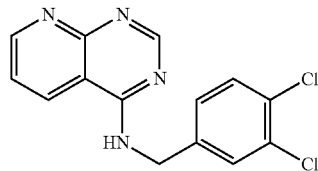 [SMILES: Clc1ccc(CNc2ncnc3ncccc23)cc1Cl]

Product 45 (200 mg, 1.20 mmol) was dissolved in 1,4-dioxane (12 mL) followed by the addition of 3,4 dichlorobenzylamine (0.32 mL, 2.40 mmol, 2.0 eq.). The mixture was left under stirring overnight at ambient temperature. The 1,4-dioxane was evaporated and the residue obtained taken up in water (20 mL) and extracted with dichloromethane (2×20 mL). The organic phase was dried over magnesium sulfate, filtered and concentrated in vacuo. The crude product was chromatographed on silica gel (gradient CH$_2$Cl$_2$ to CH$_2$Cl$_2$/MeOH 95:05) to give the title product 46 (234 mg, 64%) in the form of a white solid. $R_f$ (CH$_2$Cl$_2$/MeOH 97:03): 0.13. $^1$H NMR (250 MHz, DMSO-d$_6$) δ 9.14 (t, J=5.5 Hz, 1H), 9.01 (dd, J=4.4, 1.8 Hz, 1H), 8.73 (dd, J=8.3, 1.8 Hz, 1H), 8.60 (s, 1H), 7.64 (d, J=1.8 Hz, 1H), 7.58 (dt, J=8.2, 2.1 Hz, 2H), 7.36 (dd, J=8.3, 2.0 Hz, 1H), 4.78 (d, J=5.8 Hz, 2H). $^{13}$C NMR (101 MHz, DMSO-d$_6$) δ 160.7, 158.2 (×2), 155.8, 140.3, 132.5, 130.9, 130.5, 129.4, 129.3, 127.6, 121.5, 109.7, 42.9. IR (Diamond ATR, cm$^{-1}$) ν 3195, 2972, 2359, 1574, 1472, 1414, 1334, 1276, 1207, 1112, 1032, 977, 897. HRMS (EI-MS) m/z calculated for C$_{14}$H$_{10}$Cl$_2$N$_4$ [M+H]$^+$: 305.035528, found: 305.035763. $T_m$>260° C.

Example 34: N-(1,2,3,4-Tetrahydronaphthalen-1-yl)pyrido[2,3-d]pyrimidin-4-amine (47)

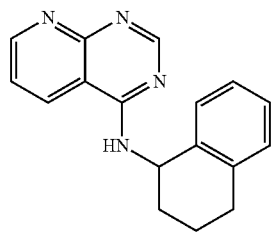 [SMILES: c1ccc2c(c1)CCCC2Nc1ncnc2ncccc12]

Product 47 was synthesised as described for 46 from 45 (152 mg, 0.92 mmol) to give the title product 47 (120 mg, 43%) in the form of a white solid. $R_f$ (CH$_2$Cl$_2$/MeOH 98:02): 0.38. $^1$H NMR (400 MHz, DMSO-d$_6$) δ 8.98 (dd, J=4.3, 1.8 Hz, 1H), 8.85-8.74 (m, 2H), 8.64 (s, 1H), 7.50 (dd, J=8.2, 4.3 Hz, 1H), 7.24-7.06 (m, 4H), 5.79-5.66 (m, 1H), 2.92-2.70 (m, 2H), 2.12-1.73 (m, 4H). $^{13}$C NMR (101 MHz, DMSO-d$_6$) δ 160.4, 158.5, 158.4, 155.6, 137.4, 137.0, 132.7, 128.9, 128.0, 126.9, 125.9, 121.2, 109.6, 48.5, 29.3, 28.9, 20.4. IR (Diamond ATR, cm$^{-1}$) ν 3248, 2929, 1560, 1529, 1416, 1334, 1279, 1110, 924, 848. HRMS (EI-MS) m/z calculated for C$_{17}$H$_{16}$N$_4$ [M+H]$^+$: 277.144773, found: 277.145128. T$_m$: 254-256° C.

Example 35: (S)-2-Methyl-N-(1,2,3,4-tetrahydronaphthalen-1-yl)pyrido [3,2-d]pyrimidin-4-amine (48)

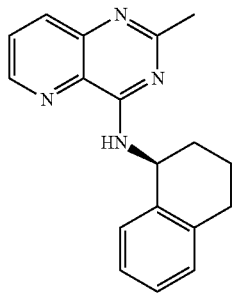

Product 48 was obtained as described for 30 from product 19 (100 mg, 0.32 mmol) to give the title product 48 in the form of a white solid (93 mg, 65%). $^1$H NMR (250 MHz, CDCl$_3$) δ 1.81-1.98 (m, 3H), 2.06-2.25 (m, 1H), 2.64 (s, 3H), 2.71-2.92 (m, 2H), 5.64 (m, 2H), 7.03-7.18 (m, 2H), 7.26-7.39 (m, 3H), 7.53 (dd, J=8.4, 4.2 Hz, 1H), 7.99 (dd, J=8.5, 1.6 Hz, 1H), 8.51 (dd, J=4.3, 1.6 Hz, 1H). $^{13}$C NMR (101 MHz, CDCl$_3$) δ 166.0, 158.9, 147.2, 144.7, 137.7, 136.9, 135.0, 130.6, 129.3, 128.9, 127.6, 127.4, 126.3, 48.3, 29.8, 29.4, 27.0, 20.2. IR (Diamond ATR, cm$^{-1}$) ν 3385, 2928, 1578, 1530, 1440, 1413, 1366, 1339, 1297, 1162, 1114, 1001, 825. [α]$^{20}_D$=−31.3 (c=0.003, CH$_2$Cl$_2$). T$_m$: 103-105° C.

Example 36: (S)-2-Fluoro-N-(1,2,3,4-tetrahydronaphthalen-1-yl)pyrido [3,2-d]pyrimidin-4-amine (49)

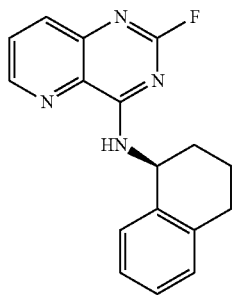

Product 19 (200 mg, 0.64 mmol) was dissolved in NMP (4 mL) under an argon atmosphere and the addition made of anhydrous potassium fluoride (187 mg, 3.21 mmol, 5.0 eq.) and 18-crown-6 (17 mg, 0.064 mmol, 0.1 eq.). The mixture was brought to 230° C. under microwave radiation for 2 hours. The reaction mixture was taken up with water (20 mL) and extracted with ethyl acetate (2×20 mL). The organic phase was dried over magnesium sulfate and concentrated in vacuo. The crude product was purified by silica gel chromatography (eluting gradient EP to EP/AcOEt 80/20) to give the title product 49 in the form of a white solid (95 mg, 50%). $^1$H NMR (400 MHz, CDCl$_3$) δ 8.58 (dd, J=4.3, 1.5 Hz, 1H), 8.01 (dd, J=8.5, 1.5 Hz, 1H), 7.68 (d, J=8.5 Hz, 1H), 7.63 (dd, J=8.5, 4.3 Hz, 1H), 7.36-7.29 (m, 1H), 7.24-7.14 (m, 3H), 5.60 (dt, J=8.7, 5.8 Hz, 1H), 2.97-2.78 (m, 2H), 2.28-2.18 (m, 1H), 2.09-1.89 (m, 3H). $^{13}$C NMR (101 MHz, CDCl$_3$) δ 19.9, 29.1, 29.5, 49.0, 126.4, 127.7, 128.3, 128.8, 129.3, 130.5, 130.8, 135.0, 135.0, 135.6, 137.7, 145.9, 146.1, 147.3, 147.3, 159.5, 161.6, 162.2, 162.4. $^{19}$F NMR (400 MHz, CDCl$_3$) 5-43.33. IR (Diamond ATR, cm$^{-1}$) ν3371, 3353, 2929, 1611, 1586, 1568, 1550, 1489, 1438, 1405, 1350, 1328, 1297, 1085, 819, 769, 736. HRMS (EI-MS) m/z calculated for C$_{17}$H$_{16}$FN$_4$ [M+H]$^+$: 295.135207, found: 295.135351. [α]$^{20}_D$=−25.6 (c=0.003, CH$_2$Cl$_2$). T$_m$: 154-156° C.

Example 37: 2-Chloro-N-(3,4-dihydroquinolin-1(2H)-yl)pyrido[3,2-d]pyrimidin-4-amine (52)

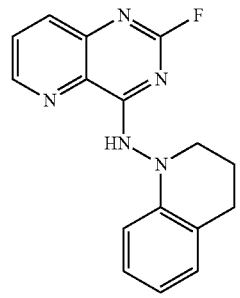

Product 52 was synthesized as described for 6 from 2 (205 mg, 1.02 mmol) and from compound 50 (159 mg, 1.07 mmol, 1.05 eq.) to give the title product 52 in the form of a yellowish solid (191 mg, 60%). $^1$H NMR (400 MHz, DMSO-d$_6$) δ 10.85 (s, 1H), 8.87 (dd, J=4.2, 1.6 Hz, 1H), 8.13 (dd, J=8.5, 1.6 Hz, 1H), 7.92 (dd, J=8.5, 4.2 Hz, 1H), 7.00 (d, J=7.3 Hz, 1H), 6.94 (t, J=7.7 Hz, 1H), 6.66 (t, J=7.3 Hz, 1H), 6.60 (d, J=8.2 Hz, 1H), 3.54 (s, 2H), 2.78 (t, J=6.3 Hz, 2H), 2.14-2.01 (m, 2H). $^{13}$C NMR (101 MHz, DMSO-d$_6$) δ 22.2, 27.0, 50.4, 112.5, 118.7, 122.9, 127.1, 129.3, 129.6, 130.2, 135.1, 145.7, 146.2, 149.6, 157.8, 161.3. IR (Diamond ATR, cm$^{-1}$) ν 3238, 3063, 2945, 2921, 2888, 2856, 1597, 1577, 1515, 1488, 1473, 1455, 1282, 1233, 1212, 1170, 1091, 803. HRMS (EI-MS) m/z calculated for C$_{16}$H$_{15}$ClN$_5$ [M+H]$^+$: 312.09, found: 312.101050. T$_m$: 85-87° C.

Example 38: N-(3,4-Dihydroquinolin-1(2H)-yl)pyrido[3,2-d]pyrimidin-4-amine (53)

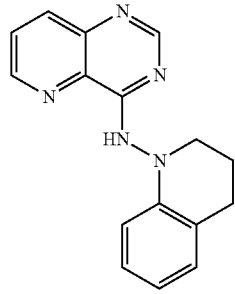

Product 53 was obtained as described for 7 from 52 (67 mg, 0.21 mmol) to give the title product 53 in the form of a yellow solid (40 mg, 68%). $^1$H NMR (400 MHz, CDCl$_3$) δ 2.20-2.36 (m, 2H), 2.91 (t, J=6.4 Hz, 2H), 3.65 (s, 2H), 6.75-6.90 (m, 2H), 6.99-7.12 (m, 2H), 7.75 (dd, J=8.5, 4.2 Hz, 1H), 8.20 (dd, J=8.5, 1.6 Hz, 1H), 8.64 (s, 1H), 8.76 (s, 1H), 8.78 (dd, J=4.3, 1.6 Hz, 1H). $^{13}$C NMR (101 MHz, CDCl$_3$) δ 22.2, 26.9, 51.5, 76.7, 77.0, 77.2, 77.3, 113.1, 119.9, 123.7, 127.1 128.0, 129.3, 131.2, 136.0, 144.5, 145.3, 148.6, 156.6, 159.0. IR (Diamond ATR, cm$^{-1}$) ν 3238, 3063, 2945, 2921, 2888, 2856, 1597, 1577, 1515, 1488, 1473, 1455, 1435, 1370, 1282, 1233, 1212, 1170, 1091, 803, 757. HRMS (EI-MS) m/z calculated for C$_{16}$H$_{16}$N$_5$ [M+H]$^+$: 278.13, found: 278.140203. T$_m$: 179-180° C.

Example 39: 2-Chloro-N-{6,7,8,9-tetrahydro-5H-benzo[7]annulen-5-yl}pyrido [3,2-d] pyrimidin-4-amine (55)

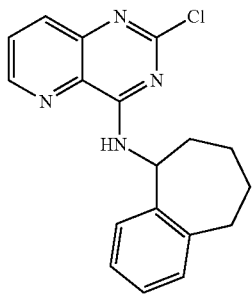 [SMILES: Clc1nc(NC2CCCCc3ccccc32)c2ncccc2n1]

Product 55 was synthesised as described for 6 from 2 (122 mg, 0.61 mmol) and from compound 54 (119 mg, 0.81 mmol, 1.05 eq.) then triethylamine (0, 94 mL, 0.67 mmol, 1.05 eq.) to give the title product 55 in the form of a brown solid (116 mg, 60%). R$_f$ (EP/AcOEt 70:30): 0.28. $^1$H NMR (250 MHz, CDCl$_3$) δ 8.53 (m, 1H), 7.84 (m, 1H), 7.80-7.71 (m, 1H), 7.50 (m, 1H), 7.20-7.12 (m, 1H), 7.03-6.91 (m, 3H), 3.96 (q, J=7.1 Hz, 6H), 3.55 (q, J=7.0 Hz, 1H), 2.83 (t, J=5.6 Hz, 2H). $^{13}$C NMR (100 MHz, CDCl$_3$) ppm: 159.7, 158.5, 148.3, 145.6, 141.5, 140.7, 135.0, 130.7, 130.4, 128.3, 127.6, 126.9, 126.4, 55.1, 36.3, 33.3, 27.6, 2159.7, 158.5, 148.3, 145.6, 141.5, 140.7, 135.0, 130.7, 130.4, 128.3, 127.6, 126.9, 126.4, 55.1, 36.3, 33.3, 27.6, 27.5. IR (Diamond ATR, cm$^{-1}$) ν 3368, 2919, 2851, 1585, 1544, 1190, 1152, 1129, 976, 871. HRMS (EI-MS) m/z calculated for C$_{18}$H$_{17}$ClN$_4$ [M+H]$^+$: 325.1213, found: m/z 325.1214. T$_m$: 122-124° C.

Example 40: N-{6,7,8,9-tetrahydro-5H-benzo[7]annulen-5-yl}pyrido[3,2-d]pyrimidin-4-amine (56)

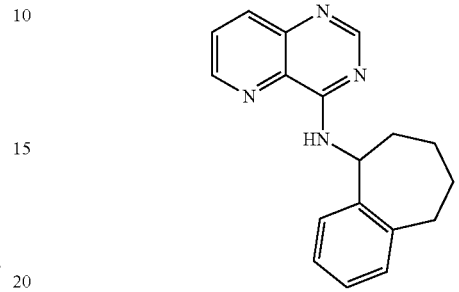

Product 56 was synthesized as described for 7 from 55 (60 mg, 0.19 mmol) to give the title product 56 in the form of an amorphous yellow solid (40 mg, 68%). R$_f$ (EP/AcOEt 70:30): 0.3 $^1$H NMR (250 MHz, CDCl$_3$) δ 8.84-8.72 (m, 1H), 8.63 (s, 1H), 8.13 (d, J=8.4 Hz, 1H), 7.70 (dd, J=8.7, 4.4 Hz, 2H), 7.32 (d, J=7.2 Hz, 2H), 7.24-7.08 (m, 3H), 5.65 (t, J=8.8 Hz, 1H), 3.15-2.87 (m, 2H), 2.24-1.94 (m, 4H). $^{13}$C NMR (100 MHz, CDCl$_3$) δ 158.5, 156.4, 148.0, 144.1, 141.3, 141.2, 135.7, 131.9, 130.1, 127.5, 127.1, 126.2, 125.6, 54.3, 36.0, 33.9, 28.1, 27.4. IR (Diamond ATR, cm$^{-1}$) ν 3403, 2923, 1574, 1534, 1359, 827, 747, 685. HRMS (EI-MS) m/z calculated for C$_{18}$H$_{18}$N$_4$ [M+H]$^+$: 291.1605, found: m/z 291.1604. T$_m$: 104-106° C.

Example 41: 2-Chloro-N-(7-nitro-1,2,3,4-tetrahydronaphthalen-1-yl)pyrido[3,2-d]pyrimidin-4-amine (58)

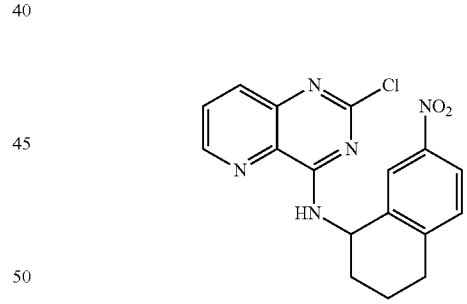

Product 58 was synthesized as described for 6 from 2 (95 mg, 0.47 mmol) and from compound 57 (96 mg, 0.50 mmol, 1.05 eq.) to give the title product 58 in the form of a yellowish solid (132 mg, 78%). R$_f$ (EP/AcOEt 70:30): 0.6. $^1$H NMR (250 MHz, CDCl$_3$) δ 8.60 (dt, J=4.3, 1.5 Hz, 1H), 8.20 (d, J=2.2 Hz, 1H), 8.05-7.93 (m, 2H), 7.64 (ddd, J=8.5, 4.3, 0.9 Hz, 1H), 7.56 (d, J=9.1 Hz, 1H), 7.31-7.20 (m, 1H), 5.64 (t, J=8.1 Hz, 1H), 2.90 (dq, J=14.3, 6.7 Hz, 2H), 2.32-2.16 (m, 1H), 1.28-1.13 (m, 2H), 0.91-0.75 (m, 1H). $^{13}$C NMR 100 MHz, CDCl$_3$) δ 165.94, 160.1, 158.1, 155.4, 153.1, 148.8, 148.5, 146.4, 145.7, 145.6, 137.5, 136.8, 136.0, 135.0, 130.4, 128.5, 123.9, 122.3, 48.6, 29.5, 29.4, 29.2, 19.6. IR (Diamond ATR, cm$^{-1}$) ν 3395, 3059, 3027, 2929, 2907, 2843, 1601, 1556, 1493, 1452, 1376, 1276, 1142, 1128, 1069, 995, 901, 889, 756. T$_m$: 134-136° C.

Example 42: 2N-(7-nitro-1,2,3,4-tetrahydronaphthalen-1-yl)pyrido[3,2-d]pyrimidin-4-amine (59)

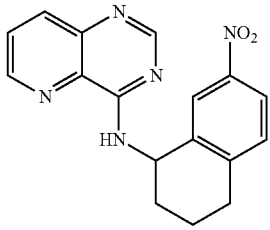 [SMILES: O=[N+]([O-])c1ccc2c(c1)C(Nc1ncnc3cccnc13)CCC2]

Product 59 was synthesized as described for 7 from 58 (85 mg, 0.24 mmol) to give the title product 59 in the form of a yellow solid (40 mg, 68%). $R_f$ (EP/AcOEt 50:50): 0.7. $^1$H NMR (250 MHz, CDCl$_3$) δ 8.79-8.65 (m, 2H), 8.30-8.24 (m, 1H), 8.17 (dd, J=8.5, 1.6 Hz, 1H), 8.06 (dd, J=8.5, 2.5 Hz, 1H), 7.70 (dd, J=8.5, 4.3 Hz, 1H), 7.45 (m, 2H), 5.76 (q, J=7.7, 6.5 Hz, 1H), 3.12-2.88 (m, 2H), 2.29-1.77 (m, 4H). $^{13}$C NMR (100 MHz, CDCl$_3$) δ 148.3, 138.4, 130.2, 127.9, 123.8, 122.2, 48.2, 29.5, 29.4. IR (Diamond ATR, cm$^{-1}$) ν 3384, 2951, 2871, 1559, 1537, 1515, 1343, 1311. HRMS (EI-MS) m/z calculated for Cl$_7$H$_{15}$N$_5$O$_2$ [M+H]$^+$: 322.1299, found m/z: 322.1298. T$_m$: 160-162° C.

Example 43: 2-Chloro-N-(3,4-dihydro-2H-1-benzopyran-4-yl)pyrido[3,2-d]pyrimidin-4-amine (61)

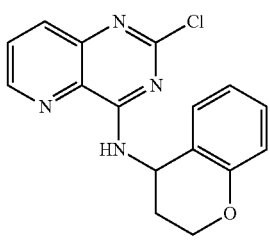 [SMILES: Clc1nc(NC2CCOc3ccccc32)c2ncccc2n1]

Product 61 was synthesized as described for 6 from 2 (3.04 mmol, 1.0 eq.) and solubilized in 90 mL of THF and compound 60 (3.38 mmol, 1.0 eq.) to give product 61 in the form of a pinkish solid with a yield of 62% (615 mg). $R_f$ (EP/AcOEt 50:50): 0.32. $^1$H NMR (250 MHz, CDCl$_3$) δ 8.35 (tt, J=3.9, 1.7 Hz, 1H, NH), 7.78 (dt, J=8.6, 1.8 Hz, 1H), 7.59-7.35 (m, 2H), 7.12-6.87 (m, 2H), 6.73-6.51 (m, 2H), 5.34 (m, 1H, CH), 2.28-1.95 (m, 2H, CH$_2$), 1.31-0.89 (m, 1H, CH). $^{13}$C NMR (101 MHz, CDCl$_3$) δ 160.0, 158.4, 155.2, 148.5, 145.8, 135.1, 130.6, 129.7, 129.5, 128.5, 121.2, 121.0, 117.4, 63.2, 45.0, 28.5. IR (Diamond ATR, cm$^{-1}$) ν 3389, 1573, 1437, 1390, 1278, 1224, 1126, 936, 873. HRMS (EI-MS) m/z calculated for C$_{16}$H$_{13}$ClN$_4$O [M+H]$^+$: 313.0853, found m/z: 313.0851. T$_m$: 152-154° C.

Example 44: N-(3,4-dihydro-2H-1-benzopyran-4-yl)pyrido[3,2-d]pyrimidin-4-amine (62)

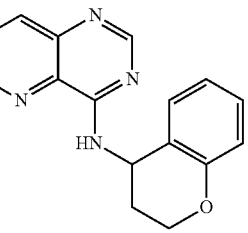

Product 62 was synthesized as described for 7 from 61 (300 mg, 0.96 mmol) to give the title product 62 in the form of a white solid (25 mg, 10%). $R_f$ (EP/AcOEt 50:50): 0.33. $^1$H NMR (250 MHz, CDCl$_3$) δ 8.72-8.57 (m, 1H), 8.10 (dd, J=8.5, 1.6 Hz, 1H), 7.64 (dd, J=8.5, 4.2 Hz, 1H), 7.42 (d, J=7.8 Hz, 1H), 7.31-7.14 (m, 2H), 6.94-6.81 (m, 2H), 5.61-5.49 (m, 1H), 2.50-2.16 (m, 1H), 1.35-1.11 (m, 2H), 0.93-0.76 (m, 2H). $^{13}$C NMR (101 MHz, CDCl$_3$) δ 159.0, 156.3, 155.2, 148.3, 144.4, 135.9, 131.9, 129.6, 129.5, 127.8, 121.9, 120.9, 117.3, 77.3, 63.3, 44.7, 29.7, 28.6. IR (Diamond ATR, cm$^{-1}$) ν3389, 2925, 1577, 1487, 1529, 1453, 1435, 1361, 1304, 1250, 1224, 1115, 1065, 1021, 828. HRMS (EI-MS) m/z calculated for Cl$_6$H$_{14}$N$_4$O [M+H]$^+$: 279.1240, found m/z: 279.1239. T$_m$: 86-88° C.

Example 45: 2-chloro-N-(4,5,6,7-tetrahydro-1-benzofuran-4-yl)pyrido[3,2-d]pyrimidin-4-amine (64)

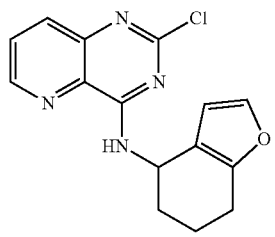 [SMILES: Clc1nc(NC2CCCc3occc32)c2ncccc2n1]

Product 64 was synthesized as described for 6 from 2 (0.99 mmol, 1.0 eq.) and from compound 63 (1.56 mmol, 1.0 eq.) to give product 64 in the form of a beige solid with a yield of 62% (185 mg). $R_f$ (EP/AcOEt 50:50): 0.71. $^1$H NMR (250 MHz, CDCl$_3$) δ 8.61 (dd, J=4.3, 1.5 Hz, 1H) δ 8.05-7.96 (m, 1H), 7.71-7.55 (m, 1H), 7.30-7.19 (m, 3H), 6.33 (d, J=2.0 Hz, 1H), 2.65 (d, J=5.9 Hz, 2H), 1.94 (m, 4H). $^{13}$C NMR (101 MHz, CDCl$_3$) δ 160.1, 158.5, 153.0, 148.2, 145.7, 141.3, 135.0, 130.7, 128.3, 117.2, 109.4, 44.8, 30.9, 29.6, 22.9, 19.9. IR (Diamond ATR, cm$^{-1}$) ν3394, 1601, 1576, 1549, 1469, 1398, 1375, 1283, 1137, 1036, 891, 872, 694, 568, 510. HRMS (EI-MS) Cl$_5$H$_{13}$ClN$_4$O [M+H]$^+$, calculated m/z 301.0850, found m/z: 301.0851. T$_m$: 168-170° C.

Example 46: N-(4,5,6,7-Tetrahydro-1-benzofuran-4-yl)pyrido[3,2-d]pyrimidin-4-amine (65)

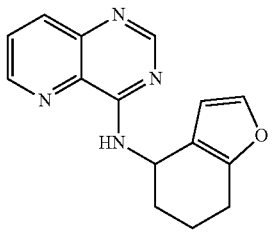 [SMILES: c1cnc2c(NC3CCCc4occc43)ncnc2c1]

Product 65 was synthesized as described for 7 from 64 (100 mg, 0.33 mmol) to give the title product 65 in the form of a white solid (83 mg, 95%). $R_f$ (EP/AcOEt 50:50): 0.42. $^1$H NMR (250 MHz, CDCl$_3$) δ 8.80-8.60 (m, 1H), 8.12 (dd, J=8.5, 1.6 Hz, 1H), 7.66 (dd, J=8.5, 4.2 Hz, 1H), 7.40-7.24 (m, 1H), 6.37 (d, J=1.9 Hz, 1H), 5.44 (ddd, J=7.7, 6.0, 4.1 Hz, 1H), 2.81-2.09 (m, 2H), 2.08-1.71 (m, 2H), 1.44-1.13 (m, 2H). $^{13}$C NMR (100 MHz, CDCl$_3$) δ 148.1, 141.1, 135.8, 132.0, 127.6, 109.4, 44.4, 29.6, 22.9, 19.9. IR (Diamond ATR, cm$^{-1}$) v392, 2930, 1579, 1537, 1476, 1362, 1294, 1105, 1026, 828, 686. HRMS (EI-MS) Cl$_5$H$_{15}$N$_{40}$ [M+H]$^+$, calculated m/z: 267.1240, found m/z: 267.1239. $T_m$: 142-144° C.

Example 47: N-Cyclohexyl-2-(3,5-dimethylpyrazol-1-yl)pyrido[3,2-d]pyrimidin-4-amine (66)

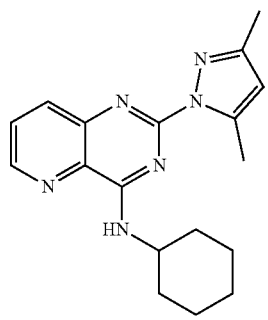 [SMILES: Cc1cc(C)n(-c2nc(NC3CCCCC3)c3ncccc3n2)n1]

Product 22 (151 mg, 0.576 mmol) was dissolved in 10 mL of dioxane followed by the addition of hydrazine monohydrate (0.976 mL, 20.7 mmol, 36 eq.). After overnight refluxing, the reaction mixture was dried under vacuum. The crude product was taken up in 10 mL of ethyl acetate. The organic phase was washed with water (3×10 mL), dried over MgSO$_4$, filtered and evaporated under vacuum. The crude product was dissolved in 10 mL of ethanol, and 2,4-pendadione (0.063 mL, 0.67 mmol, 1.05 eq.) was added. After overnight refluxing, the solvent was evaporated under reduced pressure and flash purification performed on silica eluting with petroleum ether/ethyl acetate (50:50). Product 66 was obtained with a yield of 72% in the form of a colourless oil. $R_f$ (EP/AcOEt 30:70): 0.33. $^1$H NMR (400 MHz, CDCl$_3$) δ 8.57 (m, 1H), 8.21 (m, 1H), 7.63-7.51 (m, 1H), 7.20 (d, J=8.4 Hz, 1H), 6.06-5.98 (m, 1H), 4.12 (sl, 1H), 2.73 (s, 3H), 2.35 (s, 3H), 2.18-2.08 (m, 2H), 1.90-1.78 (m, 2H), 1.73-1.64 (m, 1H), 1.41 (m, 4H), 1.33-1.19 (m, 1H). 13C NMR (101 MHz, CDCl$_3$) δ 159.5, 154.5, 150.8, 146.8, 145.7, 142.6, 135.9, 130.3, 127.8, 110.0, 77.4, 77.3, 77.1, 76.7, 50.1, 32.6, 25.5, 24.9, 15.7, 13.9. IR (Diamond ATR, cm$^{-1}$) v 3380, 2924, 2851, 1604, 1584, 1541, 1441, 1412, 1376, 1123, 1035, 972, 946, 873, 822. HRMS (EI-MS) C$_{18}$H$_{22}$N$_6$ [M+H]$^+$, calculated m/z 345.179815, found m/z 345.179809.

Example 48: 2-(3,5-Dimethylpyrazol-1-yl)-N-tetralin-1-yl-pyrido[3,2-d]pyrimidin-4-amine (67)

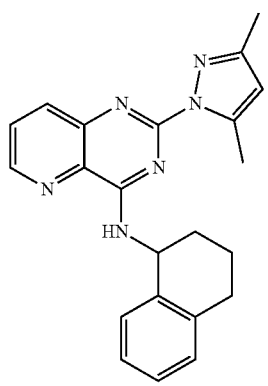 [SMILES: Cc1cc(C)n(-c2nc(NC3CCCc4ccccc43)c3ncccc3n2)n1]

Product 67 was obtained as described for 66 from 6 (76 mg, 0.24 mmol) to give the title product 67 with a yield of 85% in the form of a colourless oil. $R_f$ (DCM/MeOH 96:4): 0.5. $^1$H NMR (250 MHz, CDCl$_3$) δ 8.53 (dd, J=4.3, 1.5 Hz, 1H), 8.24 (dd, J=8.5, 1.5 Hz, 1H), 7.65-7.47 (m, 2H), 7.34 (d, J=7.0 Hz, 1H), 7.18 (m, 3H), 5.58 (dt, J=8.5, 5.8 Hz, 1H), 2.93-2.79 (m, 2H), 2.74 (s, 3H), 2.36 (s, 3H), 2.26-1.82 (m, 5H). $^{13}$C NMR (63 MHz, CDCl$_3$) δ 159.8, 154.5, 151.0, 147.0, 145.9, 142.7, 137.7, 2×136.0, 130.3, 129.3, 128.8, 127.9, 127.6, 126.4, 110.1, 77.5, 77.2, 77.0, 76.5, 49.2, 29.69, 29.2, 20.0, 15.9, 13.9. IR (Diamond ATR, cm$^{-1}$) v 3356, 2922, 1604, 1583, 1558, 1540, 1469, 1440, 1411, 1385, 1357, 1300, 1158, 1123, 1035, 971, 874. HRMS (EI-MS) C$_{22}$H$_{22}$N$_6$ [M+H]$^+$, calculated m/z 371.197871, found m/z 371.197768.

Example 49: 2-Chloro-N-cyclohexyl-7-methyl-pyrido[3,2-d]pyrimidin-4-amine (70)

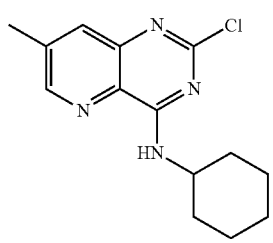 [SMILES: Cc1cnc2c(NC3CCCCC3)nc(Cl)nc2c1]

Product 69 (80 mg, 0.375 mmol) was dissolved in anhydrous THF (6 mL) and the mixture placed at 0° C. The successive addition was made of cyclohexanamine (0.046 mL, 0.41 mmol, 1.1 eq.) then triethylamine (0.48 mL, 0.41 mmol, 1.1 eq.) and the mixture left under stirring overnight at ambient temperature. The THF was evaporated and the residue obtained taken up in saturated NaHCO$_3$ solution and extracted with dichloromethane. The organic phase was dried over magnesium sulfate, filtered and concentrated in vacuo. The crude product was chromatographed on silica gel (eluting gradient EP to EP/AcOEt 80:20) to give the title product 70 in the form of a yellowish solid (70 mg, 67%). $R_f$ (EP/AcOEt 30:70): 0.7. $^1$H NMR (400 MHz, CDCl$_3$) δ 8.50 (d, J=2.0 Hz, 1H), 7.77 (dd, J=2.0, 0.9 Hz, 1H), 7.19 (d, J=8.6 Hz, 1H), 4.22 (m, 1H), 2.53 (d, J=0.9 Hz, 3H), 2.17-2.07 (m, 2H), 1.84 (m, 1H), 1.76-1.62 (m, 2H), 1.57-1.23 (m, 5H). $^{13}$C NMR (101 MHz, CDCl$_3$) δ 159.9, 158.6, 149.6, 145.5, 138.9, 133.8, 128.6, 77.3, 77.2, 77.0, 76.7, 49.3, 32.7, 25.5, 24.7, 18.9. IR (Diamond ATR, cm$^{-1}$) ν 3381, 2922, 2849, 1578, 1442, 1368, 1329, 1275, 1202, 1156, 1124, 943, 728. HRMS (EI-MS) Cl$_4$H$_{17}$ClN$_4$ [M+H]$^+$, calculated m/z 277.121451, found m/z 277.121264. $T_m$: 144-146° C.

Example 50: N-Cyclohexyl-2-(3,5-dimethylpyrazol-1-yl)-7-methyl-pyrido[3,2-d]pyrimidin-4-amine (71)

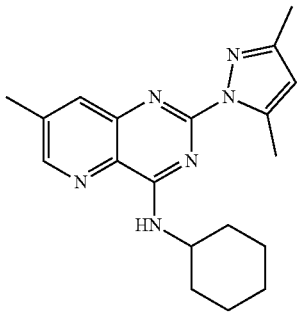 [SMILES: Cc1cnc2c(NC3CCCCC3)nc(-n3nc(C)cc3C)nc2c1]

Product 70 (60 mg, 0.217 mmol) was dissolved in 10 mL of dioxane, followed by the addition of hydrazine monohydrate (0.367 mL, 7.8 mmol, 36 eq.). After overnight refluxing, the reaction mixture was dried under vacuum. The crude product was taken up in 10 mL of ethyl acetate. The organic phase was washed with water (3×10 mL), dried over MgSO$_4$, filtered and evaporated under vacuum. The crude product was dissolved in 10 mL of ethanol, and 2,4-pendadione (0.025 mL, 0.29 mmol, 1.05 eq.) was added. After overnight refluxing, the solvent was evaporated under reduced pressure. The organic phase was washed with saline solution (5×15 mL), dried over MgSO$_4$, filtered and evaporated under vacuum. The crude product was finally purified on silica eluting with EP/ethyl acetate (50:50). Product 71 was obtained with a yield of 41% in the form of a colourless oil. $R_f$(EP/AcOEt 30:70): 0.33. $^1$H NMR (400 MHz, CDCl$_3$) δ 8.41 (d, J=2.0 Hz, 1H), 7.97 (dd, J=2.0, 1.1 Hz, 1H), 7.11 (d, J=8.3 Hz, 1H), 6.02 (s, 1H), 4.11 (m, 1H), 2.73 (s, 3H), 2.48 (s, 3H), 2.35 (d, J=1.1 Hz, 3H), 2.13 (m, 2H), 1.83 (m, 2H), 1.69 (m, 1H), 1.54-1.22 (m, 5H). $^{13}$C NMR (101 MHz, CDCl$_3$) δ 159.5, 154.6, 150.7, 148.5, 145.6, 142.5, 138.3, 134.9, 128.2, 109.9, 77.4, 77.3, 77.10, 76.8, 50.0, 32.7, 25.6, 24.9, 18.9, 15.6, 13.9. IR (Diamond ATR, cm$^{-1}$) ν 3390, 2926, 2852, 1712, 1585, 1538, 1448, 1407, 1376, 1351, 1152, 1104, 972, 940, 888. HRMS (EI-MS) C$_{19}$H$_{24}$N$_6$ [M+H]$^+$, calculated m/z 337.213521, found m/z 337.213503.

Example 51: 2-Chloro-7-methyl-N-tetralin-1-yl-pyrido[3,2-d]pyrimidin-4-amine (72)

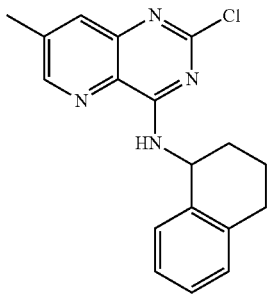 [SMILES: Cc1cnc2c(NC3CCCc4ccccc43)nc(Cl)nc2c1]

Product 69 (80 mg, 0.375 mmol) was dissolved in anhydrous THF (6 mL) and the mixture placed at 0° C. The successive addition was made of 1,2,3,4-tetrahydronaphthylamine (0.06 mL, 0.041 mmol), 1.1 petroleum ether and triethylamine (0.48 mL, 0.41 mmol, 101 eq.), and the mixture left under stirring overnight at ambient temperature. The THF was evaporated and the residue obtained taken up in saturated NaHCO$_3$ solution (20 mL) and extracted with dichloromethane (2×20 mL). The combined organic phase was dried over magnesium sulfate, filtered and concentrated in vacuo. The crude product was chromatographed on silica gel (eluting gradient: EP to EP/AcOEt 80:20) to give the title product 72 in the form of a yellowish solid (70 mg, 67%). $R_f$ (EP/AcOEt 30:70): 0.68. $^1$H NMR (400 MHz, CDCl$_3$) 58.49-8.38 (m, 1H), 7.76 (dt, J=2.0, 1.0 Hz, 1H), 7.46 (d, J=9.0 Hz, 1H), 7.35-7.06 (m, 4H), 5.59 (dt, J=9.0, 5.9 Hz, 1H), 2.85 (q, J=5.9 Hz, 2H), 2.48 (s, 3H), 2.29-1.81 (m, 4H). $^{13}$C NMR (63 MHz, CDCl$_3$) δ 160.2, 158.7, 150.0, 145.8, 139.2, 137.9, 136.1, 134.0, 129.5, 129.0, 128.7, 127.8, 126.5, 48.9, 29.8, 29.4, 20.1, 19.1. IR (Diamond ATR, cm$^{-1}$) ν 3271, 2930, 2861, 1577, 1537, 1466, 1389, 1322, 1271, 1190, 1127, 1035, 956, 873, 822. HRMS (EI-MS) Cl$_8$H$_{17}$ClN$_4$ [M+H]$^+$, calculated m/z 325.121451, found m/z 325.121362. $T_m$: 185-166° C.

Example 52: 2-(3,5-Dimethylpyrazol-1-yl)-7-methyl-N-tetralin-1-yl-pyrido[3,2-d]pyrimidin-4-amine (73)

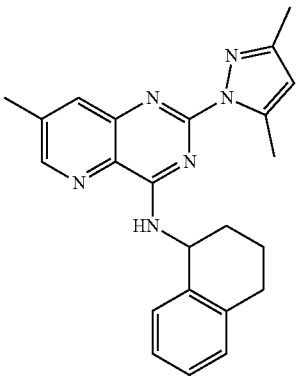 [SMILES: Cc1cnc2c(NC3CCCc4ccccc43)nc(-n3nc(C)cc3C)nc2c1]

Product 72 (67 mg, 0.206 mmol) was dissolved in 10 mL of dioxane followed by the addition of hydrazine monohydrate (0.357 mL, 7.4 mmol, 36 eq.). After overnight refluxing, the reaction mixture was dried under vacuum. The crude product was taken up in 10 mL of ethyl acetate. The organic phase was washed with water (3×10 mL), dried over MgSO₄, filtered and evaporated under vacuum. The crude product was dissolved in 10 mL of ethanol, and 2,4-pentadione (0.023 mL, 0.23 mmol, 1.05 eq.) was added. After overnight refluxing, the solvent was evaporated under reduced pressure. The organic phase was washed with saline solution (5×15 mL), dried over MgSO₄, filtered and evaporated under vacuum. The crude product was finally purified on silica eluting with EP/ethyl acetate (50:50). Product 73 was obtained with a yield of 38% in the form of a yellowish oil. $R_f$ (EP/AcOEt 30:70): 0.25. ¹H NMR (400 MHz, CDCl₃) δ 8.40 (d, J=2.0 Hz, 1H), 8.03 (dd, J=2.0, 1.1 Hz, 1H), 7.48 (d, J=8.7 Hz, 1H), 7.41-7.33 (m, 1H), 7.30-7.13 (m, 3H), 6.05 (s, 1H), 5.61 (m, 1H), 2.89 (m, 2H), 2.76 (s, 3H), 2.50 (s, 3H), 2.38 (s, 3H), 2.29-2.04 (m, 2H), 2.07-1.89 (m, 2H). ¹³C NMR (101 MHz, CDCl₃) δ 159.7, 154.6, 150.8, 148.8, 145.9, 142.6, 138.5, 137.7, 136.2, 134.9, 129.3, 128.9, 128.9, 128.2, 127.6, 126.4, 110.00, 77.4, 77.3, 77.0, 76.7, 49.1, 29.7, 29.3, 20.0, 19.0, 15.9, 13.9. IR (Diamond ATR, cm⁻¹) ν 3392, 2930, 2862, 1732, 1595, 1568, 1458, 1419, 1380, 1351, 1152, 1104, 972, 940, 890. HRMS (EI-MS) $C_{23}H_{24}N_6$ [M+H]⁺, calculated m/z: 385.213521, found m/z: 385.213551.

Example 53: 7-Hexoxy-N-tetralin-1-yl-pyrido[3,2-d]pyrimidin-3-ium-4-amine chloride (74)

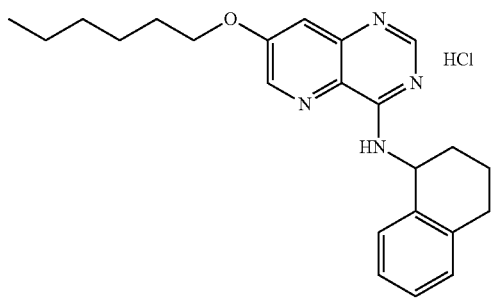 [SMILES: CCCCCCOc1cnc2c(NC3CCCc4ccccc43)ncnc2c1 ; Cl]

Compound 41 (26 mg, 0.069 mmol) was solubilised 5 mL of methanol. A solution of HCl in methanol (0.056 mL, 0.069 mmol, 1.0 eq., C=1.27 M) was added dropwise. After overnight stirring at ambient temperature, the solvent was evaporated under reduced pressure. The crude product was taken up in 5 mL of diethyl ether. After trituration, the solvent was evaporated under vacuum. This operation was performed 3 times and product 74 was obtained in the form of a white solid with quantitative yield. $R_f$ (EP/AcOEt 80:20): 0.00. ¹H NMR (400 MHz, DMSO-d₆) δ 10.34 (d, J=8.4 Hz, 1H), 8.91 (s, 1H), 8.70 (d, J=2.5 Hz, 1H), 7.67 (d, J=3.6 Hz, 1H), 7.17 (m, 4H), 5.87-5.77 (m, 1H), 4.25 (t, J=6.4 Hz, 2H), 2.91-2.72 (m, 2H), 2.08 (m, 3H), 1.83 (p, J=6.9 Hz, 3H), 1.48 (p, J=6.9 Hz, 2H), 1.34 (m, 4H), 0.94-0.86 (m, 3H). ¹³C NMR (101 MHz, DMSO-d₆) δ 159.9, 159.6, 143.5, 138.0 136.0, 129.5, 127.8, 127.6, 126.3, 123.0, 69.8, 50.3, 40.6, 40.4, 40.2, 40.0, 39.8, 39.6, 39.4, 31.4, 29.2, 29.1, 28.5, 25.4, 22.5, 21.2, 14.4. IR (Diamond ATR, cm⁻¹) ν 3330, 2929, 1626, 1606, 1565, 1435, 1417, 1369, 1348, 1268, 1236, 1041, 883. HRMS (EI-MS) $C_{23}H_{29}N_4O$ [M+H]⁺, calculated m/z: 377, 2335, found m/z: 377, 2334. $T_m$: 121-123° C.

Example 54: N-Tetralin-1-ylpyrido[3,2-d]pyrimidin-3-ium-4-amine chloride (75)

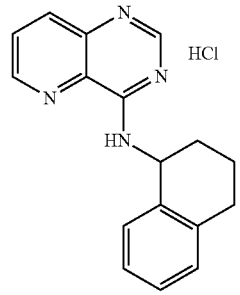

Compound 20 (42 mg, 0.151 mmol) was solubilised in 3 mL of methanol. A solution of HCl in methanol (0.122 mL, 0.151 mmol, 1.0 eq., C=M 1.27) was added dropwise. After overnight stirring at ambient temperature, the solvent was evaporated under reduced pressure. The crude product was taken up in 5 mL of diethyl ether. After trituration, the solvent was evaporated under vacuum. This operation was performed 3 times and product 75 was obtained in the form of a white solid with quantitative yield. $R_f$ (EP/AcOEt 80:20): 0.00. ¹H NMR (400 MHz, DMSO-d₆) δ 10.51 (d, J=9.2 Hz, 1H), 9.02-8.95 (m, 2H), 8.40-8.32 (m, 1H), 8.07 (dd, J=8.6, 4.3 Hz, 1H), 7.26-7.07 (m, 4H), 5.85 (q, J=8.0 Hz, 1H), 2.93-2.73 (m, 2H), 2.22-1.99 (m, 3H), 1.81 (m, 1H). ¹³C NMR (101 MHz, DMSO-d₆) δ 160.6, 152.6, 150.9, 138.0, 135.8, 130.9, 129.9, 129.5, 128.9, 127.9, 127.6, 126.3, 50.5, 29.2, 28.9, 21.1. IR (Diamond ATR, cm⁻¹) ν 3330, 2929, 1626, 1606, 1565, 1435, 1417, 1369, 1348, 1268, 1236, 1041, 883. HRMS (EI-MS) $Cl_7H_{17}N_4$ [M+H]⁺, calculated m/z: 277.1447, found m/z: 277.1448. $T_m$: 121-123° C.

Example 55: N-(1,2,3,4-tetrahydronaphthalen-1-yl)pyrimidin-2-amine (76)

2-chloropyrimidine (200 mg, 1.75 mmol) was dissolved in ethanol (2.2 mL). 1,2,3,4-tetrahydronaphthylamine (0.325 mL, 2.27 mmol, 1.05 eq.) then triethylamine (0.35 mL, 2.62 mmol, 1.05 eq.) were successively added and the mixture brought to 120° C. under microwave radiation for 5 minutes. The medium was taken up in saturated NaHCO₃ solution and extracted with dichloromethane. The organic phase was dried over magnesium sulfate, filtered and concentrated in vacuo. The crude product was chromatographed on silica gel (eluting with: EP/AcOEt 80:20) to give the title product 76 in the form of a yellowish solid (244 mg, 62%). ¹H NMR (400 MHz, CDCl₃) δ 8.34-8.08 (m, 2H), 7.39 (dd, J=7.3, 1.8 Hz, 1H), 7.25-7.10 (m, 3H), 6.53 (t, J=4.8 Hz, 1H), 5.76 (s, 1H), 5.35-5.21 (m, 1H), 2.94-2.73 (m, 2H), 2.18-2.08 (m, 1H), 2.01-1.79 (m, 3H). ¹³C NMR (101 MHz, CDCl₃) δ 19.9, 29.3, 29.9, 49.0, 76.7, 77.0, 77.2, 77.34, 110.5, 126.1, 127.1, 128.8, 129.0, 137.5, 137.6, 158.1, 161.8. IR (Diamond ATR, cm$^{-1}$): 3227, 3098, 3008, 2923, 1586, 1523, 1421, 1360, 1316, 1270, 1257, 1232, 1106, 1089, 1035, 994, 951, 925, 881. HRMS (EI-MS) m/z calculated for $C_{14}H_{16}N_3$ [M+H]$^+$: 225.13, found: 226.134048. $T_m$: 94-96° C.

Example 56: 2,7-dichloropyrido[3,2-d]pyrimidine (78)

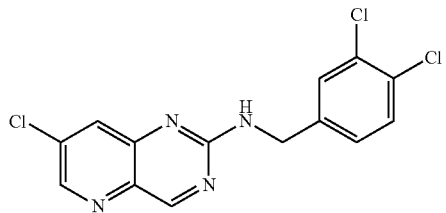 [SMILES: Clc1cnc2cnc(NCc3ccc(Cl)c(Cl)c3)nc2c1]

Product 77 (90 mg, 0.45 mmol) was dissolved in 1,4-dioxane (4 mL) and the successive addition was made 3,4 dichlorobenzylamine (0.07 mL, 0.54 mmol, 1.2 eq.) and triethylamine (0.10 mL, 0.68 mmol, 1.5 q.). The mixture was stirred under reflux overnight. The 1,4-dioxane was evaporated and the residue obtained was taken up in water and extracted with dichloromethane. The organic phase was dried over magnesium sulfate, filtered and concentrated in vacuo. The crude product was chromatographed on silica gel (gradient: petroleum ether→petroleum ether/AcOEt 70:30) to give the title product 78 (138 mg, 90%) in the form of a white solid. $^1$H NMR (250 MHz, DMSO-d$_6$) δ 9.68 (s, 1H), 9.17 (d, J=2.3 Hz, 1H), 8.68 (d, J=2.3 Hz, 1H). $^{13}$C NMR (62.5 MHz, DMSO-d$_6$) δ 164.9, 157.5, 152.7, 148.0, 137.1, 136.5, 133.7. IR (Diamond ATR, cm$^{-1}$) ν 3043, 2167, 1594, 1538, 1433, 1353, 1215, 1117, 1072, 910. HRMS (EI-MS) m/z calculated for $C_7H_3Cl_2N_3$ [M+H]$^+$: 198.9704, found: 198.9715. $T_m$: 178-180° C.

Example 57: 7-chloro-N-(3,4-dichlorobenzyl)pyrido[3,2-d]pyrimidin-2-amine (79)

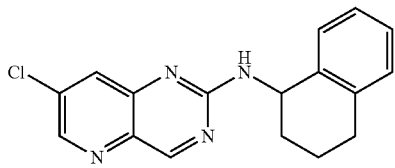 [SMILES: Clc1cnc2cnc(NC3CCCc4ccccc43)nc2c1]

Product 77 (70 mg, 0.35 mmol) was dissolved in 1,4-dioxane (3 mL). 1,2,3,4-tetrahydronaphthylamine (0.06 mL, 0.42 mmol, 1.2 eq.) and triethylamine (0.07 mL, 0.53 mmol, 1.5 eq.) were successively added and the mixture refluxed overnight under stirring. The 1,4-dioxane was evaporated and the residue obtained was taken up in water and extracted with dichloromethane. The organic phase was dried over magnesium sulfate, filtered and concentrated in vacuo. The crude product was chromatographed on silica gel (gradient: petroleum ether→petroleum ether/AcOEt 96:04) to give the title product 79 (90 mg, 83%) in the form of a yellow solid. R (petroleum ether/AcOEt 80:20): 0.18. $^1$H NMR (250 MHz, CDCl$_3$) δ 9.16 (s, 1H), 8.54 (d, J=2.2 Hz, 1H), 7.88 (s, 1H), 7.48 (d, J=1.8 Hz, 1H), 7.40 (d, J=8.2 Hz, 1H), 7.22 (dd, J=8.2, 1.9 Hz, 1H), 5.95 (s, 1H), 4.71 (d, J=6.2 Hz, 2H).

$^{13}$C NMR (101 MHz, CDCl$_3$) δ 166.7, 163.4, 148.6, 146.7, 139.1, 136.3, 135.3, 132.8, 132.2, 131.5, 130.7, 129.6, 127.0, 44.8. IR (Diamond ATR, cm$^{-1}$) ν 3266, 3094, 1602, 1584, 1538, 1392, 1269, 1130, 1080, 964, 893, 821. HRMS (EI-MS) m/z calculated for $C_{14}H_9Cl_3N_4$ [M+H]$^+$: 338.996556, found: 338.996638. $T_m$: 154-156° C.

Example 58: 2-Chloro-pyrido[2,3-d]pyrimidine (81)

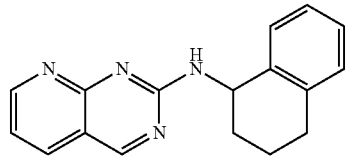 [SMILES: c1ccc2c(c1)CCCC2Nc1ncc2cccnc2n1]

Product 80 (100 mg, 0.60 mmol) was dissolved in 1,4-dioxane (7 mL) after which 1,2,3,4-tetrahydronaphthylamine (0.10 mL, 0.75 mmol, 1.2 eq.) and triethylamine (0.11 mL, 0.79 mmol, 1.5 eq.) were successively added and the mixture refluxed overnight under stirring. The 1,4-dioxane was evaporated and the residue obtained was taken up in water and extracted with dichloromethane. The organic phase was dried over magnesium sulfate, filtered and concentrated in vacuo. The crude product was chromatographed on silica gel (gradient: CH$_2$Cl$_2$→CH$_2$Cl$_2$/MeOH 99.5:0.5) to give the title product 81 (116 mg, 70%) in the form of a yellow solid. R$_f$(CH$_2$Cl$_2$/MeOH 98:02): 0.28. $^1$H NMR (250 MHz, CDCl$_3$) δ 9.32 (s, 1H), 9.24 (dd, J=4.1, 1.9 Hz, 1H), 8.34 (dd, J=7.9, 1.9 Hz, 1H), 7.65 (dd, J=7.9, 4.2 Hz, 1H). $^{13}$C NMR (101 MHz, CDCl$_3$) δ 163.0, 161.1, 160.3, 157.5, 138.0, 137.1, 136.7, 129.7, 129.2, 127.3, 126.3, 118.3, 114.2, 49.1, 29.5, 29.3, 19.7. IR (Diamond ATR, cm$^{-1}$) ν 3242, 3021, 2919, 1595, 1540, 1402, 1294, 1228, 1094, 932, 883. HRMS (EI-MS) m/z calculated for $C_{17}H_{16}N_4$ [M+H]$^+$: 277.144773, found: 277.145002. $T_m$: 180-182° C.

Example 59: 2-Chloro-N-(4-fluorophenyl)pyrido[3,2-d]pyrimidin-4-amine (82)

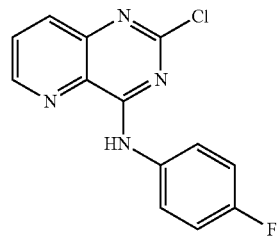 [SMILES: Fc1ccc(Nc2nc(Cl)nc3cccnc23)cc1]

Product 2 (200 mg, 1.0 mmol) was dissolved in anhydrous THF (15 mL) and the mixture placed at 0° C. after which 4-fluoroaniline (122 mg, 1.1 mmol, 1.1 eq.) and triethylamine (0.15 mL, 1.1 mmol, 1.1 eq.) were successively added and the mixture left under stirring overnight at ambient temperature. The THF was evaporated and the residue obtained taken up in saturated NaHCO$_3$ solution and extracted with dichloromethane. The organic phase was dried over magnesium sulfate, filtered and concentrated in vacuo. The crude product was chromatographed on silica gel (eluting gradient: EP→EP/AcOEt 80:20) to give the title product 82 in the form of a yellowish solid (201 mg, 73%).

Rf (petroleum ether/AcOEt 30:70): 0.34. $^1$H NMR (400 MHz, CDCl$_3$) δ 9.24 (s, 1H), 8.79 (dd, J=4.3, 1.5 Hz, 1H), 8.12 (dd, J=8.5, 1.5 Hz, 1H), 7.94-7.87 (m, 2H), 7.75 (dd, J=8.5, 4.2 Hz, 1H), 7.20-7.13 (m, 2H). $^{13}$C NMR (101 MHz, CDCl$_3$) δ 160.8, 158.4, 157.9, 157.9, 148.7, 145.8, 135.4, 133.4, 133.4, 130.4, 128.6, 122.3, 122.2, 116.0, 115.8, 77.3, 77.2, 77.0, 76.7. $^{19}$F NMR (376 MHz, CDCl$_3$) 5-117.05. IR (Diamond ATR, cm$^{-1}$) v3380, 1670, 1640, 1552, 1469, 1398, 1375, 1283, 1237, 1136, 971, 877. HRMS (EI-MS) C$_{13}$H$_9$ClN$_4$ [M+H]$^+$, calculated m/z: 275.0494, found m/z: 275.0497. T$_m$: 156-158° C.

Example 60: 2-(3,5-Dimethylpyrazol-1-yl)-N-(4-fluorophenyl)pyrido[3,2-d]pyrimidin-4-amine (83)

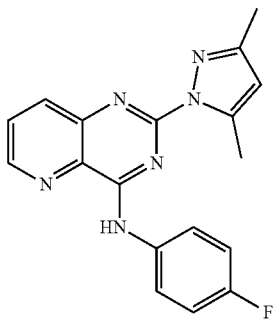 [SMILES: Cc1cc(C)n(-c2nc(Nc3ccc(F)cc3)c3ncccc3n2)n1]

Product 82 (85, 0.576 mmol) was dissolved in 10 mL of dioxane followed by the addition of hydrazine monohydrate (0.976 mL, 20.7 mmol, 36 eq.). After overnight refluxing, the reaction mixture was dried under vacuum. The crude product was taken up in 10 mL of ethyl acetate. The organic phase was washed with water (3×10 mL), dried over MgSO$_4$, filtered and evaporated under vacuum. The crude product was dissolved in 10 mL of ethanol, and 2,4-pendadione (0.063 mL, 0.67 mmol, 1.05 eq.) was added. After overnight refluxing, the solvent was evaporated under reduced pressure. The organic phase was washed with saline solution (5×15 mL), dried over MgSO$_4$, filtered and evaporated under vacuum. The crude was finally purified on silica eluting with petroleum ether/ethyl acetate (50:50). Product 83 was obtained with a yield of 32% in the form of yellowish solid. R$_f$ (petroleum ether/AcOEt 30:70): 0.33. $^1$H NMR (400 MHz, CDCl$_3$) δ 9.17 (s, 1H), 8.71 (dd, J=4.3, 1.5 Hz, 1H), 8.28 (dd, J=8.5, 1.5 Hz, 1H), 7.84-7.74 (m, 2H), 7.70 (dd, J=8.5, 4.3 Hz, 1H), 7.19-7.06 (m, 2H), 6.04 (s, 1H), 2.59 (s, 3H), 2.37 (s, 3H). $^{13}$C NMR (101 MHz, CDCl$_3$) δ 161.0, 158.5, 158.3, 154.0, 151.2, 147.6, 145.9, 142.6, 136.2, 133.5, 133.5, 130.0, 128.3, 123.6, 123.5, 115.8, 115.6, 110.0, 77.3, 77.2, 77.0, 76.7, 29.69, 15.4, 13.9. $^{19}$F NMR (376 MHz, CDCl$_3$) 5-117.05. IR (Diamond ATR, cm$^{-1}$) v 3356, 2922, 1606, 1587, 1567, 1544, 1505, 1470, 1444, 1420, 1380, 1351, 1311, 1283, 1137, 1036, 891. HRMS (EI-MS) C$_{18}$H$_{15}$FN$_6$ [M+H]$^+$, calculated m/z: 335.141499, found m/z: 335.141422. T$_m$: 176-178° C.

Example 61: 2-Chloro-N-(1,2,3,4-tetrahydronaphthalen-1-yl)pyrido[2,3-d]pyrimidin-4-amine (84)

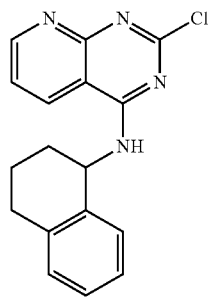 [SMILES: Clc1nc(NC2CCCc3ccccc32)c2cccnc2n1]

Product 43 (280 mg, 1.4 mmol) was dissolved in anhydrous THF (6 mL) and the mixture placed at 0° C. The successive addition was made of 1,2,3,4-tetrahydronaphthylamine (0.19 mL, 1.4 mmol, 1.0 eq.) and triethylamine (0.14 mL, 1.4 mmol, 1.0 eq.) and the mixture left under stirring overnight at ambient temperature. The THF was evaporated and the residue obtained taken up in saturated NaHCO$_3$ solution and extracted with dichloromethane. The organic phase was dried over magnesium sulfate, filtered and concentrated in vacuo. The crude product was chromatographed on silica gel (gradient CH$_2$Cl$_2$ to CH$_2$Cl$_2$/MeOH 99:1) to give the title product 84 in the form of a yellowish solid (162 mg, 40%). R$_f$ (CH$_2$Cl$_2$/MeOH 99:1): 0.22. $^1$H NMR (400 MHz, DMSO-d6) δ 9.27 (d, J=8.2 Hz, 1H), 8.98 (dd, J=4.4, 1.9 Hz, 1H), 8.84 (dd, J=8.2, 1.9 Hz, 1H), 7.55 (dd, J=8.2, 4.4 Hz, 1H), 7.27-7.10 (m, 4H), 5.69-5.58 (m, 1H), 2.93-2.74 (m, 2H), 2.15-1.75 (m, 4H). $^{13}$C NMR (101 MHz, DMSO-d$_6$) δ 162.0, 160.7, 159.5, 156.7, 137.9, 133.7, 129.4, 128.5, 127.6, 126.5, 122.0, 109.0, 49.5, 29.5, 29.3, 20.7. IR (Diamond ATR, cm$^{-1}$) v 3294, 2942, 2359, 1600, 1559, 1526, 1478, 1452, 1351, 1284, 1240, 1202, 1161, 1047, 955, 942. HRMS (EI-MS) C$_{17}$H$_{15}$ClN$_4$ [M+H]$^+$, calculated m/z: 311.1058, found m/z: 311.1060.

General procedure B: Compound 85 is dissolved in 5 mL of anhydrous THF to give a yellow solution to which the desired amine is added. The solution becomes turbid. Triethylamine is added and the solution left at ambient temperature for 2 hours under vigorous stirring. Disappearance of the starting reagent is monitored by TLC, and on completion of the reaction the THF is evaporated. The deposit obtained is taken up in 30 mL of water and the product extracted with 3×20 mL ethyl acetate.

The organic phases are combined and washed with saturated aqueous NaCl solution and finally dried over MgSO$_4$. After filtering, the solvent is evaporated and the product purified on a silica column.

Example 62: N-(1-Naphtyl)pyrido[3,2-d]pyrimidin-4-amine (86)

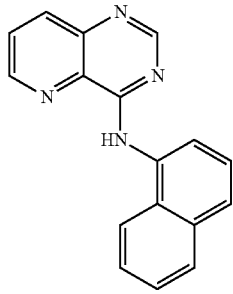 [SMILES: c1ccc2c(Nc3ncnc4cccnc34)cccc2c1]

Compound 86 was obtained following procedure B with compounds 85 (200 mg; 1 mmol), naphthylamine (246 mg; 1.7 mmol) and triethylamine (0.28 mL; 2 mmol). The product was purified on a silica column using a solvent system of 60% petroleum ether and 40% ethyl acetate. The product was obtained in the form of a yellow solid (106 mg; 38%). Rf (EP/AcOEt 50:50): 0.41. $^1$H NMR (400 MHz, DMSO-$d_6$) δ 10.48 (1H; br s; NH), 8.99 (1H; m), 8.44 (1H; s), 8.23 (1H; m), 7.95 (4H; m), 7.83 (1H; m), 7.55 (3H; m). $^{13}$C NMR (100 MHz, DMSO-$d_6$) δ 159.4, 155.7, 149.4, 144.6, 135.8, 134.1, 134.0, 131.5, 129.2, 128.7, 128.3, 126.4, 126.3, 126.2, 125.8, 123.7, 122.9. IR (Diamond ATR, cm$^{-1}$) ν 3347, 3056, 1584, 1538, 1372, 1302, 783, 761, 678, 598. HRMS (EI-MS): m/z calculated for $C_{17}H_{13}N_4$ [M+H]$^+$: 273.1134, found: 273.1136. $T_m$: 180-182° C.

Example 63: N-(2,3-dihydro-1H-inden-1-yl)pyrido[3,2-d]pyrimidin-4-amine (87)

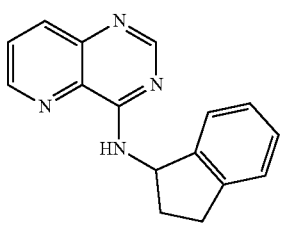 [SMILES: c1ccc2c(c1)CCC2Nc1ncnc2cccnc12]

Compound 87 was obtained following procedure B with compounds 1-Indanamine 96 (60 mg; 0.45 mmol), 85 (53 mg; 0.27 mmol) and triethylamine (0.08 mL; 0.53 mmol). The product was purified on a silica column with 99% CH$_2$Cl$_2$ and 1% MeOH solvent system. The product was obtained in the form of a yellow solid (57 mg; 81%). R$_f$ (EP/AE 50:50): 0.52. $^1$H NMR (400 MHz, CDCl$_3$) δ 8.69 (s, 1H), 8.65 (m, 1H), 8.10 (m, 1H), 7.64 (m, 1H), 7.30 (m, 5H), 5.93 (m, 1H), 3.09 (m, 1H), 2.99 (m, 1H), 2.77 (m, 1H), 2.05 (m, 1H). $^{13}$C NMR (100 MHz, CDCl$_3$) δ 159.7, 156.6, 148.3, 144.5, 143.7, 143.1, 135.9, 132.1, 128.3, 127.8, 126.9, 125.0, 124.4, 55.9, 34.1, 30.5. IR (Diamond ATR, cm$^{-1}$) ν 3367, 2950, 1581, 1481, 1446, 1379, 1362, 1313, 763, 741, 594. HRMS (EI-MS): m/z calculated for $C_{16}H_{15}N_4$ [M+H]$^+$: 263.1291, found: 263.1292. $T_m$: 135-137° C.

Example 64: N-(5-methoxy-1,2,3,4-tetrahydronaphthalen-1-yl)pyrido[3,2-d]pyrimidin-4-amine (88)

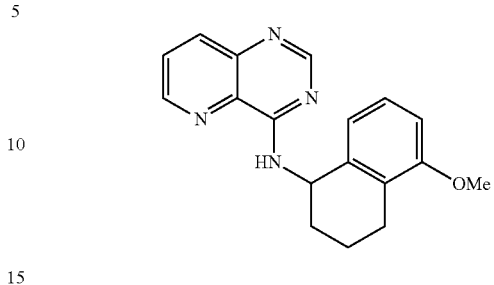

Compound 88 was obtained following procedure B with compounds 5-methoxy-1,2,3,4-tetrahydro-1-Naphthalenamine 97 (50 mg; 0.28 mmol), 85 (33 mg; 0.17 mmol) and triethylamine (0.05 mL; 0.33 mmol). The product was purified on a silica column with 99% CH$_2$Cl$_2$ and 1% MeOH solvent system. The product was obtained in the form of a yellow solid (41 mg; 80%). R$_f$ (CH$_2$Cl$_2$/MeOH 98:2): 0.35. $^1$H NMR (400 MHz, CDCl$_3$) δ 8.68 (s, 1H), 8.63 (m, 1H), 8.09 (m, 1H), 7.63 (m, 1H), 7.45 (m, 1H), 7.14 (m, 1H), 6.97 (m, 1H), 6.77 (m, 1H), 5.61 (m, 1H), 3.85 (s, 3H), 2.75 (m, 2H), 2.15 (m, 1H), 2.05 (m, 1H), 1.94 (m, 2H). $^{13}$C NMR (100 MHz, CDCl$_3$) δ 159.2, 157.3, 156.7, 148.2, 144.5, 137.7, 135.9, 132.2, 127.7, 127.0, 126.7, 120.9, 108.7, 55.5, 48.8, 29.2, 23.1, 19.5. IR (Diamond ATR, cm$^{-1}$) ν 3352, 2943, 1578, 1461, 1380, 1309, 1249, 1094, 1014, 764, 656. HRMS (EI-MS): m/z calculated for $C_{18}H_{19}N_4O$ [M+H]$^+$: 307.1553, found: 307.1552. $T_m$: 135-137° C.

Example 65: N-(7-methoxy-1,2,3,4-tetrahydronaphthalen-1-yl)pyrido[3,2-d]pyrimidin-4-amine (89)

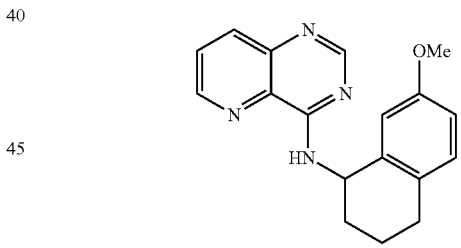

Compound 89 was obtained following procedure B with compounds 7-methoxy-1,2,3,4-tetrahydronaphthalen-1-amine 98 (70 mg; 0.4 mmol), 85 (47 mg; 0.24 mmol) and triethylamine (0.07 mL; 0.47 mmol). The product was purified on a silica column with 99% CH$_2$Cl$_2$ and 1% MeOH solvent system. The product was obtained in the form of a white solid (65 mg; 92%). R$_f$ (CH$_2$Cl$_2$/MeOH 98:2): 0.32. $^1$H NMR (400 MHz, CDCl$_3$) δ 8.66 (1H; s), 8.57 (1H; m), 8.06 (1H; m), 7.58 (1H; m), 7.49 (1H; m), 7.11 (1H; m), 6.95 (1H; m), 6.73 (1H; m), 5.59 (1H; m), 3.82 (3H; s), 2.69 (2H; m), 2.13 (1H; m), 2.00 (1H; m), 1.89 (2H; m). $^{13}$C NMR (100 MHz, CDCl$_3$) δ 159.1, 157.2, 156.6, 148.1, 144.4, 137.6, 135.8, 132.1, 127.6, 126.8, 126.6, 120.8, 108.6, 55.4, 48.7, 29.1, 23.0, 19.4. IR (Diamond ATR, cm$^{-1}$) ν 3352, 2942, 1577, 1541, 1309, 1094, 797, 720, 527. HRMS (EI-MS): m/z calculated for $C_{18}H_{19}N_4O$ [M+H]$^+$: 307.1553, found: 307.1554. $T_m$: 143-145° C.

Example 66: N-(7-fluoro-1,2,3,4-tetrahydronaphthalen-1-yl)pyrido[3,2-d]pyrimidin-4-amine (90)

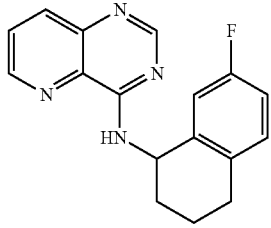 [SMILES: Fc1ccc2c(c1)C(Nc1ncnc3cccnc13)CCC2]

Compound 90 was obtained following procedure B with compounds 7-fluoro-1,2,3,4-tetrahydro-1-Naphthalen-1-amine 99 (200 mg; 1.2 mmol), 85 (142 mg; 0.72 mmol) and triethylamine (0.2 mL; 1.44 mmol). The product was purified on a silica column with 99% $CH_2Cl_2$ and 1% MeOH solvent system. The product was obtained in the form of a colourless oil (196 mg; 93%). $R_f$ ($CH_2Cl_2$/MeOH 98:2): 0.30. $^1$H NMR (250 MHz, CDCl$_3$) δ 8.66 (s, 1H), 8.63 (m, 1H), 8.09 (m, 1H), 7.62 (m, 1H), 7.43 (m, 1H), 7.05 (m, 2H), 6.87 (m, 1H), 5.61 (m, 1H), 2.78 (m, 2H), 2.19 (m, 1H), 1.94 (m, 3H). $^{13}$C NMR (62.5 MHz, CDCl$_3$) δ 161.3 (J=244.0 Hz), 159.3, 156.5, 148.3, 144.5, 138.5 (J=6.0 Hz), 135.9, 133.1 (J=3.0 Hz), 132.0, 130.6 (J=8.0 Hz), 127.8, 114.9 (J=20.0 Hz), 114.6 (J=20.0 Hz), 48.6, 29.6, 28.7, 20.4. IR (Diamond ATR, cm$^{-1}$) v 3249, 2929, 1577, 1531, 1361, 1105, 919, 827, 685. HRMS (EI-MS): m/z calculated for $C_{17}H_{16}N_4F$ [M+H]$^+$: 295.1354, found: 295.1353. $T_m$: 79-81° C.

Example 67: N-(4,5,6,7-tetrahydrobenzo[b]thiophen-4-yl)pyrido[3,2-d]pyrimidin-4-amine (91)

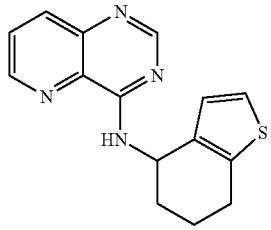 [SMILES: c1cnc2c(NC3CCCc4sccc43)ncnc2c1]

Compound 91 was obtained following procedure B with compounds 4,5,6,7-tetrahydrobenzo[b]thiophen-4-amine 100 (130 mg; 0.85 mmol), 85 (99 mg; 0.5 mmol) and triethylamine (0.14 mL; 1 mmol). The product was purified on a silica column with 96% $CH_2Cl_2$ and 4% MeOH solvent system. The product was obtained in the form of a white solid (98 mg; 70%). $R_f$ ($CH_2Cl_2$/MeOH 95:5): 0.77. $^1$H NMR (400 MHz, CDCl$_3$) δ 8.65 (s, 1H), 8.60 (m, 1H), 8.07 (m, 1H), 7.61 (m, 1H), 7.40 (m, 1H), 7.06 (m, 1H), 6.91 (m, 1H), 5.52 (m, 1H), 2.84 (m, 2H), 2.18 (m, 1H), 1.98 (m, 3H). $^{13}$C NMR (100 MHz, CDCl$_3$) δ 159.1, 156.5, 148.2, 144.4, 139.1, 135.9, 135.2, 132.1, 127.7, 126.8, 122.9, 46.3, 29.5, 25.0, 21.00. IR (Diamond ATR, cm$^{-1}$) v 3379, 2924, 1600, 1583, 1364, 1150, 1111, 829, 686, 582. HRMS (EI-MS): m/z calculated for $C_{15}H_{15}N_4S$ [M+H]$^+$: 283.1012, found: 283.1012. $T_m$: 149-151° C.

Example 68: N-(6-methoxy-1,2,3,4-tetrahydronaphthalen-1-yl)pyrido[3,2-d]pyrimidin-4-amine (92)

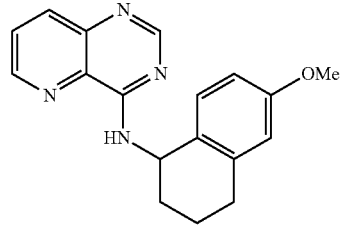 [SMILES: COc1ccc2c(c1)CCCC2Nc1ncnc2cccnc12]

Compound 92 was obtained following procedure B with compounds 6-methoxy-1,2,3,4-tetrahydronaphthalen-1-amine (100 mg; 0.565 mmol), 85 (66 mg; 0.33 mmol) and triethylamine (0.1 mL; 0.66 mmol). The product was purified on a silica column with 96% $CH_2Cl_2$ and 4% MeOH solvent system. The product was obtained in the form of a white solid (91 mg; 89%). Rf ($CH_2Cl_2$/MeOH 95:5): 0.62. $^1$H NMR (250 MHz, CDCl$_3$) δ 8.64 (m, 1H), 8.57 (m, 1H), 8.05 (m, 1H), 7.57 (m, 1H), 7.42 (m, 1H), 7.22 (m, 1H), 6.68 (m, 1H), 6.64 (m, 1H), 5.53 (m, 1H), 3.75 (m, 3H), 2.78 (m, 2H), 2.16 (m, 1H), 2.09 (m, 1H), 1.95 (m, 2H). $^{13}$C NMR (62.5 MHz, CDCl$_3$) δ 159.0, 158.8, 156.5, 148.1, 144.4, 139.1, 135.8, 132.1, 130.2, 128.6, 127.6, 113.6, 112.7, 55.3, 48.2, 29.7, 29.6, 19.9. IR (Diamond ATR, cm$^{-1}$) v 3414, 2956, 2830, 1609, 1575, 1294, 1234, 1111, 920, 838, 685, 632. HRMS (EI-MS): m/z calculated for $C_{18}H_{19}N_4O$ [M+H]$^+$: 307.1553, found: 307.1554. $T_n$: 104-106° C.

Example 69: N-(4,4-dimethyl-1,2,3,4-tetrahydronaphthalen-1-yl)pyrido[3,2-d]pyrimidin-4-amine 90 (93)

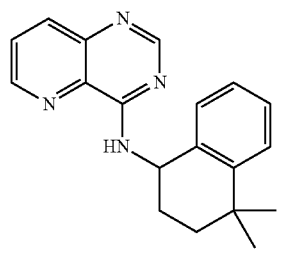 [SMILES: CC1(C)CCC(Nc2ncnc3cccnc23)c2ccccc21]

Compound 93 was obtained following procedure B with compounds 4,4-dimethyl-1,2,3,4-tetrahydronaphthalen-1-amine 101 (111 mg; 0.64 mmol), 85 (74 mg; 0.37 mmol) and triethylamine (0.11 mL; 0.74 mmol). The product was purified on a silica column with isocratic 100% $CH_2Cl_2$ system. The product was obtained in the form of a yellow solid (10 mg; 9%). $R_f$ ($CH_2Cl_2$/MeOH 95:5): 0.42. $^1$H NMR (250 MHz, CDCl$_3$) δ 8.65 (s, 1H), 8.69 (m, 1H), 8.12 (m, 1H), 7.65 (m, 1H), 7.43 (m, 2H), 7.29 (m, 2H), 7.15 (m, 1H), 5.60 (m, 1H), 2.26 (m, 1H), 2.07 (m, 1H), 1.84 (m, 2H), 1.40 (s, 3H), 1.34 (s, 3H). $^{13}$C NMR (62.5 MHz, CDCl$_3$) δ 159.4, 156.7, 148.3, 146.5, 144.5, 136.0, 135.5, 132.2, 128.6, 128.0, 127.8, 127.1, 126.3, 49.6, 35.8, 34.1, 31.8, 31.7, 26.2. IR (Diamond ATR, cm$^{-1}$) v 3227, 2960, 1578, 1479, 1270, 1148, 807, 686, 612. HRMS (EI-MS): m/z calculated for $C_{19}H_{21}N_4$ [M+H]$^+$: 305.1760, found: 305.1757. $T_m$: 200-202° C.

General procedure C: compound 19 is dissolved in 5 mL of dioxane to give a yellow solution to which the desired amine and triethylamine are added. The solution becomes turbid and is heated to 90° C. for 2 days. Disappearance of the starting reagent is monitored by TLC, and on completion of the reaction the solution is diluted with 30 mL ethyl acetate. After two washes with water, the organic phases are combined and washed with saturated aqueous NaCl solution and finally dried over $MgSO_4$. After filtering, the solvent is evaporated and the product is purified on a silica column.

Example 70: ((S)—N-(1,2,3,4-tetrahydronaphthalen-1-yl)-2-(1H-1,2,4-triazol-1-yl)pyrido[3,2-d]pyrimidin-4-amine (94)

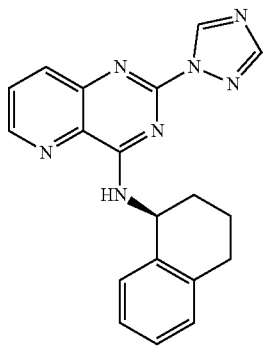 [SMILES: c1ccc2c(c1)CCC[C@@H]2Nc1nc(-n2cncn2)nc2cccnc12]

Compound 94 was obtained following procedure C with compounds 19 (100 mg; 0.32 mmol), 1,2,4-triazole (30 mg; 0.4 mmol) and triethylamine (0.05 mL; 0.4 mmol). The product was purified on a silica column with 97% $CH_2Cl_2$ and 3% MeOH solvent system. The product was obtained in the form of a white solid (62 mg; 56%). Rf ($CH_2Cl_2$/MeOH 94:6): 0.38. $^1$H NMR (400 MHz, $CDCl_3$) δ 9.30 (s, 1H), 8.64 (m, 1H), 8.26 (m, 1H), 8.18 (s, 1H), 7.72 (m, 1H), 7.68 (m, 1H), 7.36 (m, 1H), 7.22 (m, 3H), 5.69 (m, 1H), 2.92 (m, 2H), 2.27 (m, 1H), 2.15 (m, 1H), 1.99 (m, 2H). $^{13}$C NMR (100 MHz, $CDCl_3$) δ 160.3, 153.5, 151.4, 148.1, 145.3, 144.2, 137.8, 136.1, 135.7, 131.4, 129.5, 128.8, 128.6, 127.9, 126.6, 49.4, 29.5, 29.3, 20.1. IR (Diamond ATR, $cm^{-1}$) ν 3500, 2929, 1585, 1503, 1423, 1386, 1000, 940, 870, 734, 670. HRMS (EI-MS): m/z calculated for $C_{19}H_{18}N_7$ $[M+H]^+$: 344.1618, found: 344.1617. $T_m$: 171-173° C.

Example 71: (S)-2-(1H-imidazol-1-yl)-N-(1,2,3,4-tetrahydronaphthalen-1-yl)pyrido[3,2-d]pyrimidin-4-amine (95)

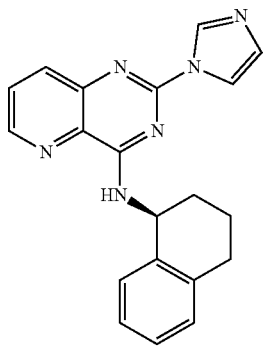 [SMILES: c1ccc2c(c1)CCC[C@@H]2Nc1nc(-n2ccnc2)nc2cccnc12]

Compound 95 was obtained following procedure C with compounds 19 (100 mg; 0.32 mmol), imidazole (30 mg; 0.4 mmol) and triethylamine (0.05 mL; 0.4 mmol). The product was purified on a silica column eluting with 94% $CH_2Cl_2$ and 6% MeOH. The product was obtained in the form of a white solid (71 mg; 65%). $R_f$ ($CH_2Cl_2$/MeOH 90:10): 0.75. $^1$H NMR (250 MHz, $CDCl_3$) δ 8.70 (s, 1H), 8.56 (m, 1H), 8.03 (m, 1H), 7.99 (s, 1H), 7.63 (m, 2H), 7.36 (m, 1H), 7.19 (m, 4H), 5.65 (m, 1H), 2.90 (m, 2H), 2.26 (m, 1H), 2.15 (m, 1H), 1.97 (m, 2H). $^{13}$C NMR (62.5 MHz, $CDCl_3$) δ 160.2, 151.8, 147.4, 145.5, 137.8, 136.7, 136.1, 135.2, 131.0, 130.2, 129.5, 128.9, 128.3, 127.8, 126.5, 117.0, 49.2, 29.6, 29.4, 20.1. IR (Diamond ATR, $cm^{-1}$) ν 3340, 2934, 1549, 1426, 1315, 1036, 1014, 819, 737, 649. HRMS (EI-MS): m/z calculated for $C_{20}H_{19}N_6$ $[M+H]^+$: 343.1665, found: 343.1666. $T_m$: 187-189° C.

Example 72: N-(6-(Methoxymethoxy)-1,2,3,4-tetrahydronaphthalen-1-yl)pyrido[3,2-d]pyrimidin-4-amine (104)

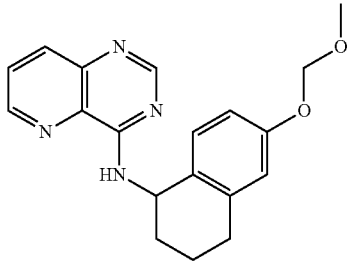 [SMILES: COCOc1ccc2c(c1)CCCC2Nc1ncnc2cccnc12]

Compound 104 was obtained following procedure B with compound 103 (70 mg, 0.34 mmol, 1.7 eq.), 85 (40 mg, 0.20 mmol, 1.0 eq.) and triethylamine (0.06 mL, 0.40 mmol, 2.0 eq.). The residue was purified by silica gel chromatography (gradient system 0 to 90% AE/100 to 10% PE). The product was obtained in the form of a white solid (55 mg, 81%). $R_f$ (PE/AE 10:90): 0.42. $^1$H NMR (400 MHz, $CDCl_3$) δ 8.67 (s, 1H), 8.65 (dd, J=4.0, 2.0 Hz, 1H), 8.10 (dd, J=8.0, 2.0 Hz, 1H), 7.64 (dd, J=8.0, 4.0 Hz, 1H), 7.41 (dd, J=8.0 Hz, 1H, NH), 7.27 (d, J=3.0 Hz, 1H), 6.85 (d, J=3.0 Hz, 1H), 6.83 (s, 1H), 5.57 (m, 1H), 5.16 (s, 2H), 3.48 (s, 3H), 2.83 (m, 2H), 2.17 (m, 1H), 2.07 (m, 1H), 1.93 (m, 2H). $^{13}$C NMR (101 MHz, $CDCl_3$) δ 159.1, 156.7, 156.5, 148.2, 144.5, 139.4, 135.9, 132.2, 130.4, 130.0, 127.7, 116.2, 115.0, 94.5, 56.1, 48.3, 29.8, 29.7, 19.9. IR (Diamond ATR, $cm^{-1}$) ν 3405, 2926, 2903, 2869, 1575, 1436, 1317, 1043, 924, 863, 643. HRMS (EI-MS): m/z calculated for $C_{19}H_{21}N_4O_2$ $[M+H]^+$: 337.1659, found: 337.1660. $T_m$: 109-111° C.

Example 73: 5-(pyrido[3,2-d]pyrimidin-4-ylamino)-5,6,7,8-tetrahydro-naphthalen-2-ol (104')

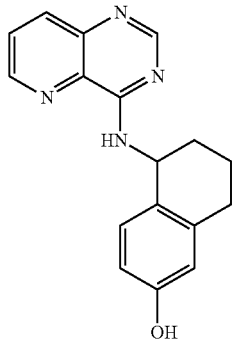 [SMILES: Oc1ccc2c(c1)CCCC2Nc1ncnc2cccnc12]

Compound 104 was dissolved in 5 mL of MeOH and a few drops of concentrated HCl solution (37%) were added at ambient temperature. The mixture was stirred overnight. The mixture was diluted with 20 mL AcOEt and washed with saturated aqueous $Na_2CO_3$ solution (20 mL). The organic phase was washed with saturated aqueous NaCl solution and dried over $MgSO_4$. After filtering, the solvent was evaporated and product 104' was obtained by precipitation in pentane in the form of a white solid (91 mg, 62%). $R_f$ ($CH_2Cl_2$/MeOH 90:10): 0.51. $^1H$ NMR (400 MHz, DMSO-$d_6$) δ 9.22 (s, 1H, OH), 8.76 (dd, J=4.0, 2.0 Hz, 1H), 8.54 (s, 1H), 8.12 (m, 2H), 7.83 (dd, J=8.0, 4.0 Hz, 1H), 6.99 (d, J=9.0 Hz, 1H, NH), 6.52 (m, 2H), 5.50 (m, 1H), 2.71 (m, 2H), 1.99 (m, 2H), 1.91 (m, 1H), 1.73 (m, 1H). $^{13}C$ NMR (101 MHz, DMSO-$d_6$) δ 158.8, 156.1, 156.0, 148.5, 144.1, 138.5, 135.4, 131.3, 129.0, 128.2, 127.3, 114.8, 113.5, 47.7, 29.2, 29.0, 20.2. IR (Diamond ATR, $cm^{-1}$) ν 3343, 2929, 1584, 1545, 1439, 1237, 742. HRMS (EI-MS): m/z calculated for $C_{17}H_{17}N_4O$ $[M+H]^+$: 293.1396, found: 293.1397. $T_m$: 233-235° C.

Example 74: 1-(pyrido[3,2-d]pyrimidin-4-ylamino)-1,2,3,4-tetrahydro-naphthalen-2-ol (107)

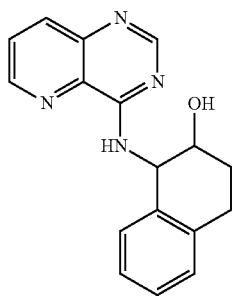 [SMILES: OC1CCc2ccccc2C1Nc1ncnc2cccnc12]

Compound 107 was obtained following procedure B with compound 106 (135 mg, 0.83 mmol, 1.7 eq.), 85 (100 mg, 0.50 mmol, 1.0 eq.) and triethylamine (0.14 mL, 1.0 mmol, 2.0 eq.). The residue was purified by silica gel chromatography (gradient system 0 to 2% MeOH/100 to 98% $CH_2Cl_2$). The product was obtained in the form of a white solid (24 mg, 16%). $R_f$ ($CH_2Cl_2$/MeOH 95:5): 0.40. $^1H$ NMR (400 MHz, $CDCl_3$) δ 8.64 (dd, J=4.0, 2.0 Hz, 1H), 8.62 (s, 1H), 8.10 (dd, J=8.0, 2.0 Hz, 1H), 7.65 (dd, J=8.0, 4.0 Hz, 1H), 7.53 (d, J=7.5 Hz, 1H, NH), 7.35 (m, 1H), 7.22 (m, 3H), 5.44 (t, J=7.5 Hz, 1H), 5.15 (br s, 1H, OH), 4.12 (m, 1H), 2.94 (m, 2H), 2.25 (m, 1H), 1.99 (m, 1H). $^{13}C$ NMR (101 MHz, $CDCl_3$) δ 160.6, 155.8, 148.7, 144.5, 137.5, 136.0, 134.9, 131.9, 129.0, 128.4, 128.1, 127.9, 127.0, 73.9, 58.0, 30.2, 27.7. IR (Diamond ATR, $cm^{-1}$) ν 3264, 2928, 1583, 1438, 1304, 1111, 827, 684. HRMS (EI-MS): m/z calculated for $C_{17}H_{17}N_4O$ $[M+H]^+$: 293.1396, found: 293.1398. $T_m$: 90-92° C.

Example 75: N-(7-Fluoro-1,2,3,4-tetrahydronaphthalen-1-yl)pyrido[3,2-d]pyrimidin-4-amine (110)

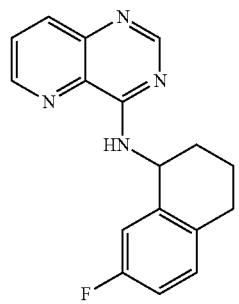 [SMILES: Fc1ccc2c(c1)C(Nc1ncnc3cccnc13)CCC2]

Compound 110 was obtained following procedure B with compounds 109 (200 mg, 1.2 mmol, 1.7 eq.), 85 (142 mg, 0.72 mmol, 1.0 eq.) and triethylamine (0.2 mL, 1.44 mmol, 2.0 eq.). The residue was purified by silica gel chromatography (eluting with $CH_2Cl_2$/MeOH 99:1). The product was obtained in the form of a colourless oil (196 mg, 93%). $R_f$ ($CH_2Cl_2$/MeOH 98:2): 0.30. $^1H$ NMR (400 MHz, $CDCl_3$) δ 8.66 (s, 1H), 8.63 (m, 1H), 8.09 (dd, J=8.0, 1.7 Hz, 1H), 7.62 (dd, J=8.0, 4.0 Hz, 1H), 7.43 (br d, J=5.0 Hz, 1H, NH), 7.05 (m, 2H), 6.87 (td, J=8.0, 3.0 Hz, 1H), 5.61 (q, J=8.0 Hz, 1H), 2.78 (m, 2H), 2.19 (m, 1H), 1.94 (m, 3H). $^{13}C$ NMR (101 MHz, $CDCl_3$) δ 161.3 (J=244.0 Hz), 159.3, 156.5, 148.3, 144.5, 138.5 (J=6.0 Hz), 135.9, 133.1 (J=3.0 Hz), 132.0, 130.6 (J=8.0 Hz), 127.8, 114.9 (J=20.0 Hz), 114.6 (J=20.0 Hz), 48.6, 29.6, 28.7, 20.4. IR (Diamond ATR, $cm^{-1}$) n 3249, 2929, 1577, 1531, 1361, 1105, 919, 827, 685. HRMS (EI-MS): m/z calculated for $C_{17}H_{16}N_4F$ $[M+H]^+$: 295.1354, found: 295.1353. $T_m$: 78-80° C.

Example 76: (S)—N-(1,2,3,4-Tetrahydronaphthalen-1-yl)-2-(1H-1,2,4-triazol-1-yl)pyrido[3,2-d]pyrimidin-4-amine (111)

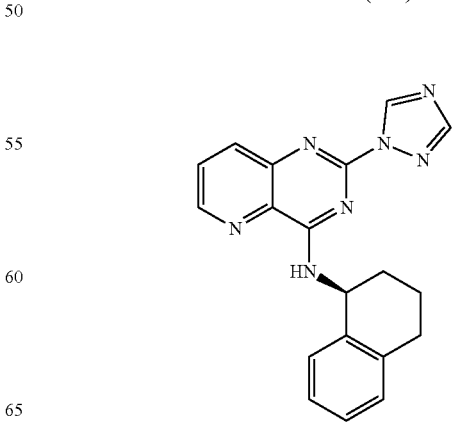

111

Compound 111 was obtained following procedure C with compounds 19 (100 mg, 0.32 mmol, 1.0 eq.), 1,2,4-triazole (30 mg, 0.4 mmol, 1.0 eq.) and triethylamine (0.05 mL, 0.4 mmol, 1.0 eq.). The residue was purified by silica gel chromatography (eluting with $CH_2Cl_2$/MeOH 97:3). The product was obtained in the form of a white solid (62 mg, 56%). $R_f$ ($CH_2Cl_2$/MeOH 94:6): 0.38. $T_m$: 170-172° C. $^1$H NMR (400 MHz, CDCl$_3$) δ 9.30 (s, 1H), 8.64 (m, 1H), 8.26 (dt, J=8.0, 1.0 Hz, 1H), 8.18 (s, 1H), 7.72 (br d, J=5.0 Hz, 1H, NH), 7.68 (m, 1H), 7.36 (d, J=8.0 Hz, 1H), 7.22 (m, 3H), 5.69 (q, J=6.0 Hz, 1H), 2.92 (m, 2H), 2.27 (m, 1H), 2.15 (m, 1H), 1.99 (m, 2H). $^{13}$C NMR (101 MHz, CDCl$_3$) δ 160.3, 153.5, 151.4, 148.1, 145.3, 144.2, 137.8, 136.1, 135.7, 131.4, 129.5, 128.8, 128.6, 127.9, 126.6, 49.4, 29.5, 29.3, 20.1. IR (Diamond ATR, cm$^{-1}$) n 3500, 2929, 1585, 1503, 1423, 1386, 1000, 940, 870, 734, 670. HRMS (EI-MS): m/z calculated for $C_{19}H_{18}N_7$ [M+H]$^+$: 344.1618, found: 344.1617.

Example 77: (S)-2-(1H-Imidazol-1-yl)-N-(1,2,3,4-tetrahydronaphthalen-1-yl)pyrido[3,2-d]pyrimidin-4-amine (112)

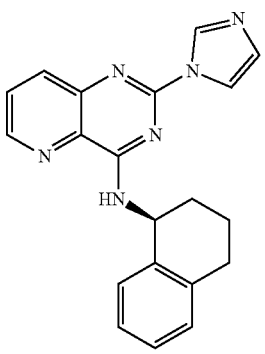 [SMILES: c1ccc2c(c1)CCC[C@@H]2Nc1nc(-n2ccnc2)nc2cccnc12]

Compound 112 was obtained following procedure C with compounds 19 (100 mg, 0.32 mmol, 1.0 eq.), imidazole (30 mg, 0.4 mmol, 1.0 eq.) and triethylamine (0.05 mL, 0.4 mmol, 1.0 eq.). The residue was purified by silica gel chromatography (eluting with $CH_2Cl_2$/MeOH 94:6). The product was obtained in the form of a white solid (71 mg, 65%). $R_f$($CH_2Cl_2$/MeOH 90:10): 0.75. $^1$H NMR (400 MHz, CDCl$_3$) δ 8.70 (s, 1H), 8.56 (m, 1H), 8.03 (dd, J=8.0, 2.0 Hz, 1H), 7.99 (s, 1H), 7.63 (m, 2H), 7.36 (d, J=8.0 Hz, 1H), 7.19 (m, 4H), 5.65 (q, J=6.0 Hz, 1H), 2.90 (m, 2H), 2.26 (m, 1H), 2.15 (m, 1H), 1.97 (m, 2H). $^{13}$C NMR (101 MHz, CDCl$_3$) δ 160.2, 151.8, 147.4, 145.5, 137.8, 136.7, 136.1, 135.2, 131.0, 130.2, 129.5, 128.9, 128.3, 127.8, 126.5, 117.0, 49.2, 29.6, 29.4, 20.1. IR (Diamond ATR, cm$^{-1}$) n 3340, 2934, 1549, 1426, 1315, 1036, 1014, 819, 737, 649. HRMS (EI-MS): m/z calculated for $C_{20}H_{19}N_6$ [M+H]$^+$: 343.1665, found: 343.1666. $T_m$: 186-188° C.

Example 78: N-Tetralin-2-ylpyrido[3,2-d]pyrimidin-4-amine (118)

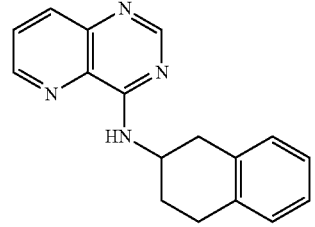 [SMILES: c1ccc2c(c1)CCC(Nc1ncnc3cccnc13)C2]

Compound 118 was obtained following procedure B with compound 117 (200 mg, 1.36 mmol, 1.7 eq.), 85 (158 mg, 0.8 mmol, 1.0 eq.) and triethylamine (0.22 mL, 16. mmol, 2.0 eq.). The residue was purified by silica gel chromatography (eluting gradient: 0 to 80% AcOEt/100 to 20% PE). The product was obtained in the form of a white solid (205 mg, 93%). $R_f$(PE/AcOEt 20:80): 0.34. $^1$H NMR (400 MHz, CDCl$_3$) δ 8.64 (m, 2H), 8.09 (dd, J=8.0, 2.0 Hz, 1H), 7.63 (dd, J=8.0, 4.0 Hz, 1H), 7.27 (br d, J=8.0 Hz, 1H, NH), 7.14 (m, 4H), 4.70 (m, 1H), 3.35 (dd, J=16.0, 5.0 Hz, 1H), 3.01 (m, 2H), 2.92 (dd, J=16.0, 8.0 Hz, 1H), 2.30 (m, 1H), 2.01 (m, 1H). $^{13}$C NMR (101 MHz, CDCl$_3$) δ 159.3, 156.5, 148.1, 144.3, 135.9, 135.5, 134.1, 132.1, 129.5, 128.9, 127.7, 126.3, 126.0, 46.5, 35.6, 28.7, 27.5. IR (Diamond ATR, cm$^{-1}$) n 3380, 2927, 1586, 1542, 1367, 1311, 1137, 776. HRMS (EI-MS): m/z calculated for $C_{17}H_{17}N_4$ [M+H]$^+$: 277.1447, found: 277.1448. $T_m$ 123-125° C.

Example 79: tert-Butyl N-[1-(pyrido[3,2-d]pyrimidin-4-ylamino)tetralin-6-yl]carbamate (119)

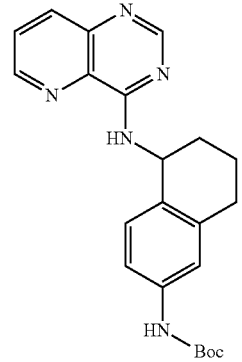 [SMILES: CC(C)(C)OC(=O)Nc1ccc2c(c1)CCCC2Nc1ncnc2cccnc12]

Compound 119 was obtained following procedure B with compound 116 (80 mg, 0.35 mmol, 1.7 eq.), 85 (44 mg, 0.22 mmol, 1 eq.) and triethylamine (0.06 mL, 0.45 mmol, 2 eq.). The residue was purified by silica gel chromatography (eluting gradient: 0 to 90% AcOEt/100 to 10% PE). The product was obtained in the form of a colourless oil (50 mg, 57%). $R_f$ (PE/AcOEt 90:10): 0.35. $^1$H NMR (400 MHz, CDCl$_3$) δ 8.64 (s, 1H), 8.62 (dd, J=4.0, 2.0 Hz, 1H), 8.08 (dd, J=8.0, 2.0 Hz, 1H), 7.62 (dd, J=8.0, 4.0 Hz, 1H), 7.39 (d, J=8.0 Hz, 1H, NH), 7.29 (s, 1H), 7.23 (d, J=3.0 Hz, 1H), 7.02 (d, J=3.0 Hz, 1H), 6.65 (s, 1H), (m, 1H), 2.82 (m, 2H), 2.14 (m, 1H), 2.03 (m, 1H), 1.90 (m, 2H), 1.49 (s, 9H). $^{13}$C NMR (101 MHz, CDCl$_3$) δ 159.1, 156.6, 152.9, 148.2, 144.5, 138.7, 137.7, 135.9, 132.1, 131.1, 129.6, 127.7, 118.8, 117.0, 80.6, 60.5, 48.4, 29.8, 29.6, 28.4, 20.0, 14.3. IR (Diamond ATR, cm$^{-1}$) n 2931, 1732, 1537, 1298, 1154, 828, 686. HRMS (EI-MS): m/z calculated for C$_{22}$H$_{26}$N$_5$O$_2$ [M+H]$^+$: 392.2080, found: 392.2081.

Example 80: tert-Butyl 4-(pyrido[3,2-d]pyrimidin-4-ylamino)-4,5,6,7-tetrahydroindole-1-carboxylate (120)

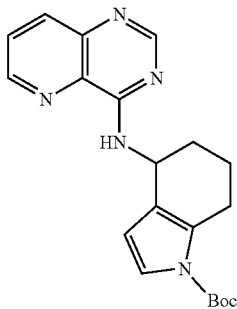 [SMILES: CC(C)(C)OC(=O)n1ccc2c1CCCC2Nc1ncnc2cccnc12]

Compound 120 was obtained following procedure B with compound 115 (74 mg, 0.31 mmol, 1.7 eq.), 85 (36 mg, 0.18 mmol, 1.0 eq.) and triethylamine (0.05 mL, 0.36 mmol, 2.0 eq.). The residue was purified by silica gel chromatography (eluting gradient: 0 to 90% AcOEt/100 to 10% PE). The product was obtained in the form of a colourless oil (60 mg, 91%). R$_f$ (PE/AcOEt 90:10): 0.38. $^1$H NMR (400 MHz, CDCl$_3$) δ 8.64 (s, 1H), 8.62 (d, J=4.0 Hz, 1H), 8.06 (dd, J=8.0, 2.0 Hz, 1H), 7.60 (ddd, J=8.0, 4.0, 2.0 Hz, 1H), 7.33 (d, J=8.0 Hz, 1H, NH), 7.14 (d, J=4.0 Hz, 1H), 6.13 (m, 1H), 5.39 (m, 1H), 2.88 (m, 2H), 2.11 (m, 1H), 1.92 (m, 3H), 1.58 (s, 9H). $^{13}$C NMR (101 MHz, CDCl$_3$) δ 159.2, 156.5, 149.5, 148.1, 144.4, 135.8, 132.2, 131.8, 127.6, 122.3, 120.3, 109.9, 83.6, 45.1, 29.3, 28.2, 24.6, 20.3. IR (Diamond ATR, cm$^1$) n 3389, 2975, 2937, 1733, 1534, 1297, 1119, 828, 716, 685. HRMS (EI-MS): m/z calculated for C$_{20}$H$_{24}$N$_5$o$_2$ [M+H]$^+$: 366.1924, found: 366.1925.

Example 81: 2-Pyrrolidin-1-yl-N-[(1S)-tetralin-1-yl] pyrido[3,2-d]pyrimidin-4-amine (121)

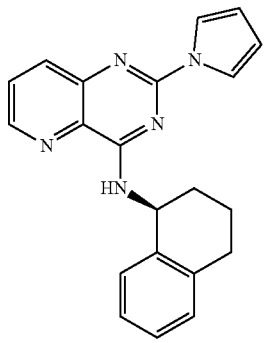 [SMILES: c1ccc2c(c1)CCC[C@@H]2Nc1nc(-n2cccc2)nc2cccnc12]

Compound 121 was obtained following procedure C with compounds 19 (100 mg, 0.32 mmol, 1.0 eq.), pyrrole (0.03 mL, 0.4 mmol, 1 eq.) and potassium tert-butylate (45 mg, 0.4 mmol, 1.0 eq.). The residue was purified by silica gel chromatography (eluting with PE/AcOEt 90:10). The product was obtained in the form of a white solid (24 mg, 22%). R$_f$ (PE/AcOEt 90:10): 0.21. $^1$H NMR (400 MHz, CDCl$_3$) δ 8.51 (dd, J=4.0, 2.0 Hz, 1H), 8.01 (dd, J=8.0, 2.0 Hz, 1H), 7.92 (m, 2H), 7.58 (dd, J=8.0, 4.0 Hz, 1H), 7.49 (d, J=8.0 Hz, 1H, NH), 7.39 (m, 1H), 7.20 (m, 3H), 6.34 (m, 2H), 5.70 (m, 1H), 2.90 (m, 2H), 2.24 (m, 1H), 2.13 (m, 1H), 1.97 (m, 2H). $^{13}$C NMR (101 MHz, CDCl$_3$) δ 160.0, 153.3, 146.4, 145.9, 137.8, 136.5, 135.0, 130.8, 129.4, 129.1, 128.0, 127.7, 126.5, 119.6, 111.4, 48.9, 31.0, 29.7, 20.2. IR (Diamond ATR, cm$^{-1}$) n 3851, 3743, 3381, 2935, 2853, 1545, 1430, 1064, 855, 758. HRMS (EI-MS): m/z calculated for C$_{21}$H$_{20}$N$_5$ [M+H]$^+$: 342.1713, found: 342.1714. T$_m$: 131-133° C.

Example 82: N-(4,5,6,7-Tetrahydro-1H-indol-4-yl) pyrido[3,2-d]pyrimidin-4-amine (122)

Compound 120 (51 mg, 0.14 mmol) was dissolved in 4 mL of CH$_2$Cl$_2$ and 1 mL TFA was added to the round-bottom flask. After vigorous overnight stirring at ambient temperature, a few milliliters of 2 M NaOH solution were added and the mixture stirred at ambient temperature for 1 hour. The product was extracted with 3×15 mL AcOEt and the organic phases combined and dried over MgSO$_4$. After filtering and evaporation, the residue was purified by silica gel chromatography (eluting gradient: 0 to 5% MeOH/100 to 95% CH$_2$Cl$_2$). The product was obtained in the form of an orange solid (22 mg, 60%). Rf (CH2Cl2/MeOH 95:5): 0.22. $^1$H NMR (400 MHz, CDCl3) δ 8.70-8.55 (m, 2H), 8.06 (dd, J=8.5, 1.6 Hz, 1H), 7.66-7.52 (m, 1H), 7.39 (m, 1H), 7.13-7.11 (d, J=8.1 Hz, 1H), 6.55-6.47 (m, 2H), 5.55-5.47 (m, 1H), 2.67-84 (m, 2H), 2.151.94 (m, 3H), 1.85-1.92 (m, 2H). $^{13}$C NMR (101 MHz, CDCl3) δ: 159.0, 156.7, 148.1, 145.8, 139.9, 135.9, 132.2, 130.3, 127.7, 126.5, 114.9, 48.4, 29.8, 28.5; 19.9. IR (Diamond ATR, cm$^{-1}$) n): 3396, 3190, 2921, 1577, 1541, 1357, 1306, 826, 685. HRMS (+ESI): m/z calculated for C$_{15}$H$_{16}$N$_5$ [M+H]$^+$: found: T$_m$: 166-168° C.

Example 83: N1-pyrido[3,2-d]pyrimidin-4-yltetralin-1,6-diamine (123)

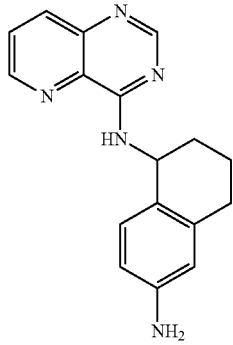 [SMILES: Nc1ccc2c(c1)CCCC2Nc1ncnc2cccnc12]

Compound 119 (60 mg, 0.15 mmol) was dissolved in 4 mL of CH$_2$Cl$_2$ and 1 mL TFA was added to the round-bottom flask. After overnight vigorous stirring at ambient temperature, a few milliliters of 2 M NaOH solution were added and the mixture stirred for 1 hour at ambient temperature. The product was extracted with 3×15 mL AcOEt and the organic phases combined and dried over MgSO$_4$. After filtering and evaporation, the residue was purified by silica gel chromatography (eluting gradient: 0 to 5% MeOH/100 to 95% CH$_2$Cl$_2$). The product was obtained in the form of an orange solid (28 mg, 68%). R$_f$ (CH$_2$Cl$_2$/MeOH 95:5): 0.26. $^1$H NMR (400 MHz, CDCl$_3$) δ 8.65 (s, 1H), 8.63 (dd, J=4.0, 2.0 Hz, 1H), 8.09 (dd, J=8.0, 2.0 Hz, 1H), 7.63 (dd, J=8.0, 4.0 Hz, 1H), 7.40 (br d, 1H, NH), 7.12 (d, J=8.0 Hz, 1H), 6.51 (dd, J=8.0, 2.0 Hz, 1H), 6.49 (d, J=2.0 Hz, 1H), 5.50 (dt, J=8.0, 5.0 Hz, 1H), 3.63 (br s, 2H, NH$_2$), 2.76 (m, 2H), 2.13 (m, 1H), 2.05 (m, 1H), 1.90 (m, 2H). $^{13}$C NMR (101 MHz, CDCl$_3$) δ 159.1, 156.7, 148.2, 145.8, 144.5, 139.0, 135.9, 132.3, 130.3, 127.7, 126.6, 114.9, 113.9, 48.4, 29.9, 29.6, 20.0. IR (Diamond ATR, cm$^{-1}$) n 3438, 3395, 3306, 3190, 2921, 1541, 1306, 1119, 826, 685, 550. HRMS (EI-MS): m/z calculated for C$_{17}$H$_{18}$N$_5$ [M+H]$^+$: 292.1556, found: 292.1558. T$_m$: 181-183° C.

Example 84: N-(8-Methoxytetralin-1-yl)pyrido[3,2-d]pyrimidin-4-amine (126)

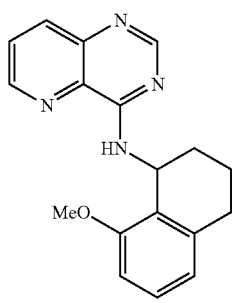 [SMILES: COc1cccc2c1C(Nc1ncnc3cccnc13)CCC2]

Compound 126 was obtained following procedure B with compound 124 (167 mg, 0.38 mmol, 1.7 eq.), 85 (46 mg, 0.23 mmol, 1.0 eq.) and triethylamine (0.07 mL, 0.45 mmol, 2.0 eq.). The residue was purified by silica gel chromatography (eluting gradient: 0 to 90% AcOEt/100 to 10% PE). The product was obtained in the form of an orange solid (58 mg, 82%). R$_f$ (PE/AcOEt 80:20): 0.29. $^1$H NMR (400 MHz, CDCl$_3$) δ 8.70 (s, 1H), 8.58 (dd, J=4.0, 2.0 Hz, 1H), 8.07 (dd, J=8.0, 2.0 Hz, 1H), 7.59 (dd, J=8.0, 4.0 Hz, 1H), 7.26 (br d, J=3.0 Hz, 1H, NH), 7.21 (t, J=8.0 Hz, 1H), 6.77 (d, J=8.0 Hz, 1H), 6.69 (d, J=8.0 Hz, 1H), 5.69 (m, 1H), 3.64 (s, 3H), 2.84 (m, 2H), 2.36 (m, 1H), 1.85 (m, 3H). $^{13}$C NMR (101 MHz, CDCl$_3$) δ 158.7, 158.5, 156.7, 147.9, 144.3, 139.5, 135.8, 132.3, 128.6, 127.5, 124.2, 121.5, 107.9, 55.6, 43.2, 29.3, 28.5, 18.3. IR (Diamond ATR, cm$^{-1}$) n 3386, 2927, 1466, 1436, 1250, 977, 892, 780, 585. HRMS (EI-MS): m/z calculated for C$_{18}$H$_{19}$N$_4$O [M+Na]$^+$: 307.1553, found: 307.1553. T$_m$: 147-149° C.

Example 85: N-(6,7-Dimethoxytetralin-1-yl)pyrido[3,2-d]pyrimidin-4-amine (127)

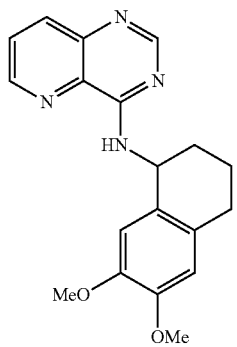 [SMILES: COc1cc2c(cc1OC)C(Nc1ncnc3cccnc13)CCC2]

Compound 127 was obtained following procedure B with compound 125 (105 mg, 0.51 mmol, 1.7 eq.), 85 (60 mg, 0.30 mmol, 1.0 eq.) and triethylamine (0.08 mL, 0.60 mmol, 2.0 eq.). The residue was purified by silica gel chromatography (eluting gradient: 0 to 90% AcOEt/100 to 10% PE). The product was obtained in the form of a white solid (73 mg, 72%). R$_f$ (PE/AcOEt 80:20): 0.32. $^1$H NMR (400 MHz, CDCl$_3$) δ 8.64 (s, 1H), 8.62 (dd, J=4.0, 2.0 Hz, 1H), 8.08 (dd, J=8.0, 2.0 Hz, 1H), 7.62 (dd, J=8.0, 4.0 Hz, 1H), 7.43 (br d, J=3.0 Hz, 1H, NH), 6.81 (s, 1H), 6.61 (s, 1H), 5.51 (m, 1H), 3.85 (s, 3H), 3.74 (s, 3H), 2.76 (m, 2H), 2.10 (m, 2H), 1.90 (m, 2H). $^{13}$C NMR (101 MHz, CDCl$_3$) δ 159.0, 156.5, 148.7, 148.2, 147.7, 144.4, 135.9, 132.2, 130.2, 128.0, 127.7, 111.8, 111.6, 56.1, 56.0, 48.4, 29.5, 29.0, 19.8. IR (Diamond ATR, cm$^{-1}$) n 3409, 2828, 1671, 1537, 1437, 1294, 1165, 1020, 942, 870, 789, 685. HRMS (EI-MS): m/z calculated for C$_{19}$H$_{21}$N$_4$O$_2$ [M+Na]$^+$: 337.1659, found: 337.1659. T$_m$: 117-119° C.

Example 86: N-[5-(Methoxymethoxy)tetralin-1-yl]pyrido[3,2-d]pyrimidin-4-amine (130)

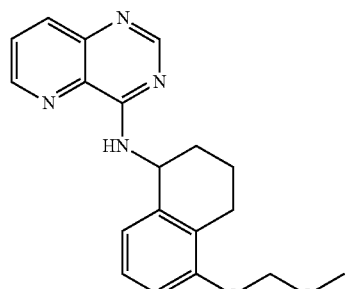

Compound 130 was obtained following procedure B with compound 129 (120 mg, 0.58 mmol, 1.7 eq.), 85 (68 mg, 0.34 mmol, 1.0 eq.) and triethylamine (0.10 mL, 0.68 mmol, 2.0 eq.). The residue was purified by silica gel chromatography (eluting gradient: 0 to 90% AcOEt/100 to 10% PE). The product was obtained in the form of a colourless oil (73 mg, 63%). $R_f$ (PE/AcOEt 20:80): 0.42. $^1$H NMR (400 MHz, CDCl$_3$) δ 8.65 (s, 1H), 8.62 (dd, J=4.0, 2.0 Hz, 1H), 8.09 (dd, J=8.0, 2.0 Hz, 1H), 7.62 (dd, J=8.0, 4.0 Hz, 1H), 7.46 (br d, J=3.0 Hz, 1H, NH), 7.06 (t, J=8.0 Hz, 1H), 7.00 (t, J=2.0 Hz, 1H), 6.92 (t, J=8.0, 2.0 Hz, 1H), 5.58 (m, 1H), 5.07 (m, 2H), 3.39 (s, 3H), 2.79 (m, 2H), 2.16 (m, 1H), 2.00 (m, 1H), 1.95 (m, 2H). $^{13}$C NMR (101 MHz, CDCl$_3$) δ 159.2, 156.6, 155.7, 148.2, 144.5, 137.6, 135.9, 132.1, 131.2, 130.3, 127.7, 116.5, 116.0, 94.7, 56.0, 48.9, 29.6, 28.6, 20.3. IR (Diamond ATR, cm$^{-1}$) n 3384, 2929, 1578, 1477, 1360, 1075, 1000, 920, 828, 803, 686. HRMS (EI-MS): m/z calculated for $C_{19}H_{21}N_4O_2$ [M+H]$^+$: 337.1659, found: 337.1658.

Example 87: 1-(Pyrido[3,2-d]pyrimidin-4-ylamino)tetralin-5-ol (131)

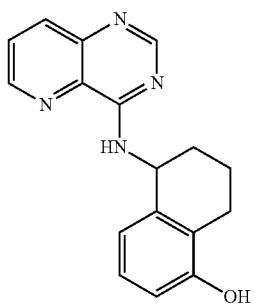 [SMILES: Oc1cccc2c1CCCC2Nc1ncnc2cccnc12]

Compound 130 (60 mg, 0.18 mmol) was dissolved in 5 mL MeOH and a few drops of concentrated HCl (37% in water) were added at ambient temperature. The mixture stirred overnight. The mixture was diluted with 20 mL AcOEt and washed with saturated aqueous Na$_2$CO$_3$ solution. The organic phase was washed with saturated aqueous NaCl solution and dried over MgSO$_4$. After filtering, the solvent was evaporated and product 131 was obtained by precipitation in pentane in the form of a white solid (42 mg, 81%). $R_f$ (AcOEt 100): 0.29. $^1$H NMR (400 MHz, DMSO-d$_6$) δ 8.98 (br s, 1H, OH), 8.79 (dd, J=4.0, 2.0 Hz, 1H), 8.54 (s, 1H), 8.37 (br d, J=3.0 Hz, 1H, NH), 8.14 (dd, J=8.0, 2.0 Hz, 1H), 7.84 (dd, J=8.0, 4.0 Hz, 1H), 6.93 (d, J=8.0 Hz, 1H), 6.58 (m, 2H), 5.56 (m, 1H), 2.69 (m, 2H), 2.02 (m, 2H), 1.93 (m, 1H), 1.76 (m, 1H). $^{13}$C NMR (101 MHz, DMSO-d$_6$) δ 159.1, 156.0, 155.3, 148.5, 144.2, 138.1, 135.4, 131.4, 129.7, 128.3, 127.3, 114.4, 113.4, 59.7, 48.4, 29.0, 20.8. IR (Diamond ATR, cm$^{-1}$) n 3362, 2928, 2680, 2593, 1584, 1509, 1451, 1361, 1237, 1189, 1158, 1130, 870, 825, 800, 616, 529. HRMS (EI-MS): m/z calculated for $C_{12}H_{18}NO_2$ [M+H]$^+$: 293.1396, found: 293.1398. $T_m$: 249-251° C.

Example 88: 6-Chloro-N-[(1S)-tetralin-1-yl]pyrido[3,2-d]pyrimidin-4-amine (133)

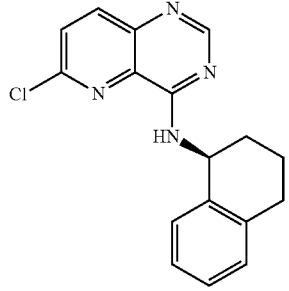 [SMILES: Clc1ccc2ncnc(N[C@H]3CCCc4ccccc43)c2n1]

Compound 132 (120 mg, 0.6 mmol) was dissolved in 5 mL of anhydrous THF after which (S)-(+)-1,2,3,4-tetrahydro-1-naphthylamine (0.09 mL, 0.6 mmol) and triethylamine (0.1 mL; 0.72 mmol) were added. The solution was stirred for 24 h at ambient temperature. Disappearance of the starting reagent was monitored by TLC, and on completion of the reaction the THF was evaporated. The deposit obtained was taken up in 30 mL of water and the product extracted with 3×20 mL ethyl acetate. The organic phases were combined and washed with saturated aqueous NaCl solution (20 mL) and finally dried over MgSO$_4$. After filtering, the solvent was evaporated and the residue purified on silica gel (eluting gradient: 0 to 40% AcOEt/100 to 60% PE). The product was obtained in the form of a beige solid (154 mg, 83%). $R_f$ (PE/AcOEt 50:50): 0.32. $^1$H NMR (400 MHz, CDCl$_3$) δ 8.67 (s, 1H), 8.04 (d, J=8.0 Hz, 1H), 7.59 (d, J=8.0 Hz, 1H), 7.32 (m, 1H), 7.18 (m, 4H), 5.64 (m, 1H), 2.87 (m, 2H), 2.20 (m, 1H), 1.99 (m, 3H). $^{13}$C NMR (101 MHz, CDCl$_3$) δ 158.3, 156.9, 148.8, 143.8, 139.1, 137.9, 136.2, 131.5, 129.5, 129.2, 128.9, 127.7, 126.5, 48.9, 29.7, 29.4, 20.2. IR (Diamond ATR, cm$^{-1}$) n 3373, 2922, 2859, 1583, 1540, 1471, 1374, 1342, 1124, 864, 753, 636. HRMS (EI-MS): m/z calculated for $C_{17}H_{16}ClN_4$ [M+H]$^+$: 311.1058, found: 311.1056. $T_m$: 115-117° C.

Example 89: 7-Bromo-N-[(1S)-tetralin-1-yl]pyrido[3,2-d]pyrimidin-4-amine (135)

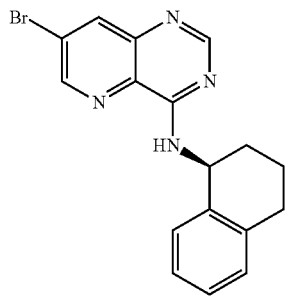 [SMILES: Brc1cnc2c(N[C@H]3CCCc4ccccc43)ncnc2c1]

Compound 134 (540 mg, 2.12 mmol) was dissolved in 5 mL of anhydrous THF and the addition made of (S)-(+)-1,2,3,4-tetrahydro-1-naphthylamine (0.31 mL, 2.12 mmol) and triethylamine (0.35 mL, 2.54 mmol). The solution was stirred overnight at 80° C. Disappearance of the starting reagent was monitored by TLC, and on completion of the reaction the THF was evaporated. The deposit obtained was taken up in 30 mL of saturated aqueous NaHCO₃ solution and the product extracted with 3×20 mL ethyl acetate. The organic phases were combined and washed with saturated aqueous NaCl solution (20 mL) and finally dried over MgSO₄. After filtering, the solvent was evaporated and the residue purified on silica gel (eluting gradient: 0 to 50% AcOEt/100 to 50% PE). The product was obtained in the form of a yellow solid (574 mg, 73%). $R_f$(PE/AcOEt 50:50): 0.51. ¹H NMR (400 MHz, CDCl₃) δ 8.66 (s, 1H), 8.60 (d, J=8.0 Hz, 1H), 8.24 (d, J=8.0 Hz, 1H), 7.40 (br d, J=3.0 Hz, 1H, NH), 7.31 (m, 1H), 7.16 (m, 3H), 5.62 (m, 1H), 2.85 (m, 2H), 2.20 (m, 1H), 2.02 (m, 1H), 1.93 (m, 2H). ¹³C NMR (101 MHz, CDCl₃) δ 159.1, 157.6, 149.3, 145.3, 137.8, 137.6, 136.2, 130.3, 129.4, 128.8, 127.7, 126.4, 124.1, 48.8, 29.7, 29.3, 20.1. IR (Diamond ATR, cm⁻¹) n 3946, 1571, 1524, 1452, 1531, 1299, 1122, 873, 748. HRMS (EI-MS): m/z calculated for $C_{17}H_{16}BrN_4$ [M+H]⁺: 355.0553, found: 355.0552. $T_m$: 82-84° C.

Example 90: N-Tetralin-1-ylthieno[3,2-d]pyrimidin-4-amine (136)

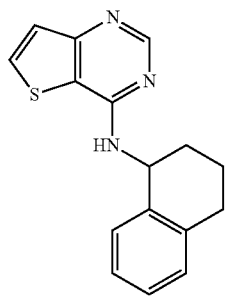 [SMILES: c1ccc2c(c1)CCCC2Nc1ncnc2ccsc12]

4-chlorothieno[3,2-d]pyrimidine (200 mg, 1.17 mmol, 1.0 eq.) was dissolved in 5 mL of anhydrous CH₃CN and the addition made 1,2,3,4-tetrahydro-1-naphthylamine (0.34 mL, 2.35 mmol, 2.0 eq.) and diisopropylethylamine (0.25 mL; 1.41 mmol, 1.2 eq.). The solution was stirred under reflux for 5 h. Disappearance of the starting reagent was monitored by TLC, and on completion of the reaction the CH₃CN was evaporated. The deposit obtained was taken up in 30 mL of saturated aqueous NaHCO₃ solution and the product extracted with 3×20 mL ethyl acetate. The organic phases were combined and washed with saturated aqueous NaCl solution (20 mL) and finally dried over MgSO₄. After filtering, the solvent was evaporated and the residue purified on silica gel (eluting gradient: 0 to 50% AcOEt/100 to 50% PE). The product was obtained in the form of a white solid (184 mg, 56%). $R_f$(PE/AcOEt 50:50): 0.25. ¹H NMR (400 MHz, CDCl₃) δ 8.68 (s, 1H), 7.70 (d, J=8.0 Hz, 1H), 7.44 (d, J=8.0 Hz, 1H), 7.36 (m, 1H), 7.20 (m, 3H), 5.69 (m, 1H), 5.07 (br d, J=3.0 Hz, 1H, NH), 2.87 (m, 2H), 2.21 (m, 1H), 2.03 (m, 1H), 1.93 (m, 2H). ¹³C NMR (101 MHz, CDCl₃) δ 160.1, 156.8, 155.3, 138.1, 136.8, 130.9, 129.5, 129.1, 127.7, 126.6, 125.7, 115.2, 49.0, 30.2, 29.5, 20.1. IR (Diamond ATR, cm⁻¹): 2928, 1578, 1535, 1496, 1442, 1302, 1040, 792, 719. HRMS (EI-MS): m/z calculated for $C_{16}H_{16}N_3S$ [M+H]⁺: 282.1059, found: 282.1058. $T_m$: 178-180° C.

Example 91: N-Tetralin-1-yl-7H-pyrrolo[2,3-d]pyrimidin-4-amine (137)

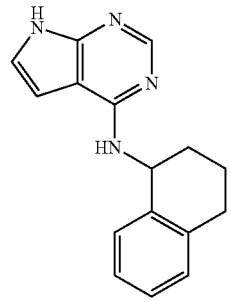 [SMILES: c1ccc2c(c1)CCCC2Nc1ncnc2[nH]ccc12]

In a sealed tube, 4-chloro-7H-pyrrolo[3,2-d]pyrimidine (200 mg, 1.31 mmol, 1.0 eq.) was dissolved in 6 mL of isopropanol and the addition was made of 1,2,3,4-tetrahydro-1-naphthylamine (0.22 mL, 1.5 mmol, 1.2 eq.) and diisopropylethylamine (0.68 mL; 3.93 mmol, 3.0 eq.). The reaction was initiated in a microwave reactor for 1 h at 160° C. Disappearance of the starting reagent was monitored by TLC, and on completion of the reaction the solution was diluted with 50 mL of AcOEt. The solution was washed with 50 mL of water then 50 mL of saturated aqueous NaCl solution and dried over MgSO₄. After filtering, the solvent was evaporated and the residue purified on silica gel (eluting gradient: 0 to 80% AcOEt/100 to 20% PE). The product was obtained in the form of a white solid (148 mg, 43%). $R_f$ (PE/AcOEt 20:80): 0.20. ¹H NMR (400 MHz, CD₃OD) 8.16 (s, 1H), 7.28 (m, 1H), 7.14 (m, 3H), 7.07 (d, J=8.0 Hz, 1H), 6.62 (d, J=8.0 Hz, 1H), 5.57 (m, 1H), 2.88 (m, 2H), 2.16 (m, 1H), 1.97 (m, 3H). ¹³C NMR (101 MHz, CD₃OD) 157.6, 152.2, 150.5, 138.8, 130.0, 129.5, 128.0, 127.0, 122.2, 104.3, 100.2, 31.5, 30.4, 21.6. IR (Diamond ATR, cm⁻¹) n 3189, 3095, 2931, 2852, 1584, 1473, 1354, 1321, 1160, 1138, 897, 819, 656. HRMS (EI-MS): m/z calculated for $Cl_6H_{17}N_4$[M+H]⁺: 265.1447, found: 265.1445. $T_m$: 226-228° C.

Example 92: N-Tetralin-1-ylthieno[2,3-d]pyrimidin-4-amine (138)

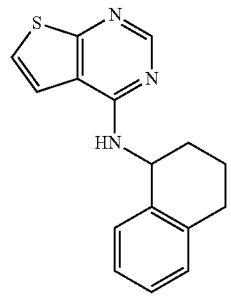 [SMILES: c1ccc2c(c1)CCCC2Nc1ncnc2sccc12]

4-chlorothieno[2,3-d]pyrimidine (200 mg, 1.18 mmol, 1.0 eq.) was dissolved 6 mL of anhydrous THF and the addition made of 1,2,3,4-tetrahydro-1-naphthylamine (0.25 mL, 1.77 mmol, 1.5 eq.) and diisopropylethylamine (0.34 mL, 1.77 mmol, 1.5 eq.). The solution was stirred for 48 h at ambient temperature. Disappearance of the starting reagent was monitored by TLC, and completion of the reaction the THF was evaporated. The deposit obtained was taken up in 30 mL of saturated aqueous NaHCO$_3$ solution and the product extracted with 3×20 mL ethyl acetate. The organic phases were combined and washed with saturated aqueous NaCl solution (20 mL) and finally dried over MgSO$_4$. After filtering, the solvent was evaporated and the residue purified on silica gel (eluting gradient: 0 to 40% AcOEt/100 to 60% PE). The product was obtained in the form of a white solid (168 mg, 51%). R$_f$ (PE/AcOEt 50:50): 0.32. $^1$H NMR (400 MHz, CDCl$_3$) δ 8.55 (s, 1H), 7.34 (m, 1H), 7.25 (d, J=8.0 Hz, 1H), 7.20 (m, 3H), 7.08 (d, J=8.0 Hz, 1H), 5.67 (m, 1H), 5.40 (br d, J=3.0 Hz, 1H, NH), 2.86 (m, 2H), 2.19 (m, 1H), 2.02 (m, 1H), 1.93 (m, 2H). $^{13}$C NMR (101 MHz, CDCl$_3$) δ 166.8, 156.5, 154.3, 138.0, 136.9, 129.5, 129.1, 127.7, 126.5, 123.2, 117.1, 116.2, 48.8, 30.0, 29.5, 20.1. IR (Diamond ATR, cm$^{-1}$) n 3234, 3052, 2929, 2858, 1578, 1536, 1493, 1437, 1354, 1306, 1079, 1023, 880, 738. HRMS (EI-MS): m/z calculated for Cl$_6$H$_{16}$N$_3$S [M+H]$^+$: 282.1059, found: 282.1055. T$_m$: 176-178° C.

Example 93: tert-Butyl N-[4-[4-[[(1S)-tetralin-1-yl]amino]pyrido[3,2-d]pyrimidin-7-yl]but-3-ynyl]carbamate (139)

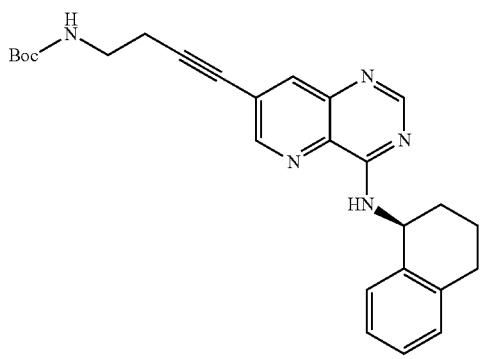 [SMILES: CC(C)(C)OC(=O)NCCC#Cc1cnc2c(N[C@H]3CCCc4ccccc43)ncnc2c1]

Compound 135 (200 mg, 0.56 mmol) was dissolved in 10 mL of CH$_3$CN and the addition made of tert-butyl but-3-yn-1-ylcarbamate (0.11 mL, 0.62 mmol), copper iodide (6.0 mg, 0.03 mmol), triphenylphosphine (8.0 mg, 0.03 mmol) and triethylamine (0.25 mL, 3.4 mmol) under vigorous stirring, and finally palladium acetate (1.5 mg, 0.0056 mmol) was added. The mixture was stirred at 80° C. for 2 hours. Disappearance of the starting reagent was monitored by TLC, and on completion of the reaction the CH$_3$CN was evaporated. The deposit obtained was taken up in 30 mL of water and the product extracted with 3×20 mL ethyl acetate. The organic phases were combined and washed with saturated aqueous NaCl solution (20 mL) and finally dried over MgSO$_4$. After filtering, the solvent was evaporated and the residue purified on silica gel (eluting gradient: 0 to 60% AcOEt/100 to 40% PE). The product was obtained in the form of a colourless oil (152 mg, 61%). R$_f$ (PE/AcOEt 50:50): 0.29. $^1$H NMR (400 MHz, CDCl$_3$) δ 8.66 (s, 1H), 8.57 (d, J=2.0 Hz, 1H), 8.05 (d, J=2.0 Hz, 1H), 7.35 (br d, J=3.0 Hz, 1H, NH), 7.32 (m, 1H), 7.18 (m, 3H), 5.61 (m, 1H), 4.92 (br s, 1H, NH), 3.41 (q, J=6.0 Hz, 2H), 2.87 (qt, J=17.0, 6.0 Hz, 2H), 2.69 (t, J=6.0 Hz, 2H), 2.19 (m, 1H), 2.00 (m, 1H), 1.98 (m, 2H), 1.46 (s, 9H). $^{13}$C NMR (101 MHz, CDCl$_3$) δ 159.0, 157.2, 155.9, 150.4, 143.8, 137.9, 137.8, 136.5, 130.5, 129.4, 129.0, 126.5, 124.7, 93.6, 79.8, 78.5, 48.8, 39.4, 29.8, 29.4, 28.5, 21.4, 20.2. IR (Diamond ATR, cm$^{-1}$) n 3373, 2931, 2231, 1698, 1574, 1525, 1389, 1364, 1319, 1283, 1162, 909, 754. HRMS (EI-MS): m/z calculated for C$_{26}$H$_{30}$N$_5$O$_2$ [M+H]$^+$: 444.2394, found: 444.2394.

Example 94: 7-(4-Aminobut-1-ynyl)-N-[(1S)-tetralin-1-yl]pyrido[3,2-d]pyrimidin-4-amine (140)

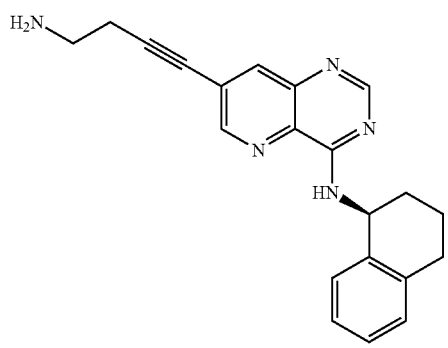 [SMILES: NCCC#Cc1cnc2c(N[C@H]3CCCc4ccccc43)ncnc2c1]

Compound 139 (130 mg, 0.3 mmol) was dissolved in 4 mL of CH$_2$Cl$_2$ and 1 mL of TFA was added to the flask. After vigorous stirring overnight at ambient temperature, a few drops of 2 M NaOH 2 M solution were added and the mixture stirred at ambient temperature for 1 hour. The product was extracted with 3×15 mL of AcOEt and the organic phases were combined and dried over MgSO$_4$. After filtering and evaporation, the product was obtained in the form of an orange solid (98 mg, 97%). R$_f$ (CH$_2$Cl$_2$/MeOH 90:10): 0.14. $^1$H NMR (400 MHz, CDCl$_3$) δ 8.65 (s, 1H), 8.56 (d, J=2.0 Hz, 1H), 8.05 (d, J=2.0 Hz, 1H), 7.35 (br d, J=3.0 Hz, 1H, NH), 7.32 (m, 1H), 7.16 (m, 3H), 5.60 (m, 1H), 2.91 (q, J=6.0 Hz, 2H), 2.87 (qt, J=17.0, 6.0 Hz, 2H), 2.62 (t, J=6.0 Hz, 2H), 2.18 (m, 1H), 1.99 (m, 1H), 1.97 (m, 2H), 1.67 (br s, 2H, NH$_2$). $^{13}$C NMR (101 MHz, CDCl$_3$) δ 159.0, 157.1, 150.4, 143.8, 137.8, 137.7, 136.4, 130.4, 129.4, 128.9, 127.6, 126.4, 124.9, 94.4, 78.5, 48.7, 41.0, 29.7, 29.4, 24.7, 20.1. IR (Diamond ATR, cm$^{-1}$) n 3367, 2934, 2225, 1577, 1530, 1322, 750, 733. HRMS (EI-MS): m/z calculated for C$_{21}$H$_{22}$N$_5$ [M+H]$^+$: 344.1869, found: 344.1870. T$_m$: 88-90° C.

Example 95: 4-(Pyrido[3,2-d]pyrimidin-4-ylamino)tetralin-1-ol (142)

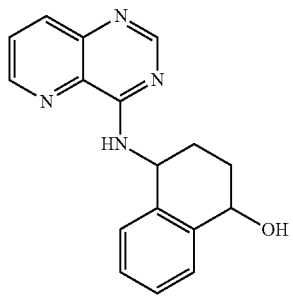 [SMILES: OC1CCC(Nc2ncnc3cccnc23)c2ccccc21]

Compound 10 (100 mg, 0.6 mmol, 1.2 eq.) was dissolved in 5 mL of anhydrous THF to give a yellow solution to which amine 141 (80 mg, 0.50 mmol, 1.0 eq.) was added. The solution became turbid. Triethylamine (0.08 mL, 0.60 mmol, 1.2 eq.) was added and the solution left at ambient temperature for 2 to 12 hours under vigorous stirring. Disappearance of the starting reagent was monitored by TLC, and on completion of the reaction the THF was evaporated. The deposit obtained was taken up in 3×20 mL ethyl acetate and the product washed with 30 mL of saturated aqueous NaHCO$_3$ solution. The organic phase was washed with saturated aqueous NaCl solution (40 mL) and finally dried over MgSO$_4$. After filtering, the solvent was evaporated and the residue purified on silica gel (eluting gradient: 0 to 60% AcOEt/100 to 40% PE). The product was obtained in the form of a white powder (32 mg, 22%). R$_f$(PE/AcOEt 30:70): 0.22. $^1$H NMR (400 MHz, CDCl$_3$) δ 8.64 (dd, J=4.0, 2.0 Hz, 1H), 8.62 (s, 1H), 8.09 (dd, J=8.0, 2.0 Hz, 1H), 7.64 (dd, J=8.0, 4.0 Hz, 1H), 7.57 (br d, J=3.0 Hz, 1H, NH), 7.51 (m, 1H), 7.32 (m, 3H), 5.57 (m, 1H), 4.86 (m, 1H), 2.67 (br s, 1H, OH), 2.29 (m, 1H), 2.16 (m, 3H). $^{13}$C NMR (101 MHz, CDCl$_3$) δ 159.4, 156.5, 148.4, 144.5, 139.6, 136.7, 136.0, 132.1, 128.8, 128.6, 128.3, 128.2, 127.9, 67.9, 48.9, 29.8, 25.3. IR (Diamond ATR, cm$^{-1}$) n 3372, 3253, 2925, 2859, 1584, 1436, 1317, 1063, 924, 826, 802, 764, 684, 590. HRMS (EI-MS): m/z calculated for Cl$_7$H$_{17}$N$_4$O [M+H]$^+$: 293.1396, found: 293.1395. T$_m$: 159-161° C.

4 enantiomers were obtained and separated (cf. Scheme 15): 142-E1, 142-E2, 142-E3 and 142-E4.

Example 96: N-Tetralin-1-ylfuro[2,3-d]pyrimidin-4-amine (143)

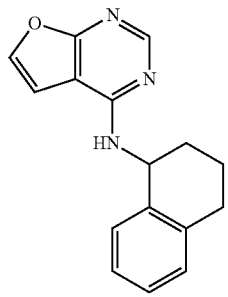 [SMILES: c1ccc2c(c1)CCCC2Nc1ncnc2occc12]

4-chlorofuro[2,3-d]pyrimidine (200 mg, 1.3 mmol, 1.0 eq.) was dissolved in 5 mL of anhydrous THF and the addition made of 1,2,3,4-tetrahydro-1-naphthylamine (0.28 mL, 1.95 mmol, 1.5 eq.) and diisopropylethylamine (0.35 mL, 1.95 mmol, 1.5 eq.). The solution was stirred for 24 h at ambient temperature. Disappearance of the starting reagent was monitored by TLC, and on completion of the reaction the THF was evaporated. The deposit obtained was taken up in 30 mL of saturated aqueous NaHCO$_3$ solution and the product extracted with 3×20 mL ethyl acetate. The organic phases were combined and washed with saturated aqueous NaCl solution (20 mL) and finally dried over MgSO$_4$. After filtering, the solvent was evaporated and the residue purified on silica gel (eluting gradient: 0 to 30% AcOEt/100 to 70% PE). The product was obtained in the form of a white solid (61 mg, 18%). R$_f$(PE/AcOEt 60:40): 0.33. $^1$H NMR (400 MHz, CDCl$_3$) δ 8.40 (s, 1H), 7.47 (d, J=2.0 Hz, 1H), 7.33 (m, 1H), 7.18 (m, 3H), 6.61 (d, J=2.0 Hz, 1H), 5.51 (br s, 1H), 5.49 (br s, 1H) 2.85 (m, 2H), 2.16 (m, 1H), 2.02 (m, 1H), 1.90 (m, 2H). $^{13}$C NMR (101 MHz, CDCl$_3$) δ 166.9, 157.1, 154.3, 141.2, 137.9, 136.7, 129.4, 129.1, 127.7, 126.5, 102.9, 100.7, 49.2, 30.2, 29.4, 19.9. IR (Diamond ATR, cm$^{-1}$) n 3281, 3103, 2929, 1589, 1488, 1343, 1143, 760, 739. HRMS (EI-MS): m/z calculated for Cl$_6$H$_{16}$N$_3$O [M+H]$^+$: 266.1287, found: 266.1286. T$_m$: 166-168° C.

Example 97: N-Tetralin-1-ylfuro[3,2-d]pyrimidin-4-amine (144)

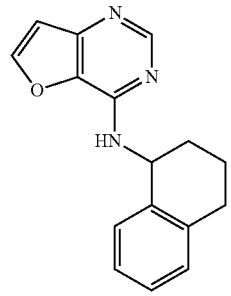 [SMILES: c1ccc2c(c1)CCCC2Nc1ncnc2ccoc12]

4-chlorofuro[3,2-d]pyrimidine (200 mg, 1.30 mmol, 1.0 eq.) was dissolved in 5 mL of anhydrous THF and the addition made of 1,2,3,4-tetrahydro-1-naphthylamine (0.28 mL, 1.95 mmol, 1.2 eq.) and diisopropylethylamine (0.35 mL; 1.95 mmol, 1.2 eq.). The solution was left under stirring for 24 h at ambient temperature. Disappearance of the starting reagent was monitored by TLC, and on completion of the reaction the THF was evaporated. The deposit obtained was taken up in 30 mL of saturated aqueous NaHCO$_3$ solution and the product extracted with 3×20 mL ethyl acetate. The organic phases were combined and washed with saturated aqueous NaCl solution (20 mL) and finally dried over MgSO$_4$. After filtering, the solvent was evaporated and the residue purified on silica gel (eluting gradient: 0 to 40% AcOEt/100 to 60% PE). The product was obtained in the form of a white solid (124 mg, 36%). R$_f$ (PE/AcOEt 50:50): 0.42. $^1$H NMR (400 MHz, CDCl$_3$) δ 8.51 (s, 1H), 7.69 (d, J=2.0 Hz, 1H), 7.35 (m, 1H), 7.19 (m, 3H), 6.85 (d, J=2.0 Hz, 1H), 5.61 (m, 1H), 5.45 (br d, J=3.0 Hz, 1H, NH), 2.85 (m, 2H), 2.19 (m, 1H), 2.02 (m, 1H), 1.97 (m, 2H). $^{13}$C NMR (101 MHz, CDCl$_3$) δ 154.1, 149.7, 148.2, 148.1, 137.8, 136.8, 134.1, 129.4, 129.0, 127.7, 126.5, 108.3, 48.7, 30.4, 29.4, 20.0. IR (Diamond ATR, cm$^{-1}$) n 3169, 3117, 3046, 2923, 2858, 1621, 1330, 1110, 898, 795, 588. HRMS (EI-MS): m/z calculated for Cl$_6$H$_{16}$N$_3$O [M+H]$^+$: 266.1288, found: 266.1287. T$_m$: 149-151° C.

Example 98: N-Tetralin-1-ylthiazolo[5,4-d]pyrimidin-7-amine (145)

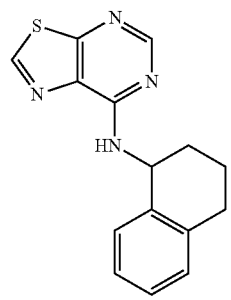 [SMILES: c1ccc2c(c1)CCCC2Nc1ncnc2scnc12]

7-chlorothiazolo[5,4-d]pyrimidine (200 mg, 1.16 mmol, 1.0 eq.) was dissolved in 6 mL of anhydrous THF and the addition made of 1,2,3,4-tetrahydro-1-naphthylamine (0.33 mL, 2.32 mmol, 2.0 eq.) and triethylamine (0.97 mL, 7.0 mmol, 6.0 eq.). The solution was left under stirring for 48 h at ambient temperature. Disappearance of the starting reagent was monitored by TLC, and on completion of the reaction the THF was evaporated. The deposit obtained was taken up 30 mL of saturated aqueous $NaHCO_3$ solution and the product extracted with 3×20 mL ethyl acetate. The organic phases were combined and washed with saturated aqueous NaCl solution (20 mL) and finally dried over $MgSO_4$. After filtering, the solvent was evaporated and the residue purified on silica gel (eluting gradient: 0 to 40% AcOEt/100 to 60% PE). The product was obtained in the form of a white solid (257 mg, 78%). $R_f$(PE/AcOEt 50:50): 0.38. $^1$H NMR (400 MHz, $CDCl_3$) δ 8.67 (s, 1H), 8.57 (s, 1H), 7.33 (m, 1H), 7.17 (m, 3H), 6.49 (br d, J=3.0 Hz, 1H, NH), 5.64 (m, 1H), 2.85 (m, 2H), 2.19 (m, 1H), 1.96 (m, 1H), 1.92 (m, 2H). $^{13}$C NMR (101 MHz, $CDCl_3$) δ 161.3, 155.7, 155.4, 150.4, 137.8, 136.5, 130.9, 129.4, 128.9, 127.6, 126.4, 48.7, 30.0, 29.4, 20.0. IR (Diamond ATR, $cm^{-1}$) n 3438, 3044, 2930, 2860, 1576, 1531, 1422, 1098, 996, 805, 746. HRMS (EI-MS): m/z calculated for $C_{15}H_{15}N_4S$ $[M+H]^+$: 283.1012, found: 283.1010. $T_m$: 111-113° C.

Example 99: N-Tetralin-1-ylimidazo[2,1-f][1,2,4]triazin-4-amine (147)

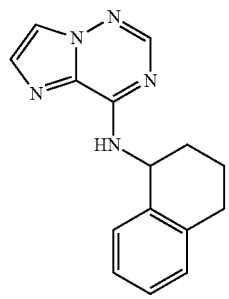 [SMILES: c1ccc2c(c1)CCCC2Nc1ncnn2ccnc12]

4-chlorofuro[3,2-d]pyrimidine (200 mg, 1.30 mmol, 1.0 eq.) was dissolved in 5 mL of anhydrous THF and the addition made of 1,2,3,4-tetrahydro-1-naphthylamine (0.37 mL, 2.6 mmol, 2.0 eq.) and diisopropylethylamine (0.45 mL; 2.6 mmol, 2.0 eq.). The solution became turbid and set in 3 h. Disappearance of the starting reagent was monitored by TLC, and on completion of the reaction the solution was diluted with 50 mL of ethyl acetate. The solution was washed with 30 mL of saturated aqueous $NaHCO_3$ solution then with 30 mL of saturated aqueous NaCl solution (20 mL) and finally dried over $MgSO_4$. After filtering, the solvent was evaporated and the residue purified on silica gel (eluting gradient: 0 to 40% AcOEt/100 to 60% PE). The product was obtained in the form of a white solid (335 mg, 97%). $R_f$ (PE/AcOEt 50:50): 0.34. $^1$H NMR (400 MHz, $CDCl_3$) δ 8.13 (s, 1H), 7.63 (d, J=2.0 Hz, 1H), 7.43 (br d, J=3.0 Hz, 1H, NH), 7.25 (m, 1H), 7.23 (d, J=2.0 Hz, 1H), 7.16 (m, 1H), 7.08 (m, 2H), 5.58 (m, 1H), 2.77 (t, J=6.0 Hz, 2H), 2.15 (m, 1H), 1.92 (m, 2H). $^{13}$C NMR (101 MHz, $CDCl_3$) δ 151.7, 149.4, 137.6, 135.6, 130.9, 129.3, 129.2, 128.7, 127.6, 126.2, 117.8, 48.7, 29.7, 29.2, 20.0. IR (Diamond ATR $cm^{-1}$) n 3154, 2941, 1603, 1477, 1147, 922, 738, 509. HRMS (EI-MS): m/z calculated for $C_{15}H_{16}N_5$ $[M+H]^+$: 266.1400, found: 266.1399. $T_m$: 135-137° C.

Example 100: 7-Methyl-N-[(1S)-tetralin-1-yl]pyrido[3,2-d]pyrimidin-4-amine (149)

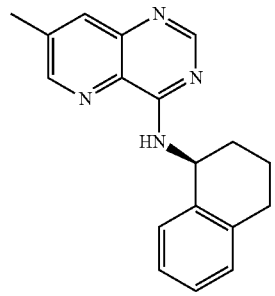 [SMILES: Cc1cnc2c(N[C@H]3CCCc4ccccc43)ncnc2c1]

Compound 148 (80 mg, 0.50 mmol, 1.0 eq.) was dissolved in 5 mL of anhydrous THF and the addition made of (S)-(+)-1,2,3,4-tetrahydro-1-naphthylamine (0.1 mL, 0.67 mmol, 1.3 eq.) and triethylamine (0.1 mL, 0.67 mmol, 1.3 eq.). The solution was stirred for 3 h at ambient temperature. Disappearance of the starting reagent was monitored by TLC, and on completion of the reaction the THF was evaporated. The deposit obtained was taken up in 30 mL of saturated aqueous $NaHCO_3$ solution and the product extracted with 3×20 mL ethyl acetate. The organic phases were combined and washed with saturated aqueous NaCl solution (20 mL) and finally dried over $MgSO_4$. After filtering, the solvent was evaporated and the residue purified on silica gel (eluting gradient: 0 to 50% AcOEt/100 to 50% PE). The product was obtained in the form of a yellow solid (110 mg, 85%). $R_f$(PE/AcOEt 50:50): 0.40. $^1$H NMR (400 MHz, $CDCl_3$) δ 8.64 (s, 1H), 8.44 (m, 1H), 7.84 (m, 1H), 7.39 (br d, J=3.0 Hz, 1H, NH), 7.33 (m, 1H), 7.16 (m, 3H), 5.62 (m, 1H), 2.84 (m, 2H), 2.49 (s, 3H), 2.19 (m, 1H), 2.01 (m, 1H), 1.95 (m, 2H). $^{13}$C NMR (101 MHz, $CDCl_3$) δ 159.1, 156.7, 149.8, 144.4, 138.2, 137.8, 136.6, 134.7, 130.0, 129.3, 128.9, 127.5, 126.4, 48.6, 29.8, 29.4, 20.1, 19.0. IR (Diamond ATR, $cm^{-1}$) n 3386, 2926, 1577, 1529, 1312, 882, 684. HRMS (EI-MS): m/z calculated for $C_{18}H_{19}N_4$ $[M+H]^+$: 291.1604, found: 291.1602. $T_m$: 129-131° C.

Example 101: 4-[[(1S)-Tetralin-1-yl]amino]pyrido[3,2-d]pyrimidin-6-ol (151)

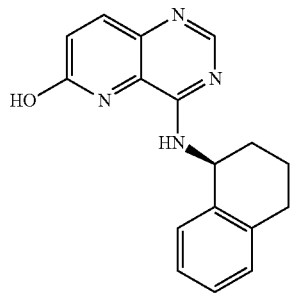 [SMILES: Oc1ccc2ncnc(N[C@H]3CCCc4ccccc43)c2n1]

In a sealed tube, compound 133 (50 mg, 0.16 mmol) was dissolved in 5 mL of DMSO to which TBAF (1 mL, 1 M in THF) was added. The tube was heated under microwave radiation to 120° C. for 1 h. On completion of the reaction, the solution was cooled down to ambient temperature and 30 mL of ethyl acetate were added. The solution was washed with 20 mL of water and 20 mL of saturated aqueous NaCl solution, and finally dried over MgSO$_4$. After filtering, the solvent was evaporated to obtain the product in the form of a yellow solid (35 mg, 74%). R$_f$ (PE/AcOEt 50:50): 0.25. $^1$H NMR (400 MHz, CDCl$_3$) δ 8.51 (s, 1H), 7.76 (d, J=8.0 Hz, 1H), 7.49 (br d, J=7.0 Hz, 1H, NH), 7.22 (m, 3H), 7.08 (m, 1H), 6.19 (d, J=8.0 Hz, 1H), 5.56 (m, 1H), 2.89 (m, 2H), 2.10 (m, 3H), 1.89 (m, 1H). $^{13}$C NMR (101 MHz, CDCl$_3$) δ 163.8, 153.5, 151.0, 142.8, 138.6, 138.0, 136.3, 129.6, 129.2, 127.5, 126.6, 126.2, 119.7, 49.2, 29.4, 29.2, 19.4. IR (Diamond ATR, cm$^{-1}$) n 3360, 3022, 2931, 2854, 1633, 1591, 1439, 1102, 907, 848, 748. HRMS (EI-MS): m/z calculated for Cl$_7$H$_{17}$N$_{40}$ [M+H]$^+$: 293.1396, found: 293.1397. T$_m$: 253-255° C.

Example 102: 4-(Pyrido[3,2-d]pyrimidin-4-ylamino) tetralin-1-one (152)

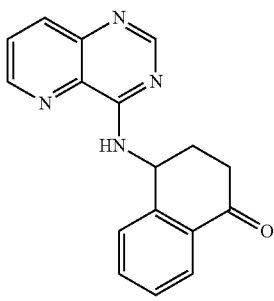 [SMILES: O=C1CCC(Nc2ncnc3cccnc23)c2ccccc21]

Compound 142 (50 mg, 0.17 mmol) was dissolved in 7 mL of CH$_2$Cl$_2$ and Dess-Martin periodinane (110 mg, 0.26 mmol, 1.5 eq.) was added. The solution was stirred at ambient temperature for 2 h. On completion of the reaction, the solution was diluted with 10 mL of saturated aqueous NaHCO$_3$ solution and 10 mL of saturated aqueous Na$_2$S$_2$O$_3$ solution, and the product extracted with 30 mL of CH$_2$Cl$_2$. The organic phase was dried over MgSO$_4$ and after filtering the solvent was evaporated. The product was purified by silica gel chromatography (eluting with CH$_2$Cl$_2$/MeOH 95:5). The product was obtained in the form of a white solid (42 mg, 84%). R$_f$ (PE/AcOEt 20:80): 0.23. $^1$H NMR (400 MHz, CDCl$_3$) δ 8.70 (dd, J=4.0, 2.0 Hz, 1H), 8.69 (s, 1H), 8.13 (dd, J=8.0, 2.0 Hz, 1H), 7.69 (dd, J=8.0, 4.0 Hz, 1H), 7.54 (m, 1H), 7.45 (m, 3H), 5.88 (td, J=49.0, 4.0 Hz, 1H), 2.92 (m, 1H), 2.80 (m, 1H), 2.57 (m, 1H), 2.39 (m, 1H). $^{13}$C NMR (101 MHz, CDCl$_3$) δ 196.9, 159.7, 156.4, 148.6, 144.7, 143.3, 136.2, 134.3, 132.3, 131.9, 128.5, 128.1, 127.7, 127.4, 48.7, 36.6, 29.7. IR (Diamond ATR, cm$^{-1}$) n 3375, 2872, 1677, 1577, 1356, 1146, 776, 683. HRMS (EI-MS): m/z calculated for C$_{17}$H$_{15}$N$_{40}$ [M+H]$^+$: 291.1240, found: 291.1239. T$_m$: 158-160° C.

Example 103: N-(6-Fluorotetralin-1-yl)pyrido[3,2-d]pyrimidin-4-amine (157)

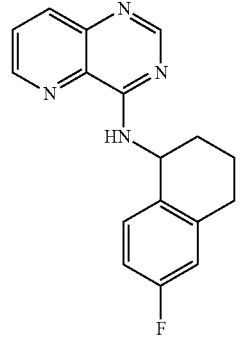 [SMILES: Fc1ccc2c(c1)CCCC2Nc1ncnc2cccnc12]

Compound 10 (150 mg, 0.91 mmol, 1.2 eq.) was dissolved in 5 mL of anhydrous THF to give a yellow solution to which 154 (90 mg, 0.54 mmol, 1.0 eq.) was added. The solution became turbid. Trimethylamine (0.16 mL, 1.1 mmol, 2.0 eq.) was added and the solution left at ambient temperature for 2 to 12 hours under vigorous stirring. Disappearance of the starting reagent was monitored by TLC, and on completion of the reaction the THF was evaporated. The deposit obtained was taken up in 3×20 mL ethyl acetate and the product washed with 30 mL of saturated aqueous NaHCO$_3$ solution. The organic phase was washed with saturated aqueous NaCl solution (40 mL) and finally dried over MgSO$_4$. After filtering, the solvent was evaporated and the residue purified on silica gel (eluting gradient: 0 to 60% AcOEt/100 to 40% PE). The product was obtained in the form of a yellow solid (132 mg, 83%). R$_f$ (PE/AcOEt 50:50): 0.31. $^1$H NMR (400 MHz, CDCl$_3$) δ 8.66 (s, 1H), 8.61 (dd, J=4.0, 2.0 Hz, 1H), 8.08 (dd, J=8.0, 2.0 Hz, 1H), 7.62 (dd, J=8.0, 4.0 Hz, 1H), 7.40 (br d, J=7.0 Hz, 1H, NH), 7.29 (m, 1H), 6.82 (m, 2H), 5.58 (m, 1H), 2.82 (m, 2H), 2.16 (m, 1H), 2.03 (m, 1H), 1.92 (m, 2H). $^{13}$C NMR (101 MHz, CDCl$_3$) δ 162.0 (d, J=246.0 Hz), 159.1, 156.5, 148.2, 144.5, 140.0 (d, J=7.0 Hz), 135.9, 132.3 (d, J=3.0 Hz), 132.0, 130.7 (d, J=8.0 Hz), 127.8, 115.4 (d, J=21.0 Hz), 113.6 (d, J=20.0 Hz), 48.1, 29.7, 29.53 (d, J=2.0 Hz), 19.8. $^{19}$F NMR (376 MHz, CDCl$_3$) 5-115.1 (1F). IR (Diamond ATR, cm$^{-1}$) n 3400, 2954, 2928, 1576, 1498, 1356, 1302, 1134, 870, 841, 798, 682. HRMS (EI-MS): m/z calculated for C$_{17}$H$_{16}$FN$_4$ [M+H]$^+$: 295.1354, found: 295.1353. T$_m$: 135-137° C.

Example 104: 7-Fluoro-N-[(1S)-tetralin-1-yl]pyrido[3,2-d]pyrimidin-4-amine (158)

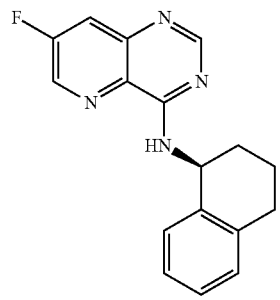 [SMILES: Fc1cnc2c(N[C@H]3CCCc4ccccc43)ncnc2c1]

Compound 155 (5 mg, 0,027 mmol, 1 eq.) was dissolved in 5 mL of anhydrous THF and the addition was made of (S)-(+)-1,2,3,4-tetrahydro-1-naphthylamine (0.005 mL, 0.033 mmol, 1.2 eq.) and triethylamine (0.005 mL, 0.033 mmol, 1.2 eq.). The solution was left under stirring overnight at ambient temperature. Disappearance of the starting reagent was monitored by TLC, and on completion of the reaction the THF was evaporated. The deposit obtained was taken up in 30 mL of saturated aqueous NaHCO$_3$ solution and the product extracted with 3×20 mL ethyl acetate. The organic phases were combined and washed with saturated aqueous NaCl solution (20 mL) and finally dried over MgSO$_4$. After filtering, the solvent was evaporated and the residue purified on silica gel (eluting gradient: 0 to 40% AcOEt/100 to 60% PE). The product was obtained in the form of a white solid (5.6 mg, 70%). R$_f$ (PE/AcOEt 50:50): 0.49. $^1$H NMR (400 MHz, CDCl$_3$) δ 8.66 (s, 1H), 8.51 (d, J=3.0 Hz, 1H), 7.73 (dd, J=9.0, 3.0 Hz, 1H), 7.36 (br d, J=7.0 Hz, 1H, NH), 7.33 (m, 1H), 7.18 (m, 3H), 5.63 (m, 1H), 2.88 (m, 2H), 2.21 (m, 1H), 2.00 (m, 1H), 1.97 (m, 2H). $^{13}$C NMR (101 MHz, CDCl$_3$) δ 161.3 (d, J=263.0 Hz), 158.9, 157.8, 146.0 (d, J=9.0 Hz), 139.0, 138.7, 137.9, 136.4, 129.2 (d, J=56.0 Hz), 129.0 (d, J=2.0 Hz), 127.7, 126.5, 119.4 (d, J=16.0 Hz), 48.8, 29.8, 29.4, 20.2. $^{19}$F NMR (376 MHz, CDCl$_3$) 5-118.8 (1F). IR (Diamond ATR, cm$^{-1}$) n 3294, 3052, 2922, 2852, 1615, 1527, 1439, 1269, 1119, 942, 890, 748, 674, 557. HRMS (EI-MS): m/z calculated for C$_{17}$H$_{16}$FN$_4$ [M+H]$^+$: 295.1353, found: 295.1354. T$_m$: 108-110° C.

Example 105: N-Tetralin-1-ylbenzofuro[3,2-d]pyrimidin-4-amine (159)

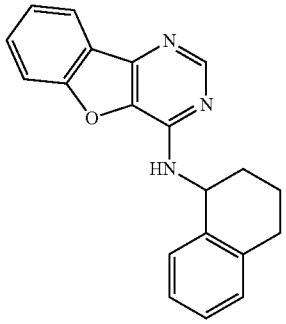 [SMILES: c1ccc2c(c1)CCCC2Nc1ncnc2c1oc1ccccc12]

Compound 156 (50 mg, 0.25 mmol, 1.0 eq.) was dissolved in 5 mL of anhydrous THF and the addition was made of 1,2,3,4-tetrahydro-1-naphthylamine (0.042 mL, 0.3 mmol, 1.2 eq.) and triethylamine (0.041 mL, 0.3 mmol, 1.2 eq.). The solution was left under stirring for 12 h at ambient temperature. Disappearance of the starting reagent was monitored by TLC, and on completion of the reaction the THF was evaporated. The deposit obtained was taken up in 30 mL of saturated aqueous NaHCO$_3$ solution and the product extracted with 3×20 mL ethyl acetate. The organic phases were combined and washed with saturated aqueous NaCl solution (20 mL) and finally dried over MgSO$_4$. After filtering, the solvent was evaporated and the residue purified on silica gel (eluting gradient: 0 to 30% AcOEt/100 to 70% PE). The product was obtained in the form of an orange solid (60 mg, 78%). R$_f$ (PE/AcOEt 40:60): 0.42. $^1$H NMR (400 MHz, CDCl$_3$) δ 8.66 (s, 1H), 8.16 (dt, J=8.0, 1.0 Hz, 1H), 7.56 (m, 2H), 7.41 (m, 2H), 7.20 (m, 3H), 5.68 (m, 1H), 5.60 (br d, J=8.0 Hz, 1H, NH), 2.87 (m, 2H), 2.21 (m, 1H), 2.08 (m, 1H), 1.95 (m, 2H). $^{13}$C NMR (101 MHz, CDCl$_3$) δ 156.5, 153.9, 148.8, 145.9, 137.9, 136.8, 135.0, 129.9, 129.4, 129.1, 127.7, 126.5, 123.9, 121.8, 112.5, 48.7, 30.2, 29.4, 19.9. IR (Diamond ATR, cm$^{-1}$) n 3230, 3026, 2932, 1602, 1498, 1400, 1158, 1099, 988, 741. HRMS (EI-MS): m/z calculated for C$_{20}$H$_{18}$N$_3$O [M+H]$^+$: 316.1444, found: 316.1445. T$_m$: 152-154° C.

Example 106: tert-Butyl N-[2-[[4-[[(1S)-tetralin-1-yl]amino]pyrido[3,2-d]pyrimidin-7-yl]amino]ethyl] carbamate (160)

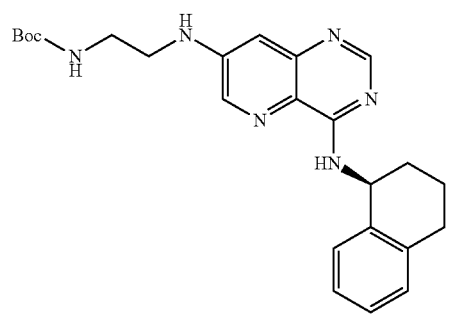 [SMILES: CC(C)(C)OC(=O)NCCNc1cnc2c(N[C@H]3CCCc4ccccc43)ncnc2c1]

In a sealed tube 10 mL, compound 135 (120 mg, 0.34 mmol, 1.0 eq.) was dissolved in 2.5 mL of toluene and 2.5 mL of dioxane before successively adding N-bocethylenediamine (0.11 mL, 0.68 mmol, 2.0 eq.), CS$_2$CO$_3$ (221 mg, 0.68 mmol, 2.0 eq.), xantphos (40 mg, 0.06 mmol, 0.2 eq.) and Pd$_2$(dba)$_3$ (31 mg, 0.034 mmol, 0.1 eq.). The reaction was carried out in a microwave reactor at 130° C. under vigorous stirring for one hour. On completion of the reaction, disappearance of the starting bromine compound was verified by TLC and the solution diluted with 5 mL ethyl acetate and filtered through Celite®. After filtering, the solvent was evaporated and the residue purified on silica gel (eluting gradient: 0 to 90% AcOEt/100 to 10% PE). The product was obtained in the form of an orange solid (105 mg, 72%). R$_f$ (PE/AcOEt 10:90): 0.24. $^1$H NMR (400 MHz, CDCl$_3$) δ 8.52 (s, 1H), 8.04 (d, J=3.0 Hz, 1H), 7.33 (m, 1H), 7.12 (m, 4H), 6.87 (m, 1H), 5.57 (m, 1H), 5.27 (br s, 1H, NH), 5.08 (br s, 1H, NH), 3.44 (m, 2H), 3.30 (m, 2H), 2.83 (m, 2H), 2.18 (m, 1H), 1.97 (m, 1H), 1.95 (m, 2H), 1.43 (s, 9H). $^{13}$C NMR (101 MHz, CDCl$_3$) δ 158.7, 157.3, 156.9, 147.6, 146.3, 139.8, 137.8, 137.0, 129.3, 129.0, 127.4, 126.3, 123.4, 108.7, 80.2, 48.4, 44.9, 39.6, 30.0, 29.4, 28.5, 20.2. IR (Diamond ATR, cm$^{-1}$): 2929, 1689, 1575, 1515, 1330, 1163, 731. HRMS (EI-MS): m/z calculated for C$_{24}$H$_{31}$N$_6$O$_2$ [M+H]$^+$: 435.2503, found: 435.2502. T$_m$: 87-89° C.

Example 107: N<sub>7</sub>-(2-Aminoethyl)-N<sub>4</sub>-[(1S)-tetralin-1-yl]pyrido[3,2-d]pyrimidine-4,7-diamine (161)

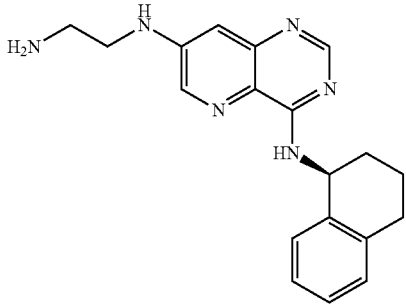 [SMILES: NCCNc1cnc2c(N[C@H]3CCCc4ccccc43)ncnc2c1]

Compound 160 (80 mg, 0.18 mmol) was dissolved in 4 mL of CH$_2$Cl$_2$ and 1 mL of TFA was added to the flask. After overnight vigorous stirring at ambient temperature, a few milliliters of 2 M NaOH solution were added and the mixture stirred at ambient temperature for 1 hour. The product was extracted with 3×15 mL AcOEt and the organic phases were combined and dried over MgSO$_4$. After filtering and evaporation, the residue was purified by silica gel chromatography (gradient 0 to 100% AcOEt/100 to 0% PE). The product was obtained in the form of a white solid (22 mg, 36%). Rf (PE/AcOEt 70:30): 0.15. $^1$H NMR (400 MHz, CDCl$_3$) δ 8.31 (s, 1H), 8.18 (d, J=3.0 Hz, 1H), 7.23 (d, J=8.0 Hz, 1H), 7.11 (m, 3H), 6.81 (d, J=3.0 Hz, 1H), 5.51 (t, J=6.0 Hz, 1H), 3.28 (t, J=6.0 Hz, 2H), 2.91 (t, J=6.0 Hz, 2H), 2.81 (m, 2H), 2.13 (m, 1H), 1.95 (m, 2H), 1.86 (m, 1H). $^{13}$C NMR (101 MHz, CDCl$_3$) δ 159.9, 156.9, 150.2, 147.0, 141.8, 138.7, 137.8, 130.2, 129.3, 128.3, 127.1, 123.2, 107.3, 49.9, 46.3, 41.0, 31.0, 30.2, 21.5 HRMS (+ESI): m/z calculated for Cl$_9$H$_{23}$N$_6$ [M+H]$^+$: 335.1979, found: 335.1977.

Example 108: 6-Hexoxy-N-[(1S)-tetralin-1-yl]pyrido[3,2-d]pyrimidin-4-amine (162)

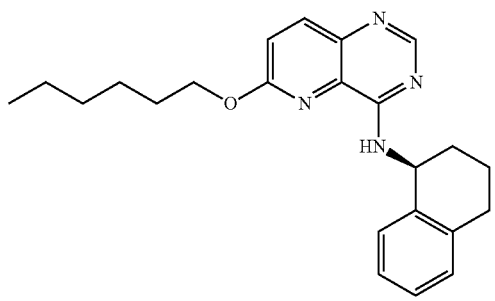 [SMILES: CCCCCCOc1ccc2ncnc(N[C@H]3CCCc4ccccc43)c2n1]

Compound 133 (100 mg, 0.32 mmol, 1.0 eq.) was dissolved in 1 mL of n-hexanol in a round-bottom flask, and the successive addition was made of Pd2(dba)3 (1.4 mg, 0.002 mmol, 0.02 eq.), KOH (27 mg, 0.28 mmol, 2.0 eq.) and Bippyphos (3.2 mg, 0.006 mmol, 0.02 eq.). The mixture was heated to 100° C. for 4 h. The reaction medium was diluted with 20 mL of water and the product extracted with 3×20 mL CH$_2$Cl$_2$. The organic phases were combined and dried over MgSO4, and the solvent evaporated after filtration. The residue was purified by silica gel chromatography (gradient 0 to 100% AcOEt/100 to 0% PE). The product was obtained in the form of an orangish oil (61 mg, 51%). R$_f$ (PE/AcOEt 50:50): 0.11. $^1$H NMR (400 MHz, CDCl$_3$) δ 8.61 (s, 1H), 8.00 (d, J=9.0 Hz, 1H), 7.43-7.36 (m, 1H), 7.29-7.12 (m, 4H), 6.93 (d, J=9.0 Hz, 1H), 5.73-5.62 (m, 1H), 4.31 (t, J=6.6 Hz, 2H), 3.02-2.82 (m, 2H), 2.37-2.23 (m, 1H), 2.08-1.90 (m, 3H), 1.85-1.73 (m, 2H), 1.51-1.14 (m, 9H). $^{13}$C NMR (101 MHz, CDCl3) δ 161.4, 158.2, 154.0, 141.2, 138.9, 137.7, 137.2, 129.2, 128.4, 128.3, 127.3, 126.3, 119.3, 77.3, 77.2, 77.0, 76.7, 66.8, 48.5, 31.5, 30.2, 29.7, 29.4, 29.3, 28.6, 25.7, 22.5, 20.5, 13.9. IR (Diamond ATR, cm$^{-1}$): 3401, 2927, 2857, 1613, 1582, 1526, 1486, 1405, 1348, 1265, 1103, 841, 745. HRMS (+ESI): m/z calculated for C$_{23}$H$_{29}$N$_4$O [M+H]$^+$: 377.2336, found: 377.2335.

Example 109: tert-Butyl N-[2-[2-[4-(tetralin-1-ylamino)pyrido[3,2-d]pyrimidin-6-yl]oxyethoxy]ethyl]carbamate (163)

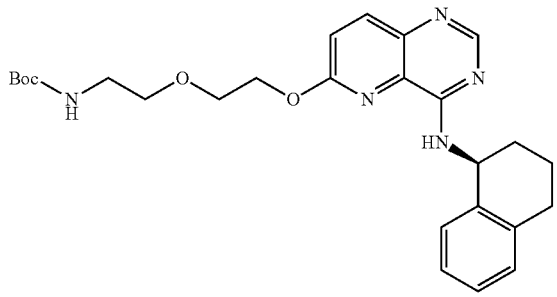 [SMILES: CC(C)(C)OC(=O)NCCOCCOc1ccc2ncnc(N[C@H]3CCCc4ccccc43)c2n1]

Compound 133 (110 mg, 0.35 mmol, 1.0 eq.) was dissolved in 0.5 mL of N-boc-2-(2-hydroxyethoxy)-ethylamine after which Pd2(dba)3 (7.3 mg, 0.008 mmol, 0.02 eq.), KOH (40 mg, 0.7 mmol, 2.0 eq.) and Bippyphos (3.5 mg, 0.007 mmol, 0.02 eq.) were successively added to the round-bottom flask. The mixture was heated to 100° C. for 4 h. The reaction medium was diluted with 20 mL of water and the product extracted with 3×20 mL CH$_2$Cl$_2$. The organic phases were combined and dried over MgSO4, and the solvent evaporated after filtration. The residue was purified by silica gel chromatography (gradient 0 to 40% AcOEt/100 to 60% PE). The product was obtained in the form of a colourless oil (153 mg, 90%). Rf (PE/AcOEt 50:50): 0.62. $^1$H NMR 1H (400 MHz, CDCl$_3$) δ 8.62 (s, 1H), 8.03 (d, J=9.0 Hz, 1H), 7.38 (m, 1H), 7.21 (m, 4H), 6.88 (d, J=9.0 Hz, 1H), 5.68 (q, J=7.2, 6.1, 6.1 Hz, 1H), 4.93 (s, 1H), 4.47 (m, 2H), 3.83 (m, 2H), 3.60 (m, 2H), 3.34 (q, J=5.4, 5.3, 5.3 Hz, 2H), 3.91 (d, J=7.6 Hz, 2H), 2.29 (m, 1H), 1.98 (m, 2H), 1.45 (s, 9H), 1.23 (m, 2H). $^{13}$C NMR (101 MHz, CDCl$_3$) 160.9, 158.1, 154.2, 141.5, 139.2, 137.7, 137.1, 129.2, 128.4, 127.3, 126.3, 119.2, 77.3, 77.2, 77.0, 76.6, 70.3, 68.9, 65.7, 48.5, 30.1, 29.3, 28.3, 20.5. HRMS (+ESI): m/z calculated for C$_{26}$H$_{34}$N$_5$O$_4$ [M+H]$^+$: 480.2605, found: 480.2605.

Example 110: 6-[2-(2-Aminoethoxy)ethoxy]-N-tetralin-1-yl-pyrido[3,2-d]pyrimidin-4-amine (164)

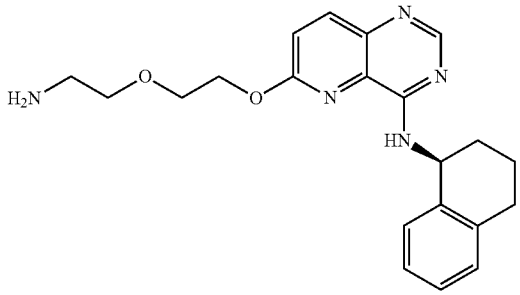 [SMILES: NCCOCCOc1ccc2ncnc(N[C@H]3CCCc4ccccc43)c2n1]

Compound 163 (150 mg, 0.31 mmol) was dissolved in 4 mL of $CH_2Cl_2$ and 1 mL of TFA was added to the round-bottom flask. After overnight vigorous stirring at ambient temperature, a few milliliters of 2 M NaOH solution were added and the mixture stirred at ambient temperature for 1 hour. The product was extracted with 3×15 mL AcOEt and the organic phases were combined and dried over $MgSO_4$. After filtering and evaporation, the residue was purified by silica gel chromatography (gradient 0 to 60% AcOEt/100 to 40% PE). The product was obtained in the form of a colourless oil (42 mg, 36%). Rf (PE/AcOEt 50:50): 0.10.

Example 111: N-(5,6,7,8-tetrahydroquinolin-8-yl)pyrido[3,2-d]pyrimidin-4-amine (165)

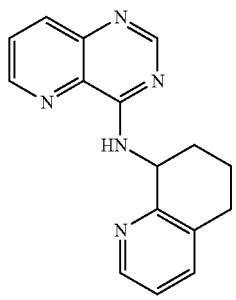

Compound 165 was obtained following procedure B with 5,6,7,8-tetrahydroquinolin-8-amine (70 mg, 0.47 mmol, 1.2 eq.), 10 (60 mg, 0.37 mmol, 1.0 eq.) and triethylamine (0.07 mL, 0.47 mmol, 1.2 eq.). The residue was purified by silica gel chromatography (gradient 0 to 50% AcOEt/100 to 50% PE). The product was obtained in the form of a grey solid (82 mg, 82%). $R_f$ (PE/AcOEt 50:50): 0.29. $^1$H NMR (400 MHz, CDCl3) δ 8.69 (m, 2H), 7.49 (dd, J=4.7, 1.6 Hz, 1H), 8.10 (dd, J=8.5, 1.6 Hz, 1H), 8.01 (d, J=6.8 Hz, 1H), 7.64 (dd, J=8.4, 4.2 Hz, 1H), 7.49 (m, 1H), 7.17 (dd, J=7.7, 4.6 Hz, 1H), 5.43 (m, 1H), 2.90 (m, 2H), 2.68 (m, 2H), 1.92 (m, 4H). $^{13}$C NMR (101 MHz, CDCl3) δ 159.6, 156.4, 155.2, 148.1, 147.5, 144.2, 137.1, 135.7, 133.1, 132.4, 127.5, 122.5, 76.7 51.5, 29.1, 28.4, 19.8. IR (Diamond Smart iTR, cm-1, neat): 3402, 2043, 2946, 1574, 1531, 1442, 1380, 1357, 1294, 804, 684. HRMS (+ESI): m/z calculated for $C_{16}H_{16}N_5$ $[M+H]^+$: 278.1400, found: 278.1398. $T_m$: 155-157° C.

BIOLOGICAL PROPERTIES OF THE COMPOUNDS OF THE INVENTION

Materials and Methods

Cell Lines Used to Screen the Molecules on the Activity of SKCa Channels (Small Conductance Calcium-Activated Potassium Channel; SK1, SK2 and SK3) and IKCa Channels (Intermediate Conductance Calcium-Activated Potassium Channel, SK4)

Use was made of the HEK 293 T line, a foetal kidney line which was immortalised with the T antigen of the SC40 simian virus. This cell line is widely used on account of the ease with which these cells can be transfected with plasmids or other transfection vectors. Four stable lines were used for patch clamp experiments: HEK-hSK1, HEK-rSK2, HEK-rSK3 and HEK-IKCa/SK4 which respectively overexpress the SK1, SK2, SK3 and SK4 channels. The lines were obtained via stable transduction (Girault et al., *Current Cancer Drug Targets*, 2011, 11, 1111-25) and are those already routinely used to assay SK3 modulators (Potier et al. *Br J Pharmacol*. 2011 January; 162(2):464-79; Sevrain et al., *Med. Chem. Commun.*, 2012, 3, 1471-1478; Sevrain et al., *Organic & Biomolecular Chemistry*, 2013 Jul. 21; 11(27):4479-87, Berthe W, Sevrain C M, Chantôme A, Bouchet A M, Gueguinou M, Fourbon Y, Potier-Cartereau M, Haelters J P, Couthon-Gourvès H, Vandier C, Jaffrès P A. ChemMedChem. 2016 Jul. 19; 11(14):1531-9). A further advantage of this line lies in the fact that it does not natively express SKCa channels. These lines therefore enabled us without difficulty to examine the effect of the molecules on the SK3 channel, and also the selectivity thereof by means of the patch clamp technique. The inhibitory activity of the non-toxic molecules was assayed on the activity of the SK3 channel. The selectivity of the molecules was determined by patch clamp on HEK cell models stably expressing the SK3 channel but also the SK1, SK2, SK3 or IKCa/SK4 channels.

Electrophysiology/Patch-Clamp

Patch clamp is a technique allowing measurement of the activity of ion channels by recording macroscopic (whole cell configuration) or microscopic (e.g. inside out configuration) ionic currents through the plasma membrane. For assay of the effect of the molecules on the SKCa/IKCa channels, two complementary techniques were used: conventional, manual patch clamp and automated patch clamp with the Nanion NPC-16 Patchliner Quattro (4 channels) (Potier et al., *Mol Cancer Ther* 2006, 5, 2946-53; Chantome et al., *Exp Cell Res* 2009, 315, 3620-30; Potier et al., *Biochem Biophys Res Commun* 2010, 397, 42-7; Girault et al., *Current Cancer Drug Targets*, 2011, 11, 1111-25; Sevrain et al., *Med. Chem. Commun.*, 2012, 3, 1471-1478; Sevrain et al., *Organic & Biomolecular Chemistry*, 2013 Jul. 21; 11(27):4479-87; Chantome et al., *Cancer Research*, 2013 Aug. 1; 73(15):4852-61, Gueguinou M, Crottès D, Chantôme A, Rapetti-Mauss R, Potier-Cartereau M, Clarysse L, Girault A, Fourbon Y, Jézéquel P, Guérin-Charbonnel C, Fromont G, Martin P, Pellissier B, Schiappa R, Chamorey E, Mignen O, Uguen A, Borgese F, Vandier C, Soriani O. Oncogene. 2017 Jan. 23. doi: 10.1038/onc.2016.501, Berthe W, Sevrain C M, Chantôme A, Bouchet A M, Gueguinou M, Fourbon Y, Potier-Cartereau M, Haelters J P, Couthon-Gourvès H, Vandier C, Jaffrès P A. ChemMedChem. 2016 Jul. 19; 11(14):1531-9, Guéguinou M, Harnois T, Crottes D, Uguen A, Deliot N, Gambade A, Chantôme A, Haelters J P, Jaffrès P A, Jourdan M L, Weber G, Soriani O, Bougnoux P, Mignen O, Bourmeyster N, Constantin B, Lecomte T, Vandier C, Potier-Cartereau M. Oncotarget. 2016 Jun. 14; 7(24):36168-36184. doi: 10.18632/oncotarget.8786).

For conventional patch clamp, the micropipette is filled with an intrapipette medium—IPM (see composition below) and allows measurement of ionic currents at the same time as allowing maintaining of membrane potential (voltage clamp). The experimental device was composed of an anti-vibration table supporting an inverted microscope (Nikon, Eclipse TE 300). The Petri dish (Corning Incorporated, USA), containing the cells was placed on a plexiglass plate attached to the microscope stage. The pipette was connected to the amplifier (Axopatch 200B) as reference electrode which allowed closing of the electrical circuit. The amplifier, which ensures current-voltage conversion, was itself connected to an analogue-digital digitizer (Digidata 1322A, Axon Instruments, USA). Control over potential and the recording and monitoring of currents were computer-assisted and driven by PClamp 8.1 software (Axon Instruments, USA). The pipettes were of hard glass on a vertical puller (PP-830, Narishige) and generally had a resistance of between 3-5 MΩ for the whole-cell configuration. For the whole-cell configuration, the cells were held in physiological saline solution or PSS, having the composition (in mM): NaCl 140, KCl 4, $MgCl_2$ 1, $CaCl_2$ 2, D-Glc 11.1, HEPES 10. The pH was adjusted to 7.4 with NaOH and the glass pipette filled with IPM having the composition (in mM) of K-glutamate 125, KCl 20, $CaCl_2$ 0.37, $MgCl_2$ 1, MgATP 1, EGTA 1, HEPES 10, and the pH adjusted to 7.2 with KOH. The intrapipette medium (IPM) was composed of a solution containing (in mM) KCl 140, EGTA 5, HEPES 10 and $MgCl_2$ 1 (pH 7.4/KOH). Several protocols were followed: i) a square pulse protocol at 10 mV (500 msec) allowing the construction of current-voltage relations (I/V) from −100 mV to +100 mV starting from a holding potential of −70 mV, and a ramp protocol allowing incrementation of imposed potential from −100 mV to +100 mV within a given time (500 msec).

The technique of choice to determine molecules inhibiting the activity of ion channels is the patch-clamp technique. However, this technique which is manual is time-consuming and only gives low yields. Automation of patch-clamp brought a revolution in the study and screening of ion channels and has allowed the envisaging of assays with much faster flow rate and much higher yield. There exist several automatic patch clamp devices based on the use of chips. The latter, called «planar» patch-clamp or 2D were developed by Nanion including in particular the Patchliner in which the patch pipette conventionally used is replaced by a chip having a hole and mimicking the end portion of a patch pipette. It is this automated device and more specifically the NPC-16 Patchliner Quattro (4 channels) which was used to assay the molecules on the SK1/SK2/KCa channels. The activity of the SK3 channel was assayed using the conventional patch clamp technique.

In Vivo Acute and Repeat Dose Toxicity

For acute toxicity, compound 20 was prepared in a DMSO/PEG300/Water mixture (5:45 50) and injected via intra-peritoneal route at 10 ml/kg with doses of 0, 1, 5, 10, 25 and 50 mg/kg, each dose group comprising 2 mice. Throughout the study, the animals were weighed and observed daily for 12 days. After 12 days, the animals were euthanised and the organs subjected to macroscopic observation.

For repeat dose toxicity, the study was divided into two steps over a time of four weeks. The tested product was administered via intraperitoneal injection to non-tumour bearing female NMRI mice aged 6 weeks (Janvier, France). Injections were given daily for 15 days. At this stage, some of the mice were sacrificed for observation of macroscopic effects of the compounds on internal organs. The remaining group was kept in animal housing over the two following weeks. Throughout this period the behaviour of the mice was monitored. At the end of this second step, sacrificing allowed examination of the effects of the molecules on internal organs and of the reversible or irreversible nature of any detected toxicity.

Six groups of 4 mice were formed and compound 20 was prepared in a DMSO/PEG300/Water mixture (5:45:50) at 10 ml/kg:

- Group 20 5: group treated via intraperitoneal injection of compound 20 at 5 mg/kg, 5 times per week for 15 days. The total injected dose was 50 mg/kg (5×10 days).
- Group 20 7.5: group treated via intraperitoneal injection of compound 20 at 7.5 mg/kg, 5 times per week for 15 days. The total injected dose was 75 mg/kg (7.5×10 days).
- Group 20 12.5: group treated via intraperitoneal injection of compound 20 at 12.5 mg/kg, 5 times per week for 15 days. The total injected dose was 125 mg/kg (12.5×10 days).
- Group 20 17.5: group treated via intraperitoneal injection of compound 20 at 17.5 mg/kg, 5 times per week for 15 days. The total injected dose was 175 mg/kg (17.5×10 days).
- Group 20 25: group treated via intraperitoneal injection of compound 20 at 25 mg/kg, 5 times per week for 15 days. The total injected dose was 250 mg/kg (25×10 days).
- Control group: group given intraperitoneal injections of DMSO/PEG300/Water at 10 ml/kg, 5 times per week for 15 days.

After the 2-week period, blood samples were taken from one half of the animals, and their organs macroscopically examined after euthanasia. After the 4-week period, the remaining animals were euthanised and the organs macroscopically examined.

In Vivo Mouse Model of Orthotopic Xenograft: Assay on Capacity of the Molecules to Reduce Tumour Development This model allowed study on a metastatic cancer with development of the primary tumour and formation of metastases in parallel with primary tumour development. For this assay, female NMRI nude mice aged four weeks were used. To prepare the graft, the terminal end bud of the mice was cauterised with an electrical scalpel and 2 million cells expressing the SK3 channel and luciferase (MDA-MB-435s-Luc) implanted therein. Luciferase allows in vivo monitoring of tumour development via optical imaging (Girault et al., *Current Cancer Drug Targets*, 2011, 11, 1111-25; Chantome et al., *Cancer Research*, 2013 Aug. 1; 73(15):4852-61).

Two groups of mice were formed and compound 20 was prepared in a DMSO/PEG300/Water mixture (5:45:50) at 10 ml/kg:

- Group 20 1: group treated via intraperitoneal injection of compound 20 at 1 mg/kg, three times per week for 14 weeks; and
- Control group: group given injections with equivalent vehicle dilution (DMSO/ethanol), three times per week for 15 weeks.

Development of the primary tumour was monitored in two manners: size measurement with a calliper rule (length×width×thickness) and measurement of bioluminescence with a bio-imaging device.

If the primary tumour reached a size of 900 mm³, it was fully excised to best approach a clinical situation and exclude this variable which could impact the development of metastases. The experiment was continued with injections of compound 20 and monitoring of the development of metastases via BLI with front and back imaging of the mice.

The weight of the mice, bioluminescence and tumour size measurements were carried out every week to monitor tumour changes and metastases. For imaging, the mice were anaesthetised with isoflurane.

After about 15 weeks, the mice were sacrificed. Luciferin was injected before sacrifice to allow whole-animal imaging and imaging of each organ examined (bone, liver, lymph node, brain, colon).

Results

Effect of Compound 20 on Development of the Primary Tumour and Metastases.

Among the different variables collected, the weight of the mice allowed verification of the non-toxicity of compound 20 over time. Weight was no longer taken into account after excision of the primary tumour to avoid distortion of the mean. We obtained identical weight progression in the mice as a function of the groups. At 10 weeks, there was no significant difference in weight between the two groups. In xenografted mice, this confirms the apparent non-toxicity of compound 20 at 1 mg/kg.

The volume and BLI of the primary tumour were measured weekly. BLI reflects the number of MDA-MB-435s cells at the implantation site. Gradual growth of primary tumours was found in the different groups with both monitoring methods: BLI and calliper rule. Tumour volume at week 7 was measured by a different operator which accounts for inflection of the curve. Tumour volume did not differ between groups at the time of primary tumour excision.

After 15 weeks, the animals were euthanised and the metastases visualized ex vivo in different organs.

All the mice (Controls and compound 20 at 1 mg/kg) developed lung metastases.

However, compound 20 at 1 mg/kg reduced the number of bone metastases and fully stopped the development of ovarian and uterine metastases (FIGS. 1 and 2). FIGS. 1 and 2 give the percentage metastases in control mice and in the mice given compound 20 at 1 mg/kg.

| Compound | % SK3 inhibition | % SK2 inhibition |
| --- | --- | --- |
| NS8593 | IC50: 87 nM ± 12<br>Stroebaek et al, 2006: 90 nM ± 8<br>Jenkins et al, 2011: 104 nM ± 34 | ND |
| 4 | 10 µM: 3.6% ± 3.6 ((N = 2) | ND |
| 5 | 10 µM: 7.7% ± 2 (N = 4) | ND |
| 79 | 10 µM: 27% ± 3.9% (N = 4) | ND |
| 7 | 10 µM: 83.4 ± 3.2 (N = 8)<br>100 nM: 81.3 ± 1.0 (N = 3)<br>10 nM: 56.1 ± 4.8 (N = 3)<br>1 nM: 42.2 ± 6.4 (N = 6) | 10 µM: 95.6 ± 1.2 (N = 9)<br>100 nM: 91.5 ± 1.6 (N = 9)<br>10 nM: 89.3 ± 3.2 (N = 8)<br>1 nM: 35.0 ± 9.2 (N = 7) |
| 6 | 10 µM: 2.65% ± 4.8 (N = 2) | ND |
| 47 | 10 µM: 7.54 ± 10.1 (N = 3) | ND |
| 14 | 10 µM: 1.52 ± 8.81 (N = 2) | ND |
| 18 | 10 µM: 89.9 ± 3.1 (N = 3)<br>100 nM: 96.0 ± 0.9 (N = 4)<br>10 nM: 59.7 ± 4.1 (N = 3)<br>1 nM: 44.7 ± 5.5 (N = 4) | 10 µM: 97.05 ± 1.08 (N = 5)<br>100 nM: 92.9 ± 1.9 (N = 5)<br>10 nM: 81.4 ± 7.8 (N = 4)<br>1 nM: 36.7 ± 9.9 (N = 3) |
| 20 | 10 µM: 92.8 ± 1.4 (N = 8)<br>10 nM: 45.5 ± 8.8 (N = 3) | 10 µM: 91.8 ± 4.1 (N = 5)<br>100 nM: 91.2 ± 1.6 (N = 10) |
| 30 | 10 µM: 87.2 ± 3.0 (N = 7)<br>500 nM: 52.9 ± 9.1 (N = 5)<br>50 nM: 35.5 ± 6.7 (N = 5) | 10 µM: 95.05 ± 2.2 (N = 6) |
| 32 | 500 nM: 27.73 ± 6.13 (N = 4)<br>50 nM: 23.57 ± 1.81 (N = 4) | ND |
| 34 | 500 nM: 40.4 ± 9.6 (N = 4)<br>50 nM: 32.9 ± 10.0 (N = 5) | 10 µM: 94.8 ± 1.2 (N = 7)<br>100 nM: 92.7 ± 4.8 (N = 2) |
| 33 | 10 µM: 71.5 ± 7.4 (N = 5)<br>100 nM: 53.2 ± 10.9 (N = 5)<br>50 nM: 30.5 ± 6.9 (N = 5) | ND |
| 35 | ND | 10 µM: 91.4 ± 2.3 (N = 4)<br>100 nM: 83.7 ± 4.2 (N = 2) |
| 38 | 10 µM: 73.98 ± 2.93<br>100 nM: 51.9 ± 4.39<br>50 nM: 31.36 ± 6.09 | ND |
| 23 | 10 µM: 8.4 ± 5.5 (N = 2) | 10 µM: 1 ± 22 (N = 2) |
| 29 | 10 µM: 46.0 ± 2.5 (N = 3) | 10 µM: 16.2 ± 12.7 (N = 2) |
| 40 | 10 µM: 82.2 ± 2.2 (N = 4)<br>100 nM: 11.9 ± 1.9 (N = 2) | 10 µM: 88.1 (N = 1)<br>100 nM: 25.6 (N = 1) |
| 53 | 10 µM: 62.2 ± 3.9 (N = 5)<br>100 nM: 41.9 ± 6.9 (N = 8)<br>50 nM: 29.2 ± 2.7 (N = 12)<br>500 nM: 94.2 ± 1.4 (N = 4)<br>10 nM: 42.6 ± 3.7 (N = 3)<br>1 nM: 7.4 ± 3.0 (N = 3) | 50 nM: 29.25 ± 2.68 (N = 12)<br>100 nM: 41.92 ± 6.99 (N = 5)<br>500 nM: 43.17 ± 2.97 (N = 8)<br>10 µM: 62.21 ± 3.95 (N = 5) |
| 62 | 50 nM: 32.09 ± 2.3 (N = 3)<br>100 nM: 46.84 ± 6.82 (N = 3)<br>10 µM: 54.38 ± 4.85 (N = 3) | ND |
| 67 | 100 nM: 35.3 ± 9.4 (N = 5)<br>1 µM: 82.4 ± 7.1 (N = 4)<br>500 nM: 39.3 ± 10.4 (N = 3) | ND |

-continued

| Compound | % SK3 inhibition | % SK2 inhibition |
|---|---|---|
| 49 | 500 nM: 75.8 ± 8.6 (N = 5)<br>250 nM: 83.1 ± 3.0 (N = 4)<br>100 nM: 37.1 ± 9.4 (N = 5) | ND |
| 74 | 500 nM: 48.55 ± 8.8 (N = 3)<br>50 nM: 18.45 ± 2.45 (N = 3) | ND |
| 75 | 10 µM: 88.81 ± 1.16 (N = 2)<br>100 nM: 85.42 ± 6.35 (N = 2)<br>10 nM: 92.43 ± 0.78 (N = 2) | 10 µM: 93.3 (N = 1)<br>100 nM: 80 (N = 1) |
| 86 | 500 nM: 18 ± 2.3 (N = 5)<br>50 nM: −9.01 ± 2.2 | ND |
| 87 | 500 nM: 47.44 ± 2.3 (N = 3)<br>50 nM: 22.92 ± 4.6 (N = 3) | ND |
| 88 | 500 nM: 54.81 ± 8.43 (N = 4)<br>50 nM: 25.75 ± 11.01 (N = 4) | ND |
| 90 | 500 nM: 39.87 ± 7.82 (N = 4)<br>50 nM: 16.07 ± 2.47(N = 4) | ND |
| 93 | 50 nM: 45.85 ± 11.2<br>100 nM: 53.55 ± 9.92<br>10 µM: 71.83 ± 7.37 | ND |
| 103 | 10 µM: 83.83 ± 6.71 (N = 4)<br>500 nM: 46.91 ± 6.45 (N = 3)<br>100 nM: 57.85 ± 7.82 (N = 3)<br>50 nM: 30.69 ± 6.94 (N = 6) | ND |
| 107 | 10 µM: 54.74 ± 6.82 (N = 6)<br>100 nM: 46.78 ± 7.7 (N = 8)<br>50 nM: 29.74 ± 5.5 (N = 8) | ND |
| 133 | 50 nM: 38.97 ± 4.68 (N = 5)<br>100 nM: 56.34 ± 7.3 (N = 4)<br>10 µM: 67.31 ± 10.04 (N = 3) | ND |
| 142-E1 | 50 nM: 35.27 ± 3.63 (N = 5)<br>100 nM: 44.55 ± 5.67 (N = 5)<br>10 µM: 57.16 ± 5.51 (N = 4) | ND |
| 142-E2 | 50 nM: 35.72 ± 1.79 (N = 4)<br>100 nM: 59.42 ± 3.43 (N = 4)<br>10 µM: 75.11 ± 2.87 (N = 4) | ND |
| 142-E3 | 50 nM: 30.69 ± 3.07 (N = 4)<br>100 nM: 49.71 ± 4.48 (N = 4)<br>10 µM: 58.9 ± 6.08 (N = 4) | ND |
| 142-E4 | 50 nM: 21.9 ± 2.32 (N = 3)<br>100 nM: 37.97 ± 3.99 (N = 3)<br>10 µM: 48.28 ± 5.99 (N = 3) | ND |
| 152 | 50 nM: 24.42 ± 1.68 (N = 3)<br>100 nM: 41.48 ± 8.7 (N = 3)<br>10 µM: 61.19 ± 8.1 (N = 3) | ND |
| 157 | 50 nM: 32.04 ± 1.39 (N = 3)<br>100 nM: 51.13 ± 1.01 (N = 3)<br>10 µM: 53.99 ± 2.19 (N = 3) | ND |
| 158 | 50 nM: 35.84 ± 5.97 (N = 4)<br>100 nM: 64.14 ± 3.06 (N = 4)<br>10 µM: 84.83 ± 5.56 (N = 4) | ND |

The invention claimed is:

1. A method for treating breast cancer, melanoma, prostate cancer, colorectal cancer, or urotherial carcinoma, said method comprising administering to a subject in need thereof a compound having formula (III-4):

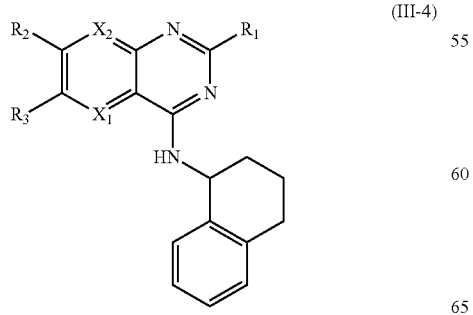

where:
either $X_1$ is a nitrogen atom and $X_2$ is a $C(R_4)$ group, or $X_1$ is a $C(R_5)$ group and $X_2$ is a nitrogen atom, or $X_1$ and $X_2$ are a nitrogen atom, $R_4$ and $R_5$ each independently being H or a substituent selected from the group consisting of: halogen atoms, $(C_1\text{-}C_6)$(cyclo)alkyl groups, $NR_aR_b$ groups, and $OR_a$ groups, $R_a$ and $R_b$ each independently being H or $(C_1\text{-}C_6)$alkyl group, $R_1$ is H, a $(C_1\text{-}C_6)$alkyl group or a radical selected from the group consisting of: —$OR_a$, —$NHR_a$, —$NR_aR_b$, —NH—C(=O)$R_a$, —C(=O)$R_a$, —C(=O)$OR_a$, —NH—CN, —C(=O)$NR_aR_b$, Cl, F, CN and nitrogen-containing and/or oxygen-containing heterocycles, said nitrogen-containing heterocycles and/or said oxygen-containing heterocycles having 5 atoms, and wherein $R_a$ and $R_b$ each independently being H, a $(C_1\text{-}C_6)$alkyl group or $(C_3\text{-}C_6)$cycloalkyl group;

$R_2$ and $R_3$ are each independently H or a substituent selected from the group consisting of: halogen atoms, (C$_1$-C$_6$)(cyclo)alkyl groups, NR$_a$R$_b$ groups, and OR$_a$ groups, R$_a$ and R$_b$ each independently being H or (C$_1$-C$_6$)alkyl group;

said compound of formula (III-4) being in pure stereoisomer form, or in the form of a mixture of enantiomers and/or diastereoisomers.

2. The method according to claim 1, where R$_3$ is H.

3. The method according to claim 1, where R$_2$ and R$_3$ are H.

4. The method according to claim 1, wherein said compound is selected from among:

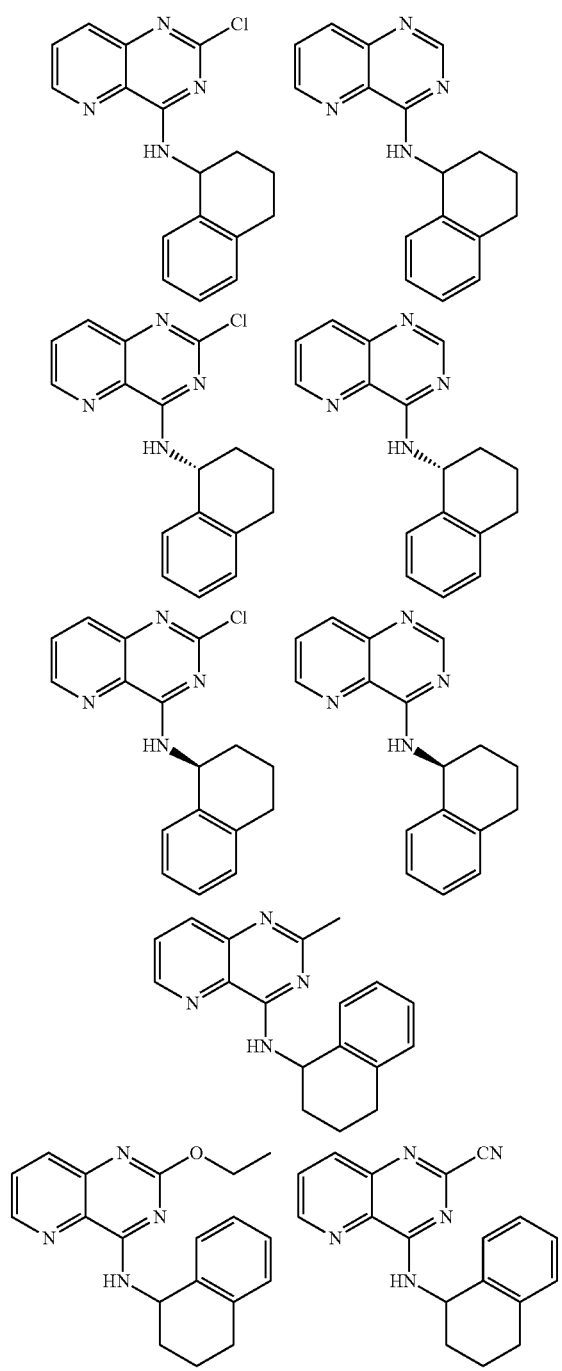

-continued

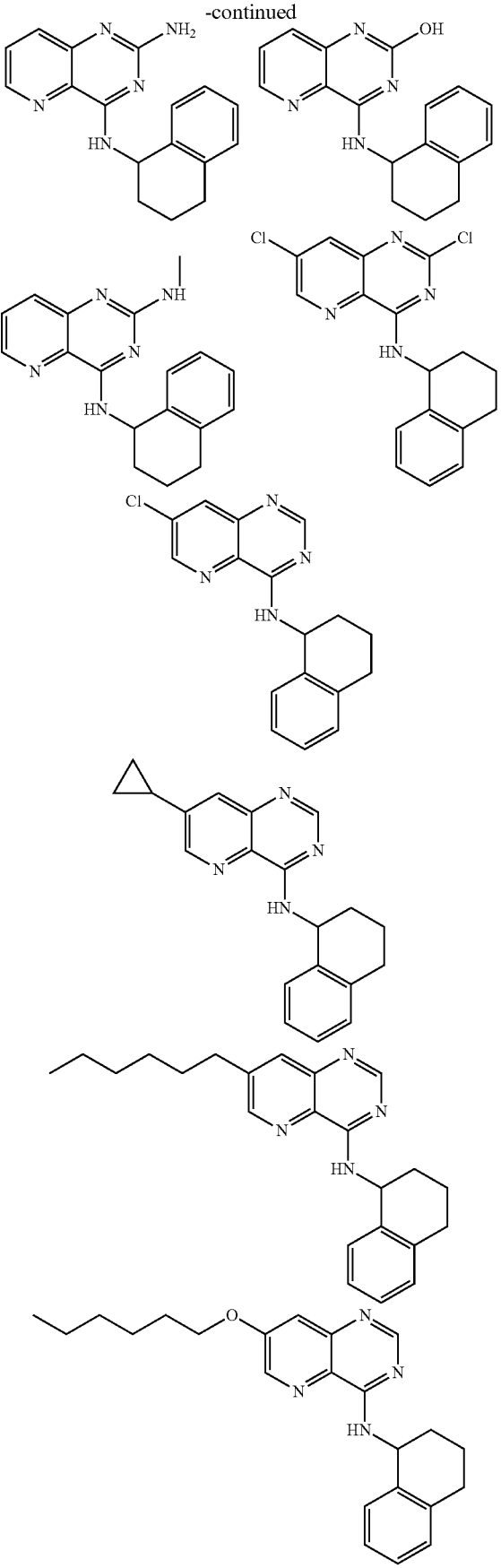

143
-continued
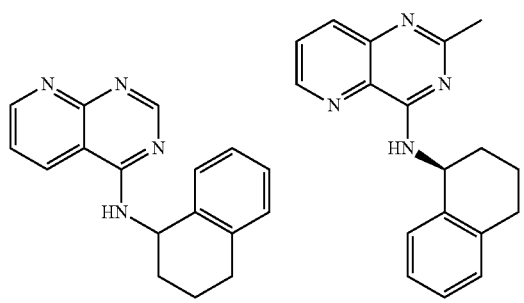
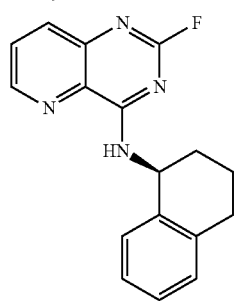
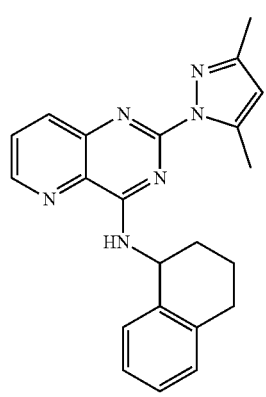
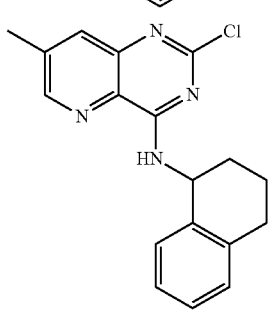
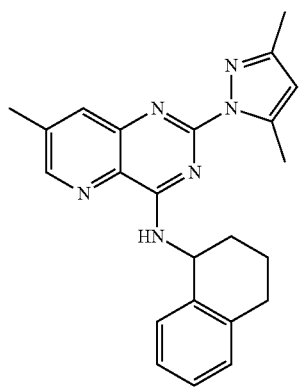
144
-continued
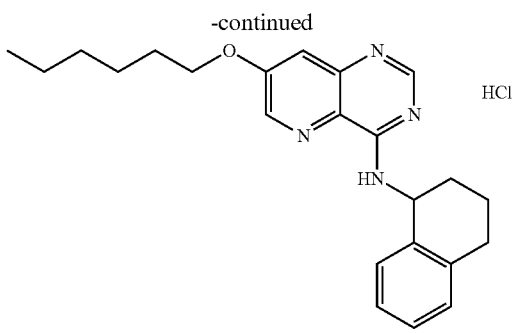
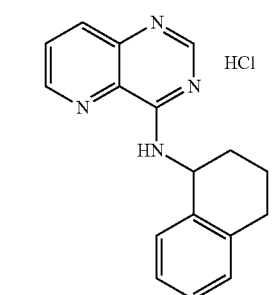
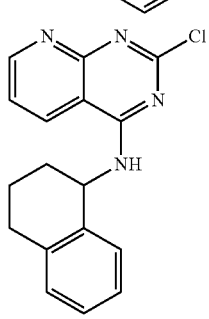
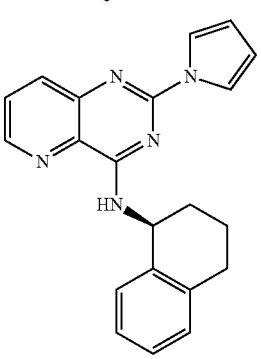
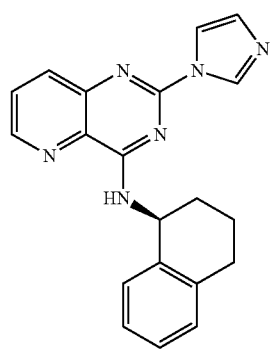

145
-continued
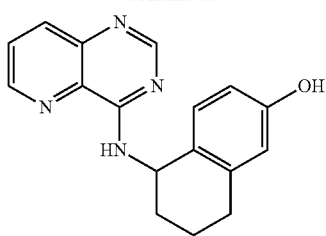
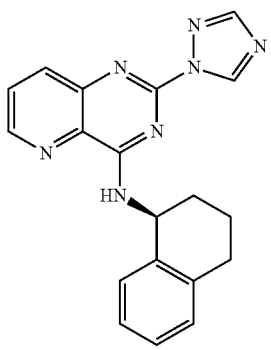
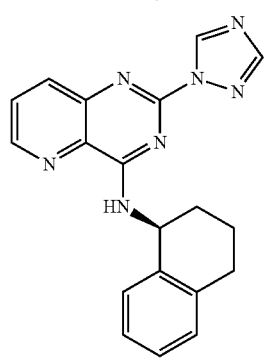
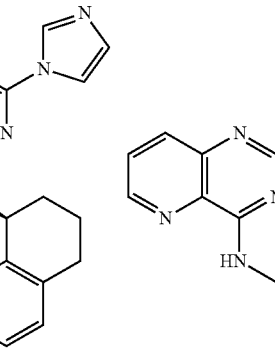
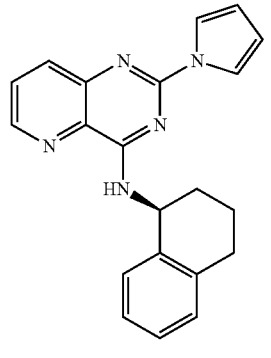 [SMILES: c1ccc2c(c1)CCC[C@@H]2Nc1nc(-n2cccc2)nc2cccnc12]
146
-continued
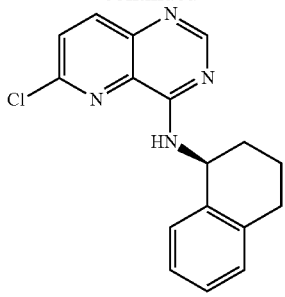
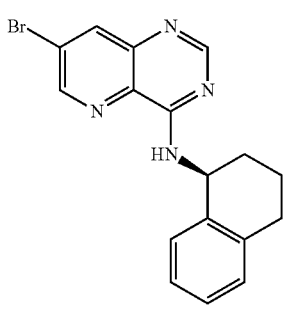
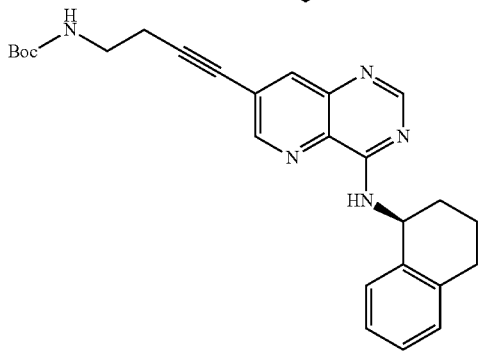
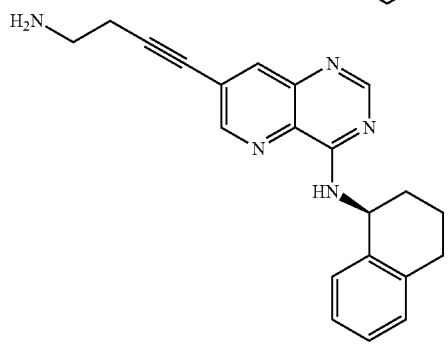
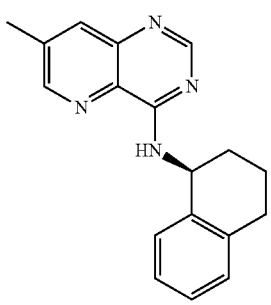

147
-continued

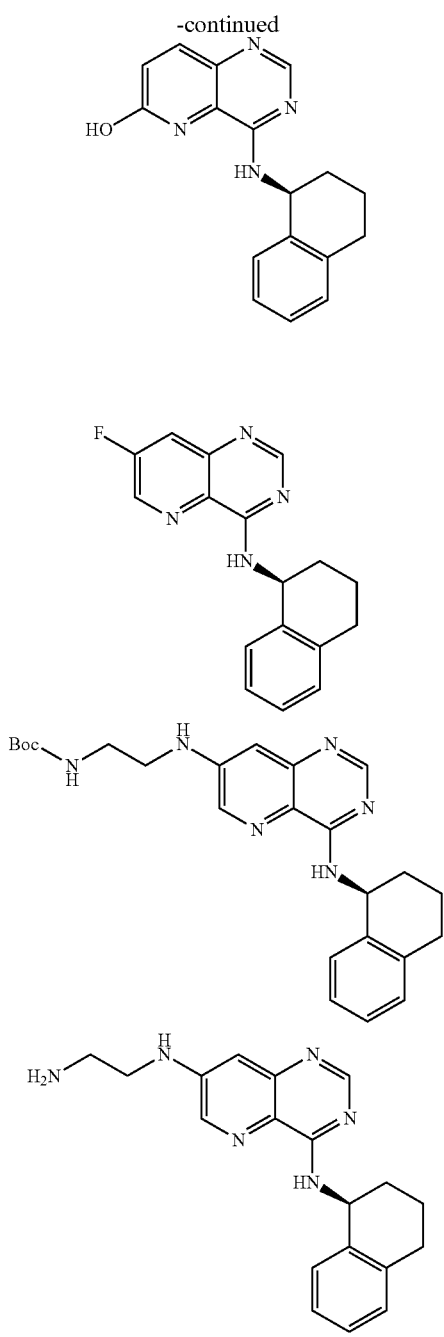

148
-continued

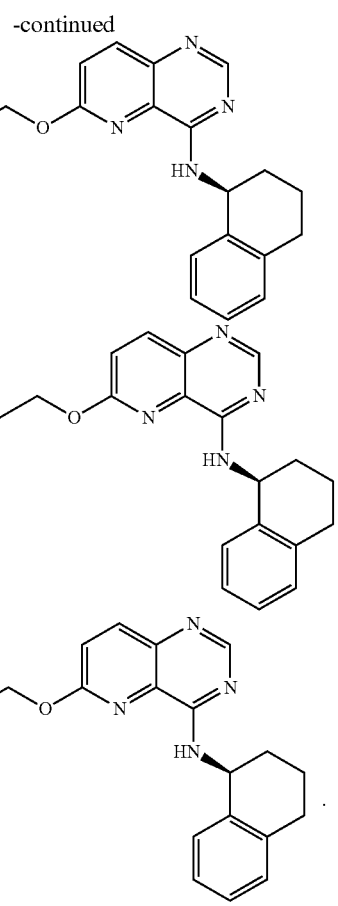

5. The method according to claim 1, wherein the cancer is breast cancer.

6. The method according to claim 1, wherein $R_1$ is H, a $(C_1$-$C_6)$alkyl group or a radical selected from the group consisting of: —$OR_a$, —$NHR_a$, —$NR_aR_b$, —NH—C(=O) $R_a$, —C(=O)$R_a$, —C(=O)O$R_a$, —NH—CN, —C(=O) $NR_aR_b$, Cl, F, CN and nitrogen-containing and/or oxygen-containing heterocycles, $R_a$ and $R_b$ each independently being H, a $(C_1$-$C_6)$alkyl group or $(C_3$-$C_6)$cycloalkyl group, and wherein said nitrogen-containing and/or oxygen-containing heterocycles are selected from heteroaryl and heterocycloalkyl groups having 5 atoms.

7. The method according to claim 6, wherein the heteroaryl group having 5 atoms is selected from the group consisting of: pyrrolyl, pyrazolyl, 1,2,3-triazolyl, 1,2,4-triazolyl, and tetrazolyl.

\* \* \* \* \*